(12) United States Patent
Van Buuren et al.

(10) Patent No.: US 12,258,581 B2
(45) Date of Patent: *Mar. 25, 2025

(54) T CELL MANUFACTURING COMPOSITIONS AND METHODS

(71) Applicants: BioNTech US Inc., Cambridge, MA (US); STICHTING HET NEDERLANDS KANKER INSTITUUT—ANTONI VAN LEEUWENHOEK ZIEKENHIS, Amsterdam (NL)

(72) Inventors: Marit M. Van Buuren, Belmont, MA (US); Divya Reddy Lenkala, Watertown, MA (US); Joost Huibert Van Den Burg, Amsterdam (NL); Jessica Kohler, Boston, MA (US); Matthew Goldstein, Jamaica Plain, MA (US); Ed Fritsch, Concord, MA (US); Renate De Boer, Diemen (NL); Ton Schumacher, Aloemehomal (NL); Noor Bakker, Stuyvesantstraat (NL)

(73) Assignees: BioNTech US Inc., Cambridge, MA (US); Stichting Het Nederlands Kanker Instituut—Antoni Van Leeuwenhoek Ziekenhis, Amsterdam (NL)

( * ) Notice: Subject to any disclaimer, the term of this patent is extended or adjusted under 35 U.S.C. 154(b) by 534 days.

This patent is subject to a terminal disclaimer.

(21) Appl. No.: 17/494,633

(22) Filed: Oct. 5, 2021

(65) Prior Publication Data

US 2022/0177840 A1  Jun. 9, 2022

Related U.S. Application Data

(63) Continuation of application No. 16/735,555, filed on Jan. 6, 2020, now Pat. No. 11,162,072, which is a continuation of application No. PCT/US2018/059896, filed on Nov. 8, 2018.

(60) Provisional application No. 62/737,625, filed on Sep. 27, 2018, provisional application No. 62/618,445, filed on Jan. 17, 2018, provisional application No. 62/588,590, filed on Nov. 20, 2017, provisional application No. 62/583,229, filed on Nov. 8, 2017.

(51) Int. Cl.
*C12N 5/0783* (2010.01)
*A61K 39/00* (2006.01)
*A61P 35/00* (2006.01)

(52) U.S. Cl.
CPC ........ *C12N 5/0636* (2013.01); *A61K 39/4611* (2023.05); *A61K 39/464401* (2023.05); *A61K 39/46449* (2023.05); *A61P 35/00* (2018.01); *A61K 2039/572* (2013.01); *C12N 2501/26* (2013.01); *C12N 2501/998* (2013.01)

(58) Field of Classification Search
None
See application file for complete search history.

(56) References Cited

U.S. PATENT DOCUMENTS

| | | | |
|---|---|---|---|
| 5,391,377 | A | 2/1995 | Barnwell |
| 5,849,589 | A | 12/1998 | Tedder et al. |
| 5,994,126 | A | 11/1999 | Steinman et al. |
| 6,406,705 | B1 | 6/2002 | Davis et al. |
| 7,276,478 | B2 | 10/2007 | Sivakumar et al. |
| 9,476,055 | B2 | 10/2016 | Sahin et al. |
| 9,809,797 | B2 | 11/2017 | Yee et al. |
| 11,162,072 | B2 | 11/2021 | Van Buuren et al. |
| 11,183,272 | B2 | 11/2021 | Rooney et al. |
| 2009/0285843 | A1 | 11/2009 | Simard et al. |
| 2010/0330056 | A1 | 12/2010 | Yee et al. |
| 2015/0104441 | A1 | 4/2015 | Olweus et al. |
| 2017/0037370 | A1 | 2/2017 | Kaiser et al. |
| 2017/0224800 | A1 | 8/2017 | Tran et al. |
| 2018/0273602 | A1 | 9/2018 | Alten et al. |
| 2019/0024050 | A1 | 1/2019 | Yee et al. |
| 2019/0119639 | A1 | 4/2019 | Oelke et al. |
| 2022/0177840 | A1 | 6/2022 | Van Buuren et al. |
| 2022/0280621 | A1 | 9/2022 | Van Buuren et al. |
| 2023/0374455 | A1 | 11/2023 | Juneja et al. |

FOREIGN PATENT DOCUMENTS

| | | |
|---|---|---|
| EP | 2749639 A1 | 7/2014 |
| EP | 3335725 A1 | 6/2018 |
| JP | 2018526034 A | 9/2018 |
| RU | 2447900 C2 | 4/2012 |
| RU | 2793344 C2 | 3/2023 |
| WO | WO-9403205 A1 | 2/1994 |
| WO | WO-9420127 A1 | 9/1994 |
| WO | WO-2006015497 A1 | 2/2006 |
| WO | WO-2006110582 A1 | 10/2006 |

(Continued)

OTHER PUBLICATIONS

Ali, et al., "Induction of neoantigen-reactive T cells from healthy donors", Nature Protocols (2019).

(Continued)

*Primary Examiner* — Michail A Belyavskyi
(74) *Attorney, Agent, or Firm* — Wilson Sonsini Goodrich & Rosati

(57) ABSTRACT

The generation of antigen specific T cells by controlled ex vivo induction or expansion can provide highly specific and beneficial T cell therapies. The present disclosure provides T cell manufacturing methods and therapeutic T cell compositions which can be used for treating subjects with cancer and other conditions, diseases and disorders personal antigen specific T cell therapy.

21 Claims, 49 Drawing Sheets

(56) References Cited

FOREIGN PATENT DOCUMENTS

| WO | WO-2011143656 A2 | 11/2011 |
|---|---|---|
| WO | WO-2012159643 A1 | 11/2012 |
| WO | WO-2013118899 A1 | 8/2013 |
| WO | WO-2015095811 A2 | 6/2015 |
| WO | WO-2017015427 A1 | 1/2017 |
| WO | WO-2017026389 A1 | 2/2017 |
| WO | WO-2017044661 A1 | 3/2017 |
| WO | WO-2017044859 A1 | 3/2017 |
| WO | WO-2017177337 A1 | 10/2017 |
| WO | WO-2017184590 A1 | 10/2017 |
| WO | WO-2019094642 A1 | 5/2019 |
| WO | WO-2020047449 A2 | 3/2020 |
| WO | WO-2020132586 A1 | 6/2020 |
| WO | WO-2020227546 A1 | 11/2020 |
| WO | WO-2022036137 A1 | 2/2022 |
| WO | WO-2023064930 A1 | 4/2023 |
| WO | WO-2024124222 A1 | 6/2024 |

OTHER PUBLICATIONS

Al-Kadhimi, Zaid. et al. The Use of Clinical Grade Magnetic Beads to Deplete Immune Suppressive Elements from Autologous Peripheral Blood Hematopoietic Stem Cell Grafts Enhances T Cell Immune Responses. Blood 112(11):2311, 1-3 (2008).
Allison AC. The Mode of Action of Immunological Adjuvants. Developments in Biological Standardization vol. 92: pp. 3-11 (1998).
Andersen, et al., "Dissection of T-cell Antigen Specificity in Human Melanoma" Cancer Res; 72(7) Apr. 1, 2012, p. 1642-1650.
Bernhard et al., Generation of Immunostimulatory Dendritic Cells From Human CD34+ Hematopoietic Progenitor Cells of the Bone Marrow and Peripheral Blood, Cancer Res. 55:1099-104 (1995).
Bishop, MR, et al., High-dose therapy and peripheral blood progenitor cell transplantation: effects of recombinant human granulocyte-macrophage colony-stimulating factor on the autograft, Blood, vol. 83, No. 2, pp. 610-616 (1994).
Bollard et al., "Sustained complete Responses in Patients With Lymphoma Receiving Autologous Cytotoxic T Lymphocytes Targeting Epstein-Barr Virus Latent Membrane Proteins", Journal of Clinical Oncology 32:8 (2014).
Borish, Larry. et al. Cytokines and chemokines. J Allergy Clin Immunol 111(2 Suppl):S460-475 (2003).
Busch, Robert, et al., Degenerate Binding of Immunogenic Peptides to Hla-dr Proteins on B Cell Surfaces. International Immunology 2:443-451 (1990).
Carreno et al., "IL-12p70-producing patient DC vaccine elicits Tc1-polarized immunity" J. Clin Invest 123(8):3383-3394, Vole 123, No. 8 (2013).
Ceppellini, R, et al., Binding of labelled influenza matrix peptide to HLA DR in living B lymphoid cells. Nature 339(6223):392-394 (1989).
Cerundolo, V, et al., The Binding Affinity and Dissociated Rates of Peptides for Class I Major Histocompatibility Complex Molecules. European Journal of Immunology 21:2069-2075 (1991).
Chae, Young Kwang. et al. Current landscape and future of dual anti-CTLA4 and PD-1/PD-L1 blockade immunotherapy in cancer; lessons learned from clinical trials with melanoma and non-small cell lung cancer (NSCLC). J Immunother Cancer 6(1):39, 1-27 (2018).
Christinck, E Rosemary et al. Peptide Binding to Class I MHC on Living Cells and Quantitation of Complexes Required for CTL Lysis. Nature vol. 352,6330: pp. 67-70 (1991).
Del Guercio, M F, et al., Binding of a Peptide Antigen to Multiple HLA Alleles Allows Definition of an A2-Like Supertype. Journal of Immunology 154(2):685-693 (1995).
Dupuis, M., et al., Dendritic Cells Internalize Vaccine Adjuvant after Intramuscular Injection, Cell Immunol. 1998; 186(1):18-27.
EP20801696.4 Extended European Search Report dated May 22, 2023.

Erdmann et al., "Automated closed-system manufacturing of human monocyte-derived dendritic cells for cancer immunotherapy", Journal of Immunological Methods 463:89-96 (2018).
European Patent Application No. 19849341.3 Extended European Search Report issued on Apr. 8, 2022.
Fix., Oral controlled release technology for peptides: status and future prospects. Pharm Res., 13(12):1760-1764 (1996).
Freudenthal, et al. The distinct surface of human blood dendritic cells, as observed after an improved isolation method. Proc Natl Acad Sci U S A. Oct. 1990;87(19):7698-702.
Fritsch et al., "HLA-binding properties of tumor neoepitopes in humans", Cancer Immunol Res p. 1-27 (2014).
Gabrilovich, Dmitry I et al. IL-12 and Mutant P53 Peptide-Pulsed Dendritic Cells for the Specific Immunotherapy of Cancer. Journal of Immunotherapy With Emphasis on Tumor Immunology vol. 19,6: pp. 414-418 (1996).
Gamvrellis, Anita, et al., Vaccines that Facilitate Antigen Entry into Dendritic Cells. Immunology and Cell Biology 82(5):506-516 (2004).
Gattinoni et al., "A human memory T-cell subset with stem cell-like properties", Nat. Med. 17(10): 1290-1297 (2012).
Gilboa, Eli, "The Making of a Tumor Rejection Antigen", Immunity. 11:263-270 (1999).
Gjertsen et al., Cytotoxic CD4+ and CD8+ T lymphocytes, generated by mutant p21-ras (12Val) peptide vaccination of a patient, recognize 12Val-dependent nested epitopes present within the vaccine peptide and kill autologous tumour cells carrying this mutation. Int J Cancer. Sep. 4, 1997;72(5):784-90. doi: 10.1002/(sici)1097-0215(19970904)72:5784::aid-ijc143.0.co;2-9. PMID: 9311595.
Gururangan, Sridharan et al. Total tumor RNA pulsed dendritic cells plus adoptive transfer of ex-vivo enriched autologous T-lymphocytes in the treatment of children with primary brain tumors. Neuroimmunology and Neuroinflammation 5(10):45, 1-15 (2018).
Hamanishi, Junzo. et al. PD-1/PD-L1 blockade in cancer treatment: perspectives and issues. Int J Clin Oncol 21(3):462-473 (2016).
Hammer, Juergen, et al., Precise Prediction of Major Histocompatibility Complex Class II-peptide Interaction Based on Peptide Side Chain Scanning. The Journal of experimental medicine 180(6):2353-2358 (1994).
Hill, C Mark, et al., Conformational and Structural Characteristics of Peptides Binding to HLA-DR Molecules. Journal of immunology 147(1):189-197 (1991).
Hill, C Mark, et al., Exploration of Requirements for Peptide Binding to HLA DRB10101 and DRBI*0401. Journal of immunology 152(6):2890-2898 (1994).
JP2021566008 Office Action dated May 29, 2023, and an English translation.
Kharkevich, D A, Pharmacology: Textbook, 10th Ed. Corrected, Revised and Supplemented. GEOTAR-Media 73-74 (2010).
Khilko, S N, et al., Direct Detection of Major Histocompatibility Complex Class I Binding to Antigenic Peptides Using Surface Plasmon Resonance. Peptide Immobilization and Characterization of Binding Specificity. The Journal of Biological Chemistry 268(21): 15425-15434 (1993).
Kholodov et al. Clinical Pharmacokinetics. Moscow, Medicine pp. 83-98, 134-138, 160, 378-380 (1985).
Klebanoff et al. Sorting through subsets: Which T cell poulations mediate highly effective adoptive immunotherapy? J Immunother 35(9):651-660 (2012).
Koski et al., "CD14+ Monocytes as Dendritic Cell Precursors: Diverse Maturation-Inducing Pathways Lead to Common Activation of NF-kB/ReIB", Critical Reviews in Immunology, 21:179-189 (2001).
KR20217040167 Office Action dated Dec. 27, 2023, and an English translation.
Krieg, Arthur M. Therapeutic Potential of Toll-like Receptor 9 Activation. Nature Reviews Drug Discovery vol. 5,6: pp. 471-484 (2006).
Kurd, et al., "T cell selection in the thymus: a spatial and temporal perspective" Immunol Rev (2016); 271(1): p. 114-126.
Lauss, Martin. et al. Mutational and putative neoantigen load predict clinical benefit of adoptive T cell therapy in melanoma. Nat Commun 8(1):1738, 1-11 (2017).

(56) References Cited

OTHER PUBLICATIONS

Leen et al., "Cytotoxic T lymphocyte therapy with donor T cells prevents and treats adenovirus and Epstein-Barr virus infections after haploidentical and matched unrelated stem cell transplantation", Blood 114(19): 4283-4292 (2009).
Li, H. et al., "TCRβ repertoire of CD4+ and CD8+ T cells is distinct in richness, distribution, and CDR3 amino acid composition," J Leukoc Biol., 2016, vol. 99, No. 3, pp. 505-513.
Linnemann et al., "High-throughput epitope discovery reveals frequent recognition of neo-antigens by CD4+ T cells in human melanoma", Nature Medicine 21(1): 81-87 (2015).
Lissina et al., "Priming of Qualitatively Superior Human Effector CD8+ T Cells Using TLR8 Ligand Combined with FLT3 Ligand", J. Immunol 196:256-263 (2016).
Ljunggren, H G, et al., Empty MHC Class I Molecules Come Out in the Cold. Nature 346(6283):476-480 (1990).
Maraskovsky et al., "In vivo generation of human dendritic cell subsets by Flt3 lignad", BLOOD 96(3): 878-884 (2000).
Markowicz, et al. Granulocyte-macrophage colony-stimulating factor promotes differentiation and survival of human peripheral blood dendritic cells in vitro. J Clin Invest. Mar. 1990;85(3):955-61.
Marshall, K W, et al., Role of the Polymorphic Residues in HLA-DR Molecules in Allele-specific Binding of Peptide Ligands. Journal of Immunology 152(10):4946-4957 (1994).
Marshall, Keith W et al. Role of the Polymorphic Residues in HLA-DR Molecules in Allele-specific Binding of Peptide Ligands. The Journal of Immunology vol. 152, 10: pp. 4946-4957 (1994).
Matsumura, Noriomi. et al. Immunostimulatory effect of Fms-like tyrosine kinase 3 ligand on peripheral monocyte-derived dendritic cells and natural killer cells: utilization for ovarian cancer treatment. Oncology Reports 19(2):505-515 (2008).
Mosca, Paul J, et al., Dendritic Cell Vaccines. Frontiers in Bioscience 12:4050-4060 (2007).
Nair et al., "Isolation and Generation of Human Dendritic Cells", Curr. Protoc. Immunol. (2012).
O'Doherty, et al. Dendritic cells freshly isolated from human blood express CD4 and mature into typical immunostimulatory dendritic cells after culture in monocyte-conditioned medium. J Exp Med. Sep. 1, 1993;178(3):1067-76.
Parker, K C, et al., The Beta 2-microglobulin Dissociation Rate is an Accurate Measure of the Stability of MHC Class I Heterotrimers and Depends on Which Peptide is Bound. Journal of Immunology 149(6):1896-1904 (1992).
PCT/US2018/59896 International Search Report and Written Opinion dated Mar. 4, 2019.
PCT/US2019/046876 International Search Report and Written Opinion issued Jan. 21, 2020.
PCT/US2021/045800 International Search Report and Written Opinion dated Dec. 22, 2021.
PCT/US2022/078161 International Search Report and Written Opinion dated Feb. 16, 2023.
PCT/US2023/083256 International Search Report and Written Opinion dated Mar. 26, 2024.
Poncette, Lucia. et al. Effective NY-ESO-1-specific MHC II-restricted T cell receptors from antigen-negative hosts enhance tumor regression. J Clin Invest 129(1):324-335. (2019) Published online Dec. 10, 2018.
Reay, P A, et al., pH Dependence and Exchange of High and Low Responder Peptides Binding to a Class II MHC Molecule. 11(8):2829-2839 (1992).
RU2021135535 Office Action with Search Report dated Oct. 27, 2023, and an English translation.
Russian Patent Application No. 2021106561/10 Exam Report and Translation issued on Dec. 29, 2021.
Russian Patent Application No. 2021106561/10 Exam Report and Translation issued on May 26, 2022.
Saint-Jean, Melanie. et al. Adoptive Cell Therapy with Tumor-Infiltrating Lymphocytes in Advanced Melanoma Patients. J Immunol Res 2018:3530148, 1-10 (2018).
Sakaguchi et al., Regulatory T Cells and Immune Tolerance. Cell 133:775-787 (2008).
Samanen et al. Chemical approaches to improve the oral bioavailability of peptidergic molecules. J. Pharm. Pharmacol. 48:119-135 (1996).
Schumacher, T N , et al., Direct Binding of Peptide to Empty MHC Class I Molecules on Intact Cells and in Vitro. Cell 62(3):563-567 (1990).
Selezneva et al.: Complex Approach to the Study of Pharmacological Agents In Vitro, Ex Vivo, In Vivo. International Research Journal. 6(37):1-13 (2015).
Serafini, Paolo et al. Phosphodiesterase-5 inhibition augments endogenous antitumor immunity by reducing myeloid-derived suppressor cell function. J Exp Med 203(12):2691-2702 (2006).
Sette, Alessandro et al. Peptide Binding to the Most Frequent HLA-A Class I Alleles Measured by Quantitative Molecular Binding Assays. Molecular Immunology vol. 31, 11: pp. 813-822 (1994).
Sidney, J, et al., Measurement of MHC/peptide Interactions by Gel Filtration. Current Protocols in Immunology Chapter 18:Unit 18.3:47 Pages (2013).
Stronen et al., "Dendritic Cells Engineered to Express Defined Allo-HLA Peptide Complexes Induce Antigen-specific Cytotoxic T Cells Efficiently Killing Tumour Cells", Scandinavian Journal of Immunology 69, pp. 319-328 (2009).
Thillier, Yann et al. Synthesis of 5' cap-0 and cap-1 RNAs using solid-phase chemistry coupled with enzymatic methylation by human (guanine-$N^7$)-methyl transferase. RNA 18(4):856-868 (2012).
Townsend, A, et al., Assembly of MHC Class I Molecules Analyzed in Vitro. Cell 62(2):285-295 (1990).
Van Buuren et al., "High sensitivity of cancer exome-based CD8 T cell neo-antigen identification", OncoImmunology 3 (2014).
Verdegaal, Els. E.M. Adoptive cell therapy: a highly successful individualized therapy for melanoma with great potential for other malignancies. Curr Opin Immunol 39:90-95 (2016).
Wang et al. Identification of T-cell Receptors Targeting KRAS-Mutated Human Tumors. Cancer Immunol Res. Mar. 2016;4(3):204-14. doi: 10.1158/2326-6066.CIR-15-0188. Epub Dec. 23, 2015. PMID: 26701267; PMCID: PMC4775432.
Wilde, Susanne. et al. Dendritic cells pulsed with RNA encoding allogeneic MHC and antigen induce T cells with superior antitumor activity and higher TCR functional avidity. Blood 114(10):2131-2139 (2009).
Yarchoan, Mark. et al. Targeting neoantigens to augment antitumour immunity. Nat Rev Cancer 17(4):209-222 (2017).
Young, et al. Dendritic cells stimulate primary human cytolytic lymphocyte responses in the absence of CD4+ helper T cells. J Exp Med. Apr. 1, 1990;171(4):1315-32.

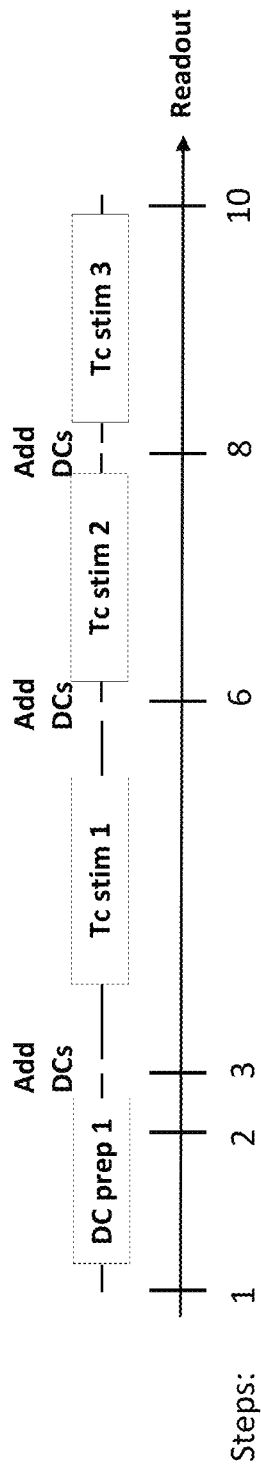
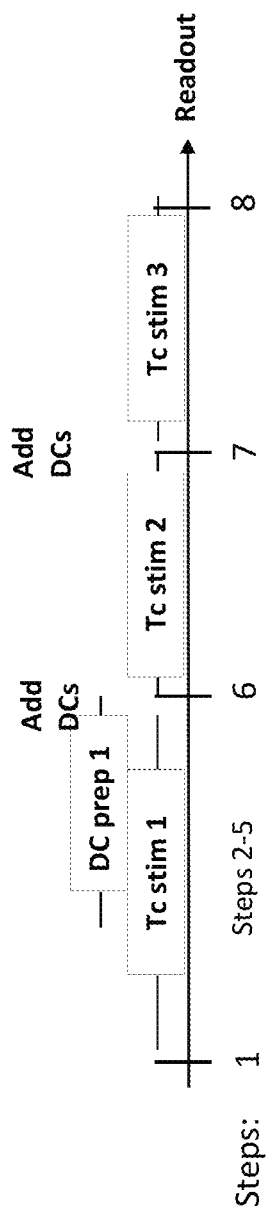
FIG. 1A
FIG. 1B

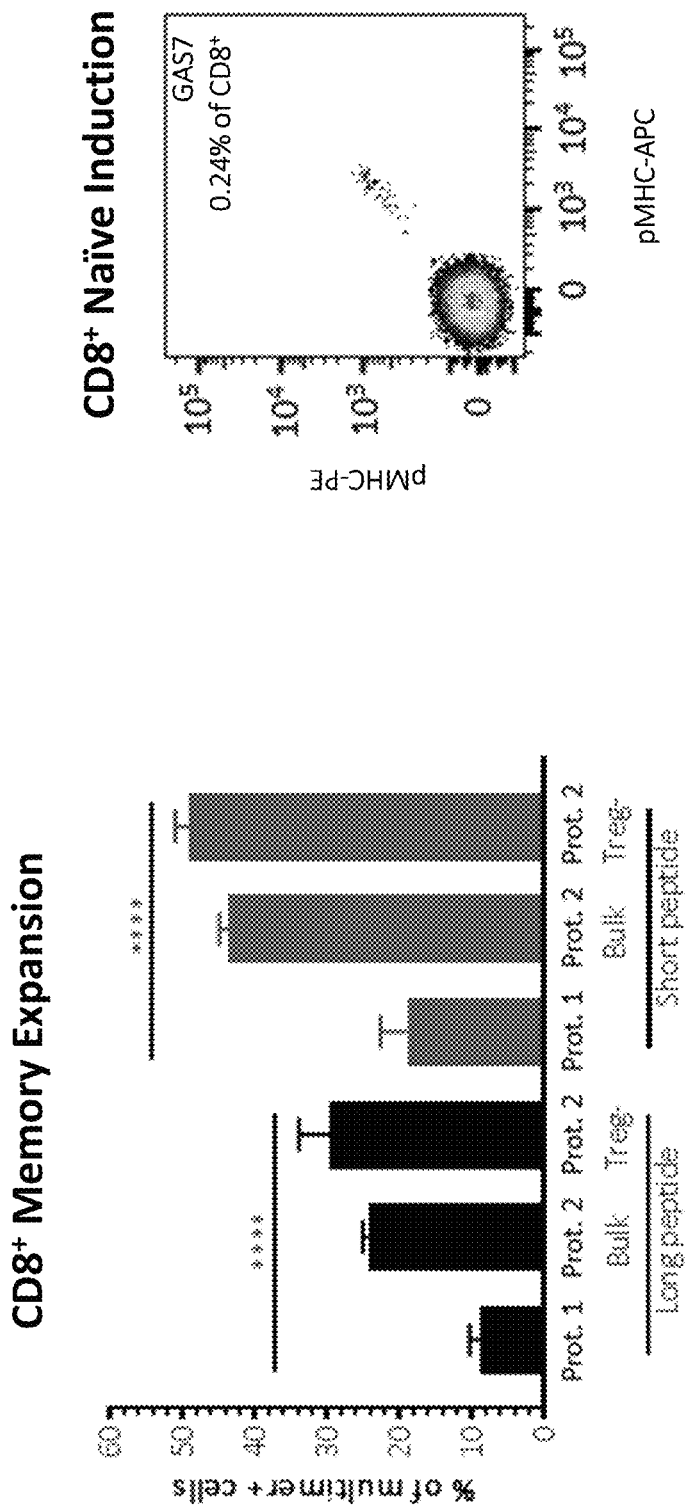

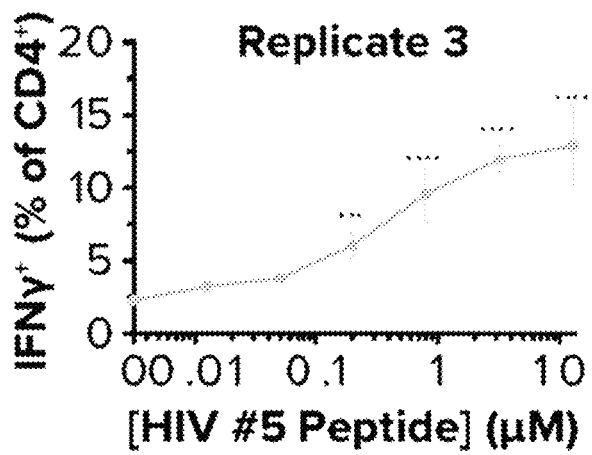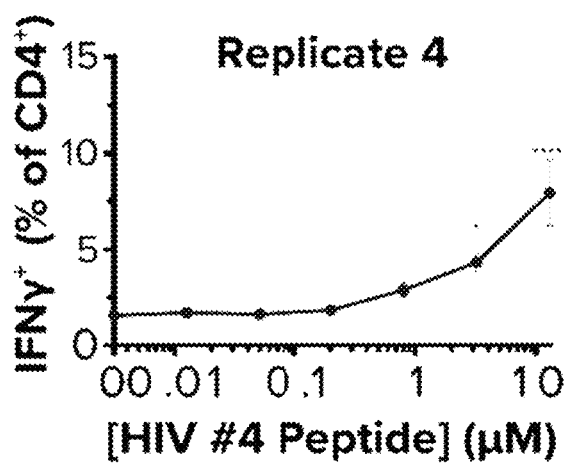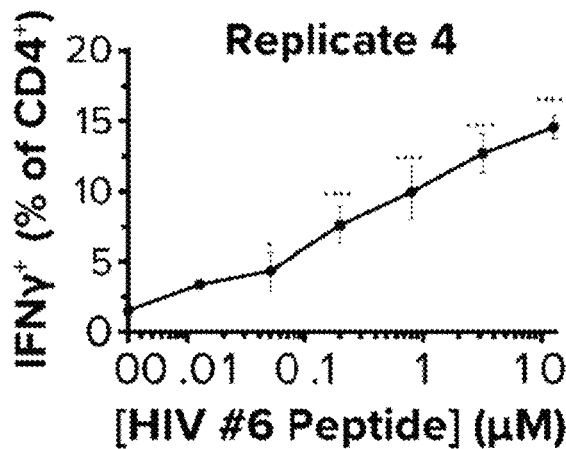
FIG. 30C

T CELL MANUFACTURING COMPOSITIONS AND METHODS

CROSS-REFERENCE

This application is a continuation application of the U.S. patent application U.S. Ser. No. 16/735,555 filed on Jan. 6, 2020, which is a continuation of international patent application PCT/US2018/059896 filed on Nov. 8, 2018, which claims benefit to U.S. Provisional Application No. 62/583,229, filed Nov. 8, 2017; U.S. Provisional Application No. 62/588,590, filed Nov. 20, 2017; U.S. Provisional Application No. 62/618,445, filed Jan. 17, 2018; and U.S. Provisional Application No. 62/737,625, filed Sep. 27, 2018, which applications are incorporated herein by reference in its entirety.

BACKGROUND

Tumor vaccines are typically composed of tumor antigens and immunostimulatory molecules (e.g., adjuvants, cytokines or TLR ligands) that work together to induce antigen-specific cytotoxic T cells (CTLs) that recognize and lyse tumor cells. Such vaccines contain either shared tissue restricted tumor antigens or a mixture of shared and patient-specific antigens in the form of whole tumor cell preparations. The shared tissue restricted tumor antigens are ideally immunogenic proteins with selective expression in tumors across many individuals and are commonly delivered to patients as synthetic peptides or recombinant proteins. In contrast, whole tumor cell preparations are delivered to patients as autologous irradiated cells, cell lysates, cell fusions, heat-shock protein preparations or total mRNA. Since whole tumor cells are isolated from the autologous patient, the cells may include patient-specific tumor antigens as well as shared tumor antigens. Finally, there is a third class of tumor antigens, neoantigens, that has rarely been used in vaccines, which consists of proteins with tumor-specific mutations (which can be patient-specific or shared) that result in altered amino acid sequences. Such mutated proteins are: (a) unique to the tumor cell as the mutation and its corresponding protein are present only in the tumor; (b) avoid central tolerance and are therefore more likely to be immunogenic; (c) provide an excellent target for immune recognition including by both humoral and cellular immunity.

Adoptive immunotherapy or adoptive cellular therapy (ACT) is the transfer of gene modified T lymphocytes to a subject for the therapy of disease. Adoptive immunotherapy has yet to realize its potential for treating a wide variety of diseases including cancer, infectious disease, autoimmune disease, inflammatory disease, and immunodeficiency. However, most, if not all adoptive immunotherapy strategies require T cell activation and expansion steps to generate a clinically effective, therapeutic dose of T cells. Due to the inherent complexity of live cell culture and patient to patient variability, current technologies for generating therapeutic doses of T cells, including engineered T cells, remain limited by cumbersome T cell manufacturing processes. Existing T cell manufacturing processes are not easily scalable, repeatable, reliable, or efficient and often produce an inferior T cell product that may be prone to exhaustion and loss of effector immune cell function. To date, engineered T cell adoptive immunotherapies have met with only limited success and routinely show variable clinical activity. Therefore, such therapies are not suitable for widespread clinical use. Accordingly, there remains a need for developing compositions and methods for expansion and induction of antigen specific T cells with a favorable phenotype and function.

SUMMARY

In some aspects, provided herein is a pharmaceutical composition comprising: a population of immune cells from a biological sample comprising at least one antigen specific T cell comprising a T cell receptor (TCR) specific to at least one antigen peptide sequence, and a pharmaceutically acceptable excipient; wherein an amount of immune cells expressing CD14 and/or CD25 in the population is proportionally different from an amount of immune cells expressing CD14 and/or CD25 in the biological sample. In some aspects, provided herein is a pharmaceutical composition comprising: a population of immune cells from a biological sample comprising at least one antigen specific T cell comprising a T cell receptor (TCR) specific to at least one antigen peptide sequence, and a pharmaceutically acceptable excipient; wherein an amount of immune cells expressing CD14 and/or CD25 in the population is different from an amount of immune cells expressing CD14 and/or CD25 in the biological sample. In some aspects, provided herein is a pharmaceutical composition comprising: a population of immune cells from a biological sample comprising at least one antigen specific T cell comprising a T cell receptor (TCR) specific to at least one antigen peptide sequence, and a pharmaceutically acceptable excipient; wherein a percentage of immune cells expressing CD14 and/or CD25 in the population is different from a percentage of immune cells expressing CD14 and/or CD25 in the biological sample. In some aspects, provided herein is a pharmaceutical composition comprising: a population of immune cells from a biological sample comprising at least one antigen specific T cell comprising a T cell receptor (TCR) specific to at least one antigen peptide sequence, and a pharmaceutically acceptable excipient; wherein a concentration of immune cells expressing CD14 and/or CD25 in the population is different from a concentration of immune cells expressing CD14 and/or CD25 in the biological sample.

In some aspects, provided herein is a composition comprising a population of immune cells from a biological sample, wherein an amount of immune cells expressing CD14 and CD25 in the population is proportionally less than an amount of immune cells expressing CD14 and CD25 in the biological sample. In some aspects, provided herein is a composition comprising a population of immune cells from a biological sample, wherein an amount of immune cells expressing CD14 and CD25 in the population is less than an amount of immune cells expressing CD14 and CD25 in the biological sample. In some aspects, provided herein is a composition comprising a population of immune cells from a biological sample, wherein a percentage of immune cells expressing CD14 and CD25 in the population is less than a percentage of immune cells expressing CD14 and CD25 in the biological sample. In some aspects, provided herein is a composition comprising a population of immune cells from a biological sample, wherein a concentration of immune cells expressing CD14 and CD25 in the population is less than a concentration of immune cells expressing CD14 and CD25 in the biological sample.

In some aspects, provided herein is a pharmaceutical composition comprising a population of immune cells comprising T cells from a biological sample, wherein the T cells comprise at least one antigen specific T cell that is an antigen presenting cell (APC) stimulated T cell and comprises a T cell receptor (TCR) specific to at least one antigen peptide sequence, wherein the APC is a FLT3L-stimulated APC; and a pharmaceutically acceptable excipient.

In some aspects, provided herein is a pharmaceutical composition comprising a population of immune cells comprising T cells from a biological sample, wherein the T cells comprise at least one antigen specific T cell comprising a T cell receptor (TCR) specific to at least one antigen peptide sequence, and a pharmaceutically acceptable excipient; wherein the at least one antigen specific T cell is at least about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total T cells, total $CD4^+$ T cells, total $CD8^+$ T cells, or total immune cells; and wherein the biological sample comprises one or more antigen specific T cells, wherein the one or more antigen specific T cells in the biological sample is at most about 0.00001%, 0.00005%, 0.0001%, 0.0005%, 0.001%, 0.005%, 0.01%, or 0.05% of total $CD4^+$ T cells, total $CD8^+$ T cells, total T cells or total immune cells of total T cells, total $CD4^+$ T cells, total $CD8^+$ T cells, or total immune cells in the biological sample. In some aspects, provided herein is a pharmaceutical composition comprising a population of immune cells comprising T cells expanded or induced from a biological sample, wherein the T cells expanded or induced from the biological sample comprise at least one antigen specific T cell comprising a T cell receptor (TCR) specific to at least one antigen peptide sequence, and a pharmaceutically acceptable excipient; wherein an amount, concentration or percentage of the at least one antigen specific T cell is at least about 1.1, 1.2, 1.3, 1.4, 1.5, 1.6, 1.7, 1.8, 1.9, 2, 2.5, 3, 3.5, 4, 4.5, 5, 5.5, 6, 6.6, 7, 7.5, 8, 8.5, 9, 9.5, 10, 11, 12, 13, 14, 15, 16, 17, 18, 19, 20, 25, 30, 35, 40, 45, 50, 55, 60, 75, 80, 85, 90, 95, 100, 125, 150, 175, 200, 225, 250, 275, 300, 325, 350, 375, 400, 425, 450, 475, 500, 600, 700, 800, 900, or 1000 greater than an amount, concentration or percentage of antigen specific T cells or total T cells in the biological sample. In some aspects, provided herein is a pharmaceutical composition comprising a population of immune cells comprising T cells from a biological sample, wherein the T cells comprise at least one antigen specific T cell comprising a T cell receptor (TCR) specific to at least one antigen peptide sequence, and a pharmaceutically acceptable excipient; wherein the at least one antigen specific T cell comprises expanded or induced antigen specific T cells that are expanded or induced at least about 1.1, 1.2, 1.3, 1.4, 1.5, 1.6, 1.7, 1.8, 1.9, 2, 2.5, 3, 3.5, 4, 4.5, 5, 5.5, 6, 6.6, 7, 7.5, 8, 8.5, 9, 9.5, 10, 11, 12, 13, 14, 15, 16, 17, 18, 19, 20, 25, 30, 35, 40, 45, 50, 55, 60, 75, 80, 85, 90, 95, 100, 125, 150, 175, 200, 225, 250, 275, 300, 325, 350, 375, 400, 425, 450, 475, 500, 600, 700, 800, 900, or 1000 fold from the biological sample. In some aspects, provided herein is a pharmaceutical composition comprising a population of immune cells comprising $CD4^+$ T cells from a biological sample, wherein the $CD4^+$ T cells comprise at least one antigen specific $CD4^+$ T cell comprising a T cell receptor (TCR) specific to at least one antigen peptide sequence, and a pharmaceutically acceptable excipient; wherein the at least one antigen specific $CD4^+$ T cell is at least about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total T cells, total $CD4^+$ T cells, total $CD8^+$ T cells, or total immune cells; and wherein the biological sample comprises one or more antigen specific $CD4^+$ T cells, wherein the one or more antigen specific $CD4^+$ T cells in the biological sample is at most about 0.00001%, 0.00005%, 0.0001%, 0.0005%, 0.001%, 0.005%, 0.01%, or 0.05% of total $CD4^+$ T cells, total $CD8^+$ T cells, total T cells or total immune cells of total T cells, total $CD4^+$ T cells, total $CD8^+$ T cells, or total immune cells in the biological sample. In some embodiments, a pharmaceutical composition comprises a population of immune cells comprising $CD4^+$ T cells from a biological sample, wherein the $CD4^+$ T cells comprise at least one antigen specific $CD4^+$ T cell comprising a T cell receptor (TCR) specific to at least one antigen peptide sequence, and a pharmaceutically acceptable excipient; wherein the at least one antigen specific $CD4^+$ T cell is at least about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total $CD4^+$ T cells; and wherein the biological sample comprises one or more antigen specific $CD4^+$ T cells, wherein the one or more antigen specific $CD4^+$ T cells in the biological sample is at most about 0.00001%, 0.00005%, 0.0001%, 0.0005%, 0.001%, 0.005%, 0.01%, or 0.05% of total $CD4^+$ T cells in the biological sample. In some aspects, provided herein is a pharmaceutical composition comprising a population of immune cells comprising $CD4^+$ T cells expanded or induced from a biological sample, wherein the $CD4^+$ T cells expanded or induced from the biological sample comprise at least one antigen specific $CD4^+$ T cell comprising a T cell receptor (TCR) specific to at least one antigen peptide sequence, and a pharmaceutically acceptable excipient; wherein an amount, concentration or percentage of the at least one antigen specific T cell is at least about 1.1, 1.2, 1.3, 1.4, 1.5, 1.6, 1.7, 1.8, 1.9, 2, 2.5, 3, 3.5, 4, 4.5, 5, 5.5, 6, 6.6, 7, 7.5, 8, 8.5, 9, 9.5, 10, 11, 12, 13, 14, 15, 16, 17, 18, 19, 20, 25, 30, 35, 40, 45, 50, 55, 60, 75, 80, 85, 90, 95, 100, 125, 150, 175, 200, 225, 250, 275, 300, 325, 350, 375, 400, 425, 450, 475, 500, 600, 700, 800, 900, or 1000 greater than an amount, concentration or percentage of antigen specific $CD4^+$ T cells, total $CD4^+$ T cells, or total T cells in the biological sample. In some aspects, provided herein is a pharmaceutical composition comprising a population of immune cells comprising $CD4^+$ T cells from a biological sample, wherein the $CD4^+$ T cells comprise at least one antigen specific $CD4^+$ T cell comprising a T cell receptor (TCR) specific to at least one antigen peptide sequence, and a pharmaceutically acceptable excipient; wherein the at least one antigen specific $CD4^+$ T cell comprises expanded or induced antigen specific $CD4^+$ T cells that are expanded or induced at least about 1.1, 1.2, 1.3, 1.4, 1.5, 1.6, 1.7, 1.8, 1.9, 2, 2.5, 3, 3.5, 4, 4.5, 5, 5.5, 6, 6.6, 7, 7.5, 8, 8.5, 9, 9.5, 10, 11, 12, 13, 14, 15, 16, 17, 18, 19, 20, 25, 30, 35, 40, 45, 50, 55, 60, 75, 80, 85, 90, 95, 100, 125, 150, 175, 200, 225, 250, 275, 300, 325, 350, 375, 400, 425, 450, 475, 500, 600, 700, 800, 900, or 1000 fold from the biological sample. In some aspects, provided herein is a pharmaceutical composition comprising a population of immune cells comprising $CD4^+$ T cells from a biological sample depleted of CD25 expressing cells or CD25 and CD14 expressing cells, wherein the $CD4^+$ T cells comprise at least one antigen specific $CD4^+$ T cell comprising a T cell receptor (TCR) specific to at least one antigen peptide sequence, and a pharmaceutically acceptable excipient; wherein the at least one antigen specific $CD4^+$ T cell comprises expanded or induced antigen specific $CD4^+$ T cells that are expanded or induced at least about 1.1, 1.2, 1.3, 1.4, 1.5, 1.6, 1.7, 1.8, 1.9, 2, 2.5, 3, 3.5, 4, 4.5, 5, 5.5, 6, 6.6, 7, 7.5, 8, 8.5, 9, 9.5, 10, 11, 12, 13, 14, 15, 16, 17, 18, 19, 20, 25, 30, 35, 40, 45, 50, 55, 60, 75, 80, 85, 90, 95, 100, 125, 150, 175, 200, 225, 250, 275, 300, 325, 350, 375, 400, 425, 450, 475, or 500 fold higher compared from the biological sample. In some aspects, provided herein is a pharmaceutical composition comprising a population of immune cells comprising $CD8^+$ T cells from a biological sample, wherein the $CD8^+$ T cells comprise at least one antigen specific $CD8^+$ T cell comprising a T cell receptor (TCR) specific to at least one antigen peptide sequence, and a pharmaceutically acceptable excipient; wherein the at least one antigen specific $CD8^+$ T cell is at least about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total T cells, total $CD4^+$ T cells, total $CD8^+$ T cells, or total immune cells; and wherein the biological sample comprises one or more antigen specific $CD8^+$ T cells, wherein the one or more antigen specific $CD8^+$ T cells in the biological sample is at most about 0.00001%, 0.00005%, 0.0001%, 0.0005%, 0.001%, 0.005%, 0.01%, or 0.05% of total $CD4^+$ T cells, total $CD8^+$ T cells, total T cells or total immune cells of total T cells, total $CD4^+$ T cells, total $CD8^+$ T cells, or total immune cells in the biological sample. In some embodiments, a pharmaceutical composition comprises a population of immune cells comprising $CD8^+$ T cells from a biological sample, wherein the $CD8^+$ T cells comprise at least one antigen specific $CD8^+$ T cell comprising a T cell receptor (TCR) specific to at least one antigen peptide sequence, and a pharmaceutically acceptable excipient; wherein the at least one antigen specific $CD8^+$ T cell is at least about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total $CD8^+$ T cells; and wherein the biological sample comprises one or more antigen specific $CD4^+$ T cells, wherein the one or more antigen specific $CD8^+$ T cells in the biological sample is at most about 0.00001%, 0.00005%, 0.0001%, 0.0005%, 0.001%, 0.005%, 0.01%, or 0.05% of total $CD8^+$ T cells in the biological sample. In some aspects, provided herein is a pharmaceutical composition comprising a population of immune cells comprising $CD8^+$ T cells expanded or induced from a biological sample, wherein the $CD8^+$ T cells expanded or induced from the biological sample comprise at least one antigen specific $CD8^+$ T cell comprising a T cell receptor (TCR) specific to at least one antigen peptide sequence, and a pharmaceutically acceptable excipient; wherein an amount, concentration or percentage of the at least one antigen specific T cell is at least about 1.1, 1.2, 1.3, 1.4, 1.5, 1.6, 1.7, 1.8, 1.9, 2, 2.5, 3, 3.5, 4, 4.5, 5, 5.5, 6, 6.6, 7, 7.5, 8, 8.5, 9, 9.5, 10, 11, 12, 13, 14, 15, 16, 17, 18, 19, 20, 25, 30, 35, 40, 45, 50, 55, 60, 75, 80, 85, 90, 95, 100, 125, 150, 175, 200, 225, 250, 275, 300, 325, 350, 375, 400, 425, 450, 475, 500, 600, 700, 800, 900, or 1000 greater than an amount, concentration or percentage of antigen specific $CD8^+$ T cells, total $CD8^+$ T cells, or total T cells in the biological sample. In some aspects, provided herein is a pharmaceutical composition comprising a population of immune cells comprising $CD8^+$ T cells from a biological sample, wherein the $CD8^+$ T cells comprise at least one antigen specific $CD8^+$ T cell comprising a T cell receptor (TCR) specific to at least one antigen peptide sequence, and a pharmaceutically acceptable excipient; wherein the at least one antigen specific $CD8^+$ T cell comprises expanded or induced antigen specific $CD4^+$ T cells that are expanded or induced at least about 1.1, 1.2, 1.3, 1.4, 1.5, 1.6, 1.7, 1.8, 1.9, 2, 2.5, 3, 3.5, 4, 4.5, 5, 5.5, 6, 6.6, 7, 7.5, 8, 8.5, 9, 9.5, 10, 11, 12, 13, 14, 15, 16, 17, 18, 19, 20, 25, 30, 35, 40, 45, 50, 55, 60, 75, 80, 85, 90, 95, 100, 125, 150, 175, 200, 225, 250, 275, 300, 325, 350, 375, 400, 425, 450, 475, 500, 600, 700, 800, 900, or 1000 fold from the biological sample. In some aspects, provided herein is a pharmaceutical composition comprising a population of immune cells comprising $CD8^+$ T cells from a biological sample, wherein the $CD8^+$ T cells comprise at least one antigen specific $CD8^+$ T cell comprising a T cell receptor (TCR) specific to at least one antigen peptide sequence, and a pharmaceutically acceptable excipient; wherein the at least one antigen specific $CD8^+$ T cell comprises expanded or induced antigen specific $CD8^+$ T cells that are expanded or induced at least about 1.1, 1.2, 1.3, 1.4, 1.5, 1.6, 1.7, 1.8, 1.9, 2, 2.5, 3, 3.5, 4, 4.5, 5, 5.5, 6, 6.6, 7, 7.5, 8, 8.5, 9, 9.5, 10, 11, 12, 13, 14, 15, 16, 17, 18, 19, 20, 25, 30, 35, 40, 45, 50, 55, 60, 75, 80, 85, 90, 95, 100, 125, 150, 175, 200, 225, 250, 275, 300, 325, 350, 375, 400, 425, 450, 475, 500, 600, 700, 800, 900, or fold from the biological sample.

In some embodiments, the at least one antigen specific T cell comprises at least one APC-stimulated T cell. In some embodiments, the amount of immune cells expressing CD14 and/or CD25 in the population is proportionally less than the amount of immune cells expressing CD14 and/or CD25 in the biological sample. In some embodiments, the amount of immune cells expressing CD14 and/or CD25 in the population is proportionally more than the amount of immune cells expressing CD14 and/or CD25 in the biological sample. In some embodiments, the percentage of immune cells expressing CD14 and/or CD25 in the population is less than the percentage of immune cells expressing CD14 and/or CD25 in the biological sample. In some embodiments, the percentage of immune cells expressing CD14 and/or CD25 in the population is more than the percentage of immune cells expressing CD14 and/or CD25 in the biological sample. In some embodiments, the concentration of immune cells expressing CD14 and/or CD25 in the population is less than the concentration of immune cells expressing CD14 and/or CD25 in the biological sample. In some embodiments, the concentration of immune cells expressing CD14 and/or CD25 in the population is more than the concentration of immune cells expressing CD14 and/or CD25 in the biological sample.

In some embodiments, the biological sample is from a subject. In some embodiments, the subject is a human. In some embodiments, the subject has a disease or disorder. In some embodiments, the disease or disorder is cancer. In some embodiments, the cancer is selected from the group consisting of ovarian cancer, lung cancer and melanoma.

In some embodiments, the at least one antigen specific T cell comprises at least one $CD4^+$ T cell. In some embodiments, the at least one antigen specific T cell comprises at least one $CD8^+$ T cell. In some embodiments, the at least one antigen specific T cell comprises at least one CD4 enriched T cell. In some embodiments, the at least one antigen specific T cell comprises at least one CD8 enriched T cell. In some embodiments, the at least one antigen specific T cell comprises a memory T cell. In some embodiments, the at least one antigen specific T cell comprises a naïve T cell. In some embodiments, the at least one antigen specific T cell comprises a memory $CD4^+$ T cell. In some embodiments, the at least one antigen specific T cell comprises an expanded memory $CD4^+$ T cell. In some embodiments, the at least one antigen specific T cell comprises a naïve $CD4^+$ T cell. In some embodiments, the at least one antigen specific T cell comprises an induced naïve $CD4^+$ T cell. In some embodiments, the at least one antigen specific T cell comprises a memory $CD8^+$ T cell. In some embodiments, the at least one antigen specific T cell comprises an expanded memory $CD8^+$ T cell. In some embodiments, the at least one antigen specific T cell comprises a naïve CD8+ T cell. In some embodiments, the at least one antigen specific T cell comprises an induced naïve CD8+ T cell.

In some embodiments, the at least one antigen-specific T cell is stimulated in a medium comprising IL-7, IL-15, an indoleamine 2,3-dioxygenase-1 (IDO) inhibitor, an anti-PD-1 antibody, IL-12, or a combination thereof. In some embodiments, the IDO inhibitor is epacadostat, navoximod, 1-methyltryptophan, or a combination thereof.

In some embodiments, the at least one antigen peptide sequence comprises a mutation selected from (A) a point mutation, (B) a splice-site mutation, (C) a frameshift mutation, (D) a read-through mutation, (E) a gene-fusion mutation, and combinations thereof. In some embodiments, the at least one antigen peptide sequence binds to the HLA protein of a subject with a greater affinity than a corresponding wild-type peptide. In some embodiments, the at least one antigen peptide sequence binds to the HLA protein of a subject with a $K_D$ or an $IC_{50}$ less than 500 nM, 250 nM, 150 nM, 100 nM, 50 nM, 25 nM or 10 nM. In some embodiments, each of the at least one antigen peptide sequence binds to a protein encoded by an HLA allele expressed by a subject. In some embodiments, the TCR binds to a peptide-HLA complex with a $K_D$ or an $IC_{50}$ of less than 500 nM, 250 nM, 150 nM, 100 nM, 50 nM, 25 nM or 10 nM. In some embodiments, each of the at least one antigen peptide sequence comprises a mutation that is not present in non-cancer cells of a subject. In some embodiments, each of the at least one antigen peptide sequences is encoded by a gene or an expressed gene of a subject's cancer cells.

In some embodiments, one or more of the at least one antigen peptide sequence has a length of at least 8; 9; 10; 11; 12; 13; 14; 15; 16; 17; 18; 19; 20; 21; 22; 23; 24; 25; 26; 27; 28; 29; 30; 40; 50; 60; 70; 80; 90; 100; 150; 200; 250; 300; 350; 400; 450; 500; 600; 700; 800; 900; 1,000; 1,500; 2,000; 2,500; 3,000; 4,000; 5,000; 7,500; or 10,000 naturally occurring amino acids. In some embodiments, one or more of the at least one antigen peptide sequence binds to a protein encoded by a class I HLA allele and has a length of from 8-12 naturally occurring amino acids. In some embodiments, one or more of the at least one antigen peptide sequence binds to a protein encoded by a class II HLA allele and has a length of from 16-25 naturally occurring amino acids.

In some embodiments, the at least one antigen peptide sequence comprises a plurality of antigen peptide sequences. In some embodiments, the plurality of antigen peptide sequences comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, 300, 350, 400, 450, or 500 antigen peptide sequences. In some embodiments, the antigen is a neoantigen, a tumor associated antigen, an overexpressed antigen, a viral antigen, a minor histocompatibility antigen or a combination thereof.

In some embodiments, the APC is one or more APC preparations. In some embodiments, the APC comprises an APC loaded with one or more antigen peptides comprising one or more of the at least one antigen peptide sequence. In some embodiments, the APC is an autologous APC, an allogenic APC, or an artificial APC. In some embodiments, the APC comprises a dendritic cell (DC). In some embodiments, the APC is derived from a CD14+ monocyte. In some embodiments, the APC is a CD14 enriched APC. In some embodiments, the APC is a CD141 enriched APC. In some embodiments, the CD14+ monocyte is enriched from a biological sample from a subject comprising PBMCs. In some embodiments, the CD14+ monocyte is stimulated with one or more cytokines or growth factors. In some embodiments, the one or more cytokines or growth factors comprise GM-CSF, IL-4, FLT3L, TNF-α, IL-1β, PGE1, IL-6, IL-7, IFN-α, R848, LPS, ss-rna40, poly I:C, or a combination thereof.

In some embodiments, the CD14+ monocyte is from a second biological sample comprising PBMCs. In some embodiments, the second biological sample is from the same subject.

In some embodiments, the biological sample comprises peripheral blood mononuclear cells (PBMCs).

In some embodiments, the at least one antigen specific T cell comprises a plurality of antigen specific T cells. In some embodiments, a percentage of the at least one antigen specific T cell in the composition is at least about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total T cells or total immune cells. In some embodiments, a percentage of at least one antigen specific CD8+ T cell in the composition is at least about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4+ T cells, total CD8+ T cells, total T cells or total immune cells. In some embodiments, a percentage of at least one antigen specific CD4+ T cell in the composition is at least about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4+ T cells, total CD8+ T cells, total T cells or total immune cells. In some embodiments, a percentage of the at least one antigen specific T cell in the biological sample is at most about 0.00001%, 0.00005%, 0.0001%, 0.0005%, 0.001%, 0.005%, 0.01%, 0.05%, 0.1% or 0.5% of total CD4+ T cells, total CD8+ T cells, total T cells or total immune cells. In some embodiments, a percentage of at least one antigen specific CD8+ T cell in the biological sample is at most about 0.00001%, 0.00005%, 0.0001%, 0.0005%, 0.001%, 0.005%, 0.01%, 0.05%, 0.1% or 0.5% of total CD4+ T cells, total CD8+ T cells, total T cells or total immune cells. In some embodiments, a percentage of at least one antigen specific CD4+ T cell in the biological sample is at most about 0.00001%, 0.00005%, 0.0001%, 0.0005%, 0.001%, 0.005%, 0.01%, 0.05%, 0.1% or 0.5% of total CD4+ T cells, total CD8+ T cells, total T cells or total immune cells.

In some embodiments, the pharmaceutical composition comprises: a population of immune cells from a biological sample comprising at least one antigen specific T cell comprising a T cell receptor (TCR) specific to at least one antigen peptide sequence, and a pharmaceutically acceptable excipient; wherein an amount of immune cells expressing CD19 and/or CD16 in the population is different from an amount of immune cells expressing CD19 and/or CD16 in the biological sample. In some embodiments, the pharmaceutical composition comprises: a population of immune cells from a biological sample comprising at least one antigen specific T cell comprising a T cell receptor (TCR) specific to at least one antigen peptide sequence, and a pharmaceutically acceptable excipient; wherein an amount of immune cells expressing CD19 and/or CD16 in the population is less than an amount of immune cells expressing CD19 and/or CD16 in the biological sample.

In some aspects, provided herein is a method of treatment comprising administering a composition described herein to a subject with a disease or disorder.

In some aspects, provided herein is a method of using a composition described herein, for the manufacture of a medicament for use in therapy.

In one aspect, provided herein is a method of preparing at least one antigen specific T cell comprising a T cell receptor (TCR) specific to at least one antigen peptide sequence, the method comprising incubating an APC with a population of immune cells from a biological sample depleted of cells expressing CD25 or CD14 and CD25, wherein the at least one antigen specific T cell comprises an amount of expanded or induced antigen specific T cells that is at least about 1.1, 1.2, 1.3, 1.4, 1.5, 1.6, 1.7, 1.8, 1.9, 2, 2.5, 3, 3.5, 4, 4.5, 5, 5.5, 6, 6.6, 7, 7.5, 8, 8.5, 9, 9.5, 10, 11, 12, 13, 14, 15, 16, 17, 18, 19, 20, 25, 30, 35, 40, 45, 50, 55, 60, 75, 80, 85, 90, 95, 100, 125, 150, 175, 200, 225, 250, 275, 300, 325, 350, 375, 400, 425, 450, 475, or 500 fold higher than an amount of antigen specific T cells expanded or induced using a method comprising incubating an APC with a population of immune cells from a biological sample depleted of cells expressing CD14. In one aspect, provided herein is a method of preparing at least one antigen specific $CD4^+$ T cell comprising a T cell receptor (TCR) specific to at least one antigen peptide sequence, the method comprising incubating an APC with a population of immune cells from a biological sample depleted of cells expressing CD25 or CD14 and CD25, wherein the at least one antigen specific $CD4^+$ T cell comprises an amount of expanded or induced antigen specific $CD4^+$ T cells that is at least about 1.1, 1.2, 1.3, 1.4, 1.5, 1.6, 1.7, 1.8, 1.9, 2, 2.5, 3, 3.5, 4, 4.5, 5, 5.5, 6, 6.6, 7, 7.5, 8, 8.5, 9, 9.5, 10, 11, 12, 13, 14, 15, 16, 17, 18, 19, 20, 25, 30, 35, 40, 45, 50, 55, 60, 75, 80, 85, 90, 95, 100, 125, 150, 175, 200, 225, 250, 275, 300, 325, 350, 375, 400, 425, 450, 475, or 500 fold higher than an amount of antigen specific $CD4^+$ T cells expanded or induced using a method comprising incubating an APC with a population of immune cells from a biological sample depleted of cells expressing CD14. In one aspect, provided herein is a method of preparing at least one antigen specific $CD8^+$ T cell comprising a T cell receptor (TCR) specific to at least one antigen peptide sequence, the method comprising incubating an APC with a population of immune cells from a biological sample depleted of cells expressing CD25 or CD14 and CD25, wherein the at least one antigen specific $CD8^+$ T cell comprises an amount of expanded or induced antigen specific $CD8^+$ T cells that is at least about 1.1, 1.2, 1.3, 1.4, 1.5, 1.6, 1.7, 1.8, 1.9, 2, 2.5, 3, 3.5, 4, 4.5, 5, 5.5, 6, 6.6, 7, 7.5, 8, 8.5, 9, 9.5, 10, 11, 12, 13, 14, 15, 16, 17, 18, 19, 20, 25, 30, 35, 40, 45, 50, 55, 60, 75, 80, 85, 90, 95, 100, 125, 150, 175, 200, 225, 250, 275, 300, 325, 350, 375, 400, 425, 450, 475, or 500 fold higher than an amount of antigen specific $CD8^+$ T cells expanded or induced using a method comprising incubating an APC with a population of immune cells from a biological sample depleted of cells expressing CD14.

In some embodiments, the biological sample is further depleted of CD19 expressing cells. In some embodiments, the biological sample is further depleted of CD19 expressing cells. In some embodiments, the APC is a FLT3L-stimulated APC. In some embodiments, incubating the population of immune cells is performed in a medium containing IL-7, IL-15, or a combination thereof. In some embodiments, the medium further comprises an indoleamine 2,3-dioxygenase-1 (IDO) inhibitor, an anti-PD-1 antibody, IL-12, or a combination thereof. In some embodiments, the IDO inhibitor is epacadostat, navoximod, 1-methyltryptophan, or a combination thereof.

In one aspect, provided herein is a method of preparing a pharmaceutical composition comprising at least one antigen specific T cell comprising a T cell receptor (TCR) specific to at least one antigen peptide sequence, the method comprising: incubating FMS-like tyrosine kinase 3 receptor ligand (FLT3L) with a population of immune cells from a biological sample for a first time period; and thereafter incubating at least one T cell of the biological sample with an APC, wherein the at least one antigen specific T cell comprises an amount of expanded or induced antigen specific T cells that is at least about 1.1, 1.2, 1.3, 1.4, 1.5, 1.6, 1.7, 1.8, 1.9, 2, 2.5, 3, 3.5, 4, 4.5, 5, 5.5, 6, 6.6, 7, 7.5, 8, 8.5, 9, 9.5, 10, 11, 12, 13, 14, 15, 16, 17, 18, 19, 20, 25, 30, 35, 40, 45, 50, 55, 60, 75, 80, 85, 90, 95, 100, 125, 150, 175, 200, 225, 250, 275, 300, 325, 350, 375, 400, 425, 450, 475, or 500 fold higher than an amount of antigen specific T cells expanded or induced using a method that does not comprise incubating FMS-like tyrosine kinase 3 receptor ligand (FLT3L) with a population of immune cells from a biological sample for a first time period; and that does comprise incubating at least one T cell of the biological sample with an APC thereafter. In one aspect, provided herein is a method of preparing a pharmaceutical composition comprising at least one antigen specific $CD4^+$ T cell comprising a T cell receptor (TCR) specific to at least one antigen peptide sequence, the method comprising: incubating FMS-like tyrosine kinase 3 receptor ligand (FLT3L) with a population of immune cells from a biological sample for a first time period; and thereafter incubating at least one $CD4^+$ T cell of the biological sample with an APC, wherein the at least one antigen specific $CD4^+$ T cell comprises an amount of expanded or induced antigen specific $CD4^+$ T cells that is at least about 1.1, 1.2, 1.3, 1.4, 1.5, 1.6, 1.7, 1.8, 1.9, 2, 2.5, 3, 3.5, 4, 4.5, 5, 5.5, 6, 6.6, 7, 7.5, 8, 8.5, 9, 9.5, 10, 11, 12, 13, 14, 15, 16, 17, 18, 19, 20, 25, 30, 35, 40, 45, 50, 55, 60, 75, 80, 85, 90, 95, 100, 125, 150, 175, 200, 225, 250, 275, 300, 325, 350, 375, 400, 425, 450, 475, or 500 fold higher than an amount of antigen specific $CD4^+$ T cells expanded or induced using a method that does not comprise incubating FMS-like tyrosine kinase 3 receptor ligand (FLT3L) with a population of immune cells from a biological sample for a first time period; and that does comprise incubating at least one $CD4^+$ T cell of the biological sample with an APC thereafter. In one aspect, provided herein is a method of preparing a pharmaceutical composition comprising at least one antigen specific $CD8^+$ T cell comprising a T cell receptor (TCR) specific to at least one antigen peptide sequence, the method comprising: incubating FMS-like tyrosine kinase 3 receptor ligand (FLT3L) with a population of immune cells from a biological sample for a first time period; and thereafter incubating at least one $CD8^+$ T cell of the biological sample with an APC, wherein the at least one antigen specific $CD8^+$ T cell comprises an amount of expanded or induced antigen specific $CD8^+$ T cells that is at least about 1.1, 1.2, 1.3, 1.4, 1.5, 1.6, 1.7, 1.8, 1.9, 2, 2.5, 3, 3.5, 4, 4.5, 5, 5.5, 6, 6.6, 7, 7.5, 8, 8.5, 9, 9.5, 10, 11, 12, 13, 14, 15, 16, 17, 18, 19, 20, 25, 30, 35, 40, 45, 50, 55, 60, 75, 80, 85, 90, 95, 100, 125, 150, 175, 200, 225, 250, 275, 300, 325, 350, 375, 400, 425, 450, 475, or 500 fold higher than an amount of antigen specific $CD8^+$ T cells expanded or induced using a method that does not comprise incubating FMS-like tyrosine kinase 3 receptor ligand (FLT3L) with a population of immune cells from a biological sample for a first time period; and that does comprise incubating at least one CD8⁺ T cell of the biological sample with an APC thereafter.

In one aspect, provided herein is a method of preparing at least one antigen specific T cell comprising a T cell receptor (TCR) specific to at least one antigen peptide sequence, the method comprising incubating an APC with a population of immune cells from a biological sample depleted of cells expressing CD14 and/or CD25.

In one aspect, provided herein is a method of preparing at least one antigen specific T cell comprising a T cell receptor (TCR) specific to at least one antigen peptide sequence, the method comprising incubating a FMS-like tyrosine kinase 3 receptor ligand (FLT3L)-stimulated APC with a population of immune cells from a biological sample.

In one aspect, provided herein is a method of preparing a pharmaceutical composition comprising at least one antigen specific T cell comprising a T cell receptor (TCR) specific to at least one antigen peptide sequence, the method comprising: incubating FMS-like tyrosine kinase 3 receptor ligand (FLT3L) with a population of immune cells from a biological sample for a first time period; and thereafter incubating at least one T cell of the biological sample with an APC.

In one aspect, provided herein is a method of preparing at least one antigen specific T cell comprising a T cell receptor (TCR) specific to at least one antigen peptide sequence, the method comprising incubating a population of immune cells from a biological sample with one or more APC preparations for one or more separate time periods of less than 28 days from incubating the population of immune cells with a first APC preparation of the one or more APC preparations, wherein at least one antigen specific memory T cell is expanded, or at least one antigen specific naïve T cell is induced.

In one aspect, provided herein is a method of preparing at least one antigen specific T cell comprising a T cell receptor (TCR) specific to at least one antigen peptide sequence, the method comprising incubating a population of immune cells from a biological sample with 3 or less APC preparations for 3 or less separate time periods, wherein at least one antigen specific memory T cell is expanded or at least one antigen specific naïve T cell is induced.

In some embodiments, the population of immune cells is from a biological sample depleted of CD14 and/or CD25 expressing cells.

In some embodiments, the APC is a FLT3L-stimulated APC. In some embodiments, at least one of the APC preparations comprises a FLT3L-stimulated APC. In some embodiments, at least two of the APC preparations comprise a FLT3L-stimulated APC. In some embodiments, at least three of the APC preparations comprise a FLT3L-stimulated APC. In some embodiments, each of the APC preparations comprises a FLT3L-stimulated APC.

In some embodiments, the APC comprises one or more APC preparations. In some embodiments, the APC preparations comprise 3 or less APC preparations. In some embodiments, the APC preparations are incubated with the immune cells sequentially within one or more separate time periods. In some embodiments, the biological sample is from a subject. In some embodiments, the subject is a human. In some embodiments, the subject has a disease or disorder. In some embodiments, the disease or disorder is cancer. In some embodiments, the cancer is selected from the group consisting of ovarian cancer, lung cancer and melanoma.

In some embodiments, the at least one antigen specific T cell comprises at least one CD4⁺ T cell. In some embodiments, the at least one antigen specific T cell comprises at least one CD8⁺ T cell. In some embodiments, at least one antigen specific T cell comprises at least one CD4 enriched T cell. In some embodiments, at least one antigen specific T cell comprises at least one CD8 enriched T cell. In some embodiments, the at least one antigen specific T cell comprises at least one memory T cell. In some embodiments, the at least one antigen specific T cell comprises at least one naïve T cell. In some embodiments, the at least one antigen specific T cell comprises at least one memory CD4⁺ T cell. In some embodiments, the at least one antigen specific T cell comprises at least one naïve CD4⁺ T cell. In some embodiments, the at least one antigen specific T cell comprises at least one memory CD8⁺ T cell. In some embodiments, the at least one antigen specific T cell comprises at least one naïve CD8⁺ T cell.

In some embodiments, the at least one antigen peptide sequence comprises a mutation selected from (A) a point mutation, (B) a splice-site mutation, (C) a frameshift mutation, (D) a read-through mutation, (E) a gene-fusion mutation, and combinations thereof. In some embodiments, the at least one antigen peptide sequence comprises a point mutation and binds to the HLA protein of a subject with a greater affinity than a corresponding wild-type peptide. In some embodiments, the at least one antigen peptide sequence binds to the HLA protein of a subject with a $K_D$ or an $IC_{50}$ of less than 500 nM, 250 nM, 150 nM, 100 nM, 50 nM, 25 nM or 10 nM. In some embodiments, each of the at least one antigen peptide sequence binds to a protein encoded by an HLA allele expressed by a subject. In some embodiments, the TCR binds to a peptide-HLA complex with a $K_D$ or an $IC_{50}$ of less than 500 nM, 250 nM, 150 nM, 100 nM, 50 nM, 25 nM or 10 nM. In some embodiments, each of the at least one antigen peptide sequences comprises a mutation that is not present in non-cancer cells of a subject. In some embodiments, each of the at least one antigen peptide sequences is encoded by gene or an expressed gene of a subject's cancer cells. In some embodiments, one or more of the at least one antigen peptide sequence has a length of at least 8; 9; 10; 11; 12; 13; 14; 15; 16; 17; 18; 19; 20; 21; 22; 23; 24; 25; 26; 27; 28; 29; 30; 40; 50; 60; 70; 80; 90; 100; 150; 200; 250; 300; 350; 400; 450; 500; 600; 700; 800; 900; 1,000; 1,500; 2,000; 2,500; 3,000; 4,000; 5,000; 7,500; or 10,000 naturally occurring amino acids. In some embodiments, one or more of the at least one antigen peptide sequence binds to a protein encoded by a class I HLA allele and has a length of from 8-12 naturally occurring amino acids. In some embodiments, one or more of the at least one antigen peptide sequence binds to a protein encoded by a class II HLA allele and has a length of from 16-25 naturally occurring amino acids. In some embodiments, the at least one antigen peptide sequence comprises a plurality of antigen peptide sequences. In some embodiments, the plurality of antigen peptide sequences comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, 300, 350, 400, 450, or 500 antigen peptide sequences. In some embodiments, the antigen is a neoantigen, a tumor associated antigen, a viral antigen, a minor histocompatibility antigen or a combination thereof.

In some embodiments, a method comprises depleting cells expressing CD14 and/or CD25 from the biological sample. In some embodiments, depleting cells expressing CD14 and/or CD25 comprises binding a CD14 and/or CD25 binding agent to an APC or an APC of the APC preparations. In some embodiments, the CD14 and/or CD25 binding agent is biotinylated. In some embodiments, depleting cells expressing CD14 and/or CD25 further comprises binding an anti-biotin reagent on a solid support to the CD14 and/or CD25 binding agent. In some embodiments, the CD14 and/or CD25 binding agent is attached to a solid support.

In some embodiments, the APC or an APC of the APC preparations comprises an APC loaded with one or more antigen peptides comprising one or more of the at least one antigen peptide sequence. In some embodiments, the APC or an APC of the APC preparations is an autologous APC or an allogenic APC. In some embodiments, the APC or an APC of the APC preparations comprises a dendritic cell (DC). In some embodiments, the APC or an APC of the APC preparations is derived from a CD14$^+$ monocyte. In some embodiments, the APC or an APC of the APC preparations is enriched from a biological sample. In some embodiments, the APC or an APC of the APC preparations is stimulated with one or more cytokines or growth factors. In some embodiments, the one or more cytokines or growth factors comprise GM-CSF, IL-4, FLT3L, TNF-α, IL-1β, PGE1, IL-6, IFN-α, R848, LPS, ss-rna40, poly I:C, or a combination thereof.

In some embodiments, the APC or an APC of the APC preparations is from a second biological sample. In some embodiments, the second biological sample is from the same subject. In some embodiments, the biological sample comprises peripheral blood mononuclear cells (PBMCs).

In some embodiments, the at least one antigen specific T cell comprises a plurality of antigen specific T cells. In some embodiments, a percentage of the at least one antigen specific T cell is at least about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4$^+$ T cells, total CD8$^+$ T cells, total T cells or total immune cells. In some embodiments, a percentage of at least one antigen specific CD8$^+$ T cell is at least about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4$^+$ T cells, total CD8$^+$ T cells, total T cells or total immune cells. In some embodiments, a percentage of at least one antigen specific CD4$^+$ T cell is at least about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4$^+$ T cells, total CD8$^+$ T cells, total T cells or total immune cells. In some embodiments, a percentage of the at least one antigen specific T cell in the biological sample is at most about 0.00001%, 0.00005%, 0.0001%, 0.0005%, 0.001%, 0.005%, 0.01%, 0.05%, 0.1% or 0.5% of total CD4$^+$ T cells, total CD8$^+$ T cells, total T cells or total immune cells. In some embodiments, a percentage of at least one antigen specific CD8$^+$ T cell in the biological sample is at most about 0.00001%, 0.00005%, 0.0001%, 0.0005%, 0.001%, 0.005%, 0.01%, 0.05%, 0.1% or 0.5% of total CD4$^+$ T cells, total CD8$^+$ T cells, total T cells or total immune cells. In some embodiments, a percentage of at least one antigen specific CD4$^+$ T cell in the biological sample is at most about 0.00001%, 0.00005%, 0.0001%, 0.0005%, 0.001%, 0.005%, 0.01%, 0.05%, 0.1% or 0.5% of total CD4$^+$ T cells, total CD8$^+$ T cells, total T cells or total immune cells.

In some embodiments, the method further comprises administering one or more of the at least one antigen specific T cell to a subject.

In some embodiments, a total time period of the separate time periods is less than 28 days. In some embodiments, incubating comprises incubating a first APC preparation of the APC preparations to the T cells for more than 7 days. In some embodiments, a method comprises incubating the APC or one or more of the APC preparations with a first medium comprising at least one cytokine or growth factor for a first time period. In some embodiments, the at least one cytokine or growth factor comprises GM-CSF, IL-4, FLT3L, TNF-α, IL-1β, PGE1, IL-6, IFN-α, R848, LPS, ss-rna40, poly I:C, or any combination thereof. In some embodiments, a method comprises incubating one or more of the APC preparations with at least one peptide for a second time period. In some embodiments, a method comprises incubating the APC or one or more of the APC preparations with a second medium comprising one or more cytokines or growth factors for a third time period, thereby obtaining a matured APC. In some embodiments, the one or more cytokines or growth factors comprises GM-CSF, IL-4, FLT3L, TNF-α, IL-1β, PGE1, IL-6, IFN-α, R848, LPS, ss-rna40, poly I:C, or a combination thereof. In some embodiments, the method further comprises removing the one or more cytokines or growth factors of the second medium after the third time period and before a start of the fourth time period.

In some embodiments, the method is performed ex vivo.

In some embodiments, the biological sample is freshly obtained from a subject or is a frozen sample.

In some embodiments, the method comprises obtaining a biological sample from a subject comprising at least one APC and at least one PBMC.

In some embodiments, the method comprises depleting cells expressing CD14 and/or CD25 from a biological sample, thereby obtaining a CD14 and/or CD25 cell depleted sample.

In some embodiments, the method comprises incubating a CD14 and/or CD25 cell depleted sample with FLT3L for a first time period.

In some embodiments, the method comprises incubating at least one peptide with a CD14 and/or CD25 cell depleted sample for a second time period, thereby obtaining a first matured APC peptide loaded sample.

In some embodiments, the method comprises incubating a first matured APC peptide loaded sample with at least one PBMC for a third time period, thereby obtaining a first stimulated PBMC sample.

In some embodiments, the method comprises incubating a PBMC of a first stimulated PBMC sample with a FLT3L-stimulated APC of a matured APC sample for a fourth time period, thereby obtaining a second stimulated PBMC sample.

In some embodiments, the method comprises incubating a PBMC of a first stimulated PBMC sample with FLT3L and a second APC peptide loaded sample of a matured APC sample for a fourth time period, thereby obtaining a second stimulated PBMC sample.

In some embodiments, the method comprises incubating a PBMC of a first stimulated PBMC sample with FLT3L and a FLT3L-stimulated APC of a matured APC sample for a fourth time period, thereby obtaining a second stimulated PBMC sample.

In some embodiments, the method comprises incubating a PBMC of a second stimulated PBMC sample with a FLT3L-stimulated APC of a matured APC sample for a fifth time period, thereby obtaining a third stimulated PBMC sample.

In some embodiments, the method comprises incubating a PBMC of a second stimulated PBMC sample with FLT3L and a third APC peptide loaded sample of a matured APC sample for a fifth time period, thereby obtaining a third stimulated PBMC sample In some embodiments, the method comprises incubating a PBMC of a second stimulated PBMC sample with FLT3L and a FLT3L-stimulated APC of a matured APC sample for a fifth time period, thereby obtaining a third stimulated PBMC sample.

In some embodiments, the method comprises administering at least one T cell of a first stimulated PBMC sample to a subject in need thereof. In some embodiments, the method comprises administering at least one T cell of a second stimulated PBMC sample to a subject in need thereof. In some embodiments, the method comprises administering at least one T cell of a third stimulated PBMC sample to a subject in need thereof.

In some embodiments, incubating the PBMC of the first stimulated PBMC sample is performed in the presence of IL-7, IL-15, or a combination thereof. In some embodiments, incubating the PBMC of the first stimulated PBMC sample is performed in the presence of an indoleamine 2,3-dioxygenase-1 (IDO) inhibitor, an anti-PD-1 antibody, IL-12, or a combination thereof. In some embodiments, incubating the PBMC of the second stimulated PBMC sample is performed in the presence of IL-7, IL-15, or a combination thereof. In some embodiments, incubating the PBMC of the second stimulated PBMC sample is performed in the presence of an indoleamine 2,3-dioxygenase-1 (IDO) inhibitor, an anti-PD-1 antibody, IL-12, or a combination thereof.

In one aspect, provided herein is a method comprising: obtaining a biological sample from a subject comprising at least one antigen presenting cell (APC); enriching cells expressing CD14 from the biological sample, thereby obtaining a CD14$^+$ cell enriched sample; incubating the CD14$^+$ cell enriched sample with at least one cytokine or growth factor for a first time period; incubating at least one peptide with the CD14$^+$ cell enriched sample for a second time period, thereby obtaining an APC peptide loaded sample; incubating the APC peptide loaded sample with one or more cytokines or growth factors for a third time period, thereby obtaining a matured APC sample; incubating APCs of the matured APC sample with a CD14 and/or CD25 depleted sample comprising PBMCs for a fourth time period; incubating the PBMCs with APCs of a matured APC sample for a fifth time period; incubating the PBMCs with APCs of a matured APC sample for a sixth time period; and administering at least one T cell of the PBMCs to a subject in need thereof.

In one aspect, provided herein is a method comprising: obtaining a biological sample from a subject comprising at least one APC and at least one PBMC; depleting cells expressing CD14 and/or CD25 and/or CD19 from the biological sample, thereby obtaining a CD14 and/or CD25 and/or CD19 cell depleted sample; incubating the CD14 and/or CD25 and/or CD19 cell depleted sample with FLT3L for a first time period; incubating at least one peptide with the CD14 and/or CD25 and/or CD19 cell depleted sample for a second time period, thereby obtaining an APC peptide loaded sample; incubating the APC peptide loaded sample with the at least one PBMC for a third time period, thereby obtaining a first stimulated PBMC sample; incubating a PBMC of the first stimulated PBMC sample with an APC of a matured APC sample for a fourth time period, thereby obtaining a second stimulated PBMC sample; optionally, incubating a PBMC of the second stimulated PBMC sample with an APC of a matured APC sample for a fifth time period, thereby obtaining a third stimulated PBMC sample; administering at least one T cell of the first, the second or the third stimulated PBMC sample to a subject in need thereof.

In one aspect, provided herein is a method comprising obtaining a biological sample from a subject comprising at least one APC and at least one PBMC; depleting cells expressing CD14 and/or CD25 and/or CD19 from the biological sample, thereby obtaining a CD14 and/or CD25 and/or CD19 cell depleted sample; incubating the CD14 and/or CD25 and/or CD19 cell depleted sample with FLT3L for a first time period; incubating at least one peptide with the CD14 and/or CD25 and/or CD19 cell depleted sample for a second time period, thereby obtaining an APC peptide loaded sample; incubating the APC peptide loaded sample with the at least one PBMC for a third time period, thereby obtaining a first stimulated PBMC sample; optionally, incubating a PBMC of the first stimulated PBMC sample with a FLT3L-stimulated APC of a matured APC sample for a fourth time period, thereby obtaining a second stimulated PBMC sample; optionally, incubating a PBMC of the second stimulated PBMC sample with a FLT3L-stimulated APC of a matured APC sample for a fifth time period, thereby obtaining a third stimulated PBMC sample; and administering at least one T cell of the first, the second or the third stimulated PBMC sample to a subject in need thereof.

In one aspect, provided herein is a method comprising: obtaining a biological sample from a subject comprising at least one APC and at least one PBMC; depleting cells expressing CD14 and/or CD25 and/or CD19 from the biological sample, thereby obtaining a CD14 and/or CD25 and/or CD19 cell depleted sample; incubating the CD14 and/or CD25 and/or CD19 cell depleted sample with FLT3L for a first time period; incubating at least one peptide with the CD14 and/or CD25 and/or CD19 cell depleted sample for a second time period, thereby obtaining a first APC peptide loaded sample; incubating the first APC peptide loaded sample with the at least one PBMC for a third time period, thereby obtaining a first stimulated PBMC sample; optionally, incubating a PBMC of the first stimulated PBMC sample with FLT3L and a second APC peptide loaded sample of a matured APC sample for a fourth time period, thereby obtaining a second stimulated PBMC sample; optionally, incubating a PBMC of the second stimulated PBMC sample with FLT3L and a third APC peptide loaded sample of a matured APC sample for a fifth time period, thereby obtaining a third stimulated PBMC sample; and administering at least one T cell of the first, the second or the third stimulated PBMC sample to a subject in need thereof In one aspect, provided herein is a method comprising: obtaining a biological sample from a subject comprising at least one APC and at least one PBMC; depleting cells expressing CD14 and/or CD25 and/or CD19 from the biological sample, thereby obtaining a CD14 and/or CD25 and/or CD19 cell depleted sample; incubating the CD14 and/or CD25 and/or CD19 cell depleted sample with FLT3L for a first time period; incubating at least one peptide with the CD14 and/or CD25 and/or CD19 cell depleted sample for a second time period, thereby obtaining a first APC peptide loaded sample; incubating the first APC peptide loaded sample with the at least one PBMC for a third time period, thereby obtaining a first stimulated PBMC sample; optionally, incubating a PBMC of the first stimulated PBMC sample with FLT3L and a FLT3L-stimulated APC of a matured APC sample for a fourth time period, thereby obtaining a second stimulated PBMC sample; optionally, incubating a PBMC of the second stimulated PBMC sample with FLT3L and a FLT3L-stimulated APC of a matured APC sample for a fifth time period, thereby obtaining a third stimulated PBMC sample; administering at least one T cell of the first, the second or the third stimulated PBMC sample to a subject in need thereof.

In one aspect, provided herein is a method comprising determining expression of one or more cell markers of at least one immune cell of a stimulated immune cell sample; and determining binding of the at least one immune cell of the stimulated immune cell sample to a peptide-MHC complex; wherein determining expression and determining binding are performed simultaneously. In some embodiments, the stimulated immune cell sample is a population of immune cells stimulated with APCs comprising a peptide-MHC complex. In some embodiments, the population of immune cells is from a biological sample.

In one aspect, provided herein is a method comprising incubating a population of immune cells from a biological sample with APCs comprising a peptide-MHC complex, thereby obtaining a stimulated immune cell sample; determining expression of one or more cell markers of at least one immune cell of the stimulated immune cell sample; and determining binding of the at least one immune cell of the stimulated immune cell sample to a peptide-MHC complex; wherein determining expression and determining binding are performed simultaneously.

In some embodiments, the one or more cell markers comprise TNF-α, IFN-γ, LAMP-1, 4-1BB, IL-2, IL-17A, Granzyme B, PD-1, CD25, CD69, TIM3, LAG3, CTLA-4, CD62L, CD45RA, CD45RO, FoxP3, or any combination thereof. In some embodiments, the one or more cell markers comprise a cytokine. In some embodiments, the one or more cell markers comprise a degranulation marker. In some embodiments, the one or more cell markers comprise a cell-surface marker. In some embodiments, the one or more cell markers comprise a protein. In some embodiments, determining binding of the at least one immune cell of the stimulated immune cell sample to the peptide-MHC complex comprises determining binding of the at least one immune cell of the stimulated immune cell sample to a MHC tetramer comprising the peptide and the MHC of the peptide-MHC complex. In some embodiments, the MHC is a class I MHC or a class II MHC. In some embodiments, the peptide-MHC complex comprises one or more labels. In some embodiments, the population of immune cells from a biological sample comprises two or more samples each comprising a population of immune cells from one or more biological samples. In some embodiments, the two or more samples are labeled with two or more sample labels. In some embodiments, determining expression and determining binding comprises fluorescent activated cell sorting (FACS). In some embodiments, determining expression and determining binding comprises single cell analysis. In some embodiments, determining expression and determining binding comprises determining a percentage of immune cells that both express the one or more cell markers and that bind to the peptide-MHC complex. In some embodiments, the labels comprise a fluorophore. In some embodiments, the population of immune cells comprises a population of immune cells representative of the population of immune cells of a composition described herein.

Where aspects or embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claimed invention.

INCORPORATION BY REFERENCE

All publications, patents, and patent applications mentioned in this specification are herein incorporated by reference in their entirety for all purposes, to the same extent as if each individual publication, patent, or patent application was specifically and individually indicated to be incorporated by reference. For example, all publications and patents mentioned herein are incorporated herein by reference in their entirety for the purpose of describing and disclosing the kits, compositions, and methodologies that are described in the publications, which might be used in connection with the methods, kits, and compositions described herein. The documents discussed herein are provided solely for their disclosure prior to the filing date of the present application. Nothing herein is to be construed as an admission that the inventors described herein are not entitled to antedate such disclosure by virtue of prior invention or for any other reason.

BRIEF DESCRIPTION OF THE DRAWINGS

FIG. 1A depicts an example schematic of an antigen specific T cell manufacturing protocol.

FIG. 1B depicts an example schematic of an antigen specific T cell manufacturing protocol.

FIG. 2 depicts an example result showing fraction of antigen specific CD8$^+$ memory T cells induced by long peptide or short peptide. "Bulk" indicates the sample containing T cells used for induction is whole peripheral blood mononuclear cell (PBMC). "Treg" indicates the sample containing T cells used for induction is PBMCs depleted of CD25 expressing cells.

FIG. 3 depicts an example flow cytometry analysis showing the fraction of antigen specific CD8$^+$ naïve T cells induced with a GAS7 peptide.

FIG. 30C depicts an example result of sensitivity determination by detection and functional characterization of de novo induced CD4+ responses with multiple specificities in the same culture. Similar magnitude was observed for each response in the pool deconvolution assay. The responses to HIV #5, HIV #6 and HIV #4 demonstrated an $EC_{50}$ of 0.45 µM, 0.43 µM and 9.1 µM, respectively.

DETAILED DESCRIPTION OF THE INVENTION

Figure 4:
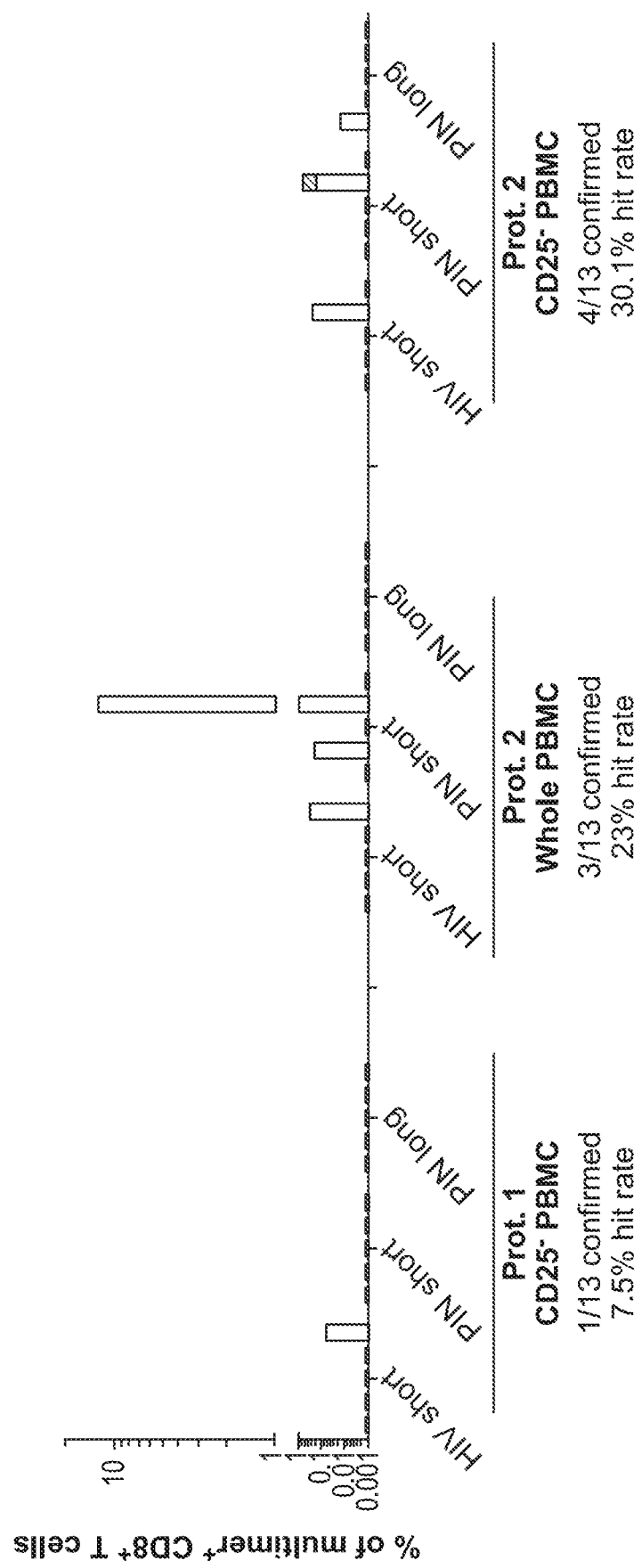
FIG. 4 depicts an example result showing antigen specific CD8$^+$ T cell responses to a peptide pool of HIV short peptides, short previously identified neoantigens (PINs), or long PINs. "Whole PBMC" indicates the sample containing T cells used for induction is whole PBMC. "CD25$^-$ PBMC" indicates the sample containing T cells used for induction is depleted of CD25$^+$ cells.

Described herein are novel immunotherapeutic agents and uses thereof based on the discovery of neoantigens arising from mutational events unique to an individual's tumor. Accordingly, the present disclosure described herein provides methods and protocols to create antigen specific immune cells, for example T cells, for use in treating disease.

Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

It is understood that terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. Nothing herein is intended as a promise.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the pertinent art. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed.

To facilitate an understanding of the present disclosure, a number of terms and phrases are defined below.

A "neoantigen" refers to a class of tumor antigens which arise from tumor-specific changes in proteins. Neoantigens encompass, but are not limited to, tumor antigens which arise from, for example, a substitution in a protein sequence, a frame shift mutation, a fusion polypeptide, an in-frame deletion, an insertion, and expression of an endogenous retroviral polypeptide.

A "neoepitope" refers to an epitope that is not present in a reference, such as a non-diseased cell, e.g., a non-cancerous cell or a germline cell, but is found in a diseased cell, e.g., a cancer cell. This includes situations where a corresponding epitope is found in a normal non-diseased cell or a germline cell but, due to one or more mutations in a diseased cell, e.g., a cancer cell, the sequence of the epitope is changed so as to result in the neoepitope.

A "reference" can be used to correlate and/or compare the results obtained in the methods of the present disclosure from a diseased specimen. Typically a "reference" may be obtained on the basis of one or more normal specimens, in particular specimens which are not affected by a disease, either obtained from an individual or one or more different individuals (e.g., healthy individuals), such as individuals of the same species. A "reference" can be determined empirically by testing a sufficiently large number of normal specimens.

A "mutation" refers to a change of or a difference in a nucleic acid sequence (e.g., a nucleotide substitution, addition or deletion) compared to a reference nucleic acid. A "somatic mutation" can occur in any of the cells of the body except the germ cells (sperm and egg) and are not passed on to children. These alterations can (but do not always) cause cancer or other diseases. In some embodiments, a mutation is a non-synonymous mutation. A "non-synonymous mutation" refers to a mutation, for (e.g., a nucleotide substitution), which does result in an amino acid change such as an amino acid substitution in the translation product. A "frameshift" occurs when a mutation disrupts the normal phase of a gene's codon periodicity (also known as "reading frame"), resulting in translation of a non-native protein sequence. It is possible for different mutations in a gene to achieve the same altered reading frame.

The term "affinity" refers to a measure of the strength of binding between two members of a binding pair (e.g., a human leukocyte antigen (HLA)-binding peptide and a class I or II HLA, or a peptide-HLA complex and a T cell receptor (TCR)). $K_D$ refers to the dissociation constant between two members of a binding pair and has units of molarity. $K_A$ refers to the affinity constant between two members of a binding pair is the inverse of the dissociation constant. Affinity may be determined experimentally, for example by surface plasmon resonance (SPR) using commercially available Biacore SPR units. $K_{off}$ refers to the off-rate constant of two members of a binding pair, (e.g., the off-rate constant of an HLA-binding peptide and a class I or II HLA, or a peptide-HLA complex and a TCR). $K_{on}$ refers to the on-rate constant of two members of a binding pair, (e.g., the on-rate constant of an HLA-binding peptide and a class I or II HLA, or a peptide-HLA complex and a TCR).

Throughout this disclosure, "binding data" results may be expressed in terms of an "$IC_{50}$." Affinity may also be expressed as the inhibitory concentration 50 ($IC_{50}$), or the concentration at which 50% of a first member of a binding pair (e.g., a peptide) is displaced. Likewise, $ln(IC_{50})$ refers to the natural log of the $IC_{50}$. For example, an $IC_{50}$ may be the concentration of a tested peptide in a binding assay at which 50% inhibition of binding of a labeled reference peptide is observed. Given the conditions in which the assays are run (e.g., limiting HLA protein concentrations and/or labeled reference peptide concentrations), these values can approximate $K_D$ values. Assays for determining binding are well known in the art and are described in detail, for example, in PCT publications WO 94/20127 and WO 94/03205, and other publications such Sidney et al., Current Protocols in Immunology 18.3.1 (1998); Sidney, et al., J. Immunol. 154:247 (1995); and Sette, et al., Mol. Immunol. 31:813 (1994). Alternatively, binding can be expressed relative to binding by a reference standard peptide. Binding can also be determined using other assay systems including those using: live cells (e.g., Ceppellini et al., Nature 339:392 (1989); Christnick et al., Nature 352:67 (1991); Busch et al., Int. Immunol. 2:443 (1990); Hill et al., J. Immunol. 147:189 (1991); del Guercio et al., J. Immunol. 154:685 (1995)), cell free systems using detergent lysates (e.g., Cerundolo et al., J. Immunol. 21:2069 (1991)), immobilized purified MHC (e.g., Hill et al., J. Immunol. 152, 2890 (1994); Marshall et al., J. Immunol. 152:4946 (1994)), ELISA systems (e.g., Reay et al., EMBO J. 11:2829 (1992)), surface plasmon resonance (e.g., Khilko et al., J. Biol. Chem. 268:15425 (1993)); high flux soluble phase assays (Hammer et al., J. Exp. Med. 180:2353 (1994)), and measurement of class I MHC stabilization or assembly (e.g., Ljunggren et al., Nature 346:476 (1990); Schumacher et al., Cell 62:563 (1990); Townsend et al., Cell 62:285 (1990); Parker et al., J. Immunol. 149:1896 (1992)).

The term "derived" when used to discuss an epitope is a synonym for "prepared." A derived epitope can be isolated from a natural source, or it can be synthesized according to standard protocols in the art. Synthetic epitopes can comprise artificial amino acid residues "amino acid mimetics," such as D isomers of natural occurring L amino acid residues or non-natural amino acid residues such as cyclohexylalanine. A derived or prepared epitope can be an analog of a native epitope. The term "derived from" refers to the origin or source, and may include naturally occurring, recombinant, unpurified, purified or differentiated molecules or cells. For example, an expanded or induced antigen specific T cell may be derived from a T cell. For example, an expanded or induced antigen specific T cell may be derived from an antigen specific T cell in a biological sample. For example, a matured APC (e.g., a professional APC) may be derived from a non-matured APC (e.g., an immature APC). For example, an APC may be derived from a monocyte (e.g., a $CD14^+$ monocyte). For example a dendritic cell may be derived from a monocyte (e.g., a $CD14^+$ monocyte). For example, an APC may be derived from a bone marrow cell.

An "epitope" is the collective features of a molecule (e.g., a peptide's charge and primary, secondary and tertiary structure) that together form a site recognized by another molecule (e.g., an immunoglobulin, T cell receptor, HLA molecule, or chimeric antigen receptor). For example, an epitope can be a set of amino acid residues involved in recognition by a particular immunoglobulin; a Major Histocompatibility Complex (MHC) receptor; or in the context of T cells, those residues recognized by a T cell receptor protein and/or a chimeric antigen receptor. Epitopes can be prepared by isolation from a natural source, or they can be synthesized according to standard protocols in the art. Synthetic epitopes can comprise artificial amino acid residues, amino acid mimetics, (such as D isomers of naturally-occurring L amino acid residues or non-naturally-occurring amino acid residues). Throughout this disclosure, epitopes may be referred to in some cases as peptides or peptide epitopes. In certain embodiments, there is a limitation on the length of a peptide of the present disclosure. The embodiment that is length-limited occurs when the protein or peptide comprising an epitope described herein comprises a region (i.e., a contiguous series of amino acid residues) having 100% identity with a native sequence. In order to avoid the definition of epitope from reading, e.g., on whole natural molecules, there is a limitation on the length of any region that has 100% identity with a native peptide sequence. Thus, for a peptide comprising an epitope described herein and a region with 100% identity with a native peptide sequence, the region with 100% identity to a native sequence generally has a length of: less than or equal to 600 amino acid residues, less than or equal to 500 amino acid residues, less than or equal to 400 amino acid residues, less than or equal to 250 amino acid residues, less than or equal to 100 amino acid residues, less than or equal to 85 amino acid residues, less than or equal to 75 amino acid residues, less than or equal to 65 amino acid residues, and less than or equal to 50 amino acid residues. In certain embodiments, an "epitope" described herein is comprised by a peptide having a region with less than 51 amino acid residues that has 100% identity to a native peptide sequence, in any increment down to 5 amino acid residues; for example 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2 or 1 amino acid residues.

A "T cell epitope" refers to a peptide sequence bound by an MHC molecule in the form of a peptide-MHC (pMHC) complex. A peptide-MHC complex can be recognized and bound by a TCR of a T cell (e.g., a cytotoxic T-lymphocyte or a T-helper cell).

A "T cell" includes $CD4^+$ T cells and $CD8^+$ T cells. The term T cell also includes both T helper 1 type T cells and T helper 2 type T cells.

An "immune cell" refers to a cell that plays a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

An "immunogenic" peptide or an "immunogenic" epitope or an "immunogenic" peptide epitope is a peptide that binds to an HLA molecule and induces a cell-mediated or humoral response, for example, a cytotoxic T lymphocyte (CTL) response, a helper T lymphocyte (HTL) response and/or a B lymphocyte response. Immunogenic peptides described herein are capable of binding to an HLA molecule and thereafter induce a cell-mediated or humoral response (e.g., a CTL (cytotoxic) response, or a HTL response) to the peptide.

A "protective immune response" or "therapeutic immune response" refers to a CTL and/or an HTL response to an antigen derived from an pathogenic antigen (e.g., a tumor antigen), which in some way prevents or at least partially arrests disease symptoms, side effects or progression. The immune response can also include an antibody response which has been facilitated by the stimulation of helper T cells.

A "T cell receptor" ("TCR") refers to a molecule, whether natural or partly or wholly synthetically produced, found on the surface of T lymphocytes (T cells) that recognizes an antigen bound to a major histocompatibility complex (MHC) molecule. The ability of a T cells to recognize an antigen associated with various diseases (e.g., cancers) or infectious organisms is conferred by its TCR, which is made up of both an alpha ($\alpha$) chain and a beta ($\beta$) chain or a gamma ($\gamma$) and a delta ($\delta$) chain. The proteins which make up these chains are encoded by DNA, which employs a unique mechanism for generating the tremendous diversity of the TCR. This multi-subunit immune recognition receptor associates with the CD3 complex and binds peptides presented by the MHC class I and II proteins on the surface of antigen-presenting cells (APCs). Binding of a TCR to a peptide on an APC is a central event in T cell activation.

As used herein, a "chimeric antigen receptor" or "CAR" refers to an antigen binding protein in that includes an immunoglobulin antigen binding domain (e.g., an immunoglobulin variable domain) and a T cell receptor (TCR) constant domain. As used herein, a "constant domain" of a TCR polypeptide includes a membrane-proximal TCR constant domain, a TCR transmembrane domain and/or a TCR cytoplasmic domain, or fragments thereof. For example, in some embodiments, a CAR is a monomer that includes a polypeptide comprising an immunoglobulin heavy chain variable domain linked to a TCR$\beta$ constant domain. In some embodiments, the CAR is a dimer that includes a first polypeptide comprising an immunoglobulin heavy or light chain variable domain linked to a TCR$\alpha$ or TCR$\beta$ constant domain and a second polypeptide comprising an immunoglobulin heavy or light chain variable domain (e.g., a $\kappa$ or $\lambda$ variable domain) linked to a TCR$\beta$ or TCR$\alpha$ constant domain.

"Major Histocompatibility Complex" or "MHC" is a cluster of genes that plays a role in control of the cellular interactions responsible for physiologic immune responses. The terms "major histocompatibility complex" and the abbreviation "MHC" can include any class of MHC molecule, such as MHC class I and MHC class II molecules, and relate to a complex of genes which occurs in all vertebrates. In humans, the MHC complex is also known as the human leukocyte antigen (HLA) complex. Thus, a "Human Leukocyte Antigen" or "HLA" refers to a human Major Histocompatibility Complex (MHC) protein (see, e.g., Stites, et al., Immunology, $8^{TH}$ Ed., Lange Publishing, Los Altos, Calif. (1994). For a detailed description of the MHC and HLA complexes, see, Paul, Fundamental Immunology, $3^{rd}$ Ed., Raven Press, New York (1993).

The major histocompatibility complex in the genome comprises the genetic region whose gene products expressed on the cell surface are important for binding and presenting endogenous and/or foreign antigens and thus for regulating immunological processes. MHC proteins or molecules are important for signaling between lymphocytes and antigen presenting cells or diseased cells in immune reactions. MHC proteins or molecules bind peptides and present them for recognition by T-cell receptors. The proteins encoded by the MHC can be expressed on the surface of cells, and display both self-antigens (peptide fragments from the cell itself) and non-self-antigens (e.g., fragments of invading microorganisms) to a T-cell. MHC binding peptides can result from the proteolytic cleavage of protein antigens and represent potential lymphocyte epitopes. (e.g., T cell epitope and B cell epitope). MHCs can transport the peptides to the cell surface and present them there to specific cells, such as cytotoxic T-lymphocytes, T-helper cells, or B cells. The MHC region can be divided into three subgroups, class I, class II, and class III. MHC class I proteins can contain an $\alpha$-chain and $\beta$2-microglobulin (not part of the MHC encoded by chromosome 15). They can present antigen fragments to cytotoxic T-cells. MHC class II proteins can contain $\alpha$- and $\beta$-chains and they can present antigen fragments to T-helper cells. MHC class III region can encode for other immune components, such as complement components and cytokines. The MHC can be both polygenic (there are several MHC class I and MHC class II genes) and polymorphic (there are multiple alleles of each gene).

"Antigen processing" or "processing" refers to the degradation of a polypeptide or antigen into procession products, which are fragments of said polypeptide or antigen (e.g., the degradation of a polypeptide into peptides) and the association of one or more of these fragments (e.g., via binding) with MHC molecules for presentation by cells, for example, antigen presenting cells, to specific T cells.

An "antigen presenting cell" (APC) refers to a cell which presents peptide fragments of protein antigens in association with MHC molecules on its cell surface. The term includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

A "receptor" refers to a biological molecule or a molecule grouping capable of binding a ligand. A receptor may serve, to transmit information in a cell, a cell formation or an organism. A receptor comprises at least one receptor unit, for example, where each receptor unit may consist of a protein molecule. A receptor has a structure which complements that of a ligand and may complex the ligand as a binding partner. The information is transmitted in particular by conformational changes of the receptor following complexation of the ligand on the surface of a cell. In some embodiments, a receptor is to be understood as meaning in particular proteins of MHC classes I and II capable of forming a receptor/ ligand complex with a ligand, in particular a peptide or peptide fragment of suitable length. A "ligand" refers to a molecule which has a structure complementary to that of a receptor and is capable of forming a complex with this receptor. In some embodiments, a ligand is to be understood as meaning a peptide or peptide fragment which has a suitable length and suitable binding motifs in its amino acid sequence, so that the peptide or peptide fragment is capable of forming a complex with MHC proteins such as MHC class I or MHC class II proteins. In some embodiments, a "receptor/ligand complex" is also to be understood as meaning a "receptor/peptide complex" or "receptor/peptide fragment complex", including a peptide- or peptide fragment-presenting MHC molecule such as MHC class I or MHC class II molecules.

A "native" or a "wild type" sequence refers to a sequence found in nature. The term "naturally occurring" as used herein refers to the fact that an object can be found in nature.

For example, a peptide or nucleic acid that is present in an organism (including viruses) and can be isolated from a source in nature and which has not been intentionally modified by man in the laboratory is naturally occurring.

The terms "peptide" and "peptide epitope" are used interchangeably with "oligopeptide" in the present specification to designate a series of residues connected one to the other, typically by peptide bonds between the α-amino and carboxyl groups of adjacent amino acid residues. A "synthetic peptide" refers to a peptide that is obtained from a non-natural source, e.g., is man-made. Such peptides can be produced using such methods as chemical synthesis or recombinant DNA technology. "Synthetic peptides" include "fusion proteins."

The term "motif" refers to a pattern of residues in an amino acid sequence of defined length, for example, a peptide of less than about 15 amino acid residues in length, or less than about 13 amino acid residues in length, for example, from about 8 to about 13 amino acid residues (e.g., 8, 9, 10, 11, 12, or 13) for a class I HLA motif and from about 6 to about 25 amino acid residues (e.g., 6, 7, 8, 9, 10, 11, 12, 13, 14, 15, 16, 17, 18, 19, 20, 21, 22, 23, 24, or 25) for a class II HLA motif, which is recognized by a particular HLA molecule. Motifs are typically different for each HLA protein encoded by a given human HLA allele. These motifs differ in their pattern of the primary and secondary anchor residues. In some embodiments, an MHC class I motif identifies a peptide of 7, 8 9, 10, 11, 12 or 13 amino acid residues in length. In some embodiments, an MHC class II motif identifies a peptide of 15, 16, 17, 18, 19, 20, 21, 22, 23, 24, 25 or 26 amino acid residues in length. A "cross-reactive binding" peptide refers to a peptide that binds to more than one member of a class of a binding pair members (e.g., a peptide bound by both a class I HLA molecule and a class II HLA molecule).

The term "residue" refers to an amino acid residue or amino acid mimetic residue incorporated into a peptide or protein by an amide bond or amide bond mimetic, or that is encoded by a nucleic acid (DNA or RNA). The nomenclature used to describe peptides or proteins follows the conventional practice. The amino group is presented to the left (the amino- or N-terminus) and the carboxyl group to the right (the carboxy- or C-terminus) of each amino acid residue. When amino acid residue positions are referred to in a peptide epitope they are numbered in an amino to carboxyl direction with the first position being the residue located at the amino terminal end of the epitope, or the peptide or protein of which it can be a part. In the formulae representing selected specific embodiments of the present invention, the amino- and carboxyl-terminal groups, although not specifically shown, are in the form they would assume at physiologic pH values, unless otherwise specified. In the amino acid structure formulae, each residue is generally represented by standard three letter or single letter designations. The L-form of an amino acid residue is represented by a capital single letter or a capital first letter of a three-letter symbol, and the D-form for those amino acid residues having D-forms is represented by a lower case single letter or a lower case three letter symbol. However, when three letter symbols or full names are used without capitals, they can refer to L amino acid residues. Glycine has no asymmetric carbon atom and is simply referred to as "Gly" or "G". The amino acid sequences of peptides set forth herein are generally designated using the standard single letter symbol. (A, Alanine; C, Cysteine; D, Aspartic Acid; E, Glutamic Acid; F, Phenylalanine; G, Glycine; H, Histidine; I, Isoleucine; K, Lysine; L, Leucine; M, Methionine; N, Asparagine; P, Proline; Q, Glutamine; R, Arginine; S, Serine; T, Threonine; V, Valine; W, Tryptophan; and Y, Tyrosine.)

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Methods of identifying nucleotide and amino acid conservative substitutions which do not eliminate peptide function are well-known in the art.

"Pharmaceutically acceptable" refers to a generally non-toxic, inert, and/or physiologically compatible composition or component of a composition. A "pharmaceutical excipient" or "excipient" comprises a material such as an adjuvant, a carrier, pH-adjusting and buffering agents, tonicity adjusting agents, wetting agents, preservatives, and the like. A "pharmaceutical excipient" is an excipient which is pharmaceutically acceptable.

According to the present disclosure, the term "vaccine" relates to a pharmaceutical preparation (pharmaceutical composition) or product that upon administration induces an immune response, for example, a cellular or humoral immune response, which recognizes and attacks a pathogen or a diseased cell such as a cancer cell. A vaccine may be used for the prevention or treatment of a disease. The term "individualized cancer vaccine" or "personalized cancer vaccine" "personal cancer vaccine" concerns a particular cancer patient and means that a cancer vaccine is adapted to the needs or special circumstances of an individual cancer patient.

The terms "polynucleotide" and "nucleic acid" are used interchangeably herein and refer to polymers of nucleotides of any length, and include DNA and RNA, for example, mRNA. The nucleotides can be deoxyribonucleotides, ribonucleotides, modified nucleotides or bases, and/or their analogs, or any substrate that can be incorporated into a polymer by DNA or RNA polymerase. In some embodiments, the polynucleotide and nucleic acid can be in vitro transcribed mRNA. In some embodiments, the polynucleotide that is administered using the methods of the invention is mRNA.

The terms "isolated" or "biologically pure" refer to material which is substantially or essentially free from components which normally accompany the material as it is found in its native state. Thus, isolated peptides described herein do not contain some or all of the materials normally associated with the peptides in their in situ environment. For example, an "isolated" epitope can be an epitope that does not include the whole sequence of the protein from which the epitope was derived. For example, a naturally-occurring polynucleotide or peptide present in a living animal is not isolated, but the same polynucleotide or peptide, separated from some or all of the coexisting materials in the natural system, is isolated. Such a polynucleotide could be part of a vector, and/or such a polynucleotide or peptide could be part of a composition, and still be "isolated" in that such vector or composition is not part of its natural environment. Isolated RNA molecules include in vivo or in vitro RNA transcripts of the DNA molecules described herein, and further include such molecules produced synthetically. In some embodiments, a polypeptide, antibody, polynucleotide, vector, cell, or composition which is isolated is substantially pure. The term "substantially pure" as used herein refers to material which is at least 50% pure (i.e., free from contaminants), at least 90% pure, at least 95% pure, at least 98% pure, or at least 99% pure.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software that can be used to obtain alignments of amino acid or nucleotide sequences are well-known in the art. These include, but are not limited to, BLAST, ALIGN, Megalign, BestFit, GCG Wisconsin Package, and variations thereof. In some embodiments, two nucleic acids or polypeptides described herein are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60 residues, at least about 60-80 residues in length or any integral value there between. In some embodiments, identity exists over a longer region than 60-80 residues, such as at least about 80-100 residues, and in some embodiments the sequences are substantially identical over the full length of the sequences being compared, such as an amino acid sequence of a peptide or a coding region of a nucleotide sequence.

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The terms "effective amount" or "therapeutically effective amount" or "therapeutic effect" refer to an amount of a therapeutic effective to "treat" a disease or disorder in a subject or mammal. The therapeutically effective amount of a drug has a therapeutic effect and as such can prevent the development of a disease or disorder; slow down the development of a disease or disorder; slow down the progression of a disease or disorder; relieve to some extent one or more of the symptoms associated with a disease or disorder; reduce morbidity and mortality; improve quality of life; or a combination of such effects.

The terms "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent or slow the development of a targeted pathologic condition or disorder. Thus those in need of treatment include those already with the disorder; those prone to have the disorder; and those in whom the disorder is to be prevented.

The term "depleted" when used to describe a cell sample (e.g., a peripheral blood mononuclear cell (PBMC) sample) refers to a cell sample in which a subpopulation of cells has been removed or depleted. For example, a immune cell sample depleted of CD25 expressing cells refers to an immune cell sample in which CD25 expressing cells have been removed or depleted. For example, one or more binding agents can be used to remove or deplete one or more cells or cell types from a sample. For example, CD14$^+$ cells can be depleted or removed from a PBMC sample, such as by using an antibody that binds to CD14.

The "stimulation" refers to a response induced by binding of a stimulatory molecule with its cognate ligand thereby mediating a signal transduction event. For example, stimulation of a T cell can refer to binding of a TCR of a T cell to a peptide-MHC complex. For example, stimulation of a T cell can refer to a step within protocol 1 or protocol 2 in which PBMCs are cultured together with peptide loaded APCs.

The term "enriched" refers to a composition or fraction wherein an object species has been partially purified such that the concentration of the object species is substantially higher than the naturally occurring level of the species in a finished product without enrichment. The term "induced cell" refers to a cell that has been treated with an inducing compound, cell, or population of cells that affects the cell's protein expression, gene expression, differentiation status, shape, morphology, viability, and the like.

Overview of T Cell Therapies and Manufacturing Thereof

Generating antigen specific T cells by controlled ex vivo induction or expansion of T cells (e.g., autologous T cells) can provide highly specific and beneficial T cell therapies (e.g., adoptive T cell therapies). The present disclosure provides T cell manufacturing methods and therapeutic T cell compositions which can be used for treating subjects with cancer and other conditions, diseases and disorders. The objective is to expand and induce antigen specific T cells with a favorable phenotype and function. The present disclosure provides compositions and methods for manufacturing of T cells which can be used for antigen specific T cell therapy (e.g., personal or personalized T cell therapies). The T cell compositions provided herein can be personal antigen specific T cell therapies.

Provided herein are methods of stimulating T cells. For example, the methods provided herein can be used to stimulate antigen specific T cells. The methods provided herein can be used to expand or induce antigen specific T cells. For example, the methods provided herein can be used to expand antigen specific memory T cells. For example, the methods provided herein can be used to induce antigen specific naïve T cells. For example, the methods provided herein can be used to expand antigen specific CD8$^+$ memory T cells. For example, the methods provided herein can be used to induce antigen specific CD8$^+$ naïve T cells. For example, the methods provided herein can be used to expand antigen specific CD4$^+$ memory T cells. For example, the methods provided herein can be used to induce antigen specific CD4$^+$ naïve T cells. Also provided herein are therapeutic compositions comprising antigen specific T cells. For example, the therapeutic compositions can comprise antigen specific memory T cells. For example, the therapeutic compositions can comprise antigen specific naïve T cells. Also provided herein are methods of use or methods of treatment using the therapeutic compositions described herein.

T Cell Compositions

Provided herein are compositions (e.g., pharmaceutical compositions) comprising a population of immune cells. The compositions can comprise at least one antigen specific T cells comprising a T cell receptor (TCR). The compositions can comprise at least one antigen specific T cells comprising a T cell receptor (TCR) specific to at least one antigen peptide sequence.

In some embodiments, the compositions provided herein comprise T cells that are stimulated by APCs, such as APCs pre-loaded with antigen peptides. The compositions can comprise a population of immune cells comprising T cells from a sample (e.g., a biological sample), wherein the T cells comprise APC-stimulated T cells. In some embodiments, a composition comprises a population of immune cells that has been incubated with one or more cytokines, growth factors or ligands, such as a ligand that binds to a cell surface receptor of an APC or a T cell. Non-limiting examples of such cytokines, growth factors and ligands include, but are not limited to, GM-CSF, IL-4, FLT3L, TNF-α, IL-1β, PGE1, IL-6, IFN-α, R848, LPS, ss-rna40, and polyI:C. In some embodiments, a composition comprises a population of immune cells that has been incubated with one or more APCs or APC preparations. For example, a composition can comprise a population of immune cells that has been incubated with one or more cytokine, growth factor and/or ligand stimulated APCs or cytokine, growth factor and/or ligand stimulated APC preparations. For example, a composition can comprise a population of immune cells that has been incubated with one or more cytokine stimulated APCs or cytokine stimulated APC preparations. For example, a composition can comprise a population of immune cells that has been incubated with one or more growth factor stimulated APCs or growth factor stimulated APC preparations. For example, a composition can comprise a population of immune cells that has been incubated with one or more ligand stimulated APCs or ligand stimulated APC preparations.

In some embodiments, the APC is an autologous APC, an allogenic APC, or an artificial APC. In some embodiments, the APC comprises a dendritic cell (DC). In some embodiments, the APC is derived from a CD14$^+$ monocyte. In some embodiments, the APCs can be obtained from skin, spleen, bone marrow, thymus, lymph nodes, peripheral blood, or cord blood. In some embodiments, the CD14$^+$ monocyte is from a biological sample from a subject comprising PBMCs. For example, a CD14$^+$ monocyte can be isolated from, enriched from, or purified from a biological sample from a subject comprising PBMCs. In some embodiments, the CD14$^+$ monocyte is stimulated with one or more cytokines or growth factors. In some embodiments, the one or more cytokines or growth factors comprise GM-CSF, IL-4, FLT3L, TNF-α, IL-1β, PGE1, IL-6, IFN-α, R848, LPS, ss-rna40, poly I:C, or a combination thereof. In some embodiments, the CD14$^+$ monocyte is from a second biological sample comprising PBMCs.

In some embodiments, the isolated populations of CD14$^+$ APCs can be enriched or substantially enriched. In some embodiments, the isolated population of CD14$^+$ APCs is at least 30%, at least 50%, at least 75%, or at least 90% homogeneous. In some embodiments, the isolated population of CD14$^+$ APCs is at least 60%, at least 75%, or at least 90% homogeneous. APCs, such as CD14$^+$ APCs can include, for example, APCs derived in culture from monocytic dendritic precursors as well as endogenously-derived APCs present in tissues such as, for example, peripheral blood, cord blood, skin, spleen, bone marrow, thymus, and lymph nodes.

CD14$^+$ APCs and cell populations substantially enriched for CD14$^+$ APCs can be isolated by methods also provided by the present invention. The methods generally include obtaining a population of cells that includes APC precursors, differentiation of the APC precursors into immature or mature APCs, and can also include the isolation of CD14$^+$ APCs from the population of differentiated immature or mature APCs.

APC precursor cells can be obtained by methods known in the art. APC precursors can be isolated, for example, by density gradient separation, fluorescence activated cell sorting (FACS), immunological cell separation techniques such as panning, complement lysis, rosetting, magnetic cell separation techniques, nylon wool separation, and combinations of such methods. Methods for immuno-selecting APCs include, for example, using antibodies to cell surface markers associated with APC precursors, such as anti-CD34 and/or anti-CD14 antibodies coupled to a substrate.

Enriched populations of APC precursors can also be obtained. Methods for obtaining such enriched precursor populations are known in the art. For example, enriched populations of APC precursors can be isolated from a tissue source by selective removal of cells that adhere to a substrate. Using a tissue source such as, e.g., bone marrow or peripheral blood, adherent monocytes can be removed from cell preparations using a commercially-treated plastic substrate (e.g., beads or magnetic beads) to obtain a population enriched for nonadherent APC precursors.

Monocyte APC precursors can also be obtained from a tissue source by using a APC precursor-adhering substrate. For example, peripheral blood leukocytes isolated by, e.g., leukopheresis, are contacted with a monocytic APC precursor-adhering substrate having a high surface area to volume ratio and the adherent monocytic APC precursors are separated. In additional embodiments, the substrate coupled can be a particulate or fibrous substrate having a high surface-to-volume ratio, such as, for example, microbeads, microcarrier beads, pellets, granules, powder, capillary tubes, microvillous membrane, and the like. Further, the particulate or fibrous substrate can be glass, polystyrene, plastic, glass-coated polystyrene microbeads, and the like.

The APC precursors can also be cultured in vitro for differentiation and/or expansion. Methods for differentiation/expansion of APC precursors are known in the art. Generally, expansion can be achieved by culturing the precursors in the presence of at least one cytokine that induces APC (e.g., dendritic cell) differentiation/proliferation. Typically, these cytokines are granulocyte colony stimulating factor (G-CSF) or granulocyte/macrophage colony stimulating factor (GM-CSF). In addition, other agents can be used to inhibit proliferation and/or maturation of non-APC cell types in the culture, thereby further enriching the population of APC precursors. Typically, such agents include cytokines such as, e.g., IL-13, IL-4, or IL-15, and the like.

The isolated populations of APC precursors are cultured and differentiated to obtain immature or mature APCs. Suitable tissue culture media include, for example, but not limited to, AIM-V®, RPMI 1640, DMEM, X-VIVO 15®, and the like. The tissue culture media is typically supplemented with amino acids, vitamins, divalent cations, and cytokines to promote differentiation of the precursors toward the APC phenotype. Typically, the differentiation-promoting cytokines are GM-CSF and/or IL-4.

Further, cultures of APC precursors during expansion, differentiation, and maturation to the APC phenotype can include plasma to promote the development of $CD14^+$ APCs. A typical plasma concentration is about 5%. In addition, where, for example, APC precursors are isolated by adherence to a substrate, plasma can be included in the culture media during the adherence step to promote the $CD14^+$ phenotype early in culture. A typical plasma concentration during adherence is about 1% or more.

The monocytic APC precursors can be cultured for any suitable time. In certain embodiments, suitable culture times for the differentiation of precursors to immature APCs can be about 1 to about 10 days, e.g., about 4 to about 7 days. The differentiation of immature APCs from the precursors can be monitored by methods known to those skilled in the art, such as by the presence or absence of cell surface markers (e.g., $CD11c^+$, $CD83^{low}$, $CD86^{-/low}$, $HLA-DR^+$). Immature APCs can also be cultured in appropriate tissue culture medium to maintain the immature APCs in a state for further differentiation or antigen uptake, processing and presentation. For example, immature APCs can be maintained in the presence of GM-CSF and IL-4.

Following differentiation from APC precursors, $CD14^+$ cells can be isolated to obtain an isolated population of $CD14^+$ APCs. Typically, where the $CD14^+$ APCs are isolated prior to maturation from enriched or substantially enriched APCs, the isolated population will be enriched or substantially enriched for immature $CD14^+$ APCs. Generally, isolation of the $CD14^+$ APCs includes contacting the cell population from which the $CD14^+$ cells are to be isolated with a CD14-specific probe. In one exemplary embodiment, CD14-expressing cells are detected by FACS using a CD14-specific probe either directly conjugated to a fluorescent molecule (e.g., FITC or PE) or with a unlabeled antibody specific for CD14 and a labeled second antibody specific for the first antibody. $CD14^+$ cells can also be separated from $CD14^{low}$ and $CD14^-$ cells by FACS sorting. Gating for $CD14^{high}$ positivity can be determined in reference to CD14 staining on, e.g., PBMC-derived monocytes. Typically, the CD14-specific binding agent is, for example, an anti-CD14 antibody (e.g., monoclonal or antigen binding fragments thereof). A number of anti-CD14 antibodies suitable for use in the present invention are well known to the skilled artisan and many can be purchased commercially.

In another embodiment, a CD14-specific probe is coupled to a substrate and the $CD14^+$ cells are isolated by affinity selection. A population of cells that includes $CD14^+$ cells is exposed to the coupled substrate and the $CD14^+$ cells are allowed to specifically adhere. Non-adhering $CD14^-$ cells are then washed from the substrate, and the adherent cells are then eluted to obtain an isolated cell population substantially enriched in $CD14^+$ APCs. The CD14-specific probe can be, for example, an anti-CD14 antibody. The substrate can be, for example, commercially available tissue culture plates or beads (e.g., glass or magnetic beads). Methods for affinity isolation of cell populations using substrate-coupled antibodies specific for surface markers are generally known.

During culture, immature APCs (either an isolated population of $CD14^-$ immature APCs or total immature APCs prior to isolation) can optionally be exposed to a predetermined antigen. Suitable predetermined antigens can include any antigen for which T-cell modulation is desired. In one embodiment, immature APCs are cultured in the presence of prostate specific membrane antigen (PSMA) for cancer immunotherapy and/or tumor growth inhibition. Other antigens can include, for example, bacterial cells, viruses, partially purified or purified bacterial or viral antigens, tumor cells, tumor specific or tumor associated antigens (e.g., tumor cell lysate, tumor cell membrane preparations, isolated antigens from tumors, fusion proteins, liposomes, and the like), recombinant cells expressing an antigen on its surface, autoantigens, and any other antigen. Any of the antigens can also be presented as a peptide or recombinantly produced protein or portion thereof. Following contact with antigen, the cells can be cultured for any suitable time to allow antigen uptake and processing, to expand the population of antigen-specific APCs, and the like.

For example, in one embodiment, the immature APCs can be cultured following antigen uptake to promote maturation of the immature APCs into mature APCs that present antigen in the context of MHC molecules. Methods for APC maturation are known. Such maturation can be performed, for example, by culture in the presence of known maturation factors, such as cytokines (e.g., TNF-α, IL-1β, or CD40 ligand), bacterial products (e.g., LPS or BCG), and the like. The maturation of immature APCs to mature APCs can be monitored by methods known in the art, such as, for example by measuring the presence or absence of cell surface markers (e.g., upregulation of CD83, CD86, and MHC molecules) or testing for the expression of mature APC specific mRNA or proteins using, for example, an oligonucleotide array.

Optionally, the immature APCs can be cultured in an appropriate tissue culture medium to expand the cell population and/or maintain the immature APCs in state for further differentiation or antigen uptake. For example, immature APCs can be maintained and/or expanded in the presence of GM-CSF and IL-4. Also, the immature APCs can be cultured in the presence of anti-inflammatory molecules such as, for example, anti-inflammatory cytokines (e.g., IL-10 and TGF-β) to inhibit immature APC maturation.

In another aspect, the isolated population of $CD14^+$ APCs are enriched for mature APCs. The isolated population of $CD14^+$ mature APCs can be obtained by culturing an isolated population of $CD14^+$ immature APCs in the presence of maturation factors as described above (e.g., bacterial products, and/or proinflammatory cytokines), thereby inducing maturation. Optionally, a mixed population of $CD14^+$ and $CD14^-$ immature APCs (differentiated from APC precursors) can be cultured to induce maturation, the maturation stage monitored as described above, and, at the appropriate stage of mature APC enrichment, the $CD14^+$ cells separated as described above to obtain an isolated population enriched or substantially enriched for $CD14^+$ mature APCs.

According to yet another aspect of the invention, APCs can be preserved, e.g., by cryopreservation either before exposure or following exposure to a prostate cancer antigen. Cryopreservation agents which can be used include but are not limited to dimethyl sulfoxide (DMSO), glycerol, polyvinylpyrrolidone, polyethylene glycol, albumin, dextran, sucrose, ethylene glycol, i-erythritol, D-ribitol, D-mannitol, D-sorbitol, i-inositol, D-lactose, choline chloride, amino acids, methanol, acetamide, glycerol monoacetate, and inorganic salts. A controlled slow cooling rate can be critical. Different cryoprotective agents and different cell types typically have different optimal cooling rates. The heat of fusion phase where water turns to ice typically should be minimal. The cooling procedure can be carried out by use of, e.g., a programmable freezing device or a methanol bath procedure. Programmable freezing apparatuses allow determination of optimal cooling rates and facilitate standard reproducible cooling. Programmable controlled-rate freezers such as Cryomed or Planar permit tuning of the freezing regimen to the desired cooling rate curve.

After thorough freezing, APCs can be rapidly transferred to a long-term cryogenic storage vessel. In a typical embodiment, samples can be cryogenically stored in liquid nitrogen (−196° C.) or its vapor (−165° C.). Considerations and procedures for the manipulation, cryopreservation, and long term storage of hematopoietic stem cells, particularly from bone marrow or peripheral blood, is largely applicable to the APCs of the invention.

Frozen cells are preferably thawed quickly (e.g., in a water bath maintained at 37-41° C.) and chilled immediately upon thawing. It may be desirable to treat the cells in order to prevent cellular clumping upon thawing. To prevent clumping, various procedures can be used, including but not limited to the addition before and/or after freezing of DNAse, low molecular weight dextran and citrate, hydroxyethyl starch, and the like. The cryoprotective agent, if toxic in humans, should be removed prior to therapeutic use of the thawed APCs. One way in which to remove the cryoprotective agent is by dilution to an insignificant concentration. Once frozen APCs have been thawed and recovered, they can be used to activate T cells as described herein with respect to non-frozen APCs.

In some embodiments, a composition comprises a population of immune cells that has been depleted of one or more types of immune cells. For example, a composition can comprise a population of immune cells that has been depleted of one or more types of immune cells that express one or more proteins, such as one or more cell surface receptors. In some embodiments, a composition comprises a population of immune cells from a biological sample comprising at least one antigen specific T cells comprising a T cell receptor (TCR) specific to at least one antigen peptide sequence, wherein an amount of CD14 and/or CD25 expressing immune cells in the population is proportionally different from an amount of immune cells expressing CD14 and/or CD25 in the biological sample. For example, a composition can comprise a population of immune cells from a biological sample comprising at least one antigen specific T cells comprising a T cell receptor (TCR) specific to at least one antigen peptide sequence, wherein an amount of CD14 expressing immune cells in the population is proportionally different from an amount of immune cells expressing CD14 in the biological sample. For example, a composition can comprise a population of immune cells from a biological sample comprising at least one antigen specific T cells comprising a T cell receptor (TCR) specific to at least one antigen peptide sequence, wherein an amount of CD25 expressing immune cells in the population is proportionally different from an amount of immune cells expressing CD25 in the biological sample. For example, a composition can comprise a population of immune cells from a biological sample comprising at least one antigen specific T cells comprising a T cell receptor (TCR) specific to at least one antigen peptide sequence, wherein an amount of CD14 and CD25 expressing immune cells in the population is proportionally different from an amount of immune cells expressing CD14 and CD25 in the biological sample. For example, a composition can comprise a population of immune cells from a biological sample, wherein an amount of immune cells expressing CD14 and CD25 in the population is proportionally less than an amount of immune cells expressing CD14 and CD25 in the biological sample.

In some embodiments, a composition comprises a population of immune cells comprising T cells from a sample (e.g., a biological sample), wherein the T cells comprise APC-stimulated T cells, wherein the APCs are FLT3L-stimulated APCs. For example, a composition can comprise a population of immune cells comprising T cells from a sample (e.g., a biological sample), wherein the T cells comprise APC-stimulated T cells and antigen specific T cells comprising a T cell receptor (TCR) specific to at least one antigen peptide sequence, wherein the APCs are FLT3L-stimulated APCs. In some embodiments, the composition comprises a population of immune cells comprising T cells from a biological sample, wherein the T cells comprise at least one antigen specific T cell that is an APC-stimulated T cell and comprises a T cell receptor (TCR) specific to at least one antigen peptide sequence, wherein the APC is a FLT3L-stimulated APC, and wherein an amount of antigen specific T cells in the population is proportionally more than an amount of antigen specific T cells in the biological sample. In some embodiments, the T cells comprise a plurality of antigen specific T cells comprising a T cell receptor (TCR) specific to at least one antigen peptide sequence. In some embodiments, the T cells comprise a plurality of antigen specific T cells comprising a plurality of T cell receptors (TCRs) specific to at least one antigen peptide sequence. In some embodiments, the T cells comprise a plurality of antigen specific T cells comprising a plurality of T cell receptors (TCRs) specific to a plurality of antigen peptide sequences. For example, the plurality of antigen specific T cells in the composition can comprise 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^2$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ antigen specific T cells. For example, the plurality T cell receptors (TCRs) specific to at least one antigen peptide sequence can comprise 10, 20, 30, 40, 50, 60, 70, 80, 90, 100, 150, 200, 250, 300, 350, 400, 450, 500, 550, 600, 650, 700, 750, 800, 850, 900, or 1000 different TCRs specific to the at least one antigen peptide sequence. For example, the plurality T cell receptors (TCRs) specific to a plurality of antigen peptide sequences can comprise 10, 20, 30, 40, 50, 60, 70, 80, 90, 100, 150, 200, 250, 300, 350, 400, 450, 500, 550, 600, 650, 700, 750, 800, 850, 900, or 1000 different TCRs specific to the plurality of antigen peptide sequences. For example, the plurality of antigen peptide sequences can comprise 10, 20, 30, 40, 50, 60, 70, 80, 90, 100, 150, 200, 250, 300, 350, 400, 450, 500, 550, 600, 650, 700, 750, 800, 850, 900, or 1000 different antigen peptide sequences.

In some embodiments, a composition or pharmaceutical composition comprises a population of immune cells from a biological sample. In some embodiments, the immune cells comprise a plurality of antigen specific T cells. In some embodiments, each of the antigen specific T cells comprises a T cell receptor (TCR) specific to at least one antigen peptide sequence. In some embodiments, a composition or pharmaceutical composition comprises a population of immune cells, wherein an amount of CD14 and/or CD25 expressing immune cells in the population is less than an amount of CD14 and/or CD25 expressing immune cells in the biological sample. In some embodiments, a pharmaceutical composition further comprises a pharmaceutically acceptable excipient.

In some embodiments, a pharmaceutical composition provided herein comprises: a population of immune cells from a biological sample comprising at least one antigen specific T cell comprising a T cell receptor (TCR) specific to at least one antigen peptide sequence, and a pharmaceutically acceptable excipient; wherein an amount of immune cells expressing CD14 and/or CD25 in the population is proportionally different from an amount of immune cells expressing CD14 and/or CD25 in the biological sample.

In some embodiments, a composition provided herein comprises a population of immune cells from a biological sample, wherein an amount of immune cells expressing CD14 and CD25 in the population is proportionally less than an amount of immune cells expressing CD14 and CD25 in the biological sample.

In some embodiments, a pharmaceutical composition provided herein comprises: a population of immune cells comprising T cells from a biological sample, wherein the T cells comprise at least one antigen specific T cell that is an APC-stimulated T cell and comprises a T cell receptor (TCR) specific to at least one antigen peptide sequence, wherein the APC is a FLT3L-stimulated APC; and a pharmaceutically acceptable excipient. In some embodiments, the at least one antigen specific T cell comprises at least one APC-stimulated T cell. In some embodiments, the amount of immune cells expressing CD14 and/or CD25 in the population is proportionally less than the amount of immune cells expressing CD14 and/or CD25 in the biological sample. In some embodiments, the amount of immune cells expressing CD14 and/or CD25 in the population is proportionally more than the amount of immune cells expressing CD14 and/or CD25 in the biological sample.

In some embodiments, the pharmaceutical composition comprises $CD4^+$ T cells, wherein a percentage of the antigen specific T cells of the $CD4^+$ T cells is at least about 2%, 3%, 4%, 5%, 10%, 20%, 30%, 40%, 50%, 60%, 70%, 80%, or 90%. In some embodiments, the pharmaceutical composition comprises naïve $CD8^+$ T cells, wherein a percentage of the antigen specific T cells of the naïve $CD8^+$ T cells is at least about 0.2%, 0.5%, 1%, 2%, 3%, 4%, 5%, 10%, 20%, 30%, 40%, 50%, 60%, 70%, 80%, or 90%. In some embodiments, the pharmaceutical composition comprises memory $CD8^+$ T cells, wherein a percentage of the antigen specific T cells of the memory $CD8^+$ T cells is at least about 0.2%, 0.5%, 1%, 2%, 3%, 4%, 5%, 10%, 20%, 30%, 40%, 50%, 60%, 70%, 80%, or 90%.

In some embodiments, the pharmaceutical composition comprises a population of immune cells comprising T cells from a biological sample, wherein the T cells comprise APC-stimulated T cells and antigen specific T cells comprising a T cell receptor (TCR) specific to at least one antigen peptide sequence, wherein the APCs are FLT3L-stimulated APCs; and a pharmaceutically acceptable excipient.

In some embodiments, the pharmaceutical composition comprises a population of immune cells comprising T cells from a biological sample, wherein the T cells comprise a plurality of neoantigen specific T cells comprising a T cell receptor (TCR) specific to at least one antigen peptide sequence, and a pharmaceutically acceptable excipient; wherein a percentage of the antigen specific T cells of the T cells is at least about 0.5%, 1%, 1.5%, 2%, 2.5%, 3%, 3.5%, 4%, 4.5%, 5%, 10%, 20%, 30%, 40%, 50%, 60%, 70%, or 80%.

In some embodiments, the neoantigen specific T cells comprise APC-stimulated T cells. In some embodiments, a percentage of CD14 and/or CD25 expressing immune cells in the population is less than a percentage of CD14 and/or CD25 expressing immune cells in the biological sample. In some embodiments, the biological sample is from a subject. In some embodiments, the subject is a human. In some embodiments, the subject has a disease or disorder. In some embodiments, the disease or disorder is cancer. In some embodiments, the neoantigen specific T cells comprise $CD4^+$ and/or $CD8^+$ T cells. In some embodiments, the neoantigen specific T cells comprise CD4-enriched T cells and/or CD8-enriched T cells. For example, a $CD4^+$ T cell or a $CD8^+$ T cell can be isolated from, enriched from, or purified from a biological sample from a subject comprising PBMCs. In some embodiments, the neoantigen specific T cells are naïve $CD4^+$ and/or naïve $CD8^+$ T cells. In some embodiments, a naïve T cell is characterized by the surface expression of L-selectin (CD62L). In some embodiments, a naïve T cell is characterized by the absence of one or more of the activation markers CD25, CD44 or CD69. In some embodiments, a naïve T cell is characterized by the absence of the memory CD45RO isoform. In some embodiments, a naïve T cell is characterized by expression of functional IL-7 receptors, consisting of subunits IL-7 receptor-α, CD127, and common-γ chain, CD132. In some embodiments, the at least one neoantigen peptide sequence comprises a mutation selected from (A) a point mutation and the cancer neoantigen peptide binds to the HLA protein of the subject with an $IC_{50}$ less than 500 nM and a greater affinity than a corresponding wild-type peptide, (B) a splice-site mutation, (C) a frameshift mutation, (D) a read-through mutation, (E) a gene-fusion mutation, and combinations thereof. In some embodiments, each of the at least one neoantigen peptide sequence binds to a protein encoded by an HLA allele expressed by the subject. In some embodiments, each of the at least one neoantigen peptide sequence comprises a mutation that is not present in non-cancer cells of the subject. In some embodiments, each of the at least one neoantigen peptide sequences is encoded by an expressed gene of the subject's cancer cells.

In some embodiments, one or more of the at least one neoantigen peptide sequence has a length of from 8-50 naturally occurring amino acids. In some embodiments, the at least one neoantigen peptide sequence comprises a plurality of neoantigen peptide sequences. In some embodiments, the plurality of neoantigen peptide sequences comprises from 2-50, 3-50, 4-50, 5-50, 6-50, 7-50, 8-50, 9-50, or 10-50 neoantigen peptide sequences.

In some embodiments, the APCs are one or more APC preparations. In some embodiments, the APCs comprise APCs loaded with one or more neoantigen peptides comprising one or more of the at least one neoantigen peptide sequence. In some embodiments, the APCs are autologous APCs or allogenic APCs.

In some embodiments, the APCs comprise dendritic cells (DCs). In some embodiments, the APCs are derived from $CD14^+$ monocytes. In some embodiments, the $CD14^+$ monocytes are enriched from the biological sample from the subject comprising PBMCs. For example, a $CD14^+$ can be isolated from, enriched from, or purified from a biological sample from a subject comprising PBMCs.

In some embodiments, the $CD14^+$ monocytes are stimulated with one or more cytokines or growth factors. In some embodiments, the one or more cytokines or growth factors comprise GM-CSF, IL-4, FLT3L, or a combination thereof. In some embodiments, the CD14$^+$ monocytes are from a second biological sample comprising PBMCs. In some embodiments, the second biological sample is from the same subject.

In some embodiments, the biological sample comprises peripheral blood mononuclear cells (PBMCs). In some embodiments, a percentage of the at least one antigen specific T cell in the composition is at least about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total T cells or total immune cells. In some embodiments, a percentage of at least one antigen specific CD8$^+$ T cell in the composition is at least about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4$^+$ T cells, total CD8$^+$ T cells, total T cells or total immune cells. In some embodiments, a percentage of at least one antigen specific CD4$^+$ T cell in the composition is at least about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4$^+$ T cells, total CD8$^+$ T cells, total T cells or total immune cells. In some embodiments, a percentage of the at least one antigen specific T cell in the biological sample is at most about 0.00001%, 0.00005%, 0.0001%, 0.0005%, 0.001%, 0.005%, 0.01%, 0.05%, 0.1% or 0.5% of total CD4$^+$ T cells, total CD8$^+$ T cells, total T cells or total immune cells. In some embodiments, a percentage of at least one antigen specific CD8$^+$ T cell in the biological sample is at most about 0.00001%, 0.00005%, 0.0001%, 0.0005%, 0.001%, 0.005%, 0.01%, 0.05%, 0.1% or 0.5% of total CD4$^+$ T cells, total CD8$^+$ T cells, total T cells or total immune cells. In some embodiments, a percentage of at least one antigen specific CD4$^+$ T cell in the biological sample is at most about 0.00001%, 0.00005%, 0.0001%, 0.0005%, 0.001%, 0.005%, 0.01%, 0.05%, 0.1% or 0.5% of total CD4$^+$ T cells, total CD8$^+$ T cells, total T cells or total immune cells. In some embodiments, a percentage of antigen specific T cells in the biological sample is at most about 0.5%. In some embodiments, a percentage of neoantigen specific CD8$^+$ T cells in the biological sample is at most about 0.5%. In some embodiments, a percentage of antigen specific CD4$^+$ T cells in the biological sample is at most about 0.5%.

In some embodiments, a percentage of antigen specific T cells in the pharmaceutical composition is at least about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4$^+$ T cells, total CD8$^+$ T cells, total T cells or total immune cells. In some embodiments, a percentage of antigen specific CD8$^+$ T cells in the pharmaceutical composition is at least about 1%, 2%, 3%, 4%, 5%, 6%, 7%, 8%, 9%, 10%, 11%, 12%, 13%, 14%, 15%, 16%, 17%, 18%, 19%, or 20% of total CD4$^+$ T cells, total CD8$^+$ T cells, total T cells or total immune cells. In some embodiments, a percentage of antigen specific naïve CD8$^+$ T cells in the pharmaceutical composition is at least about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4$^+$ T cells, total CD8$^+$ T cells, total T cells or total immune cells. In some embodiments, a percentage of antigen specific memory CD8$^+$ T cells in the pharmaceutical composition is at least about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4$^+$ T cells, total CD8$^+$ T cells, total T cells or total immune cells. In some embodiments, a percentage of antigen specific CD4$^+$ T cells in the pharmaceutical composition is at least about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4$^+$ T cells, total CD8$^+$ T cells, total T cells or total immune cells.

Methods of Manufacturing

Provided herein are methods for antigen specific T cell manufacturing. Provided herein are methods of preparing T cell compositions, such as therapeutic T cell compositions. For example, a method can comprise expanding or inducing antigen specific T cells. Preparing (e.g., inducing or expanding) T cells can also refer to manufacturing T cells, and broadly encompasses procedures to isolate, stimulate, culture, induce, and/or expand any type of T cells (e.g., CD4$^+$ T cells and CD8$^+$ T cells). In a first aspect, provided herein is a method of preparing at least one antigen specific T cell comprising a T cell receptor (TCR) specific to at least one antigen peptide sequence, the method comprising incubating an APC with a population of immune cells from a biological sample depleted of cells expressing CD14 and/or CD25.

In a second aspect, provided here is a method of preparing at least one antigen specific T cell comprising a T cell receptor (TCR) specific to at least one antigen peptide sequence, the method comprising incubating a FMS-like tyrosine kinase 3 receptor ligand (FLT3L)-stimulated APC with a population of immune cells from a biological sample.

In a third aspect, provided herein is a method of preparing a pharmaceutical composition comprising at least one antigen specific T cell comprising a T cell receptor (TCR) specific to at least one antigen peptide sequence, the method comprising: incubating FMS-like tyrosine kinase 3 receptor ligand (FLT3L) with a population of immune cells from a biological sample for a first time period; and thereafter incubating at least one T cell of the biological sample with an APC.

In a fourth aspect, provided herein is a method of preparing at least one antigen specific T cell comprising a T cell receptor (TCR) specific to at least one antigen peptide sequence, the method comprising incubating a population of immune cells from a biological sample with one or more APC preparations for one or more separate time periods of less than 28 days from incubating the population of immune cells with a first APC preparation of the one or more APC preparations, wherein at least one antigen specific memory T cell is expanded, or at least one antigen specific naïve T cell is induced.

In a fifth aspect, provided herein is a method of preparing at least one antigen specific T cell comprising a T cell receptor (TCR) specific to at least one antigen peptide sequence, the method comprising incubating a population of immune cells from a biological sample with 3 or less APC preparations for 3 or less separate time periods, wherein at least one antigen specific memory T cell is expanded or at least one antigen specific naïve T cell is induced.

In some embodiments, a method of preparing antigen specific T cells comprises a T cell receptor (TCR) specific to at least one antigen peptide sequence comprises incubating a population of immune cells from a biological sample with one or more APC preparations for one or more separate time periods, thereby stimulating T cells to become antigen specific T cells, wherein a percentage of antigen specific T cells is at least about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total $CD4^+$ T cells, total $CD8^+$ T cells, total T cells or total immune cells. In some embodiments, a method of preparing antigen specific T cells comprises a T cell receptor (TCR) specific to at least one antigen peptide sequence comprises incubating a population of immune cells from a biological sample with 3 or less APC preparations for 3 or less separate time periods, thereby stimulating T cells to become antigen specific T cells. In some embodiments, a method of preparing antigen specific T cells comprises a T cell receptor (TCR) specific to at least one antigen peptide sequence comprises incubating a population of immune cells from a biological sample with 2 or less APC preparations for 2 or less separate time periods, thereby stimulating T cells to become antigen specific T cells.

In some embodiments, a method comprises: (a) obtaining a biological sample from a subject comprising at least one antigen presenting cell (APC); (b) enriching cells expressing CD14 from the biological sample, thereby obtaining a $CD14^+$ cell enriched sample; (c) incubating the $CD14^+$ cell enriched sample with at least one cytokine or growth factor for a first time period; (d) incubating at least one peptide with the $CD14^+$ enriched sample of (c) for a second time period, thereby obtaining an APC peptide loaded sample; (e) incubating the APC peptide loaded sample with one or more cytokines or growth factors for a third time period, thereby obtaining a matured APC sample; (f) incubating APCs of the matured APC sample with a CD14 and/or CD25 depleted sample comprising PBMCs for a fourth time period; (g) incubating the PBMCs with APCs of a matured APC sample for a fifth time period; (h) incubating the PBMCs with APCs of a matured APC sample for a sixth time period; and (i) administering at least one T cell of the PBMCs to a subject in need thereof.

In some embodiments, a method comprises: (a) obtaining a biological sample from a subject comprising at least one APC and at least one PBMC; (b) depleting cells expressing CD14 and/or CD25 from the biological sample, thereby obtaining a CD14 and/or CD25 cell depleted sample; (c) incubating the CD14 and/or CD25 cell depleted sample with FLT3L for a first time period; (d) incubating at least one peptide with the CD14 and/or CD25 cell depleted sample of (c) for a second time period, thereby obtaining an APC peptide loaded sample; (e) incubating the APC peptide loaded sample with the at least one PBMC for a third time period, thereby obtaining a first stimulated PBMC sample; (f) incubating a PBMC of the first stimulated PBMC sample with an APC of a matured APC sample for a fourth time period, thereby obtaining a second stimulated PBMC sample; (g) incubating a PBMC of the second stimulated PBMC sample with an APC of a matured APC sample for a fifth time period, thereby obtaining a third stimulated PBMC sample; (h) administering at least one T cell of the third stimulated PBMC sample to a subject in need thereof.

In some embodiments, a method of preparing at least one antigen specific T cell comprising a T cell receptor (TCR) specific to at least one antigen peptide sequence comprises incubating an APC with a population of immune cells from a biological sample depleted of cells expressing CD14 and/or CD25.

In some embodiments, provided herein is a method of preparing at least one antigen specific T cell comprising a T cell receptor (TCR) specific to at least one antigen peptide sequence, the method comprising incubating a population of immune cells from a biological sample with one or more APC preparations for one or more separate time periods of less than 28 days from incubating the population of immune cells with a first APC preparation of the one or more APC preparations, wherein at least one antigen specific memory T cell is expanded, or at least one antigen specific naïve T cell is induced. In some embodiments, provided herein is a method of preparing at least one antigen specific T cell comprising a T cell receptor (TCR) specific to at least one antigen peptide sequence, the method comprising incubating a population of immune cells from a biological sample with 3 or less APC preparations for 3 or less separate time periods, wherein at least one antigen specific memory T cell is expanded or at least one antigen specific naïve T cell is induced.

In some embodiments, a method of preparing antigen specific T cells comprises a T cell receptor (TCR) specific to at least one antigen peptide sequence comprises contacting a population of immune cells (e.g., PBMCs) to APCs. In some embodiments, a method of preparing antigen specific T cells comprises a T cell receptor (TCR) specific to at least one antigen peptide sequence comprises incubating a population of immune cells (e.g., PBMCs) with APCs for a time period. In some embodiments, the population of immune cells is from a biological sample. In some embodiments, the population of immune cells is from a sample (e.g., a biological sample) depleted of CD14 expressing cells. In some embodiments, the population of immune cells is from a sample (e.g., a biological sample) depleted of CD25 expressing cells. In some embodiments, the population of immune cells is from a sample (e.g., a biological sample) depleted of CD14 expressing cells and CD25 expressing cells.

In some embodiments, a method of preparing at least one antigen specific T cell comprising a T cell receptor (TCR) specific to at least one antigen peptide sequence comprises incubating a FMS-like tyrosine kinase 3 receptor ligand (FLT3L)-stimulated APC with a population of immune cells from a biological sample. In some embodiments, provided herein is a method of preparing a pharmaceutical composition comprising at least one antigen specific T cell comprising a T cell receptor (TCR) specific to at least one antigen peptide sequence, the method comprising: incubating FMS-like tyrosine kinase 3 receptor ligand (FLT3L) with a population of immune cells from a biological sample for a first time period; and thereafter incubating at least one T cell of the biological sample with an APC.

In some embodiments, a method of preparing at least one antigen specific T cell comprising a T cell receptor (TCR) specific to at least one antigen peptide sequence comprises contacting a population of immune cells from a sample (e.g., a biological sample) with FMS-like tyrosine kinase 3 receptor ligand (FLT3L). In some embodiments, a method of preparing at least one antigen specific T cells comprises a T cell receptor (TCR) specific to at least one antigen peptide sequence comprises contacting a population of immune cells from a sample (e.g., a biological sample) with FMS-like tyrosine kinase 3 receptor ligand (FLT3L)-stimulated APCs. In some embodiments, a method of preparing at least one antigen specific T cells comprises a T cell receptor (TCR) specific to at least one antigen peptide sequence comprises incubating a population of immune cells from a sample (e.g., a biological sample) with FMS-like tyrosine kinase 3 receptor ligand (FLT3L)-stimulated APCs. In some embodiments, a method of preparing a pharmaceutical composition comprising at least one antigen specific T cell comprising a T cell receptor (TCR) specific to at least one antigen peptide sequence comprises incubating FMS-like tyrosine kinase 3 receptor ligand (FLT3L) with a population of immune cells from a biological sample (e.g., for a time period); and then contacting T cells of the biological sample to APCs. In some embodiments, a method of preparing at least one antigen specific T cell comprising a T cell receptor (TCR) specific to at least one antigen peptide sequence comprises contacting a population of immune cells from a sample (e.g., a biological sample) to one or more APC preparations. In some embodiments, a method of preparing at least one antigen specific T cell comprising a T cell receptor (TCR) specific to at least one antigen peptide sequence comprises incubating a population of immune cells from a sample (e.g., a biological sample) to one or more APC preparations for one or more separate time periods. In some embodiments, a method of preparing at least one antigen specific T cell comprising a T cell receptor (TCR) specific to at least one antigen peptide sequence comprises incubating a population of immune cells from a sample (e.g., a biological sample) to one or more APC preparations for 1, 2, 3, 4, 5, 6, 7, 8, 9 or 10 separate time periods. In some embodiments, the one or more separate time periods is less than 28 days calculated from incubating the population of immune cells with a first APC preparation of the one or more APC preparations.

In some embodiments, a method of preparing antigen specific T cells comprises a T cell receptor (TCR) specific to at least one antigen peptide sequence comprises incubating a population of immune cells to APCs for a time period, wherein the population of immune cells is from a biological sample comprising PBMCs. In some embodiments, a method of preparing antigen specific T cells comprises a T cell receptor (TCR) specific to at least one antigen peptide sequence comprises incubating a population of immune cells to APCs for a time period, wherein the population of immune cells is from a biological sample depleted of CD14 and/or CD25 expressing cells.

In some embodiments, a method of preparing antigen specific T cells comprising a T cell receptor (TCR) specific to at least one antigen peptide sequence comprises incubating a population of immune cells from a biological sample with FMS-like tyrosine kinase 3 receptor ligand (FLT3L)-stimulated APCs for a time period.

In some embodiments, a method of preparing a pharmaceutical composition comprising antigen specific T cells comprising a T cell receptor (TCR) specific to at least one antigen peptide sequence comprises incubating FMS-like tyrosine kinase 3 receptor ligand (FLT3L) with a population of immune cells from a biological sample; and then contacting T cells of the biological sample with APCs.

In some embodiments, a method of preparing antigen specific T cells comprising a T cell receptor (TCR) specific to at least one antigen peptide sequence comprises incubating a population of immune cells from a biological sample with one or more APC preparations for one or more separate time periods, thereby inducing or expanding antigen specific T cells, wherein the one or more separate time periods is less than 28 days calculated from incubating the population of immune cells with a first APC preparation of the one or more APC preparations. In some embodiments, incubating a population of immune cells from a biological sample with one or more APC preparations for one or more separate time periods is performed in a medium containing IL-7, IL-15, or a combination thereof. In some embodiments, the medium further comprises an indoleamine 2,3-dioxygenase-1 (IDO) inhibitor, an anti-PD-1 antibody, IL-12, or a combination thereof. The IDO inhibitor can be epacadostat, navoximod, 1-Methyltryptophan, or a combination thereof. In some embodiments, the IDO inhibitor may increase the number of antigen-specific $CD8^+$ cells. In some embodiments, the IDO inhibitor may maintain the functional profile of memory $CD8^+$ T cell responses. The PD-1 antibody may increase the absolute number of antigen-specific memory $CD8^+$ T cell responses. The PD-1 antibody may increase proliferation rate of the cells treated with such antibody. The additional of IL-12 can result in an increase of antigen-specific cells and/or an increase in the frequency of $CD8^+$ T cells.

In some embodiments, a method of preparing antigen specific T cells comprising a T cell receptor (TCR) specific to at least one antigen peptide sequence comprises incubating a population of immune cells comprising from a biological sample with one or more APC preparations for one or more separate time periods, thereby expanding or inducing antigen specific T cells, wherein a percentage of antigen specific T cells, antigen specific $CD4^+$ T cells, or antigen specific $CD8^+$ T cells is at least about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total T cells, total $CD4^+$ T cells, total $CD8^+$ T cells, total immune cells, or total cells.

In some embodiments, a method of preparing antigen specific T cells comprises a T cell receptor (TCR) specific to at least one antigen peptide sequence comprises incubating a population of immune cells from a biological sample with 3 or less APC preparations for 3 or less separate time periods, thereby stimulating T cells to become antigen specific T cells.

In some embodiments, the population of immune cells is from a biological sample depleted of CD14 and/or CD25 expressing cells. In some embodiments, the APCs are FMS-like tyrosine kinase 3 receptor ligand (FLT3L)-stimulated APCs. In some embodiments, the APCs comprise one or more APC preparations. In some embodiments, the APC preparations comprise 3 or less APC preparations. In some embodiments, the APC preparations are incubated with the immune cells sequentially within one or more separate time periods.

In some embodiments, the biological sample is from a subject. In some embodiments, the subject is a human. For example, the subject can be a patient or a donor. In some embodiments, the subject has a disease or disorder. In some embodiments, the disease or disorder is cancer. In some embodiments, the antigen specific T cells comprise $CD4^+$ and/or $CD8^+$ T cells. In some embodiments, the antigen specific T cells comprise CD4 enriched T cells and/or CD8 enriched T cells. For example, a CD4⁺ T cell and/or CD8⁺ T cell can be isolated from, enriched from, or purified from a biological sample from a subject comprising PBMCs. In some embodiments, the antigen specific T cells are naïve CD4⁺ and/or naïve CD8⁺ T cells. In some embodiments, the antigen specific T cells are memory CD4⁺ and/or memory CD8⁺ T cells.

In some embodiments, the at least one antigen peptide sequence comprises a mutation selected from (A) a point mutation and the cancer antigen peptide binds to the HLA protein of the subject with an $IC_{50}$ less than 500 nM and a greater affinity than a corresponding wild-type peptide, (B) a splice-site mutation, (C) a frameshift mutation, (D) a read-through mutation, (E) a gene-fusion mutation, and combinations thereof. In some embodiments, each of the at least one antigen peptide sequence binds to a protein encoded by an HLA allele expressed by the subject. In some embodiments, each of the at least one antigen peptide sequence comprises a mutation that is not present in non-cancer cells of the subject. In some embodiments, each of the at least one antigen peptide sequences is encoded by an expressed gene of the subject's cancer cells. In some embodiments, one or more of the at least one antigen peptide sequence has a length of from 8-50 naturally occurring amino acids. In some embodiments, the at least one antigen peptide sequence comprises a plurality of antigen peptide sequences. In some embodiments, the plurality of antigen peptide sequences comprises from 2-50, 3-50, 4-50, 5-50, 6-50, 7-50, 8-50, 9-50, or 10-50 antigen peptide sequences.

In some embodiments, the APCs comprise APCs loaded with one or more antigen peptides comprising one or more of the at least one antigen peptide sequence. In some embodiments, the APCs are autologous APCs or allogenic APCs. In some embodiments, the APCs comprise dendritic cells (DCs).

In some embodiments, a method comprises depleting CD14 and/or CD25 expressing cells from the biological sample. In some embodiments, depleting CD14⁺ cells comprises contacting a CD14 binding agent to the APCs. In some embodiments, the APCs are derived from CD14⁺ monocytes. In some embodiments, the APCs are enriched from the biological sample. For example, an APC can be isolated from, enriched from, or purified from a biological sample from a subject comprising PBMCs.

In some embodiments, the APCs are stimulated with one or more cytokines or growth factors. In some embodiments, the one or more cytokines or growth factors comprise GM-CSF, IL-4, FLT3L, or a combination thereof. In some embodiments, the one or more cytokines or growth factors comprise IL-4, GM-CSF, TNF-α, IL-1β, PGE1, IL-6, IL-7 or a combination thereof.

In some embodiments, the APCs are from a second biological sample. In some embodiments, the second biological sample is from the same subject.

In some embodiments, the biological sample comprises peripheral blood mononuclear cells (PBMCs). In some embodiments, a percentage of antigen specific T cells in the method is at least about 1%, 2%, 3%, 4%, 5%, 6%, 7%, 8%, 9%, 10%, 11%, 12%, 13%, 14%, 15%, 16%, 17%, 18%, 19%, or 20% of total T cells or total immune cells. In some embodiments, a percentage of antigen specific T cells in the method is from about 0.1% to about 5%, from about 5% to 10%, from about 10% to 15%, from about 15% to 20%, from about 20% to 25%, from about 25% to 30%, from about 30% to 35%, from about 35% to about 40%, from about 40% to about 45%, from about 45% to about 50%, from about 50% to about 55%, from about 55% to about 60%, from about 60% to 65%, or from about 65% to about 70% of total T cells or total immune cells. In some embodiments, a percentage of antigen specific CD8⁺ T cells in the method is at least about 1%, 2%, 3%, 4%, 5%, 6%, 7%, 8%, 9%, 10%, 11%, 12%, 13%, 14%, 15%, 16%, 17%, 18%, 19%, or 20% of total T cells or total immune cells. In some embodiments, a percentage of antigen specific naïve CD8⁺ T cells in the method is at least about 1%, 2%, 3%, 4%, 5%, 6%, 7%, 8%, 9%, 10%, 11%, 12%, 13%, 14%, 15%, 16%, 17%, 18%, 19%, or 20% of total T cells or total immune cells. In some embodiments, a percentage of antigen specific memory CD8⁺ T cells in the method is at least about 1%, 2%, 3%, 4%, 5%, 6%, 7%, 8%, 9%, 10%, 11%, 12%, 13%, 14%, 15%, 16%, 17%, 18%, 19%, or 20% of total T cells or total immune cells. In some embodiments, a percentage of antigen specific CD4⁺ T cells in the method is at least about 1%, 2%, 3%, 4%, 5%, 6%, 7%, 8%, 9%, 10%, 11%, 12%, 13%, 14%, 15%, 16%, 17%, 18%, 19%, or 20% of total T cells or total immune cells. In some embodiments, a percentage of antigen specific CD4⁺ T cells in the method is at least about 1%, 2%, 3%, 4%, 5%, 6%, 7%, 8%, 9%, 10%, 11%, 12%, 13%, 14%, 15%, 16%, 17%, 18%, 19%, or 20% of total T cells or total immune cells In some embodiments, a percentage of antigen specific T cells in the biological sample is at most about 0.5%, 1%, 2%, 3%, 4%, 5%, 6%, 7%, 8%, 9%, 10%, 11%, 12%, 13%, 14%, 15%, 16%, 17%, 18%, 19%, or 20%. In some embodiments, a percentage of antigen specific CD8⁺ T cells in the biological sample is at most about 0.5%, 1%, 2%, 3%, 4%, 5%, 6%, 7%, 8%, 9%, 10%, 11%, 12%, 13%, 14%, 15%, 16%, 17%, 18%, 19%, or 20%. In some embodiments, a percentage of antigen specific naïve CD8⁺ T cells in the biological sample is at most about 0.5%, 1%, 2%, 3%, 4%, 5%, 6%, 7%, 8%, 9%, 10%, 11%, 12%, 13%, 14%, 15%, 16%, 17%, 18%, 19%, or 20%. In some embodiments, a percentage of antigen specific memory CD8⁺ T cells in the biological sample is at most about 0.5%, 1%, 2%, 3%, 4%, 5%, 6%, 7%, 8%, 9%, 10%, 11%, 12%, 13%, 14%, 15%, 16%, 17%, 18%, 19%, or 20%. In some embodiments, a percentage of antigen specific CD4⁺ T cells in the biological sample is at most about 0.5%, 1%, 2%, 3%, 4%, 5%, 6%, 7%, 8%, 9%, 10%, 11%, 12%, 13%, 14%, 15%, 16%, 17%, 18%, 19%, or 20%.

In some embodiments, a method comprises stimulating T cells with IL-7, IL-15, or a combination thereof. In some embodiments, a method comprises stimulating T cells with IL-7, IL-15, or a combination thereof, in the presence of an IDO inhibitor, a PD-1 antibody or IL-12. In some embodiments, the method further comprises administering the antigen specific T cells to a subject.

In some embodiments, the first time period of the one or more time periods is about 1, 2 3, 4, 5, 6, 7, 8, or 9 days.

In some embodiments, a total time period of the separate time periods is less than 28 days. In some embodiments, a total time period of the separate time periods is from 20-27 days. In some embodiments, a total time period of the separate time periods is 15, 16, 17, 18, 19, 20, 21, 22, 23, 24, 25, 26, 27, 28, 29, 30, 31, 32, 33, 34, 35, 36, 37, 38, or 39 days.

In some embodiments, a method comprises incubating a first APC preparation of the APC preparations with the T cells for more than 7 days. In some embodiments, a method comprises incubating a first APC preparation of the APC preparations with the T cells for more than 7, 8, 9, 10, 11, 12, 13, 14, 15, 16, 17, 18, 19, or 20 days. In some embodiments, a method comprises incubating a first APC preparation of the APC preparations with the T cells for from 7-20, 8-20, 9-20, 10-20, 11-20, or 12-20 days. In some embodiments, a method comprises incubating a first APC preparation of the APC preparations with the T cells for about 10-15 days.

In some embodiments, a method comprises incubating a second APC preparation of the APC preparations to the T cells for 5-9 days. In some embodiments, a method comprises incubating a second APC preparation of the APC preparations to the T cells for 5, 6, 7, 8, or 9 days.

In some embodiments, a method comprises incubating a third APC preparation of the APC preparations to the T cells for 5-9 days. In some embodiments, the method comprises incubating a third APC preparation of the APC preparations to the T cells for 5, 6, 7, 8, or 9 days.

In some embodiments, a method comprises incubating a first APC preparation of the APC preparations with the T cells for about 1, 2, 3, 4, 5, 6, 7, 8, 9, 10, 11, 12, 13, 14, 15, 16, 17, 18, 19, 20, 21, or 22 days, incubating a second APC preparation of the APC preparations to the T cells for about 1, 2, 3, 4, 5, 6, 7, 8, 9, 10, 11, 12, 13, 14, 15, 16, 17, 18, 19, 20, 21, or 22 days, and incubating a third APC preparation of the APC preparations to the T cells for about 1, 2, 3, 4, 5, 6, 7, 8, 9, 10, 11, 12, 13, 14, 15, 16, 17, 18, 19, 20, 21, or 22 days.

In some embodiments, a biological sample is freshly obtained from a subject or is a frozen sample.

In some embodiments, a method comprises incubating one or more of the APC preparations with a first medium comprising at least one cytokine or growth factor for a first time period. In some embodiments, the first time period is at lease 1, 2, 3, 4, 5, 6, 7, 8, 9, 10, 11, 12, 13, 14, 15, 16, or 17, or 18 days. In some embodiments, the first time period is no more than 2, 3, 4, 5, 6, 7, 8, 9, 10, 11, 12, 13, 14, 15, 16, 17, or 18 days. In some embodiments, the first time period is at least 1, 2 3, 4, 5, 6, 7, 8, or 9 days. In some embodiments, the first time period is no more than 3, 4, 5, 6, 7, 8, 9, or 10 days. In some embodiments, the at least one cytokine or growth factor comprises GM-CSF, IL-4, FLT3L, TNF-α, IL-1β, PGE1, IL-6, IL-7, IFN-α, R848, LPS, ss-rna40, poly I:C, or any combination thereof.

In some embodiments, a method comprises incubating one or more of the APC preparations with at least one peptide for a second time period. In some embodiments, the second time period is no more than 1 hour.

In some embodiments, a method comprises incubating one or more of the APC preparations with a second medium comprising one or more cytokines or growth factors for a third time period, thereby obtaining matured APCs. In some embodiments, the one or more cytokines or growth factors comprises GM-CSF (granulocyte macrophage colony-stimulating factor), IL-4, FLT3L, TNF-α, IL-1β, PGE1, IL-6, IL-7, IFN-α, R848 (resiquimod), LPS, ss-rna40, poly I:C, CpG, or a combination thereof. In some embodiments, the third time period is no more than 2, 3, 4, 5, 6, 7, 8, 9, 10, 11, 12, 13, 14, 15, 16, 17, or 18 days. In some embodiments, the third time period is at least 1, 2, 3, 4, 5, 6, 7, 8, 9, 10, 11, 12, 13, 14, 15, 16, or 17 days. In some embodiments, the third time period is no more than 2, 3, 4, or 5 days. In some embodiments, the third time period is at least 1, 2, 3, or 4 days.

In some embodiment, the method further comprises removing the one or more cytokines or growth factors of the second medium after the third time period and before a start of the fourth time period.

In some embodiment, the method is performed ex vivo.

In some embodiments, a method of preparing T cells comprises obtaining a biological sample from a subject comprising APCs. In some embodiments, the method comprises enriching CD14$^+$ cells from a biological sample, thereby obtaining a CD14$^+$ enriched sample. In some embodiments, a method comprises incubating a CD14$^+$ enriched sample with a first medium comprising at least one cytokine or growth factor for a first time period. In some embodiments, a method comprises incubating at least one peptide with a CD14$^+$ enriched sample for a second time period, thereby obtaining an APC peptide loaded sample. In some embodiments, a method comprises incubating an APC peptide loaded sample with a second medium comprising one or more cytokines or growth factors for a third time period, thereby obtaining a matured APC sample. In some embodiments, a method comprises contacting APCs of a matured APC sample with peripheral blood mononuclear cells (PBMCs) and a third medium comprising at least one cytokine or growth factor for a fourth time period. In some embodiments, a method comprises incubating PBMCs with APCs of a matured APC sample for a fifth time period. In some embodiments, a method comprises incubating PBMCs with APCs of a matured APC sample for a sixth time period. In some embodiments, a method comprises administering T cells of PBMCs to a subject in need thereof.

In some other embodiments, a method of preparing T cells comprises obtaining a biological sample from a subject comprising APCs. In some embodiments, the method comprises enriching CD14$^+$ cells from a biological sample, thereby obtaining a CD14$^+$ enriched sample. In some embodiments, a method comprises incubating a CD14$^+$ enriched sample with a first medium comprising at least one cytokine or growth factor for at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days.

In some embodiments, a method comprises incubating at least one peptide with a CD14$^+$ enriched sample for at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days, thereby obtaining an APC peptide loaded sample. In some embodiments, a method comprises incubating an APC peptide loaded sample with a medium comprising one or more cytokines or growth factors for at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days, thereby obtaining a matured APC sample. In some embodiments, a method comprises contacting APCs of a matured APC sample with PBMCs and a medium comprising at least one cytokine or growth factor for at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days. In some embodiments, a method comprises incubating the PBMCs with APCs of a matured APC sample for at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days. In some embodiments, a method comprises incubating PBMCs with APCs of a matured APC sample for at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days. In some embodiments, the method comprises administering T cells of the PBMCs to a subject in need thereof.

In some embodiments, a method comprises: (a) obtaining a biological sample from a subject comprising at least one antigen presenting cell (APC); (b) enriching cells expressing CD14 from the biological sample, thereby obtaining a CD14⁺ cell enriched sample; (c) incubating the CD14⁺ cell enriched sample with at least one cytokine or growth factor for a first time period; (d) incubating at least one peptide with the CD14⁺ cell enriched sample of (c) for a second time period, thereby obtaining an APC peptide loaded sample; (e) incubating the APC peptide loaded sample with one or more cytokines or growth factors for a third time period, thereby obtaining a matured APC sample; (f) incubating APCs of the matured APC sample with a CD14 and/or CD25 depleted sample comprising PBMCs for a fourth time period; (g) incubating the PBMCs with APCs of a matured APC sample for a fifth time period; (h) incubating the PBMCs with APCs of a matured APC sample for a sixth time period; and (i) administering at least one T cell of the PBMCs to a subject in need thereof. In some embodiments, the first time period is at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days. In some embodiments, the second time period is at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days. In some embodiments, the third time period is at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days. In some embodiments, the fourth time period is at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days. In some embodiments, the fifth time period is at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days.

In some embodiments, a method comprises: (a) obtaining a biological sample from a subject comprising at least one APC and at least one PBMC; (b) depleting cells expressing CD14 and/or CD25 and/or CD19 from the biological sample, thereby obtaining a CD14 and/or CD25 and/or CD19 cell depleted sample; (c) incubating the CD14 and/or CD25 and/or CD19 cell depleted sample with FLT3L for a first time period; (d) incubating at least one peptide with the CD14 and/or CD25 and/or CD19 cell depleted sample of (c) for a second time period, thereby obtaining an APC peptide loaded sample; (e) incubating the APC peptide loaded sample with the at least one PBMC for a third time period, thereby obtaining a first stimulated PBMC sample; (f) incubating a PBMC of the first stimulated PBMC sample with an APC of a matured APC sample for a fourth time period, thereby obtaining a second stimulated PBMC sample; (g) optionally, incubating a PBMC of the second stimulated PBMC sample with an APC of a matured APC sample for a fifth time period, thereby obtaining a third stimulated PBMC sample; (h) administering at least one T cell of the first, the second, or the third stimulated PBMC sample to a subject in need thereof. In some embodiments, the first time period is at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days. In some embodiments, the second time period is at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days. In some embodiments, the third time period is at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days. In some embodiments, the fourth time period is at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days. In some embodiments, the fifth time period is at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days.

In some other embodiments, a method of preparing T cells comprises (a) obtaining a biological sample from a subject comprising APCs and T cells; (b) incubating the biological sample with a first medium comprising at least one cytokine or growth factor for a first time period; (c) incubating at least one peptide with the biological sample of (c) for a second time period, thereby obtaining an APC peptide loaded sample; (d) incubating the APC peptide loaded sample with a second medium comprising one or more cytokines or growth factors for a third time period, thereby obtaining a matured APC sample; (e) incubating the matured APC sample with human serum after the third time period for a fourth period of time; (f) incubating the biological sample with one or more cytokines for a fifth time period; and (g) administering T cells of the biological sample to a subject in need thereof. In some embodiments, at least one cytokine or growth factor comprises FLT3L. In some embodiments, the first time period is at least 5 hours, at least 8 hours, at least 10 hours, at least 12 hours, at least 15 hours, at least 20 hours, at least 22 hours, at least 1 day, at least 2 days, at least 3 days, at least 4 days, or at least 5 days. In some embodiments, the second time period is at least 30 minutes, 40 minutes, 50 minutes, 1 hour, 2 hours, or 3 hours. In some embodiments, the third time period is at least 10 hours, at least 12 hours, at least 15 hours, at least 20 hours, at least 22 hours, at least 1 day, at least 2 days, at least 3 days, at least 4 days, or at least 5 days. In some embodiments, the fourth time period is about 2, 3, or 4 days. In some embodiments, the fifth time period is at least 4, 5, 6, 7, 8, 9, 10, 11, or 12 days. In some embodiments, the first time period is at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days. In some embodiments, the second time period is at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days. In some embodiments, the third time period is at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days. In some embodiments, the fourth time period is at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days. In some embodiments, the fifth time period is at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days.

The induced or expanded T cells can comprise various types of T cells. In some embodiments, antigen specific T cells comprise at least one CD4$^+$ T cell. In some embodiments, antigen specific T cells comprise at least one CD8$^+$ T cell. In some embodiments, antigen specific T cells comprise at least one CD4 enriched T cell. In some embodiments, antigen specific T cells comprise at least one CD8 enriched T cell. In some embodiments, antigen specific T cells comprise at least one memory T cell. In some embodiments, antigen specific T cells comprise at least one naïve T cell. In some embodiments, antigen specific T cells comprise at least one memory CD4$^+$ T cell. In some embodiments, antigen specific T cells comprise at least one naïve CD4$^+$ T cell. In some embodiments, antigen specific T cells comprise at least one memory CD8$^+$ T cell. In some embodiments, antigen specific T cells comprise at least one naïve CD8$^+$ T cell.

Various antigen peptides can be used to induce or expand T cells. In some embodiments, a peptide comprises a mutation selected from (A) a point mutation, (B) a splice-site mutation, (C) a frameshift mutation, (D) a read-through mutation, (E) a gene-fusion mutation, and combinations thereof. In some embodiments, a peptide comprises a point mutation and binds to the HLA protein of a subject with a greater affinity than a corresponding wild-type peptide. In some embodiments, a peptide binds to the HLA protein of a subject with an $IC_{50}$ of less than 500 nM, 250 nM, 150 nM, 100 nM, 50 nM, 25 nM or 10 nM. In some embodiments, a peptide binds to the HLA protein of a subject with an $IC_{50}$ or a $K_D$ of less than 500 nM, 250 nM, 150 nM, 100 nM, 50 nM, 25 nM or 10 nM. In some embodiments, each peptide binds to a protein encoded by an HLA allele expressed by a subject. In some embodiments, a TCR of an antigen specific T cell induced or expanded binds to a peptide-HLA complex with an $IC_{50}$ or a $K_D$ of less than 500 nM, 250 nM, 150 nM, 100 nM, 50 nM, 25 nM or 10 nM. In some embodiments, the TCR binds to an peptide-HLA complex with an $IC_{50}$ or a $K_D$ of less than 500 nM, 250 nM, 150 nM, 100 nM, 50 nM, 25 nM or 10 nM. In some embodiments, each of the at least one antigen peptide sequences comprises a mutation that is not present in non-cancer cells of a subject. In some embodiments, each of the at least one antigen peptide sequences is encoded by gene or an expressed gene of a subject's cancer cells. In some embodiments, a peptide has a length of at least 8; 9; 10; 11; 12; 13; 14; 15; 16; 17; 18; 19; 20; 21; 22; 23; 24; 25; 26; 27; 28; 29; 30; 40; 50; 60; 70; 80; 90; 100; 150; 200; 250; 300; 350; 400; 450; 500; 600; 700; 800; 900; 1,000; 1,500; 2,000; 2,500; 3,000; 4,000; 5,000; 7,500; or 10,000 or more naturally occurring amino acids. In some embodiments, a peptide binds to a protein encoded by a class I HLA allele and has a length of from 8-12 naturally occurring amino acids. In some embodiments, a peptide binds to a protein encoded by a class II HLA allele and has a length of from 16-25 naturally occurring amino acids. In some embodiments, a peptide comprises a plurality of peptides. In some embodiments, the plurality of peptides comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, 300, 350, 400, 450, or 500 or more antigen peptides.

In various embodiments, APCs are used to stimulate/induce T cells. In some embodiments, an APC or an APC of an APC preparation is loaded with one or more antigen peptides. In some embodiments, an APC or an APC of an APC preparation is an autologous APC or an allogenic APC. In some embodiments, an APC or an APC of an APC preparation comprises a dendritic cell (DC). In some embodiments, the method comprises depleting cells expressing CD14 and/or CD25 from a biological sample. In some embodiments, the method comprises depleting cells expressing CD19 from a biological sample. In some embodiments, depleting cells expressing CD14 and/or CD25 comprises binding a CD14 and/or CD25 binding agent to an APC or an APC of an APC preparation. In some embodiments, the CD14 and/or CD25 binding agent is biotinylated. In some embodiments, depleting cells expressing CD14 and/or CD25 comprises binding an anti-biotin reagent on a solid support to a CD14 and/or CD25 binding agent. In some embodiments, a CD14 and/or CD25 binding agent is attached to a solid support. In some embodiments, depleting cells expressing CD19 comprises binding a CD19 binding agent to an APC or an APC of an APC preparation. In some embodiments, the CD19 binding agent is biotinylated. In some embodiments, depleting cells expressing CD19 comprises binding an anti-biotin reagent on a solid support to a CD19 binding agent. In some embodiments, a CD19 binding agent is attached to a solid support. In some embodiments, an APC or an APC of an APC preparation is derived from a CD14$^+$ monocyte. In some embodiments, an APC or an APC of an APC preparation is CD141 enriched APC or CD141 enriched dentric cell.

In some embodiments, an APC or an APC of an APC preparation is enriched from a biological sample. In some embodiments, an APC or an APC of an APC preparation is stimulated with one or more cytokines or growth factors. In some embodiments, the one or more cytokines or growth factors comprise GM-CSF, IL-4, FLT3L, TNF-α, IL-1β, PGE1, IL-6, IL-7, IFN-α, R848, LPS, ss-rna40, poly I:C, or a combination thereof. In some embodiments, an APC or an APC of an APC preparation is from a second biological sample. In some embodiments, the second biological sample is from the same subject. In some embodiments, the biological sample comprises peripheral blood mononuclear cells (PBMCs). In some embodiments, a biological sample is freshly obtained from a subject or is a frozen sample.

In some embodiments, a percentage of the at least one antigen specific T cell is at least about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4$^+$ T cells, total CD8$^+$ T cells, total T cells or total immune cells. In some embodiments, a percentage of at least one antigen specific CD8$^+$ T cell is at least about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4$^+$ T cells, total CD8$^+$ T cells, total T cells or total immune cells. In some embodiments, a percentage of at least one antigen specific CD4$^+$ T cell is at least about 0.00001%, 0.00002%, 0.00005%, 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4$^+$ T cells, total CD8$^+$ T cells, total T cells or total immune cells.

In some embodiments, a percentage of the at least one antigen specific T cell in the biological sample is at most about 0.00001%, 0.00005%, 0.0001%, 0.0005%, 0.001%, 0.005%, 0.01%, 0.05%, 0.1%, 0.2%, 0.3%, 0.4% 0.5%, 0.6%, 0.7%, 0.8%, 0.9%, or 1% of total $CD4^+$ T cells, total $CD8^+$ T cells, total T cells or total immune cells. In some embodiments, a percentage of at least one antigen specific $CD8^+$ T cell in the biological sample is at most about 0.00001%, 0.00005%, 0.0001%, 0.0005%, 0.001%, 0.005%, 0.01%, 0.05%, 0.1%, 0.2%, 0.3%, 0.4% 0.5%, 0.6%, 0.7%, 0.8%, 0.9%, or 1% of total $CD4^+$ T cells, total $CD8^+$ T cells, total T cells or total immune cells. In some embodiments, a percentage of at least one antigen specific $CD4^+$ T cell in the biological sample is at most about 0.00001%, 0.00005%, 0.0001%, 0.0005%, 0.001%, 0.005%, 0.01%, 0.05%, 0.1%, 0.2%, 0.3%, 0.4% 0.5%, 0.6%, 0.7%, 0.8%, 0.9%, or 1% of total $CD4^+$ T cells, total $CD8^+$ T cells, total T cells or total immune cells.

In some embodiments, a method further comprises administering one or more of the at least one antigen specific T cell to a subject. In some embodiments, a total time period of the separate time periods is less than 28 days. In some embodiments, incubating comprises incubating an APC preparation of the APC preparations to the T cells for more than 7 days. In some embodiments, incubating comprises incubating a first, second, third or fourth APC preparation of the APC preparations to the T cells for more than 7 days. In some embodiments, the method comprises incubating the APC or one or more of the APC preparations with a first medium comprising at least one cytokine or growth factor for a first time period. In some embodiments, the first time period is at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days. In some embodiments, the at least one cytokine or growth factor comprises GM-CSF, IL-4, FLT3L, TNF-α, IL-1, PGE1, IL-6, IL-7, IFN-α, R848, LPS, ss-rna40, poly I:C, or any combination thereof. In some embodiments, the method comprises incubating one or more of the APC preparations with at least one peptide for a second time period. In some embodiments, the second time period is at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days. In some embodiments, the method comprises incubating an APC or one or more APC with a second medium comprising one or more cytokines or growth factors for a third time period, thereby obtaining a matured APC. In some embodiments, the third time period is at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days. In some embodiments, the one or more cytokines or growth factors comprises GM-CSF, IL-4, FLT3L, TNF-α, IL-1β, PGE1, IL-6, IL-7, IFN-α, R848, LPS, ss-rna40, poly I:C, or a combination thereof. In some embodiments, the method further comprises removing the one or more cytokines or growth factors of the second medium after the third time period and before a start of the fourth time period. In some embodiments, the fourth time period is at least or at most or about 30, 40, or 50 minutes; or 1, 2, 3, 4, 5, 6, 7, 8, 9, 10, 11, 12, 13, 14, 15, 16, 17, 18, 19, 20, 21, 22, or 23 hours; or 1, 2, 3, 4, 5, 6, 7, 8, 9, 10, 11, 12, 13, 14, 15, 16, 17, 18, 19, or 20 days. In some embodiments, the antigen is a neoantigen, a tumor associated antigen, a viral antigen, a minor histocompatibility antigen or a combination thereof. In some embodiments, the method is performed ex vivo. In some embodiments, the at least one antigen specific T cell comprises a plurality of antigen specific T cells.

Antigen Presenting Cells (APCs) and Methods of Preparing

In some embodiments, a method comprises inducing or stimulating or expanding T cells with antigen presenting cells (APCs). The APCs can be pre-loaded with antigen peptides before contacting the T cells. In some embodiments, a method of expanding or inducing antigen specific T cells comprises stimulating a population of immune cells comprising T cells with APCs. In some embodiments, the population of immune cells is from a biological sample depleted of CD14 and/or CD25 expressing cells. In some embodiments, the APC is a FLT3L-stimulated APC. In some embodiments, the APC comprises one or more APC preparations. In some embodiments, at least one of the one or more APC preparations comprises a FLT3L-stimulated APC. In some embodiments, the one or more APC preparations comprise 3 or less APC preparations. In some embodiments, the one or more APC preparations are incubated with the immune cells sequentially within one or more separate time periods Antigen presenting cells (APC) present peptide fragments of protein antigens in association with MHC molecules on their cell surface. A presented peptide is associated with a MHC molecule as a peptide-MHC complex (pMHC) on the cell surface of the APC. Processing and presentation of peptide-MHC complexes can involve a series of sequential stages comprising: protease-mediated digestion of proteins; peptide transport into the endoplasmic reticulum (ER) mediated by the transporter associated with antigen processing (TAP); formation of peptide-MHC I molecules using newly synthesized MHC molecules; and transport of peptide-MHC molecules to the cell surface.

Some APCs may activate antigen specific T cells. For example, a T cell comprising a T cell receptor (TCR) that interacts with a pMHC may be activated, stimulated, induced or expanded upon formation of a TCR-pMHC. In some embodiments, an MHC (e.g., a class I MHC or a class II MHC) of an antigen presenting cell can be loaded with a peptide and presented by an APC by introducing into the APC a nucleic acid (e.g., an RNA) encoding an antigen peptide or polypeptide comprising the peptide sequence to be presented.

From a biological perspective, in order for a somatic mutation to generate an immune response several criteria need to be satisfied: the allele containing the mutation should be expressed by the cell, the mutation should be in a protein coding region and nonsynonymous, the translated protein should be cleaved by the proteasome or other cellular protein degradation pathway and an epitope containing the mutation should be presented by the MHC complex, the presented epitope should be recognized by a TCR and, finally, the TCR-pMHC complex should launch a signaling cascade that activates the T cell.

Monocytes can circulate in the bloodstream and then move into tissues where they can differentiate into macrophages and dendritic cells. Classical monocytes are typically characterized by high levels of expression of the CD14 cell surface receptor. Monocytes and B cells can be competent APCs, although their antigen presenting capacities appear to be limited to the re-activation of previously sensitized T cells. These cell types may not be capable of directly activating functionally naïve or unprimed T cell populations. Professional antigen-presenting cells are very efficient at internalizing antigen, either by phagocytosis or by receptor-mediated endocytosis, and then displaying a fragment of the antigen, bound to a MHC molecule, on their membrane. The T cell recognizes and interacts with the antigen-MHC molecule complex on the membrane of the antigen presenting cell. An additional co-stimulatory signal is then produced by the antigen presenting cell, leading to activation of the T cell. The expression of co-stimulatory molecules is a typical feature of professional antigen-presenting cells.

Professional antigen-presenting cells can be very efficient at internalizing antigen, either by phagocytosis or by receptor-mediated endocytosis, and then displaying a fragment of the antigen, bound to a MHC molecule, on their membrane. The T cell can recognize and interact with the antigen-MHC molecule complex on the membrane of the APC. An additional co-stimulatory signal can then be produced by the APC, leading to activation of the T cell. The expression of co-stimulatory molecules can be a defining feature of professional antigen-presenting cells. Examples of professional APCs can include, but are not limited to, dendritic cells (DCs), macrophages, and B-cells. Professional APCs may express high levels of MHC class II, ICAM-1 and B7-2.

One of the main types of professional antigen presenting cells is dendritic cells, which have the broadest range of antigen presentation. Other main types of professional antigen presenting cells include macrophages, B-cells, and certain activated epithelial cells. Dendritic cells are leukocyte populations that present antigens (e.g., antigens captured in peripheral tissues) to T cells via MHC class II and I antigen presentation pathways. Dendritic cells are capable of both activating naïve and previously primed T cells (e.g., memory T cells). Dendritic cells (DCs) can be leukocyte populations that present antigens captured in peripheral tissues to T cells via MHC class I and II antigen presentation pathways. Dendritic cells can be potent inducers of immune responses and the activation of these cells can be a critical step for the induction of antitumoral immunity. Dendritic cells are potent inducers of immune responses and the activation of these cells is a critical step for the induction of antitumoral immunity.

Dendritic cells can be categorized as "immature" and "mature" cells, which can be used as a simple way to discriminate between two well characterized phenotypes. However, this nomenclature should not be construed to exclude all possible intermediate stages of differentiation. Immature dendritic cells can be characterized as antigen presenting cells with a high capacity for antigen uptake and processing, which correlates with the high expression of Fcγ receptor and mannose receptor. The mature phenotype can be typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB). Mature dendritic cells may be $CD11b^+$, $CD11c^+$, $HLA-DR^+$, $CD80^+$, $CD86^+$, $CD54^+$, $CD3^-$, $CD19^-$, $CD14^-$, $CD141^+$ (BDCA-3), and/or $CD1a^+$. Dendritic cell maturation can be referred to as the status of dendritic cell activation at which such antigen presenting dendritic cells lead to T cell priming, while presentation by immature dendritic cells results in tolerance. Dendritic cell maturation can be caused by biomolecules with microbial features detected by innate receptors (e.g., bacterial DNA, viral RNA, endotoxins, etc.), pro-inflammatory cytokines (e.g., TNFs, interleukins, and interferons), ligation of CD40 on the dendritic cell surface by CD40L, and substances released from cells undergoing cell death. Further non-limiting examples of cytokines that can induce dendritic cell maturation include IL-4, GM-CSF, TNF-α, IL-1β, PGE1, and IL-6. For example, dendritic cells may be derived by culturing bone marrow cells in vitro with cytokines, such as granulocyte-macrophage colony-stimulating factor (GM-CSF) and tumor necrosis factor alpha (TNF-α). For example, dendritic cells may be derived from $CD14^+$ monocytes isolated from PBMCs. Cytokines or growth factors that can be used for deriving monocytes into dendritic cells include, but are not limited to, GM-CSF, IL-4, FLT3L, TNF-α, IL-1β, PGE1, IL-6, IL-7, IFN-α, R848, LPS, ss-rna40, and poly I:C.

Typically, non-professional antigen-presenting cells do not constitutively express MHC class II proteins. MHC class II proteins are typically expressed only upon stimulation of the non-professional antigen-presenting cells by certain cytokines such as IFN-γ.

The source of antigen-presenting cell (APC) can be typically a tissue source comprising APCs or APC precursors that are capable of expressing and presenting antigen peptides in vitro. In some embodiments, APCs are capable of proliferating and becoming professional APCs when loaded with target RNA and/or treated with the necessary cytokines or factors.

In one aspect, APC precursor cells are capable of proliferating and maturing in vitro into dendritic cells (DC). While many tissue sources may be used, typical tissue sources can comprise spleen, thymus, tissue biopsy, tumor, afferent lymph, lymph nodes, bone marrow, apheresis or leukopheresis product, and/or peripheral blood. In certain embodiments, an apheresis product, bone marrow and peripheral blood can be sources. Fetal tissue, fetal or umbilical cord blood, which is also rich in growth factors, may also be used as a source of blood for obtaining APCs and/or precursor APCs. Examples of precursor cells include, but are not limited to, embryonic stem cells, $CD34^+$ cells, monocyte progenitors, monocytes, and pre-B-cells. For example, APCs may be derived from precursor cells comprising monocytes or $CD34^+$ cells.

In one aspect, the source of APCs and/or precursor APCs can be an apheresis or leukopheresis product. Cells can be collected using apheresis procedures known in the art (e.g., Bishop et al., Blood, vol. 83, No. 2, pp. 610-616 (1994)). Apheresis product typically can contain lymphocytes, including T cells, monocytes, granulocytes, B-cells, other nucleated white blood cells, red blood cells, and platelets. In one embodiment, the cells collected by apheresis may be washed to remove the plasma fraction and to place the cells in an appropriate buffer or media for subsequent processing steps. In another embodiment of the invention, the cells can be washed with phosphate buffered saline (PBS). In an alternative embodiment, the wash solution may lack calcium and may lack magnesium or may lack many if not all divalent cations. A washing step may be accomplished by methods known to those in the art, such as by using a semi-automated "flow-through" centrifuge. After washing, the cells may be resuspended in a variety of biocompatible buffers, such as, for example, Ca-free, Mg-free PBS. Alternatively, the undesirable components of the apheresis sample may be removed and the cells directly resuspended in culture media.

APCs can be prepared from a variety of sources, including human and non-human primates, other mammals, and vertebrates. In certain embodiments, APCs can be prepared from blood of a human or non-human vertebrate. APCs can also be isolated from an enriched population of leukocytes. Populations of leukocytes can be prepared by methods known to those skilled in the art. Such methods typically include collecting heparinized blood, apheresis or leukopheresis, preparation of buffy coats, rosetting, centrifugation, density gradient centrifugation (e.g., using Ficoll, colloidal silica particles, and sucrose), differential lysis non-leukocyte cells, and filtration. A leukocyte population can also be prepared by collecting blood from a subject, defibrillating to remove the platelets and lysing the red blood cells. The leukocyte population can optionally be enriched for monocytic dendritic cell precursors.

Blood cell populations can be obtained from a variety of subjects, according to the desired use of the enriched population of leukocytes. The subject can be a healthy subject. Alternatively, blood cells can be obtained from a subject in need of immunostimulation, such as, for example, a cancer patient or other patient for which immunostimulation will be beneficial. Likewise, blood cells can be obtained from a subject in need of immune suppression, such as, for example, a patient having an autoimmune disorder (e.g., rheumatoid arthritis, diabetes, lupus, multiple sclerosis, and the like). A population of leukocytes also can be obtained from an HLA-matched healthy individual.

When blood is used as a source of APC, blood leukocytes may be obtained using conventional methods that maintain their viability. According to one aspect of the invention, blood can be diluted into medium that may or may not contain heparin or other suitable anticoagulant. The volume of blood to medium can be about 1 to 1. Cells can be concentrated by centrifugation of the blood in medium at about 1,000 rpm (150 g) at 4° C. Platelets and red blood cells can be depleted by resuspending the cells in any number of solutions known in the art that will lyse erythrocytes, for example ammonium chloride. For example, the mixture may be medium and ammonium chloride at about 1:1 by volume. Cells may be concentrated by centrifugation and washed in the desired solution until a population of leukocytes, substantially free of platelets and red blood cells, is obtained. Any isotonic solution commonly used in tissue culture may be used as the medium for separating blood leukocytes from platelets and red blood cells. Examples of such isotonic solutions can be phosphate buffered saline, Hanks balanced salt solution, and complete growth media. APCs and/or APC precursor cells may also purified by elutriation.

In one embodiment, isolation of APCs and/or precursor APCs can be performed by preincubating ficolled whole blood or apheresed peripheral blood with one or more varieties of irrelevant or non-antibody coupled paramagnetic particles (approx. 1 vial of beads or $4 \times 10^9$ beads to one batch of cells (typically from about $5 \times 10^8$ to about $2 \times 10^{10}$ cells) for about 30 minutes to 2 hours at 22 to 37° C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of isolation can be monitored by a variety of methodologies known to those of ordinary skill in the art, including flow cytometric analysis of cells before and after said isolation.

APCs may be cultured to form a primary culture in an appropriate culture container or vessel in an appropriate culture medium. In certain embodiments, the culture medium can be supplemented with one or more cytokines. The appropriate culture container or vessel may be any container with tissue culture compatible surface. Examples include various bags, flasks, roller bottles, petri dishes and multi-well containing plates made for use in tissue culture. Surfaces treated with a substance, for example collagen or poly-L-lysine, or antibodies specific for a particular cell type to promote cell adhesion may also be used provided they allow for the differential attachment of cells as described below. Surfaces may also be chemically treated, for example by ionization. Cells can be plated at an initial cell density from about $10^5$ to $10^7$ cells/cm². In one aspect, cells can be plated at $10^6$ cells/cm².

In one embodiment, the primary cultures from the selected tissue source are allowed to incubate at about 37° C. under standard tissue culture conditions of humidity, $CO_2$, and pH until a population of cells has adhered to the substrate sufficiently to allow for the separation of nonadherent cells. Some immature APCs in blood initially are nonadherent to plastic, particularly immature DC, in contrast to monocytes, so that the precursors can be separated after overnight culture. Monocytes and fibroblasts can comprise the majority of adherent cells and usually adhere to the substrate within about 30 minutes to about 24 hours. In certain aspects, nonadherent cells can be separated from adherent cells between about 1 to 16 hours. Nonadherent cells may be separated at about 1 to 2 hours. Any method which does not dislodge significant quantities of adherent cells may be used to separate the adherent from nonadherent cells. In certain aspects, the cells can be dislodged by simple shaking or pipetting. In certain aspects, pipetting can be most preferred.

Adherent cells comprising precursor APCs (e.g., monocytes) isolated according to the methods of the invention can be incubated at about 37° C. under standard tissue culture conditions of humidity, $CO_2$, and pH until a population of cells has reached an immature APC stage. In certain aspects, according to the present disclosure, adherent cells can be incubated for a period of between 4 hours and 7 days. However, one of ordinary skill in the art will readily appreciate that incubation times and conditions may vary. Immature APC may be $CD14^-$ or $CD14^+$ depending on the origin of the precursor cells. Immature APC may also express CD1a, CD40, CD86, CD54, and intermediate levels of MHC class II (levels of marker expression on sample cells can be compared by flow cytometric analysis to levels of expression on MHC class II-negative cells and cells known to express high levels of MHC class II). Immature APCs typically do not express CCR7.

In certain aspects of the present disclosure, it is not necessary to separate T cells from APCs. For example, in one embodiment, PBMC comprising APC and T cells can be exposed to antigen as described herein and the resulting antigen-specific T cells further expanded as described herein.

In certain aspects of the present invention, it is not required that the APCs or the T cells described herein be derived from an autologous source. Thus, the APCs and T cells can be obtained from a matched or unmatched donor, or from a cell line, a T cell line, or other cells grown in vitro. Methods for matching haplotypes are known in the art. Furthermore, the APCs and T cells or supernatant therefrom may be obtained from a xenogeneic source, for example, mouse, rat, non-human primate, and porcine cells may be used.

Suitable preparations of APCs include, for example, dendritic cells and monocytes. In other embodiments, the APCs can be activated non-nominal APCs, such as, for example, B cells, cells, or epithelial or endothelial cells. The APCs can be immature or mature. The APCs and T cells are typically co-cultured for about 6 to about 48 hours, although greater and lesser times are within the scope of the present invention. Co-culturing typically can be performed for a sufficient time to allow activation of T cells, but less than the time required for the differentiation and/or maturation of a significant number of immature APCs or APC precursors.

In certain embodiments, monocytic dendritic cell precursors can be isolated, for example, by contacting enriched leukocytes or monocytes with a monocytic dendritic cell precursor adhering substrate. Briefly, when a population of enriched leukocytes or monocytes is contacted with the substrate, the monocytic dendritic cell precursors, or monocytes, in the cell population can adhere to the substrate. Other leukocytes can exhibit reduced binding affinity to the substrate, thereby allowing monocytic dendritic cell precursors to be preferentially enriched on the surface of the substrate. Suitable substrates include particulate substrates, such as, for example, glass particles, plastic particles, glass-coated plastic particles, glass-coated polystyrene particles, microcapillary tubes, and microvillus membrane. The surface of the substrate can optionally be treated to enhance adherence of monocytic dendritic cell precursors to the substrate. The surface of the substrate can be coated with, for example, proteins, cytokines, plasma, and/or monocyte-binding proteins. After contacting the leukocyte- or monocyte-enriched cell population with the monocytic dendritic cell precursor adhering substrate, the monocytic dendritic cell precursors adhere to the substrate to form complexes comprising monocytic dendritic cell precursors on the substrate. Monocytic dendritic cell precursor binding can be monitored, for example, by antibody detection using anti-cell surface marker antibodies, such as, for example, anti-CD14 antibodies, by FACS forward and side scatter analysis, and the like. In some embodiments, the leukocyte population can be contacted with the substrate for about 5 to about 300 minutes, more typically about 30 to about 120 minutes. The monocytic dendritic cell precursor complexes can optionally be washed with a suitable washing buffer to remove non-specifically bound leukocytes. Suitable washing buffers include tissue culture media, phosphate buffered saline, Dulbecco's phosphate buffered saline, and the like. The media can be supplemented with amino acids, vitamins, and/or hormones to promote the viability and/or proliferation of the monocytic dendritic cell precursors. The efficacy of washing can be monitored by FACS forward and side scatter analysis of the washing buffer, by staining eluted cells for cell surface markers, and the like. Typically, the complexes can be washed several times to remove non-specifically bound leukocytes. The adhered monocytic dendritic cell precursors can be eluted from the substrate. For example, the precursors can be eluted from the substrate by treatment with phosphate buffered saline containing 0.4% EDTA or other non-toxic chelating agent. The monocytic dendritic cell precursors typically can be eluted from the substrate without the use of trypsin or other proteases.

In other embodiments, the dendritic cells can be isolated according to other methods known to the skilled artisan (e.g., O'Doherty et al., J. Exp. Med. 178:1067-76 (1993); Young and Steinman, J. Exp. Med. 171:1315-32 (1990); Freudenthal and Steinman, Proc. Natl. Acad. Sci. USA 87:7698-702 (1990); Macatonia, et al., Immunol. 67:285-89 (1989); Markowicz and Engleman, J. Clin. Invest. 85:955-61 (1990); U.S. Pat. Nos. 5,994,126 and 5,851,756). Methods for immuno-selecting dendritic cells include, e.g., using antibodies to cell surface markers associated with dendritic cell precursors, such as anti-CD34 and/or anti-CD14 antibodies coupled to a substrate (e.g., Bernhard et al., Cancer Res. 55:1099-104 (1995); Caux at al., Nature 360:258-61 (1992)) or associated with fully differentiated dendritic cells, such as, CD11c, CD54, CD83, CD80, and CD86.

In other embodiments, the APCs can be non-nominal APCs under inflammatory or otherwise activated conditions. For example, non-nominal APCs can include epithelial cells stimulated with interferon-gamma, T cells, B cells, and/or monocytes activated by factors or conditions that induce APC activity. Such non-nominal APCs can be prepared according to methods known in the art.

The APCs can be cultured, expanded, differentiated and/or, matured, as desired, according to the according to the type of APC. The APCs can be cultured in any suitable culture vessel, such as, for example, culture plates, flasks, culture bags, and bioreactors.

In certain embodiments, APCs can be cultured in suitable culture or growth medium to maintain and/or expand the number of APCs in the preparation. The culture media can be selected according to the type of APC isolated. For example, mature APCs, such as mature dendritic cells, can be cultured in growth media suitable for their maintenance and expansion. The culture medium can be supplemented with amino acids, vitamins, antibiotics, divalent cations, and the like. In addition, cytokines, growth factors and/or hormones, can be included in the growth media. For example, for the maintenance and/or expansion of mature dendritic cells, cytokines, such as granulocyte/macrophage colony stimulating factor (GM-CSF) and/or interleukin 4 (IL-4), can be added. In other embodiments, immature APCs can be cultured and/or expanded. Immature dendritic cells can they retain the ability to uptake target mRNA and process new antigen. In some embodiments, immature dendritic cells can be cultured in media suitable for their maintenance and culture. The culture medium can be supplemented with amino acids, vitamins, antibiotics, divalent cations, and the like. In addition, cytokines, growth factors and/or hormones, can be included in the growth media.

Other immature APCs can similarly be cultured or expanded. Preparations of immature APCs can be matured to form mature APCs. Maturation of APCs can occur during or following exposure to antigen peptides. In certain embodiments, preparations of immature dendritic cells can be matured. Suitable maturation factors include, for example, cytokines TNF-α, bacterial products (e.g., BCG), and the like. In another aspect, isolated APC precursors can be used to prepare preparations of immature APCs. APC precursors can be cultured, differentiated, and/or matured. In certain embodiments, monocytic dendritic cell precursors can be cultured in the presence of suitable culture media supplemented with amino acids, vitamins, cytokines, and/or divalent cations, to promote differentiation of the monocytic dendritic cell precursors to immature dendritic cells. In some embodiments, the APC precursors are isolated from PBMCs. The PBMCs can be obtained from a donor, for example, a human donor, and can be used freshly or frozen for future usage. In some embodiments, the APC is prepared from one or more APC preparations. In some embodiments, the APC comprises an APC loaded with one or more antigen peptides comprising one or more of the at least one antigen peptide sequence. In some embodiments, the APC is an autologous APC, an allogenic APC, or an artificial APC.

In some embodiments, the APC precursors are monocytes. In some embodiments, the monocytes are CD14$^+$ monocytes. In some embodiments, the monocytes are isolated by anti-CD14 antibodies. In some embodiments, the isolated monocytes are plated at $10^5$ to $10^7$ cells/well in 2 mL media. In some embodiments, the isolated monocytes are plated at about $3\times10^6$ cells/well in 2 mL media. In some embodiments, the isolated monocytes are cultured in media containing a cytokine or a growth factor. In some embodiments, the isolated monocytes are cultured in media containing GM-CSF, IL-4, FLT3L, TNF-α, IL-1β, PGE1, IL-6, IL-7, IFN-α, R848, LPS, ss-rna40, poly I:C, or a combination thereof. In some embodiments, the isolated monocytes are cultured for at least 2 days, at least 3 days, at least 4 days, at least 5 days, or at least 6 days before subjecting to maturation. In some embodiments, the monocytes are derived to dendritic cells ex vivo in culture media. In some embodiments, the derived dendritic cells are further matured ex vivo and loaded with the antigen peptides. In some embodiments, the derived dendritic cells are cultured in a medium containing one or more antigen peptides. In some embodiments, the antigen peptides are neoantigen peptides. Examples of neoantigen peptides include, but are not limited to, HIV short peptide, HIV long peptides, previously identified neoantigen (PIN) short peptides, and PIN long peptides. In some embodiments, the derived dendritic cells are cultured in a medium containing one or more neoantigen peptides for at least 30 minutes, at least 50 minutes, at least 1 hour, or at least 2 hours. In some embodiments, the derived dendritic cells are further incubated with one or more cytokines after incubating with the antigen peptides. In some embodiments, the one or more cytokine comprise GM-CSF, IL-4, FLT3L, TNF-α, IL-1β, PGE1, IL-6, IL-7, IFN-α, R848, LPS, ss-rna40, poly I:C, or a combination thereof.

In some embodiments, whole PBMCs are used to prepare APCs, which can be further used to stimulate T cells. In some embodiments, the PBMCs are cultured in a medium containing FMS-like tyrosine kinase 3 receptor ligand (FLT3L). In some embodiments, the PBMCs are depleted of T regulatory cells ($T_{reg}$ cells) and then cultured in a medium containing FLT3L. In some embodiments, the PBMCs are depleted of $CD14^+$ cells and then cultured in medium containing FLT3L. In some embodiments, the PBMCs are depleted of $CD25^+$ cells and then cultured in medium containing FLT3L. In some embodiments, the PBMCs are depleted of $CD25^+$ and $CD14^+$ cells and then cultured in medium containing FLT3L. In some embodiments, the PBMCs are depleted of $CD25^+$ cells, $CD14^+$ cells, and $CD19^+$ cells and then cultured in medium containing FLT3L. In some embodiments, the PBMCs are cultured in medium containing FLT3L and then depleted of $CD14^+$ cells. In some embodiments, the PBMCs are cultured in medium containing FLT3L and then depleted of $CD25^+$ cells. In some embodiments, the PBMCs are cultured in medium containing FLT3L and then depleted of $CD14^+$ cells and $CD25^+$ cells. In some embodiments, the isolated $CD14^+$ monocytes are cultured in a medium containing FLT3L. In some embodiments, after culturing in a medium containing FLT3L, PBMCs (whole, $CD14^+$ depleted, $CD25^+$ depleted, $CD25^+/CD14^+$ depleted, or $CD25^+/CD14^+/CD19^+$ depleted) or isolated $CD14^+$ monocytes are cultured in a medium containing one or more antigens. In some embodiments, the PBMC or isolated $CD14^+$ monocytes are cultured in a medium containing one or more maturation cytokines. Example of maturation cytokines include, but are not limited to, GM-CSF, IL-4, FLT3L, TNF-α, IL-1β, PGE1, IL-6, IL-7, IFN-α, R848, LPS, ss-rna40, poly I:C, or a combination thereof. The maturation cytokine can be added in a cell culture or medium in various concentrations. In some embodiment, a maturation cytokine is added in a cell culture or medium at a final concentration of at least 0.05 ng/mL, 0.1 ng/mL, 0.2 ng/mL, 0.3 ng/mL, 0.4 ng/mL, 0.5 ng/mL, 0.8 ng/mL, 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 12 ng/mL, 15 ng/mL, 18 ng/mL, or 20 ng/mL. In some embodiment, a maturation cytokine is added in a cell culture or medium at a final concentration of at least 0.05 μg/mL, 0.1 μg/mL, 0.2 μg/mL, 0.3 μg/mL, 0.4 μg/mL, 0.5 μg/mL, 0.8 μg/mL, 1 μg/mL, 2 μg/mL, 3 μg/mL, 4 μg/mL, 5 μg/mL, 6 μg/mL, 7 μg/mL, 8 μg/mL, 9 μg/mL, or 10 μg/mL. In some embodiment, a maturation cytokine is added in a cell culture or medium at a final concentration of at least 10 U/mL, 20 U/mL, 30 U/mL, 40 U/mL, 50 U/mL, 80 U/mL, 100 U/mL, 200 U/mL, 500 U/mL, 800 U/mL, 1000 U/mL, 1500 U/mL, 2000 U/mL, or 2500 U/mL (As used herein, enzyme unit is calculated according to manufacture's protocol). In some embodiments, the PBMC culture (either whole PBMCs or PBMCs depleted with certain cells) used for APC preparation are subject to further incubation or cytokine treatment for T cell induction or stimulation. In this case, the APC preparation (e.g., maturation and peptide loading) and T cell induction or stimulation are performed using the same cell culture. In some other cases, the APC preparation is a separate cell population from the PBMC population used for T cell stimulation.

In some embodiments, the method comprises incubating one or more APCs or one or more APC preparations with a peptide, thereby generating a peptide loaded APC sample. For example, the method can comprise incubating one or more APCs or one or more APC preparations with one or more peptides at a concentration of from 0.001-100 μM, thereby generating a peptide loaded APC sample. For example, the method can comprise incubating one or more APCs or one or more APC preparations with one or more peptides at a concentration of at least about 0.001 μM, 0.005 μM, 0.01 μM, 0.02 μM, 0.03 μM, 0.04 μM, 0.05 μM, 0.08 μM, 0.09 μM, 0.1 μM, 0.2 μM, 0.3 μM, 0.4 μM, 0.5 μM, 0.6 μM, 0.7 μM, 0.8 μM, 0.9 μM, 1 μM, 2 μM, 3 μM, 4 μM, 5 μM, 6 μM, 7 μM, 8 μM, 9 μM, 10 μM, 20 μM, 30 μM, 40 μM, 50 μM, 60 μM, 70 μM, 80 μM, 90 μM, or 100 μM. For example, the method can comprise incubating one or more APCs or one or more APC preparations with one or more peptides at a concentration of at most about 0.001 μM, 0.005 μM, 0.01 μM, 0.02 μM, 0.03 μM, 0.04 μM, 0.05 μM, 0.08 μM, 0.09 μM, 0.1 μM, 0.2 μM, 0.3 μM, 0.4 μM, 0.5 μM, 0.6 μM, 0.7 μM, 0.8 μM, 0.9 μM, 1 μM, 2 μM, 3 μM, 4 μM, 5 μM, 6 μM, 7 μM, 8 μM, 9 μM, 10 μM, 20 μM, 30 μM, 40 μM, 50 μM, 60 μM, 70 μM, 80 μM, 90 μM, or 100 μM. For example, the method can comprise incubating one or more APCs or one or more APC preparations with one or more or more peptides at a concentration of about 0.001 μM, 0.005 μM, 0.01 μM, 0.02 μM, 0.03 μM, 0.04 μM, 0.05 μM, 0.08 μM, 0.09 μM, 0.1 μM, 0.2 μM, 0.3 μM, 0.4 μM, 0.5 μM, 0.6 μM, 0.7 μM, 0.8 μM, 0.9 μM, 1 μM, 2 μM, 3 μM, 4 μM, 5 μM, 6 μM, 7 μM, 8 μM, 9 μM, 10 μM, 20 μM, 30 μM, 40 μM, 50 μM, 60 μM, 70 μM, 80 μM, 90 μM, or 100 μM. For example, the method can comprise incubating one or more APCs or one or more APC preparations with 1, 2, 3, 4, 5, 6, 7, 8, 9, 10, 11, 12, 13, 14, 15, 16, 17, 18, 19, or 20 or more peptides at a concentration of at least about 0.001 μM, 0.005 μM, 0.01 μM, 0.02 μM, 0.03 μM, 0.04 μM, 0.05 μM, 0.08 μM, 0.09 μM, 0.1 μM, 0.2 μM, 0.3 μM, 0.4 μM, 0.5 μM, 0.6 μM, 0.7 μM, 0.8 μM, 0.9 μM, 1 μM, 2 μM, 3 μM, 4 μM, 5 μM, 6 μM, 7 μM, 8 μM, 9 μM, 10 μM, 20 μM, 30 μM, 40 μM, 50 μM, 60 μM, 70 μM, 80 μM, 90 μM, or 100 μM. For example, the method can comprise incubating one or more APCs or one or more APC preparations with 1, 2, 3, 4, 5, 6, 7, 8, 9, 10, 11, 12, 13, 14, 15, 16, 17, 18, 19, or 20 or more peptides at a concentration of at most about 0.001 μM, 0.005 μM, 0.01 μM, 0.02 μM, 0.03 μM, 0.04 μM, 0.05 μM, 0.08 μM, 0.09 μM, 0.1 μM, 0.2 μM, 0.3 μM, 0.4 μM, 0.5 μM, 0.6 μM, 0.7 μM, 0.8 μM, 0.9 μM, 1 μM, 2 μM, 3 μM, 4 μM, 5 μM, 6 μM, 7 μM, 8 μM, 9 μM, 10 μM, 20 μM, 30 μM, 40

μM, 50 μM, 60 μM, 70 μM, 80 μM, 90 μM, or 100 μM. For example, the method can comprise incubating one or more APCs or one or more APC preparations with 1, 2, 3, 4, 5, 6, 7, 8, 9, 10, 11, 12, 13, 14, 15, 16, 17, 18, 19, or 20 or more peptides at a concentration of about 0.001 μM, 0.005 μM, 0.01 μM, 0.02 μM, 0.03 μM, 0.04 μM, 0.05 μM, 0.08 μM, 0.09 μM, 0.1 μM, 0.2 μM, 0.3 μM, 0.4 μM, 0.5 μM, 0.6 μM, 0.7 μM, 0.8 μM, 0.9 μM, 1 μM, 2 μM, 3 μM, 4 μM, 5 μM, 6 μM, 7 μM, 8 μM, 9 μM, 10 μM, 20 μM, 30 μM, 40 μM, 50 μM, 60 μM, 70 μM, 80 μM, 90 μM, or 100 μM.

T Cells

T cells belong to a group of white blood cells known as lymphocytes, and play a central role in cell-mediated immunity. T cells include CD4$^+$ T cells (helper T cells) and CD8$^+$ T cells (cytotoxic T cells). CD4$^+$ T cells can assist other white blood cells in immunologic processes, including maturation of B-cells and activation of cytotoxic T cells and macrophages. CD4$^+$ T cells are activated when presented with peptide antigens by MHC class II molecules expressed on the surface of antigen presenting cells (APCs). Once activated, the T cells can divide rapidly and secrete cytokines that regulate the active immune response. CD8$^+$ T cells can destroy virally infected cells and tumor cells, and can also be implicated in transplant rejection. CD8$^+$ T cells can recognize their targets by binding to antigen associated with MHC class I, which is present on the surface of nearly every cell of the body. Most T cells have a T cell receptor (TCR). The ability of T cells to recognize antigens associated with various cancers or infectious organisms is conferred by its TCR, which is made up of both an alpha (α) chain and a beta (β) chain or a gamma (γ) and a delta (δ) chain. The proteins which make up these chains are encoded by DNA, which employs a unique mechanism for generating the diversity of the TCR. This multi-subunit immune recognition receptor can associate with the CD3 complex and bind peptides presented by the MHC class I and II proteins on the surface of antigen-presenting cells (APCs). The first signal in activation of T cells can be provided by binding of the T cell receptor to a short peptide presented by the MHC on another cell. This ensures that only a T cell with a TCR specific to that peptide is activated. The partner cell is usually an antigen presenting cell such as a professional antigen presenting cell, usually a dendritic cell in the case of naïve responses, although B-cells and macrophages can be important APCs. Binding of a TCR to the antigenic peptide on the APC can be a central event in T cell activation, which occurs at an immunological synapse at the point of contact between the T cell and the APC.

Each TCR contains variable complementarity determining regions (CDRs), as well as framework regions (FRs) and a constant region. The amino acid sequence of the third complementarity-determining region (CDR3) loops of the α and β chain variable domains is largely determines the sequence diversity of αβ T cells arising from recombination between variable (Vβ), diversity (Dβ), and joining (Jβ) gene segments in the β chain locus, and between analogous Vα and Jα gene segments in the α chain locus, respectively. The existence of multiple such gene segments in the TCR α and β chain loci allows for a large number of distinct CDR3 sequences to be encoded. Independent addition and deletion of nucleotides at the Vβ-Dβ, Dβ-Jβ, and Vα-Jα junctions during the process of TCR gene rearrangement further increases CDR3 sequence diversity. In this respect, immunocompetence is reflected in the diversity of TCRs. The γδ TCR is distinctive from the αβ TCR in that it encodes a receptor that interacts closely with the innate immune system. TCRγδ, is expressed early in development, has specialized anatomical distribution, has unique pathogen and small-molecule specificities, and has a broad spectrum of innate and adaptive cellular interactions. Early in ontogeny, as the restricted subsets of TCRγδ cells populate various tissues prenatally, a biased pattern of TCRγ V and J segment expression is established.

T cells can be prepared according to methods known in the art. T cells can be an enriched T cell preparation, an APC-depleted cell preparation, or a substantially purified T cell preparation. T cells can be a mixed T cell population or a purified T cell subset. T cells can be an enriched T cell preparation containing a number or percentage of T cells that is increased with respect to an isolated population of T cells.

T cells, or a subset of T cells, can be obtained from various lymphoid tissues. T cells can be obtained from a number of sources, including peripheral blood mononuclear cells (PBMCs), bone marrow, thymus, tissue biopsy, tumor, lymph node tissue, gut associated lymphoid tissue, mucosa associated lymphoid tissue, spleen tissue, lymphoid tissue, and tumors. The term "peripheral blood lymphocytes" (PBL) and its grammatical equivalents as used herein can refer to lymphocytes that circulate in the blood (e.g., peripheral blood). Peripheral blood lymphocytes can refer to lymphocytes that are not localized to organs. Peripheral blood lymphocytes can comprise T cells, NK cells, B cell, or any combinations thereof.

The method can comprise isolating T cells from a subject. The method can comprise obtaining T cells isolated from a subject. T cells can be obtained from T cell lines. T cells can be obtained from autologous sources. T cells can be obtained from allogeneic sources. T cells may also be obtained from a xenogeneic source, for example, from mouse, rat, non-human primate, and pig.

T cells can be an APC-depleted cell preparation. T cells can be substantially free of APCs. For example, T cells can comprise T cells separated from over 75% of APCs. In some embodiments, peripheral blood mononuclear cells (PBMCs) can be obtained from blood, e.g., in heparinized vials. PBMCs can be separated from red blood cells by centrifugation and PBMCs recovered from the interface. The recovered PBMCs optionally can be washed (e.g., with PBS).

T cell purification can be achieved, for example, by positive or negative selection including, but not limited to, the use of antibodies directed to CD2, CD3, CD4, CD5, CD8, CD14, CD16, CD19 and/or CD25. A specific T cell subset, such as CD28$^+$, CD4$^+$, CD8$^+$, CD45RA$^+$, and/or CD45RO$^+$ T cells, can be isolated by positive or negative selection techniques. For example, CD45RO$^+$, CD14$^-$, and/or CD25$^-$ T cells can be isolated by positive or negative selection techniques. For example, CD45RA$^+$, CD14$^-$, and/or CD25$^-$ T cells can be isolated by positive or negative selection techniques. For example, CD3$^+$, CD14$^-$, and/or CD25$^-$ T cells can be isolated by positive or negative selection techniques. For example, CD28$^+$, CD14$^-$, and/or CD25$^-$ T cells can be isolated by positive or negative selection techniques. For example, CD4$^+$, CD14$^-$, and/or CD25$^-$ T cells can be isolated by positive or negative selection techniques. For example, CD8$^+$, CD14$^-$, and/or CD25$^-$ T cells can be isolated by positive or negative selection techniques. For example, CD14$^-$ and/or CD25$^-$ T cells can be isolated by negative selection techniques. For example, CD19$^-$ T cells can be isolated by negative selection techniques. For example, CD16$^-$ T cells can be isolated by negative selection techniques. For example, CD3$^+$ and CD28$^+$ T cells can be positively selected using CD3/CD28 conjugated magnetic beads. In one aspect of the present invention, enrichment of a T cell population by negative selection can be accomplished with a combination of antibodies directed to surface markers unique to the negatively selected cells. For example, enrichment of a T cell population can by accomplished by negative selection using an antibody directed to CD19, CD16, CD14, CD25 or any combination thereof. For example, enrichment of a T cell population can be accomplished by by negative selection using a combination of antibodies directed to CD19, CD16, CD25 and/or CD14.

For example, a T cell sample can comprise cells from a subject's circulating blood and can be obtained by apheresis or leukopheresis. A T cell sample may contain lymphocytes, including T cells, monocytes, granulocytes, B cells, other nucleated white blood cells, red blood cells, and/or platelets. Undesirable components of the T cell sample can be removed and the remaining T cells can be suspended in culture media. For example, cells can be washed to remove the plasma fraction. For example, T cells can be isolated from peripheral blood lymphocytes by lysing the red blood cells and by centrifugation through a PERCOLL™ gradient.

In various embodiments, provided herein are compositions and methods comprising T cells. In some embodiments, the T cell comprises a TCR having a TCR alpha and TCR beta chains. In some embodiments, the T cell comprises a TCR having a TCR gamma and TCR delta chains. In some embodiments, a T cell comprises a T cell receptor (TCR) specific to at least one antigen peptide sequence. In some embodiments, an antigen specific T cell comprises at least one CD4$^+$ T cell. In some embodiments, an antigen specific T cell comprises at least one CD8$^+$ T cell. In some embodiments, an antigen specific T cell comprises at least one CD4 enriched T cell. In some embodiments, an antigen specific T cell comprises at least one CD8 enriched T cell. In some embodiments, an antigen specific T cell comprises a memory T cell. In some embodiments, an antigen specific T cell comprises a naïve T cell. In some embodiments, an antigen specific T cell comprises a memory CD4$^+$ T cell. In some embodiments, an antigen specific T cell comprises a naïve CD4$^+$ T cell. In some embodiments, an antigen specific T cell a memory CD8$^+$ T cell. In some embodiments, an antigen specific T cell comprises a naïve CD8$^+$ T cell. In some embodiments, an antigen peptide sequence comprises a mutation selected from (A) a point mutation, (B) a splice-site mutation, (C) a frameshift mutation, (D) a read-through mutation, (E) a gene-fusion mutation, and combinations thereof. In some embodiments, an antigen peptide sequence binds to the HLA protein of a subject with a greater affinity than a corresponding wild-type peptide. In some embodiments, an antigen peptide sequence binds to the HLA protein of a subject with a $K_D$ or $IC_{50}$ of less than 500 nM, 250 nM, 150 nM, 100 nM, 50 nM, 25 nM or 10 nM. In some embodiment, each peptide sequence binds to a protein encoded by an HLA allele expressed by a subject. In some embodiments, a TCR of a T cell of a composition described herein binds to a peptide-HLA complex with a $K_D$ or $IC_{50}$ of less than 500 nM, 250 nM, 150 nM, 100 nM, 50 nM, 25 nM or 10 nM.

In some embodiments, the T cells are cultured in a medium containing a cytokine. Examples of cytokines include IL-7 and IL-15. In some embodiments, the cytokine in a T cell culture or a medium has a final concentration of at least 0.05 ng/mL, 0.1 ng/mL, 0.2 ng/mL, 0.3 ng/mL, 0.4 ng/mL, 0.5 ng/mL, 0.8 ng/mL, 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 12 ng/mL, 15 ng/mL, 18 ng/mL, or 20 ng/mL. In some embodiments, the IL-7 in a T cell culture or a medium has a final concentration of at least 0.05 ng/mL, 0.1 ng/mL, 0.2 ng/mL, 0.3 ng/mL, 0.4 ng/mL, 0.5 ng/mL, 0.8 ng/mL, 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 12 ng/mL, 15 ng/mL, 18 ng/mL, or 20 ng/mL. In some embodiments, the IL-15 in a T cell culture or a medium has a final concentration of at least 0.05 ng/mL, 0.1 ng/mL, 0.2 ng/mL, 0.3 ng/mL, 0.4 ng/mL, 0.5 ng/mL, 0.8 ng/mL, 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 12 ng/mL, 15 ng/mL, 18 ng/mL, or 20 ng/mL. In some embodiments, the T cells are cultured in a medium further containing FLT3L. In some embodiments, the FLT3L in a T cell culture or a medium has a final concentration of in a T cell culture or a medium has a final concentration of at least 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 12 ng/mL, 15 ng/mL, 18 ng/mL, 20 ng/mL, 30 ng/mL, 40 ng/mL, 50 ng/mL, 60 ng/mL, 70 ng/mL, 80 ng/mL, 90 ng/mL, 100 ng/mL, or 200 ng/mL. In some embodiments, the T cells are incubated, induced, or stimulated in a medium containing FLT3L for a first period time. In some embodiments, the T cells are incubated, induced, or stimulated in a medium containing additionally added FLT3L for a second period time. In some embodiments, the T cells are incubated, induced, or stimulated in a medium containing additional added FLT3L for a third period time. In some embodiments, the T cells are incubated, induced, or stimulated in a medium containing additional added FLT3L for a fourth, a fifth, or a sixth period time, with freshly added FLT3L in each time period.

Antigens

The present disclosure relates to methods for manufacturing T cells which are specific to immunogenic antigens. The present disclosure also relates to compositions comprising antigen specific T cells stimulated with APCs. In some embodiments, one or more antigen peptides are loaded on to APCs, wherein the peptide loaded APCs are then used to stimulate T cells to produce antigen specific T cells. In some embodiments, the antigens are neoantigens. In some embodiments, the APCs used for peptide loading are dendritic cells.

In some embodiments, a peptide sequence comprises a mutation that is not present in non-cancer cells of a subject. In some embodiments, a peptide is encoded by a gene or an expressed gene of a subject's cancer cells. In some embodiments, a peptide sequence has a length of at least 8; 9; 10; 11; 12; 13; 14; 15; 16; 17; 18; 19; 20; 21; 22; 23; 24; 25; 26; 27; 28; 29; 30; 40; 50; 60; 70; 80; 90; 100; 150; 200; 250; 300; 350; 400; 450; 500; 600; 700; 800; 900; 1,000; 1,500; 2,000; 2,500; 3,000; 4,000; 5,000; 7,500; or 10,000 or more naturally occurring amino acids. In some embodiments, a peptide sequence binds to a protein encoded by a class I HLA allele and has a length of from 8-12 naturally occurring amino acids. In some embodiments, a peptide sequence binds to a protein encoded by a class II HLA allele and has a length of from 16-25 naturally occurring amino acids. In some embodiments, a peptide sequence comprises a plurality of antigen peptide sequences. In some embodiments, the plurality of antigen peptide sequences comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, 300, 350, 400, 450, or 500 antigen peptide sequences.

In some embodiments, the antigens described herein are neoantigens. Candidate immunogenic neoantigen sequences can be identified by any suitable method known in the art. The methods of the present disclosure can be useful, for example, to produce therapies specific to a subject's disease or to produce vaccines to a disease. Candidate immunogenic neoantigens can be neoantigens previously identified. In some embodiments, candidate immunogenic neoantigens may not be previously identified. Candidate immunogenic neoantigens for use in the methods and compositions described herein can be specific to a subject. In some embodiments, candidate neoantigens for use in the methods and compositions described herein can be specific to a plurality of subjects.

In both animals and humans, mutated epitopes can be potentially effective in inducing an immune response or activating T cells. In one embodiment, the potentially immunogenic epitopes of an infectious agent in a subject, such as a virus, can be determined. In one embodiment, the potentially immunogenic mutated epitopes of a subject with a disease, such as cancer, can be determined. In some embodiments, a potentially immunogenic antigen or neoantigen for use in the methods described herein can be a differentiation antigen expressed in a tumor and cells of the type of tissue from which they are generated. In some embodiments, a potentially immunogenic antigen or neoantigen for use in the methods described herein can be a cancer/germ line antigens not expressed in another differentiated tissue. In some embodiments, a potentially immunogenic antigen or neoantigen for use in the methods described herein can be a mutated antigen. For example, a candidate immunogenic antigen or neoantigen peptide for use in the methods described herein can comprise a missense point mutation or a antigen or neoantigen of a fusion protein generated through tumor specific translocation of a gene segment. In some embodiments, a potentially immunogenic antigen or neoantigen for use in the methods described herein can be an overexpressed antigen. In some embodiments, a potentially immunogenic antigen or neoantigen can be found in tumors. For example, a potentially immunogenic antigen or neoantigen for use in the methods described herein can include a protein whose expression is strictly regulated in cells of differentiated normal tissue.

Potentially immunogenic mutated epitopes can be determined by genomic or exomic sequencing of tumor tissue and healthy tissue from a cancer patient using next generation sequencing technologies. For example, genes selected based on their mutation frequency and ability to act as an antigen or neoantigen can be sequenced using next generation sequencing technology. In one embodiment, sequencing data can be analyzed to identify potentially immunogenic mutated peptides that can bind to HLA molecules of the subject. In one embodiment, the data can be analyzed using a computer. In another embodiment the sequence data can be analyzed for the presence of antigen or neoantigen peptides. In one embodiment, potentially immunogenic antigen or neoantigen peptides can be determined by their affinity to MHC molecules.

Potentially immunogenic antigen or neoantigen peptides can be determined by direct protein sequencing. For example, protein sequencing of enzymatic protein digests using multidimensional mass spectrometry techniques (e.g., tandem mass spectrometry (MS/MS)) can be used to identify potentially immunogenic antigen or neoantigen peptides for use in the methods described herein.

High-throughput methods for de novo sequencing of unknown proteins may be used to identify potentially immunogenic antigen or neoantigen peptides. For example, high-throughput methods for de novo sequencing of unknown proteins, such as meta-shotgun protein sequencing, may be used to analyze the proteome of a subject's tumor to identify potentially immunogenic expressed neoantigens.

Potentially immunogenic antigen or neoantigen peptides may also be identified using MHC multimers to identify antigen-specific T cell responses. For example, high-throughput analysis of antigen-specific T cell responses in patient samples may be performed using MHC tetramer-based screening techniques. Tetramer-based screening techniques may be used for the initial identification of potentially immunogenic tumor specific antigens, or alternatively as a secondary screening protocol to assess what potentially immunogenic antigens a patient may have already been exposed to, thereby facilitating the selection of potentially immunogenic antigens for use in the methods described herein.

In some embodiments, immune cells can be analyzed or characterized. For example, immune cells of a composition described herein can be analyzed or characterized. In some embodiments, a method can comprise determining expression of one or more cell markers of at least one immune cell of a stimulated immune cell sample; and determining binding of the at least one immune cell of the stimulated immune cell sample to a peptide-MHC complex; wherein determining expression and determining binding are performed simultaneously. In some embodiments, the stimulated immune cell sample is a population of immune cells stimulated with APCs comprising a peptide-MHC complex. In some embodiments, the population of immune cells is from a biological sample. In some embodiments, a method can comprise incubating a population of immune cells from a biological sample with APCs comprising a peptide-MHC complex, thereby obtaining a stimulated immune cell sample; determining expression of one or more cell markers of at least one immune cell of the stimulated immune cell sample; and determining binding of the at least one immune cell of the stimulated immune cell sample to a peptide-MHC complex; wherein determining expression and determining binding are performed simultaneously. In some embodiments, the one or more cell markers comprise TNF-α, IFN-γ, LAMP-1, 4-1BB, IL-2, IL-17A, Granzyme B, PD-1, CD25, CD69, TIM3, LAG3, CTLA-4, CD62L, CD45RA, CD45RO, FoxP3, or any combination thereof. In some embodiments, the one or more cell markers comprise a cytokine. In some embodiments, the one or more cell markers comprise a degranulation marker. In some embodiments, the one or more cell markers comprise a cell-surface marker. In some embodiments, the one or more cell markers comprise a protein. In some embodiments, determining binding of the at least one immune cell of the stimulated immune cell sample to the peptide-MHC complex comprises determining binding of the at least one immune cell of the stimulated immune cell sample to a MHC tetramer comprising the peptide and the MHC of the peptide-MHC complex. In some embodiments, the MHC is a class I MHC or a class II MHC. In some embodiments, the peptide-MHC complex comprises one or more labels. In some embodiments, the population of immune cells from a biological sample comprises two or more samples each comprising a population of immune cells from one or more biological samples. In some embodiments, the two or more samples are labeled with two or more sample labels. In some embodiments, determining expression and determining binding comprises fluorescent activated cell sorting (FACS). In some embodiments, determining expression and determining binding comprises single cell analysis. In some embodiments, determining expression and determining binding comprises determining a percentage of immune cells that both express the one or more cell markers and that bind to the peptide-MHC complex. In some embodiments, the labels comprise a fluorophore. In some embodiments, the population of immune cells comprises a population of immune cells representative of the population of immune cells of a composition described herein. In some embodiments, immune cell populations expressing TNF-α, IFN-γ, LAMP-1, 4-1BB, IL-2, IL-17A, Granzyme B, PD-1, CD25, CD69, TIM3, LAG3, CTLA-4, CD62L, CD45RA, CD45RO, FoxP3, CD3, CD28, CD4, CD8, or any combination, and/or not expressing CD14, CD19, CD16, CD25, or any combination thereof, can be analyzed or characterized. For example, the method can comprise analyzing or characterizing a specific T cell subpopulation, such as T cell subpopulation expressing TNF-α, IFN-γ, LAMP-1, 4-1BB, IL-2, IL-17A, Granzyme B, PD-1, CD25, CD69, TIM3, LAG3, CTLA-4, CD62L, CD45RA, CD45RO, FoxP3, CD3, CD28, CD4, CD8, or any combination, and/or not expressing CD14, CD19, CD16, CD25, or any combination thereof. For example, the method can comprise analyzing or characterizing an immune cell population that does not express CD14, CD25, CD19, CD16, or any combination thereof.

In some embodiments, expression of one or more cell markers in an immune cell population can be determined. For example, the method can comprise determining expression of TNF-α, IFN-γ, LAMP-1, 4-1BB, IL-2, IL-17A, Granzyme B, PD-1, CD25, CD69, TIM3, LAG3, CTLA-4, CD62L, CD45RA, CD45RO, FoxP3, CD14, CD25, CD19, CD16 or any combination thereof. For example, a method can comprise incubating a population of immune cells from a biological sample with APCs comprising a peptide-MHC complex, thereby obtaining a stimulated immune cell sample; determining expression of TNF-α, IFN-γ, LAMP-1, 4-1BB, IL-2, IL-17A, Granzyme B, PD-1, CD25, CD69, TIM3, LAG3, CTLA-4, CD62L, CD45RA, CD45RO, FoxP3, CD14, CD25, CD19, CD16, or any combination thereof of at least one immune cell of the stimulated immune cell sample; and determining binding of the at least one immune cell of the stimulated immune cell sample to a peptide-MHC complex; wherein determining expression and determining binding are performed simultaneously.

Potentially immunogenic antigen or neoantigen peptides for use in the methods described herein can be known antigen or neoantigen sequences. For example, potentially immunogenic antigen or neoantigen peptides for use in the methods described herein can be from a database of antigen or neoantigen sequences.

In some aspects, the present disclosure provides peptides or polynucleotides encoding peptides identified using the methods described herein (e.g., a peptide with a tumor specific mutation, a viral peptide, or peptide associated with a non-cancerous disease).

In some embodiments, an optical method is used to select or identify immunogenic antigens. In some embodiments, a barcoded probe is used to select or identify immunogenic antigens. In some embodiments, a barcoded probe comprising a target specific region and a barcoded region is used to select or identify immunogenic antigens. In some embodiments the target specific region comprises a nucleic acid sequence that hybridizes to or has at least about 90%, 95% or 100% sequence complementarity to a nucleic acid sequence of a target polynucleotide.

In some embodiments, a sequencing method is used to identify immunogenic antigens. Any suitable sequencing method can be used according to the invention, for example, Next Generation Sequencing (NGS) technologies. Third Generation Sequencing methods might substitute for the NGS technology in the future to speed up the sequencing step of the method. For clarification purposes: the terms "Next Generation Sequencing" or "NGS" in the context of the present invention mean all high throughput sequencing technologies which, in contrast to the "conventional" sequencing methodology known as Sanger chemistry, read nucleic acid templates randomly in parallel along the entire genome by breaking the entire genome into small pieces. Such NGS technologies (also known as massively parallel sequencing technologies) are able to deliver nucleic acid sequence information of a whole genome, exome, transcriptome (all transcribed sequences of a genome) or methylome (all methylated sequences of a genome) in very short time periods, e.g. within 1-2 weeks, for example, within 1-7 days or within less than 24 hours and allow, in principle, single cell sequencing approaches. Multiple NGS platforms which are commercially available or which are mentioned in the literature can be used in the context of the invention e.g. those described in detail in WO 2012/159643.

In certain embodiments, an antigen or neoantigen peptide or epitope thereof can comprise, but is not limited to, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, about 120 or greater amino acid residues, and any range derivable therein. In specific embodiments, an immunogenic antigen or epitope thereof is equal to or less than 100 amino acids.

In some embodiments, an antigen or neoantigen peptide or epitope thereof for MHC Class I is 13 residues or less in length and usually consists of between about 8 and about 11 residues, particularly 9 or 10 residues. In some embodiments, an immunogenic antigen or neoantigen peptide or epitope thereof for MHC Class II is 9-24 residues in length.

A longer immunogenic peptide can be designed in several ways. In some embodiments, when HLA-binding peptides are predicted or known, a longer immunogenic peptide could consist of (1) individual binding peptides with extensions of 2-5 amino acids toward the N- and C-terminus of each corresponding gene product; or (2) a concatenation of some or all of the binding peptides with extended sequences for each. In other embodiments, when sequencing reveals a long (>10 residues) epitope sequence, e.g., a neoepitope present in a tumor (e.g. due to a frameshift, read-through or intron inclusion that leads to a novel peptide sequence), a longer neoantigen peptide could consist of the entire stretch of novel tumor-specific amino acids as either a single longer peptide or several overlapping longer peptides. In some embodiments, use of a longer peptide is presumed to allow for endogenous processing by patient cells and can lead to more effective antigen presentation and induction of T cell responses. In some embodiments, two or more peptides can be used, where the peptides overlap and are tiled over the long neoantigen peptide.

In some embodiments, an antigen or neoantigen peptide binds an HLA protein (e.g., HLA class I or HLA class II). In specific embodiments, an antigen or neoantigen peptide binds an HLA protein with greater affinity than a corresponding wild-type peptide. In specific embodiments, an antigen or neoantigen peptide has an $IC_{50}$ or $K_D$ of at least less than 5000 nM, at least less than 500 nM, at least less than 100 nM, at least less than 50 nM or less.

In some embodiments, an antigen or neoantigen peptide can be from about 8 and about 50 amino acid residues in length, or from about 8 and about 30, from about 8 and about 20, from about 8 and about 18, from about 8 and about 15, or from about 8 and about 12 amino acid residues in length. In some embodiments, an antigen or neoantigen peptide can be from about 8 and about 500 amino acid residues in length, or from about 8 and about 450, from about 8 and about 400, from about 8 and about 350, from about 8 and about 300, from about 8 and about 250, from about 8 and about 200, from about 8 and about 150, from about 8 and about 100, from about 8 and about 50, or from about 8 and about 30 amino acid residues in length.

In some embodiments, an antigen or neoantigen peptide can be at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more amino acid residues in length. In some embodiments, the neoantigen peptides can be at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 70, 80, 90, 100, 150, 200, 250, 300, 350, 400, 450, 500 or more amino acid residues in length. In some embodiments, an antigen or neoantigen peptide can be at most 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or less amino acid residues in length. In some embodiments, an antigen or neoantigen peptide can be at most 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 70, 80, 90, 100, 150, 200, 250, 300, 350, 400, 450, 500, or less amino acid residues in length.

In some embodiments, an antigen or neoantigen peptide has a total length of at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 40, at least 50, at least 60, at least 70, at least 80, at least 90, at least 100, at least 150, at least 200, at least 250, at least 300, at least 350, at least 400, at least 450, or at least 500 amino acids.

In some embodiments, an antigen or neoantigen peptide has a total length of at most 8, at most 9, at most 10, at most 11, at most 12, at most 13, at most 14, at most 15, at most 16, at most 17, at most 18, at most 19, at most 20, at most 21, at most 22, at most 23, at most 24, at most 25, at most 26, at most 27, at most 28, at most 29, at most 30, at most 40, at most 50, at most 60, at most 70, at most 80, at most 90, at most 100, at most 150, at most 200, at most 250, at most 300, at most 350, at most 400, at most 450, or at most 500 amino acids.

In some embodiments, the neoantigen peptides can have a pI value of about 0.5 and about 12, about 2 and about 10, or about 4 and about 8. In some embodiments, the neoantigen peptides can have a pI value of at least 4.5, 5, 5.5, 6, 6.5, 7, 7.5, or more. In some embodiments, the neoantigen peptides can have a pI value of at most 4.5, 5, 5.5, 6, 6.5, 7, 7.5, or less.

In some embodiments, an antigen or neoantigen peptide can have an HLA binding affinity of from about 1 µM and about 1 mM, about 100 µM and about 500 µM, about 500 µM and about 10 µM, about 1 nM and about 1 µM, or about 10 nM and about 1 µM. In some embodiments, an antigen or neoantigen peptide can have an HLA binding affinity of at least 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 700, 800, 900 µM, or more. In some embodiments, an antigen or neoantigen peptide can have an HLA binding affinity of at most 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 700, 800, 900 µM.

In some embodiments, an antigen or neoantigen peptide described herein can comprise carriers such as those well known in the art, e.g., thyroglobulin, albumins such as human serum albumin, tetanus toxoid, polyamino acid residues such as poly L-lysine, poly L-glutamic acid, influenza virus proteins, hepatitis B virus core protein, and the like.

In some embodiments, an antigen or neoantigen peptide described herein can be modified by terminal-$NH_2$ acylation, e.g., by alkanoyl ($C_1$-$C_{20}$) or thioglycolyl acetylation, terminal-carboxyl amidation, e.g., ammonia, methylamine, etc. In some embodiments these modifications can provide sites for linking to a support or other molecule.

In some embodiments, an antigen or neoantigen peptide described herein can contain modifications such as but not limited to glycosylation, side chain oxidation, biotinylation, phosphorylation, addition of a surface active material, e.g. a lipid, or can be chemically modified, e.g., acetylation, etc. Moreover, bonds in the peptide can be other than peptide bonds, e.g., covalent bonds, ester or ether bonds, disulfide bonds, hydrogen bonds, ionic bonds, etc.

In some embodiments, an antigen or neoantigen peptide described herein can contain substitutions to modify a physical property (e.g., stability or solubility) of the resulting peptide. For example, an antigen or neoantigen peptide can be modified by the substitution of a cysteine (C) with α-amino butyric acid ("B"). Due to its chemical nature, cysteine has the propensity to form disulfide bridges and sufficiently alter the peptide structurally so as to reduce binding capacity. Substituting α-amino butyric acid for C not only alleviates this problem, but actually improves binding and crossbinding capability in certain instances. Substitution of cysteine with α-amino butyric acid can occur at any residue of an antigen or neoantigen peptide, e.g., at either anchor or non-anchor positions of an epitope or analog within a peptide, or at other positions of a peptide.

In some embodiments, an antigen peptide or neoantigen peptide described herein can comprise amino acid mimetics or unnatural amino acid residues, e.g. D- or L-naphtylalanine; D- or L-phenylglycine; D- or L-2-thieneylalanine; D- or L-1, 2, 3, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-ρ-fluorophenylalanine; D- or L-ρ-biphenyl-phenylalanine; D- or L-ρ-methoxybiphenylphenylalanine; D- or L-2-indole(allyl)alanines; and, D- or L-alkylalanines, where the alkyl group can be a substituted or unsubstituted methyl, ethyl, propyl, hexyl, butyl, pentyl, isopropyl, iso-butyl, sec-isotyl, iso-pentyl, or a non-acidic amino acid residues. Aromatic rings of a non-natural amino acid include, e.g., thiazolyl, thiophenyl, pyrazolyl, benzimidazolyl, naphthyl, furanyl, pyrrolyl, and pyridyl aromatic rings. Modified peptides that have various amino acid mimetics or unnatural amino acid residues are particularly useful, as they tend to manifest increased stability in vivo. Such peptides can also possess improved shelf-life or manufacturing properties.

Peptide stability can be assayed in a number of ways. For instance, peptidases and various biological media, such as human plasma and serum, have been used to test stability.

See, e.g., Verhoef, et al., Eur. J. Drug Metab. Pharmacokinetics 11:291 (1986). Half-life of the peptides described herein is conveniently determined using a 25% human serum (v/v) assay. The protocol is as follows: pooled human serum (Type AB, non-heat inactivated) is dilapidated by centrifugation before use. The serum is then diluted to 25% with RPMI-1640 or another suitable tissue culture medium. At predetermined time intervals, a small amount of reaction solution is removed and added to either 6% aqueous trichloroacetic acid (TCA) or ethanol. The cloudy reaction sample is cooled (4° C.) for 15 minutes and then spun to pellet the precipitated serum proteins. The presence of the peptides is then determined by reversed-phase HPLC using stability-specific chromatography conditions.

In some embodiments, an antigen or neoantigen peptide described herein can be in solution, lyophilized, or can be in crystal form.

In some embodiments, an antigen or neoantigen peptide described herein can be prepared synthetically, by recombinant DNA technology or chemical synthesis, or can be isolated from natural sources such as native tumors or pathogenic organisms. Epitopes can be synthesized individually or joined directly or indirectly in a peptide. Although an antigen or neoantigen peptide described herein will be substantially free of other naturally occurring host cell proteins and fragments thereof, in some embodiments the peptide can be synthetically conjugated to be joined to native fragments or particles.

In some embodiments, the peptides can be synthesized in solution or on a solid support according to conventional techniques. Various automatic synthesizers are commercially available and can be used according to known protocols. (See, for example, Stewart & Young, Solid Phase Peptide Synthesis, 2d. Ed., Pierce Chemical Co., 1984). Further, individual peptides can be joined using chemical ligation to produce larger peptides that are still within the bounds of the invention.

Alternatively, recombinant DNA technology can be employed wherein a nucleotide sequence which encodes a peptide inserted into an expression vector, transformed or transfected into an appropriate host cell and cultivated under conditions suitable for expression. These procedures are generally known in the art, as described generally in Sambrook et al., Molecular Cloning, a Laboratory Manual, Cold Spring Harbor Press, Cold Spring Harbor, N.Y. (1989). Thus, recombinant peptides, which comprise or consist of one or more epitopes described herein, can be used to present the appropriate T cell epitope.

In one aspect, the present disclosure described herein also provides compositions comprising one, at least two, or more than two antigen peptides or neoantigen peptides. In some embodiments a composition described herein contains at least two distinct peptides. In some embodiments, the at least two distinct peptides are derived from the same polypeptide. By distinct polypeptides is meant that the peptide vary by length, amino acid sequence or both. The peptides are derived from any polypeptide known to or have been found to contain a tumor specific mutation. In some embodiments, an isolated antigen or neoantigen peptide is encoded by a gene with a point mutation resulting in an amino acid substitution of the native peptide.

Pharmaceutical Compositions

Pharmaceutical compositions can be formulated using one or more physiologically acceptable carriers including excipients and auxiliaries which facilitate processing of the active agents into preparations which can be used pharmaceutically. Proper formulation can be dependent upon the route of administration chosen. Any of the well-known techniques, carriers, and excipients can be used as suitable and as understood in the art.

In some cases, a pharmaceutical composition is formulated as cell based therapeutic, e.g., a T cell therapeutic. In some embodiments, a pharmaceutical composition comprises a peptide-based therapy, a nucleic acid-based therapy, an antibody based therapy, and/or a cell based therapy. In some embodiments, a pharmaceutical composition comprises a peptide-based therapeutic, or nucleic acid based therapeutic in which the nucleic acid encodes the polypeptides. In some embodiments, a pharmaceutical composition comprises as an antibody based therapeutic. A composition can comprise T cells specific for two or more immunogenic antigen or neoantigen peptides.

Pharmaceutical compositions can include, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration.

Acceptable carriers, excipients, or stabilizers are those that are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

Acceptable carriers are physiologically acceptable to the administered patient and retain the therapeutic properties of the compounds with/in which it is administered. Acceptable carriers and their formulations are generally described in, for example, Remington' pharmaceutical Sciences (18$^{th}$ ed. A. Gennaro, Mack Publishing Co., Easton, PA 1990). One example of carrier is physiological saline. A pharmaceutically acceptable carrier is a pharmaceutically acceptable material, composition or vehicle, such as a liquid or solid filler, diluent, excipient, solvent or encapsulating material, involved in carrying or transporting the subject compounds from the administration site of one organ, or portion of the body, to another organ, or portion of the body, or in an in vitro assay system. Acceptable carriers are compatible with the other ingredients of the formulation and not injurious to a subject to whom it is administered. Nor should an acceptable carrier alter the specific activity of the neoantigens.

In one aspect, provided herein are pharmaceutically acceptable or physiologically acceptable compositions including solvents (aqueous or non-aqueous), solutions, emulsions, dispersion media, coatings, isotonic and absorption promoting or delaying agents, compatible with pharmaceutical administration. Pharmaceutical compositions or pharmaceutical formulations therefore refer to a composition suitable for pharmaceutical use in a subject. Compositions can be formulated to be compatible with a particular route of administration (i.e., systemic or local). Thus, compositions include carriers, diluents, or excipients suitable for administration by various routes.

In some embodiments, a composition can further comprise an acceptable additive in order to improve the stability of immune cells in the composition. Acceptable additives may not alter the specific activity of the immune cells. Examples of acceptable additives include, but are not limited to, a sugar such as mannitol, sorbitol, glucose, xylitol, trehalose, sorbose, sucrose, galactose, dextran, dextrose, fructose, lactose and mixtures thereof. Acceptable additives can be combined with acceptable carriers and/or excipients such as dextrose. Alternatively, examples of acceptable additives include, but are not limited to, a surfactant such as polysorbate 20 or polysorbate 80 to increase stability of the peptide and decrease gelling of the solution. The surfactant can be added to the composition in an amount of 0.01% to 5% of the solution. Addition of such acceptable additives increases the stability and half-life of the composition in storage.

The pharmaceutical composition can be administered, for example, by injection. Compositions for injection include aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). The carrier can be a solvent or dispersion medium containing, for example, water, ethanol, polyol (for example, glycerol, propylene glycol, and liquid polyethylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as mannitol, sorbitol, and sodium chloride can be included in the composition. The resulting solutions can be packaged for use as is, or lyophilized; the lyophilized preparation can later be combined with a sterile solution prior to administration. For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as needed. Sterile injectable solutions can be prepared by incorporating an active ingredient in the required amount in an appropriate solvent with one or a combination of ingredients enumerated above, as required, followed by filtered sterilization. Generally, dispersions are prepared by incorporating the active ingredient into a sterile vehicle which contains a basic dispersion medium and the required other ingredients from those enumerated above. In the case of sterile powders for the preparation of sterile injectable solutions, the preferred methods of preparation can be vacuum drying and freeze drying which yields a powder of the active ingredient plus any additional desired ingredient from a previously sterile-filtered solution thereof.

Compositions can be conventionally administered intravenously, such as by injection of a unit dose, for example. For injection, an active ingredient can be in the form of a parenterally acceptable aqueous solution which is substantially pyrogen-free and has suitable pH, isotonicity and stability. One can prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required. Additionally, compositions can be administered via aerosolization.

When the compositions are considered for use in medicaments or any of the methods provided herein, it is contemplated that the composition can be substantially free of pyrogens such that the composition will not cause an inflammatory reaction or an unsafe allergic reaction when administered to a human patient. Testing compositions for pyrogens and preparing compositions substantially free of pyrogens are well understood to one or ordinary skill of the art and can be accomplished using commercially available kits.

Acceptable carriers can contain a compound that stabilizes, increases or delays absorption, or increases or delays clearance. Such compounds include, for example, carbohydrates, such as glucose, sucrose, or dextrans; low molecular weight proteins; compositions that reduce the clearance or hydrolysis of peptides; or excipients or other stabilizers and/or buffers. Agents that delay absorption include, for example, aluminum monostearate and gelatin. Detergents can also be used to stabilize or to increase or decrease the absorption of the pharmaceutical composition, including liposomal carriers. To protect from digestion the compound can be complexed with a composition to render it resistant to acidic and enzymatic hydrolysis, or the compound can be complexed in an appropriately resistant carrier such as a liposome. Means of protecting compounds from digestion are known in the art (e.g., Fix (1996) Pharm Res. 13:1760 1764; Samanen (1996) J. Pharm. Pharmacol. 48:119 135; and U.S. Pat. No. 5,391,377).

The compositions can be administered in a manner compatible with the dosage formulation, and in a therapeutically effective amount. The quantity to be administered depends on the subject to be treated, capacity of the subject's immune system to utilize the active ingredient, and degree of binding capacity desired. Precise amounts of active ingredient required to be administered depend on the judgment of the practitioner and are peculiar to each individual. Suitable regimes for initial administration and booster shots are also variable, but are typified by an initial administration followed by repeated doses at one or more hour intervals by a subsequent injection or other administration. Alternatively, continuous intravenous infusions sufficient to maintain concentrations in the blood are contemplated.

In some embodiments, the present invention is directed to an immunogenic composition, e.g., a pharmaceutical composition capable of raising a neoantigen-specific response (e.g., a humoral or cell-mediated immune response). In some embodiments, the immunogenic composition comprises neoantigen therapeutics (e.g., peptides, polynucleotides, TCR, CAR, cells containing TCR or CAR, dendritic cell containing polypeptide, dendritic cell containing polynucleotide, antibody, etc.) described herein corresponding to a tumor specific antigen or neoantigen.

In some embodiments, a pharmaceutical composition described herein is capable of raising a specific cytotoxic T cells response, specific helper T cell response, or a B cell response.

In some embodiments, antigen polypeptides or polynucleotides can be provided as antigen presenting cells (e.g., dendritic cells) containing such polypeptides or polynucleotides. In other embodiments, such antigen presenting cells are used to stimulate T cells for use in patients. In some embodiments, the antigen presenting cells are dendritic cells. In related embodiments, the dendritic cells are autologous dendritic cells that are pulsed with the neoantigen peptide or nucleic acid. The neoantigen peptide can be any suitable peptide that gives rise to an appropriate T cell response. In some embodiments, the T cell is a CTL. In some embodiments, the T cell is a HTL. Thus, one embodiment of the present disclosure is an immunogenic composition containing at least one antigen presenting cell (e.g., a dendritic cell) that is pulsed or loaded with one or more neoantigen polypeptides or polynucleotides described herein. In some embodiments, such APCs are autologous (e.g., autologous dendritic cells). Alternatively, peripheral blood mononuclear cells (PBMCs) isolated from a patient can be loaded with neoantigen peptides or polynucleotides ex vivo. In related embodiments, such APCs or PBMCs are injected back into the patient. The polynucleotide can be any suitable polynucleotide that is capable of transducing the dendritic cell, thus resulting in the presentation of a neoantigen peptide and induction of immunity. In some embodiments, such antigen presenting cells (APCs) (e.g., dendritic cells) or peripheral blood mononuclear cells (PBMCs) are used to stimulate a T cell (e.g., an autologous T cell). In related embodiments, the T cell is a CTL. In other related embodiments, the T cell is an HTL. In some embodiments, the T cells are CD8$^+$ T cells. In some embodiments, the T cells are CD4$^+$ T cells. Such T cells are then injected into the patient. In some embodiments, CTL is injected into the patient. In some embodiments, HTL is injected into the patient. In some embodiments, both CTL and HTL are injected into the patient. Administration of either therapeutic can be performed simultaneously or sequentially and in any order.

In some embodiments, a pharmaceutical composition (e.g., immunogenic compositions) described herein for therapeutic treatment can be formulated for parenteral, topical, nasal, oral or local administration. In some embodiments, the pharmaceutical compositions described herein are administered parenterally, e.g., intravenously, subcutaneously, intradermally, or intramuscularly. In some embodiments, the composition can be administered intratumorally. The compositions can be administered at the site of surgical excision to induce a local immune response to the tumor. In some embodiments, described herein are compositions for parenteral administration which comprise a solution of the neoantigen peptides and immunogenic compositions are dissolved or suspended in an acceptable carrier, for example, an aqueous carrier. A variety of aqueous carriers can be used, e.g., water, buffered water, 0.9% saline, 0.3% glycine, hyaluronic acid and the like. These compositions can be sterilized by conventional, well known sterilization techniques, or can be sterile filtered. The resulting aqueous solutions can be packaged for use as is, or lyophilized, the lyophilized preparation being combined with a sterile solution prior to administration. The compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The ability of an adjuvant to increase the immune response to an antigen is typically manifested by a significant increase in immune-mediated reaction, or reduction in disease symptoms. For example, an increase in humoral immunity can be manifested by a significant increase in the titer of antibodies raised to the antigen, and an increase in T cell activity can be manifested in increased cell proliferation, or cellular cytotoxicity, or cytokine secretion. An adjuvant can also alter an immune response, for example, by changing a primarily humoral or T helper 2 response into a primarily cellular, or T helper 1 response.

Suitable adjuvants are known in the art (see, WO 2015/095811) and include, but are not limited to poly(I:C), poly-ICLC, STING agonist, 1018 ISS, aluminum salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel® vector system, PLG microparticles, resiquimod, SRL172, virosomes and other virus-like particles, YF-17D, VEGF trap, R848, $-glucan, Pam3Cys, Pam3CSK4, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Several immunological adjuvants (e.g., MF59) specific for dendritic cells and their preparation have been described (Dupuis M, et al., Cell Immunol. 1998; 186(1):18-27; Allison A C; Dev Biol Stand. 1998; 92:3-11) (Mosca et al. Frontiers in Bioscience, 2007; 12:4050-4060) (Gamvrellis et al. Immunol & Cell Biol. 2004; 82: 506-516). Also cytokines can be used. Several cytokines have been directly linked to influencing dendritic cell migration to lymphoid tissues (e.g., TNF-α), accelerating the maturation of dendritic cells into efficient antigen-presenting cells for T-lymphocytes (e.g., GM-CSF, PGE1, PGE2, IL-1, IL-1β, IL-4, IL-6 and CD40L) (U.S. Pat. No. 5,849,589 incorporated herein by reference in its entirety) and acting as immunoadjuvants (e.g., IL-12) (Gabrilovich D I, et al., J Immunother Emphasis Tumor Immunol. 1996 (6):414-418).

CpG immunostimulatory oligonucleotides have also been reported to enhance the effects of adjuvants in a therapeutic setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell immunogenic pharmaceutical compositions, autologous cellular immunogenic pharmaceutical compositions and polysaccharide conjugates in both prophylactic and therapeutic immunogenic pharmaceutical compositions. Importantly, it enhances dendritic cell maturation and differentiation, resulting in enhanced activation of TH1 cells and strong cytotoxic T-lymphocyte (CTL) generation, even in the absence of CD4$^+$ T cell help. The TH1 bias induced by TLR9 stimulation is maintained even in the presence of adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially useful for inducing a strong response when the antigen is relatively weak. They can also accelerate the immune response and enabled the antigen doses to be reduced with comparable antibody responses to the full-dose immunogenic pharmaceutical composition without CpG in some experiments (Arthur M. Krieg, Nature Reviews, Drug Discovery, 5, June 2006, 471-484). U.S. Pat. No. 6,406,705 describes the combined use of CpG oligonucleotides, non-nucleic acid adjuvants and an antigen to induce an antigen-specific immune response. A commercially available CpG TLR9 antagonist is dSLIM (double Stem Loop Immunomodulator) by Mologen (Berlin, DE), which is a component of the pharmaceutical composition described herein. Other TLR binding molecules such as RNA binding TLR7, TLR8 and/or TLR9 can also be used.

Other examples of useful adjuvants include, but are not limited to, chemically modified CpGs (e.g. CpR, Idera), Poly(I:C)(e.g., polyI:CI2U), non-CpG bacterial DNA or RNA, ssRNA40 for TLR8, as well as immunoactive small molecules and antibodies such as cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab, and SC58175, which can act therapeutically and/or as an adjuvant. The amounts and concentrations of adjuvants and additives useful in the context of the present invention can readily be determined by the skilled artisan without undue experimentation. Additional adjuvants include colony-stimulating factors, such as Granulocyte Macrophage Colony Stimulating Factor (GM-CSF, sargramostim).

In some embodiments, an immunogenic composition according to the present disclosure can comprise more than one different adjuvant. Furthermore, the invention encompasses a pharmaceutical composition comprising any adjuvant substance including any of the above or combinations thereof. In some embodiments, the immunogenic composition comprises neoantigen therapeutics (e.g., peptides, polynucleotides, TCR, CAR, cells containing TCR or CAR, dendritic cell containing polypeptide, dendritic cell containing polynucleotide, antibody, etc.) and the adjuvant can be administered separately in any appropriate sequence.

Lipidation can be classified into several different types, such as N-myristoylation, palmitoylation, GPI-anchor addition, prenylation, and several additional types of modifications. N-myristoylation is the covalent attachment of myristate, a C14 saturated acid, to a glycine residue. Palmitoylation is thioester linkage of long-chain fatty acids (C16) to cysteine residues. GPI-anchor addition is glycosyl-phosphatidylinositol (GPI) linkage via amide bond. Prenylation is the thioether linkage of an isoprenoid lipid (e.g. farnesyl (C-15), geranylgeranyl (C-20)) to cysteine residues. Additional types of modifications can include attachment of S-diacylglycerol by a sulfur atom of cysteines, O-octanoyl conjugation via serine or threonine residues, S-archaeol conjugation to cysteine residues, and cholesterol attachment.

Fatty acids for generating lipidated peptides can include C2 to C30 saturated, monounsaturated, or polyunsaturated fatty acyl groups. Exemplary fatty acids can include palmitoyl, myristoyl, stearoyl and decanoyl groups. In some instances, a lipid moiety that has adjuvant property is attached to a polypeptide of interest to elicit or enhance immunogenicity in the absence of an extrinsic adjuvant. A lipidated peptide or lipopeptide can be referred to as a self-adjuvant lipopeptide. Any of the fatty acids described above and elsewhere herein can elicit or enhance immunogenicity of a polypeptide of interest. A fatty acid that can elicit or enhance immunogenicity can include palmitoyl, myristoyl, stearoyl, lauroyl, octanoyl, and decanoyl groups.

Polypeptides such as naked peptides or lipidated peptides can be incorporated into a liposome. Sometimes, lipidated peptides can be incorporated into a liposome. For example, the lipid portion of the lipidated peptide can spontaneously integrate into the lipid bilayer of a liposome. Thus, a lipopeptide can be presented on the "surface" of a liposome.

Exemplary liposomes suitable for incorporation in the formulations include, and are not limited to, multilamellar vesicles (MLV), oligolamellar vesicles (OLV), unilamellar vesicles (UV), small unilamellar vesicles (SUV), medium-sized unilamellar vesicles (MUV), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV).

Depending on the method of preparation, liposomes can be unilamellar or multilamellar, and can vary in size with diameters ranging from about 0.02 μm to greater than about 10 μm. Liposomes can adsorb many types of cells and then release an incorporated agent (e.g., a peptide described herein). In some cases, the liposomes fuse with the target cell, whereby the contents of the liposome then empty into the target cell. A liposome can be endocytosed by cells that are phagocytic. Endocytosis can be followed by intralysosomal degradation of liposomal lipids and release of the encapsulated agents.

The liposomes provided herein can also comprise carrier lipids. In some embodiments the carrier lipids are phospholipids. Carrier lipids capable of forming liposomes include, but are not limited to dipalmitoylphosphatidylcholine (DPPC), phosphatidylcholine (PC; lecithin), phosphatidic acid (PA), phosphatidylglycerol (PG), phosphatidylethanolamine (PE), phosphatidylserine (PS). Other suitable phospholipids further include distearoylphosphatidylcholine (DSPC), dimyristoylphosphatidylcholine (DMPC), dipalmitoylphosphatidyglycerol (DPPG), distearoylphosphatidyglycerol (DSPG), dimyristoylphosphatidylglycerol (DMPG), dipalmitoylphosphatidic acid (DPPA); dimyristoylphosphatidic acid (DMPA), distearoylphosphatidic acid (DSPA), dipalmitoylphosphatidylserine (DPPS), dimyristoylphosphatidylserine (DMPS), distearoylphosphatidylserine (DSPS), dipalmitoylphosphatidyethanolamine (DPPE), dimyristoylphosphatidylethanolamine (DMPE), distearoylphosphatidylethanolamine (DSPE) and the like, or combinations thereof. In some embodiments, the liposomes further comprise a sterol (e.g., cholesterol) which modulates liposome formation. The carrier lipids can be any known non-phosphate polar lipids.

A pharmaceutical composition can be encapsulated within liposomes using well-known technology. Biodegradable microspheres can also be employed as carriers for the pharmaceutical compositions of this invention.

The pharmaceutical composition can be administered in liposomes or microspheres (or microparticles). Methods for preparing liposomes and microspheres for administration to a patient are well known to those of skill in the art. Essentially, material is dissolved in an aqueous solution, the appropriate phospholipids and lipids added, along with surfactants if required, and the material dialyzed or sonicated, as necessary.

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months.

Cell-based immunogenic pharmaceutical compositions can also be administered to a subject. For example, an antigen presenting cell (APC) based immunogenic pharmaceutical composition can be formulated using any of the well-known techniques, carriers, and excipients as suitable and as understood in the art. APCs include monocytes, monocyte-derived cells, macrophages, and dendritic cells. Sometimes, an APC based immunogenic pharmaceutical composition can be a dendritic cell-based immunogenic pharmaceutical composition.

A dendritic cell-based immunogenic pharmaceutical composition can be prepared by any methods well known in the art. In some cases, dendritic cell-based immunogenic pharmaceutical compositions can be prepared through an ex vivo or in vivo method. The ex vivo method can comprise the use of autologous DCs pulsed ex vivo with the polypeptides described herein, to activate or load the DCs prior to administration into the patient. The in vivo method can comprise targeting specific DC receptors using antibodies coupled with the polypeptides described herein. The DC-based immunogenic pharmaceutical composition can further comprise DC activators such as TLR3, TLR-7-8, and CD40 agonists. The DC-based immunogenic pharmaceutical composition can further comprise adjuvants, and a pharmaceutically acceptable carrier.

An adjuvant can be used to enhance the immune response (humoral and/or cellular) elicited in a patient receiving the immunogenic pharmaceutical composition. Sometimes, adjuvants can elicit a Th1-type response. Other times, adjuvants can elicit a Th2-type response. A Th1-type response can be characterized by the production of cytokines such as IFN-γ as opposed to a Th2-type response which can be characterized by the production of cytokines such as IL-4, IL-5 and IL-10.

In some aspects, lipid-based adjuvants, such as MPLA and MDP, can be used with the immunogenic pharmaceutical compositions disclosed herein. Monophosphoryl lipid A (MPLA), for example, is an adjuvant that causes increased presentation of liposomal antigen to specific T Lymphocytes. In addition, a muramyl dipeptide (MDP) can also be used as a suitable adjuvant in conjunction with the immunogenic pharmaceutical formulations described herein.

Adjuvant can also comprise stimulatory molecules such as cytokines. Non-limiting examples of cytokines include: CCL20, α-interferon (IFNα), β-interferon (IFNβ), γ-interferon (IFNγ), platelet derived growth factor (PDGF), TNFα, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, IL-28, MHC, CD80, CD86, IL-1, IL-2, IL-4, IL-5, IL-6, IL-10, IL-18, MCP-1, MIP-1a, MIP-1-, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IκB, Inactive NIK, SAP K, SAP-I, JNK, interferon response genes, NFκB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAPI, and TAP2.

Additional adjuvants include: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IκB, Inactive NIK, SAP K, SAP-1, JNK, interferon response genes, NFκB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

In some aspects, an adjuvant can be a modulator of a toll like receptor. Examples of modulators of toll-like receptors include TLR9 agonists and are not limited to small molecule modulators of toll-like receptors such as Imiquimod. Sometimes, an adjuvant is selected from bacteria toxoids, polyoxypropylene-polyoxyethylene block polymers, aluminum salts, liposomes, CpG polymers, oil-in-water emulsions, or a combination thereof. Sometimes, an adjuvant is an oil-in-water emulsion. The oil-in-water emulsion can include at least one oil and at least one surfactant, with the oil(s) and surfactant(s) being biodegradable (metabolizable) and biocompatible. The oil droplets in the emulsion can be less than 5 m in diameter, and can even have a sub-micron diameter, with these small sizes being achieved with a microfluidiser to provide stable emulsions. Droplets with a size less than 220 nm can be subjected to filter sterilization.

In some instances, an immunogenic pharmaceutical composition can include carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances as required to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In another instances, the pharmaceutical preparation is substantially free of preservatives. In other instances, the pharmaceutical preparation can contain at least one preservative. It will be recognized that, while any suitable carrier known to those of ordinary skill in the art can be employed to administer the pharmaceutical compositions described herein, the type of carrier will vary depending on the mode of administration.

An immunogenic pharmaceutical composition can include preservatives such as thiomersal or 2-phenoxyethanol. In some instances, the immunogenic pharmaceutical composition is substantially free from (e.g., <10 µg/mL) mercurial material e.g. thiomersal-free. α-Tocopherol succinate may be used as an alternative to mercurial compounds.

For controlling the tonicity, a physiological salt such as sodium salt can be included in the immunogenic pharmaceutical composition. Other salts can include potassium chloride, potassium dihydrogen phosphate, disodium phosphate, and/or magnesium chloride, or the like.

An immunogenic pharmaceutical composition can have an osmolality of between 200 mOsm/kg and 400 mOsm/kg, between 240-360 mOsm/kg, or within the range of 290-310 mOsm/kg.

An immunogenic pharmaceutical composition can comprise one or more buffers, such as a Tris buffer; a borate buffer; a succinate buffer; a histidine buffer (particularly with an aluminum hydroxide adjuvant); or a citrate buffer. Buffers, in some cases, are included in the 5-20 or 10-50 mM range.

The pH of the immunogenic pharmaceutical composition can be between about 5.0 and about 8.5, between about 6.0 and about 8.0, between about 6.5 and about 7.5, or between about 7.0 and about 7.8.

An immunogenic pharmaceutical composition can be sterile. The immunogenic pharmaceutical composition can be non-pyrogenic e.g. containing <1 EU (endotoxin unit, a standard measure) per dose, and can be <0.1 EU per dose. The composition can be gluten free.

An immunogenic pharmaceutical composition can include detergent e.g. a polyoxyethylene sorbitan ester surfactant (known as 'Tweens'), or an octoxynol (such as octoxynol-9 (Triton X-100) or t-octylphenoxypolyethoxyethanol). The detergent can be present only at trace amounts. The immunogenic pharmaceutical composition can include less than 1 mg/mL of each of octoxynol-10 and polysorbate 80. Other residual components in trace amounts can be antibiotics (e.g. neomycin, kanamycin, polymyxin B).

An immunogenic pharmaceutical composition can be formulated as a sterile solution or suspension, in suitable vehicles, well known in the art. The pharmaceutical compositions can be sterilized by conventional, well-known sterilization techniques, or can be sterile filtered. The resulting aqueous solutions can be packaged for use as is, or lyophilized, the lyophilized preparation being combined with a sterile solution prior to administration.

Pharmaceutical compositions comprising, for example, an active agent such as immune cells disclosed herein, in combination with one or more adjuvants can be formulated to comprise certain molar ratios. For example, molar ratios of about 99:1 to about 1:99 of an active agent such as an immune cell described herein, in combination with one or more adjuvants can be used. In some instances, the range of molar ratios of an active agent such as an immune cell described herein, in combination with one or more adjuvants can be selected from about 80:20 to about 20:80; about 75:25 to about 25:75, about 70:30 to about 30:70, about 66:33 to about 33:66, about 60:40 to about 40:60; about 50:50; and about 90:10 to about 10:90. The molar ratio of an active agent such as an immune cell described herein, in combination with one or more adjuvants can be about 1:9, and in some cases can be about 1:1. The active agent such as an immune cell described herein, in combination with one or more adjuvants can be formulated together, in the same dosage unit e.g., in one vial, suppository, tablet, capsule, an aerosol spray; or each agent, form, and/or compound can be formulated in separate units, e.g., two vials, suppositories, tablets, two capsules, a tablet and a vial, an aerosol spray, and the like.

In some instances, an immunogenic pharmaceutical composition can be administered with an additional agent. The choice of the additional agent can depend, at least in part, on the condition being treated. The additional agent can include, for example, a checkpoint inhibitor agent such as an anti-PD1, anti-CTLA4, anti-PD-L1, anti CD40, or anti-TIM3 agent (e.g., an anti-PD1, anti-CTLA4, anti-PD-L1, anti CD40, or anti-TIM3 antibody); or any agents having a therapeutic effect for a pathogen infection (e.g. viral infection), including, e.g., drugs used to treat inflammatory conditions such as an NSAID, e.g., ibuprofen, naproxen, acetaminophen, ketoprofen, or aspirin. For example, the checkpoint inhibitor can be a PD-1/PD-L1 antagonist selected from the group consisting of: nivolumab (ONO-4538/BMS-936558, MDX1 106, OPDIVO), pembrolizumab (MK-3475, KEYTRUDA), pidilizumab (CT-011), and MPDL3280A (ROCHE). As another example, formulations can additionally contain one or more supplements, such as vitamin C, E or other anti-oxidants.

A pharmaceutical composition comprising an active agent such as an immune cell described herein, in combination with one or more adjuvants can be formulated in conventional manner using one or more physiologically acceptable carriers, comprising excipients, diluents, and/or auxiliaries, e.g., which facilitate processing of the active agents into preparations that can be administered. Proper formulation can depend at least in part upon the route of administration chosen. The agent(s) described herein can be delivered to a patient using a number of routes or modes of administration, including oral, buccal, topical, rectal, transdermal, transmucosal, subcutaneous, intravenous, and intramuscular applications, as well as by inhalation.

The active agents can be formulated for parenteral administration (e.g., by injection, for example bolus injection or continuous infusion) and can be presented in unit dose form in ampoules, pre-filled syringes, small volume infusion or in multi-dose containers with an added preservative. The compositions can take such forms as suspensions, solutions, or emulsions in oily or aqueous vehicles, for example solutions in aqueous polyethylene glycol.

For injectable formulations, the vehicle can be chosen from those known in art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation can also comprise polymer compositions which are biocompatible, biodegradable, such as poly(lactic-co-glycolic)acid. These materials can be made into micro or nanospheres, loaded with drug and further coated or derivatized to provide superior sustained release performance. Vehicles suitable for periocular or intraocular injection include, for example, suspensions of therapeutic agent in injection grade water, liposomes and vehicles suitable for lipophilic substances. Other vehicles for periocular or intraocular injection are well known in the art.

In some instances, pharmaceutical composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

When administration is by injection, the active agent can be formulated in aqueous solutions, specifically in physiologically compatible buffers such as Hanks solution, Ringer's solution, or physiological saline buffer. The solution can contain formulatory agents such as suspending, stabilizing and/or dispersing agents. In another embodiment, the pharmaceutical composition does not comprise an adjuvant or any other substance added to enhance the immune response stimulated by the peptide.

In addition to the formulations described previously, the active agents can also be formulated as a depot preparation. Such long acting formulations can be administered by implantation or transcutaneous delivery (for example subcutaneously or intramuscularly), intramuscular injection or use of a transdermal patch. Thus, for example, the agents can be formulated with suitable polymeric or hydrophobic materials (for example as an emulsion in an acceptable oil) or ion exchange resins, or as sparingly soluble derivatives, for example, as a sparingly soluble salt.

In some cases, pharmaceutical compositions comprising one or more agents exert local and regional effects when administered topically or injected at or near particular sites of infection. Direct topical application, e.g., of a viscous liquid, solution, suspension, dimethylsulfoxide (DMSO)-based solutions, liposomal formulations, gel, jelly, cream, lotion, ointment, suppository, foam, or aerosol spray, can be used for local administration, to produce for example local and/or regional effects. Pharmaceutically appropriate vehicles for such formulation include, for example, lower aliphatic alcohols, polyglycols (e.g., glycerol or polyethylene glycol), esters of fatty acids, oils, fats, silicones, and the like. Such preparations can also include preservatives (e.g., p-hydroxybenzoic acid esters) and/or antioxidants (e.g., ascorbic acid and tocopherol). See also Dermatological Formulations: Percutaneous absorption, Barry (Ed.), Marcel Dekker Incl, 1983. In another embodiment, local/topical formulations comprising a transporter, carrier, or ion channel inhibitor are used to treat epidermal or mucosal viral infections.

Pharmaceutical compositions can contain adjuvants such as hydrophilic or lipophilic gelling agents, hydrophilic or lipophilic active agents, preserving agents, antioxidants, solvents, fragrances, fillers, sunscreens, odor-absorbers and dyestuffs. The amounts of these various adjuvants are those conventionally used in the fields considered and, for example, are from about 0.01% to about 20% of the total weight of the composition. Depending on their nature, these adjuvants can be introduced into the fatty phase, into the aqueous phase and/or into the lipid vesicles.

Methods of Treatment

Also provided herein are methods of treating a subject with a disease, disorder or condition. A method of treatment can comprise administering a composition or pharmaceutical composition disclosed herein to a subject with a disease, disorder or condition.

The present disclosure provides methods of treatment comprising an immunogenic therapy. Methods of treatment for a disease (such as cancer or a viral infection) are provided. A method can comprise administering to a subject an effective amount of a composition comprising an immunogenic antigen specific T cells according to the methods provided herein. In some embodiments, the antigen comprises a viral antigen. In some embodiments, the antigen comprises a tumor antigen.

Non-limiting examples of therapeutics that can be prepared include a peptide-based therapy, a nucleic acid-based therapy, an antibody based therapy, a T cell based therapy, and an antigen-presenting cell based therapy.

In some other aspects, provided here is use of a composition or pharmaceutical composition for the manufacture of a medicament for use in therapy. In some embodiments, a method of treatment comprises administering to a subject an effective amount of T cells specifically recognizing an immunogenic neoantigen peptide. In some embodiments, a method of treatment comprises administering to a subject an effective amount of a TCR that specifically recognizes an immunogenic neoantigen peptide, such as a TCR expressed in a T cell.

In some embodiments, the cancer is selected from the group consisting of carcinoma, lymphoma, blastoma, sarcoma, leukemia, squamous cell cancer, lung cancer (including small cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, melanoma, endometrial or uterine carcinoma, salivary gland carcinoma, kidney or renal cancer, liver cancer, prostate cancer, vulval cancer, thyroid cancer, hepatic carcinoma, head and neck cancer, colorectal cancer, rectal cancer, soft-tissue sarcoma, Kaposi's sarcoma, B-cell lymphoma (including low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's macroglobulinemia), chronic lymphocytic leukemia (CLL), acute lymphoblastic leukemia (ALL), myeloma, Hairy cell leukemia, chronic myeloblasts leukemia, and post-transplant lymphoproliferative disorder (PTLD), abnormal vascular proliferation associated with phakomatoses, edema, Meigs' syndrome, and combinations thereof.

The methods described herein are particularly useful in the personalized medicine context, where immunogenic neoantigen peptides identified according to the methods described herein are used to develop therapeutics (such as vaccines or therapeutic antibodies) for the same individual. Thus, a method of treating a disease in a subject can comprise identifying an immunogenic neoantigen peptide in a subject according to the methods described herein; and synthesizing the peptide (or a precursor thereof); and manufacturing T cells specific for identified neoantigens; and administering the neoantigen specific T cells to the subject.

The agents and compositions provided herein may be used alone or in combination with conventional therapeutic regimens such as surgery, irradiation, chemotherapy and/or bone marrow transplantation (autologous, syngeneic, allogeneic or unrelated). A set of tumor antigens can be identified using the methods described herein and are useful, e.g., in a large fraction of cancer patients.

In some embodiments, at least one or more chemotherapeutic agents may be administered in addition to the composition comprising an immunogenic therapy. In some embodiments, the one or more chemotherapeutic agents may belong to different classes of chemotherapeutic agents.

In practicing the methods of treatment or use provided herein, therapeutically-effective amounts of the therapeutic agents can be administered to a subject having a disease or condition. A therapeutically-effective amount can vary widely depending on the severity of the disease, the age and relative health of the subject, the potency of the compounds used, and other factors.

Subjects can be, for example, mammal, humans, pregnant women, elderly adults, adults, adolescents, pre-adolescents, children, toddlers, infants, newborn, or neonates. A subject can be a patient. In some cases, a subject can be a human. In some cases, a subject can be a child (i.e. a young human being below the age of puberty). In some cases, a subject can be an infant. In some cases, the subject can be a formula-fed infant. In some cases, a subject can be an individual enrolled in a clinical study. In some cases, a subject can be a laboratory animal, for example, a mammal, or a rodent. In some cases, the subject can be a mouse. In some cases, the subject can be an obese or overweight subject.

In some embodiments, the subject has previously been treated with one or more different cancer treatment modalities. In some embodiments, the subject has previously been treated with one or more of radiotherapy, chemotherapy, or immunotherapy. In some embodiments, the subject has been treated with one, two, three, four, or five lines of prior therapy. In some embodiments, the prior therapy is a cytotoxic therapy.

In some embodiments, the disease or condition that can be treated with the methods disclosed herein is cancer. Cancer is an abnormal growth of cells which tend to proliferate in an uncontrolled way and, in some cases, to metastasize (spread). A tumor can be cancerous or benign. A benign tumor means the tumor can grow but does not spread. A cancerous tumor is malignant, meaning it can grow and spread to other parts of the body. If a cancer spreads (metastasizes), the new tumor bears the same name as the original (primary) tumor.

The methods of the disclosure can be used to treat any type of cancer known in the art. Non-limiting examples of cancers to be treated by the methods of the present disclosure can include melanoma (e.g., metastatic malignant melanoma), renal cancer (e.g., clear cell carcinoma), prostate cancer (e.g., hormone refractory prostate adenocarcinoma), pancreatic adenocarcinoma, breast cancer, colon cancer, lung cancer (e.g., non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies.

Additionally, the disease or condition provided herein includes refractory or recurrent malignancies whose growth may be inhibited using the methods of treatment of the present disclosure. In some embodiments, a cancer to be treated by the methods of treatment of the present disclosure is selected from the group consisting of carcinoma, squamous carcinoma, adenocarcinoma, sarcomata, endometrial cancer, breast cancer, ovarian cancer, cervical cancer, fallopian tube cancer, primary peritoneal cancer, colon cancer, colorectal cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, head and neck cancer, glioblastoma, glioma, squamous cell carcinoma of the head and neck, prostate cancer, pancreatic cancer, mesothelioma, sarcoma, hematological cancer, leukemia, lymphoma, neuroma, and combinations thereof. In some embodiments, a cancer to be treated by the methods of the present disclosure include, for example, carcinoma, squamous carcinoma (for example, cervical canal, eyelid, tunica conjunctiva, vagina, lung, oral cavity, skin, urinary bladder, tongue, larynx, and gullet), and adenocarcinoma (for example, prostate, small intestine, endometrium, cervical canal, large intestine, lung, pancreas, gullet, rectum, uterus, stomach, mammary gland, and ovary). In some embodiments, a cancer to be treated by the methods of the present disclosure further include sarcomata (for example, myogenic sarcoma), leukosis, neuroma, melanoma, and lymphoma. In some embodiments, a cancer to be treated by the methods of the present disclosure is breast cancer. In some embodiments, a cancer to be treated by the methods of treatment of the present disclosure is triple negative breast cancer (TNBC). In some embodiments, a cancer to be treated by the methods of treatment of the present disclosure is ovarian cancer. In some embodiments, a cancer to be treated by the methods of treatment of the present disclosure is colorectal cancer.

In some embodiments, a patient or population of patients to be treated with a pharmaceutical composition of the present disclosure have a solid tumor. In some embodiments, a solid tumor is a melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma. In some embodiments, a patient or population of patients to be treated with a pharmaceutical composition of the present disclosure have a hematological cancer. In some embodiments, the patient has a hematological cancer such as Diffuse large B cell lymphoma ("DLBCL"), Hodgkin's lymphoma ("HL"), Non-Hodgkin's lymphoma ("NHL"), Follicular lymphoma ("FL"), acute myeloid leukemia ("AML"), or Multiple myeloma ("MM"). In some embodiments, a patient or population of patients to be treated having the cancer selected from the group consisting of ovarian cancer, lung cancer and melanoma.

Specific examples of cancers that can be prevented and/or treated in accordance with present disclosure include, but are not limited to, the following: renal cancer, kidney cancer, glioblastoma multiforme, metastatic breast cancer; breast carcinoma; breast sarcoma; neurofibroma; neurofibromatosis; pediatric tumors; neuroblastoma; malignant melanoma; carcinomas of the epidermis; leukemias such as but not limited to, acute leukemia, acute lymphocytic leukemia, acute myelocytic leukemias such as myeloblastic, promyelocytic, myelomonocytic, monocytic, erythroleukemia leukemias and myclodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone cancer and connective tissue sarcomas such as but not limited to bone sarcoma, myeloma bone disease, multiple myeloma, cholesteatoma-induced bone osteosarcoma, Paget's disease of bone, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangio sarcoma, neurilemmoma, rhabdomyosarcoma, and synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease (including juvenile Paget's disease) and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; cervical carcinoma; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; colorectal cancer, KRAS mutated colorectal cancer; colon carcinoma; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as KRAS-mutated non-small cell lung cancer, non-small cell lung cancer, squamous cell carcinoma (epidermoid carcinoma), adenocarcinoma, large-cell carcinoma and small-cell lung cancer; lung carcinoma; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, androgen-independent prostate cancer, androgen-dependent prostate cancer, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acrallentiginous melanoma; kidney cancers such as but not limited to renal cell cancer, adenocarcinoma, hypernephroma, fibrosarcoma, transitional cell cancer (renal pelvis and/or uterer); renal carcinoma; Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

Kits

The methods and compositions described herein can be provided in kit form together with instructions for administration. Typically the kit can include the desired neoantigen therapeutic compositions in a container, in unit dosage form and instructions for administration. Additional therapeutics, for example, cytokines, lymphokines, checkpoint inhibitors, antibodies, can also be included in the kit. Other kit components that can also be desirable include, for example, a sterile syringe, booster dosages, and other desired excipients.

Kits and articles of manufacture are also provided herein for use with one or more methods described herein. The kits can contain one or more types of immune cells. The kits can also contain reagents, peptides, and/or cells that are useful for antigen specific immune cell (e.g. neoantigen specific T cells) production as described herein. The kits can further contain adjuvants, reagents, and buffers necessary for the makeup and delivery of the antigen specific immune cells.

The kits can also include a carrier, package, or container that is compartmentalized to receive one or more containers such as vials, tubes, and the like, each of the container(s) comprising one of the separate elements, such as the polypeptides and adjuvants, to be used in a method described herein. Suitable containers include, for example, bottles, vials, syringes, and test tubes. The containers can be formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment. A kit typically includes labels listing contents and/or instructions for use, and package inserts with instructions for use. A set of instructions can also be included.

Embodiment Paragraphs

[1] A pharmaceutical composition comprising: (a) a population of immune cells from a biological sample comprising at least one antigen specific T cell comprising a T cell receptor (TCR) specific to at least one antigen peptide sequence, and (b) a pharmaceutically acceptable excipient; wherein an amount of immune cells expressing CD14 and/or CD25 in the population is proportionally different from an amount of immune cells expressing CD14 and/or CD25 in the biological sample.

[2] A composition comprising a population of immune cells from a biological sample, wherein an amount of immune cells expressing CD14 and CD25 in the population is proportionally less than an amount of immune cells expressing CD14 and CD25 in the biological sample.

[3] A pharmaceutical composition comprising (a) a population of immune cells comprising T cells from a biological sample, wherein the T cells comprise at least one antigen specific T cell that is an APC-stimulated T cell and comprises a T cell receptor (TCR) specific to at least one antigen peptide sequence, wherein the APC is a FLT3L-stimulated APC; and (b) a pharmaceutically acceptable excipient.

[4] The composition of paragraph [1], wherein the at least one antigen specific T cell comprises at least one APC-stimulated T cell.

[5] The composition of any one of paragraphs [1], [3] and [4], wherein the amount of immune cells expressing CD14 and/or CD25 in the population is proportionally less than the amount of immune cells expressing CD14 and/or CD25 in the biological sample.

[6] The composition of any one of paragraphs [1], [3] and [4], wherein the amount of immune cells expressing CD14 and/or CD25 in the population is proportionally more than the amount of immune cells expressing CD14 and/or CD25 in the biological sample.

[7] The composition any one of paragraphs [1]-[6], wherein the biological sample is from a subject.

[8] The composition of paragraph [7], wherein the subject is a human.

[9] The composition of paragraph [7] or [8], wherein the subject has a disease or disorder.

[10] The composition of paragraph [9], wherein the disease or disorder is cancer.

[11] The composition of paragraph [10], wherein the cancer is selected from the group consisting of ovarian cancer, lung cancer and melanoma.

[12] The composition of any one of paragraphs [1]-[11], wherein the at least one antigen specific T cell comprises at least one CD4+ T cell.

[13] The composition of any one of paragraphs [1]-[12], wherein the at least one antigen specific T cell comprises at least one CD8+ T cell.

[14] The composition of any one of paragraphs [1]-[13], wherein the at least one antigen specific T cell comprises at least one CD4 enriched T cell.

[15] The composition of any one of paragraphs [1]-[14], wherein the at least one antigen specific T cell comprises at least one CD8 enriched T cell.

[16] The composition of any one of paragraphs [1]-[15], wherein the at least one antigen specific T cell comprises a memory T cell.

[17] The composition of any one of paragraphs [1]-[16], wherein the at least one antigen specific T cell comprises a naïve T cell.

[18] The composition of any one of paragraphs [1]-[17], wherein the at least one antigen specific T cell comprises a memory CD4+ T cell.

[19] The composition of any one of paragraphs [1]-[18], wherein the at least one antigen specific T cell comprises a naïve CD4+ T cell.

[20] The composition of any one of paragraphs [1]-[19], wherein the at least one antigen specific T cell comprises a memory CD8+ T cell.

[21] The composition of any one of paragraphs [1]-[20], wherein the at least one antigen specific T cell comprises a naïve CD8+ T cell.

[22] The composition of any one of paragraphs [1]-[21], wherein the at least one antigen peptide sequence comprises a mutation selected from (A) a point mutation, (B) a splice-site mutation, (C) a frameshift mutation, (D) a read-through mutation, (E) a gene-fusion mutation, and combinations thereof.

[23] The composition of any one of paragraphs [1]-[22], wherein the at least one antigen peptide sequence binds to the HLA protein of a subject with a greater affinity than a corresponding wild-type peptide.

[24] The composition of any one of paragraphs [1]-[23], wherein the at least one antigen peptide sequence binds to the HLA protein of a subject with a KD or an IC50 of less than 500 nM, 250 nM, 150 nM, 100 nM, 50 nM, 25 nM or 10 nM.

[25] The composition of any one of paragraphs [1]-[24], wherein each of the at least one antigen peptide sequence binds to a protein encoded by an HLA allele expressed by a subject.

[26] The composition of any one of paragraphs [1]-[25], wherein the TCR binds to a peptide-HLA complex with a KD or an IC50 of less than 500 nM, 250 nM, 150 nM, 100 nM, 50 nM, 25 nM or 10 nM.

[27] The composition of any one of paragraphs [1]-[26], wherein each of the at least one antigen peptide sequence comprises a mutation that is not present in non-cancer cells of a subject.

[28] The composition of any one of paragraphs [1]-[27], wherein each of the at least one antigen peptide sequences is encoded by a gene or an expressed gene of a subject's cancer cells.

[29] The composition of any one of paragraphs [1]-[28], wherein one or more of the at least one antigen peptide sequence has a length of at least 8; 9; 10; 11; 12; 13; 14; 15; 16; 17; 18; 19; 20; 21; 22; 23; 24; 25; 26; 27; 28; 29; 30; 40; 50; 60; 70; 80; 90; 100; 150; 200; 250; 300; 350; 400; 450; 500; 600; 700; 800; 900; 1,000; 1,500; 2,000; 2,500; 3,000; 4,000; 5,000; 7,500; or 10,000 naturally occurring amino acids.

[30] The composition of any one of paragraphs [1]-[29], wherein one or more of the at least one antigen peptide sequence binds to a protein encoded by a class I HLA allele and has a length of from 8-12 naturally occurring amino acids.

[31] The composition of any one of paragraphs [1]-[30], wherein one or more of the at least one antigen peptide sequence binds to a protein encoded by a class II HLA allele and has a length of from 16-25 naturally occurring amino acids.

[32] The composition of any one of paragraphs [1]-[31], wherein the at least one antigen peptide sequence comprises a plurality of antigen peptide sequences.

[33] The composition of paragraph [32], wherein the plurality of antigen peptide sequences comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, 300, 350, 400, 450, or 500 antigen peptide sequences.

[34] The composition of paragraph [3]-[33], wherein the APC is one or more APC preparations.

[35] The composition of any one of paragraphs [3]-[34], wherein the APC is a mature APC.

[36] The composition of any one of paragraphs [3]-[35], wherein the APC comprises an APC loaded with one or more antigen peptides comprising one or more of the at least one antigen peptide sequence.

[37] The composition of any one of paragraphs [3]-[36], wherein the APC is an autologous APC, an allogenic APC, or an artificial APC.

[38] The composition of any one of paragraphs [3]-[37], wherein the APC comprises a dendritic cell (DC).

[39] The composition of any one of paragraphs [4]-[38], wherein the APC is derived from a CD14+ monocyte, or is a CD14 enriched APC, or is a CD141 enriched APC.

[40] The composition of paragraph [39], wherein the CD14+ monocyte is enriched from a biological sample from a subject comprising peripheral blood mononuclear cells (PBMCs).

[41] The composition of paragraph [39] or [40], wherein the CD14+ monocyte is stimulated with one or more cytokines or growth factors.

[42] The composition of paragraph [41], wherein the one or more cytokines or growth factors comprise GM-CSF, IL-4, FLT3L, TNF-α, IL-1β, PGE1, IL-6, IL-7, IFN-α, R848, LPS, ss-rna40, poly I:C, or a combination thereof.

[43] The composition of any one of paragraphs [39]-[42], wherein the CD14+ monocyte is from a second biological sample comprising PBMCs.

[44] The composition of paragraph [43], wherein the second biological sample is from the same subject.

[45] The composition of any one of paragraphs [1]-[44], wherein the biological sample comprises peripheral blood mononuclear cells (PBMCs).

[46] The composition of any one of paragraphs [1] and [3]-[45], wherein the at least one antigen-specific T cell is stimulated in a medium comprising IL-7, IL-15, an indoleamine 2,3-dioxygenase-1 (IDO) inhibitor, an anti-PD-1 antibody, IL-12, or a combination thereof.

[47] The composition of paragraph [46], wherein the IDO inhibitor is epacadostat, navoximod, 1-methyltryptophan, or a combination thereof.

[48] The composition of any one of paragraphs [1]-[47], wherein a percentage of the at least one antigen specific T cell in the composition is at least about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total T cells or total immune cells.

[49] The composition of any one of paragraphs [1]-[48], wherein a percentage of at least one antigen specific CD8+ T cell in the composition is at least about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4+ T cells, total CD8+ T cells, total T cells or total immune cells.

[50] The composition of any one of paragraphs [1]-[49], wherein a percentage of at least one antigen specific CD4+ T cell in the composition is at least about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4+ T cells, total CD8+ T cells, total T cells or total immune cells.

[51] The composition of any one of paragraphs [1]-[50], wherein a percentage of the at least one antigen specific T cell in the biological sample is at most about 0.00001%, 0.00005%, 0.0001%, 0.0005%, 0.001%, 0.005%, 0.01%, 0.05%, 0.1% or 0.5% of total CD4+ T cells, total CD8+ T cells, total T cells or total immune cells.

[52] The composition of any one of paragraphs [1]-[51], wherein a percentage of at least one antigen specific CD8+ T cell in the biological sample is at most about 0.00001%, 0.00005%, 0.0001%, 0.0005%, 0.001%, 0.005%, 0.01%, 0.05%, 0.1% or 0.5% of total CD4+ T cells, total CD8+ T cells, total T cells or total immune cells.

[53] The composition of any one of paragraphs [1]-[52], wherein a percentage of at least one antigen specific CD4+ T cell in the biological sample is at most about 0.00001%, 0.00005%, 0.0001%, 0.0005%, 0.001%, 0.005%, 0.01%, 0.05%, 0.1% or 0.5% of total CD4+ T cells, total CD8+ T cells, total T cells or total immune cells.

[54] The composition of any one of paragraphs [1]-[53], wherein the antigen is a neoantigen, a tumor associated antigen, an overexpressed antigen, a viral antigen, a minor histocompatibility antigen or a combination thereof.

[55] The composition of any one of paragraphs [1]-[54], wherein a number of at least one antigen specific CD8+ T cell in the composition is at least about 1×106, 2×106, 5×106, 1×107, 2×107, 5×107, 1×108, 2×108, or 5×108, antigen specific CD8+ T cells.

[56] The composition of any one of paragraphs [1]-[54], wherein a number of at least one antigen specific CD4+ T cell in the composition is at least about 1×106, 2×106, 5×106, 1×107, 2×107, 5×107, 1×108, 2×108, or 5×108, antigen specific CD4+ T cells.

[57] The composition of any one of paragraphs [1]-[56], wherein the at least one antigen specific T cell comprises a plurality of antigen specific T cells.

[58] The composition of any one of paragraphs [1]-[57], wherein an amount of immune cells expressing CD19 and/or CD16 in the population is less than an amount of immune cells expressing CD19 and/or CD16 in the biological sample.

[59] A method of treatment comprising administering the composition of any one of paragraphs [1] or [3]-[58], to a subject with a disease or disorder.

[60] Use of the composition of any one of paragraphs [1] or [3]-[58], for the manufacture of a medicament for use in therapy.

[61] A method of preparing at least one antigen specific T cell comprising a T cell receptor (TCR) specific to at least one antigen peptide sequence, the method comprising incubating an APC with a population of immune cells from a biological sample depleted of cells expressing CD14 and/or CD25.

[62] A method of preparing at least one antigen specific T cell comprising a T cell receptor (TCR) specific to at least one antigen peptide sequence, the method comprising incubating a FMS-like tyrosine kinase 3 receptor ligand (FLT3L)-stimulated APC with a population of immune cells from a biological sample.

[63] A method of preparing a pharmaceutical composition comprising at least one antigen specific T cell comprising a T cell receptor (TCR) specific to at least one antigen peptide sequence, the method comprising: (a) incubating FMS-like tyrosine kinase 3 receptor ligand (FLT3L) with a population of immune cells from a biological sample for a first time period; and (b) thereafter incubating at least one T cell of the biological sample with an APC.

[64] A method of preparing at least one antigen specific T cell comprising a T cell receptor (TCR) specific to at least one antigen peptide sequence, the method comprising incubating a population of immune cells from a biological sample with one or more APC preparations for one or more separate time periods of less than 28 days from incubating the population of immune cells with a first APC preparation of the one or more APC preparations, wherein at least one antigen specific memory T cell is expanded, or at least one antigen specific naïve T cell is induced.

[65] A method of preparing at least one antigen specific T cell comprising a T cell receptor (TCR) specific to at least one antigen peptide sequence, the method comprising incubating a population of immune cells from a biological sample with 3 or less APC preparations for 3 or less separate time periods, wherein at least one antigen specific memory T cell is expanded or at least one antigen specific naïve T cell is induced.

[66] The method of any one of paragraphs [62]-[65], wherein the population of immune cells is from a biological sample depleted of CD14 and/or CD25 expressing cells.

[67] The method of paragraph [61] or [66], wherein the biological sample is further depleted of CD19 expressing cells.

[68] The method of paragraph [61] or [63], wherein the APC is a FLT3L-stimulated APC.

[69] The method of any one of paragraphs [64]-[67], wherein incubating the population of immune cells is performed in a medium containing IL-7, IL-15, or a combination thereof.

[70] The method of paragraph [69], wherein the medium further comprises an indoleamine 2,3-dioxygenase-1 (IDO) inhibitor, an anti-PD-1 antibody, IL-12, or a combination thereof.

[71] The method of paragraph [70], wherein the IDO inhibitor is epacadostat, navoximod, 1-methyltryptophan, or a combination thereof.

[72] The method of any one of paragraphs [64]-[71], wherein at least one of the APC preparations comprises a FLT3L-stimulated APC.

[73] The method of any one of paragraphs [64]-[71], wherein at least two of the APC preparations comprise a FLT3L-stimulated APC.

[74] The method of any one of paragraphs [64]-[71], wherein at least three of the APC preparations comprise a FLT3L-stimulated APC.

[75] The method of any one of paragraphs [64]-[71], wherein each of the APC preparations comprises a FLT3L-stimulated APC.

[76] The method of any one of paragraphs [61]-[63], wherein the APC comprises one or more APC preparations.

[77] The method of any one of paragraphs [61]-[76], wherein the one or more APC preparations comprise 3 or less APC preparations.

[78] The method of any one of paragraphs [64]-[77], wherein the one or more APC preparations are incubated with the immune cells sequentially within one or more separate time periods.

[79] The method of any one of paragraphs [61]-[78], wherein at least one of the one or more APC preparations are APCs from the biological sample.

[80] The method of any one of paragraphs [61]-[79], wherein the population of immune cells comprises the APC or at least one of the one or more APC preparations.

[81] The method of any one of paragraphs [61]-[79], wherein the population of immune cells does not comprise the APC, the population of immune cells does not comprise one of the one or more APC preparations.

[82] The method of any one of paragraphs [61]-[81], wherein the method comprises incubating FLT3L and at least one peptide with a population of immune cells from a biological sample, wherein the FLT3L is incubated with the population of immune cells for a first time period and wherein the at least one peptide is incubated with the population of immune cells for a first peptide stimulation time period, thereby obtaining a first stimulated T cell sample, wherein the population of immune cells comprises at least one T cell and at least one APC.

[83] The method of paragraphs [82], wherein the method comprises incubating FLT3L and at least one peptide with at least one APC, wherein the FLT3L is incubated with the at least one APC for a second time period and wherein the at least one peptide is incubated with the at least one APC for a second peptide stimulation time period, thereby obtaining a first matured APC peptide loaded sample; and incubating the first matured APC peptide loaded sample with the first stimulated T cell sample, thereby obtaining a second stimulated T cell sample.

[84] The method of paragraphs [83], wherein the method comprises incubating FLT3L and at least one peptide with at least one APC, wherein the FLT3L is incubated with the at least one APC for a third time period and wherein the at least one peptide is incubated with the at least one APC for a third peptide stimulation time period, thereby obtaining a second matured APC peptide loaded sample; and incubating the second matured APC peptide loaded sample with the second stimulated T cell sample, thereby obtaining a third stimulated T cell sample.

[85] The method of any one of paragraphs [61]-[84], wherein the biological sample is from a subject.

[86] The method of paragraph [85], wherein the subject is a human.

[87] The method of paragraph [85] or [86], wherein the subject has a disease or disorder.

[88] The method of paragraph [87], wherein the disease or disorder is cancer.

[89] The method of paragraph [88], wherein the cancer is selected from the group consisting of ovarian cancer, lung cancer and melanoma.

[90] The method of any one of paragraphs [61]-[89], wherein the at least one antigen specific T cell comprises at least one CD4+ T cell.

[91] The method of any one of paragraphs [61]-[90], wherein the at least one antigen specific T cell comprises at least one CD8+ T cell.

[92] The method of any one of paragraphs [61]-[91], wherein at least one antigen specific T cell comprises at least one CD4 enriched T cell.

[93] The method of any one of paragraphs [61]-[92], wherein at least one antigen specific T cell comprises at least one CD8 enriched T cell.

[94] The method of any one of paragraphs [61]-[93], wherein the at least one antigen specific T cell comprises at least one memory T cell.

[95] The method of any one of paragraphs [61]-[94], wherein the at least one antigen specific T cell comprises at least one naïve T cell.

[96] The method of any one of paragraphs [61]-[95], wherein the at least one antigen specific T cell comprises at least one memory CD4+ T cell.

[97] The method of any one of paragraphs [61]-[96], wherein the at least one antigen specific T cell comprises at least one naïve CD4+ T cell.

[98] The method of any one of paragraphs [61]-[97], wherein the at least one antigen specific T cell comprises at least one memory CD8+ T cell.

[99] The method of any one of paragraphs [61]-[98], wherein the at least one antigen specific T cell comprises at least one naïve CD8+ T cell.

[100] The method of any one of paragraphs [61]-[99], wherein the at least one antigen peptide sequence comprises a mutation selected from (A) a point mutation, (B) a splice-site mutation, (C) a frameshift mutation, (D) a read-through mutation, (E) a gene-fusion mutation, and combinations thereof.

[101] The method of any one of paragraphs [61]-[100], wherein the at least one antigen peptide sequence comprises a point mutation and binds to the HLA protein of a subject with a greater affinity than a corresponding wild-type peptide.

[102] The method of any one of paragraphs [61]-[101], wherein the at least one antigen peptide sequence binds to the HLA protein of a subject with an IC50 less than 500 nM, 250 nM, 150 nM, 100 nM, 50 nM, 25 nM or 10 nM.

[103] The method of any one of paragraphs [61]-[102], wherein each of the at least one antigen peptide sequence binds to a protein encoded by an HLA allele expressed by a subject.

[104] The method of any one of paragraphs [61]-[103], wherein the TCR binds to a peptide-HLA complex with an KD of less than 500 nM, 250 nM, 150 nM, 100 nM, 50 nM, 25 nM or 10 nM.

[105] The method of any one of paragraphs [61]-[104], wherein each of the at least one antigen peptide sequences comprises a mutation that is not present in non-cancer cells of a subject.

[106] The method of any one of paragraphs [61]-[105], wherein each of the at least one antigen peptide sequences is encoded by gene or an expressed gene of a subject's cancer cells.

[107] The method of any one of paragraphs [61]-[106], wherein one or more of the at least one antigen peptide sequence has a length of at least 8; 9; 10; 11; 12; 13; 14; 15; 16; 17; 18; 19; 20; 21; 22; 23; 24; 25; 26; 27; 28; 29; 30; 40; 50; 60; 70; 80; 90; 100; 150; 200; 250; 300; 350; 400; 450; 500; 600; 700; 800; 900; 1,000; 1,500; 2,000; 2,500; 3,000; 4,000; 5,000; 7,500; or 10,000 naturally occurring amino acids.

[108] The method of any one of paragraphs [61]-[107], wherein one or more of the at least one antigen peptide sequence binds to a protein encoded by a class I HLA allele and has a length of from 8-12 naturally occurring amino acids.

[109] The method of any one of paragraphs [61]-[108], wherein one or more of the at least one antigen peptide sequence binds to a protein encoded by a class II HLA allele and has a length of from 16-25 naturally occurring amino acids.

[110] The method of any one of paragraphs [61]-[109], wherein the at least one antigen peptide sequence comprises a plurality of antigen peptide sequences.

[111] The method of paragraph [110], wherein the plurality of antigen peptide sequences comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, 300, 350, 400, 450, or 500 antigen peptide sequences.

[112] The method of any one of paragraphs [61]-[111], wherein the APC or an APC of the APC preparations comprises an APC loaded with one or more antigen peptides comprising one or more of the at least one antigen peptide sequence.

[113] The method of any one of paragraphs [61]-[112], wherein the APC or an APC of the APC preparations is an autologous APC or an allogenic APC.

[114] The method of any one of paragraphs [61]-[113], wherein the APC or an APC of the APC preparations comprises a dendritic cell (DC).

[115] The method of paragraph [114], wherein the DC is a CD141+DC.

[116] The method of any one of paragraphs [61]-[114], wherein the method comprises depleting cells expressing CD14 and/or CD25 from the biological sample.

[117] The method of paragraph [116], wherein the method further comprises depleting cells expressing CD19 from the biological sample.

[118] The method of paragraph [116] or [116], wherein depleting cells expressing CD14 or CD25 or CD19 comprises binding a CD14 or CD25 or CD19 binding agent to an APC or an APC of the APC preparations.

[119] The method of paragraph [118], wherein the CD14 or CD25 or CD19 binding agent is biotinylated.

[120] The method of paragraph [118] or [119], wherein depleting cells expressing CD14 or CD25 or CD19 further comprises binding an anti-biotin reagent on a solid support to the CD14 or CD25 or CD19 binding agent.

[121] The method of any one of paragraphs [118]-[120], wherein the CD14 or CD25 or CD19 binding agent is attached to a solid support.

[122] The method of any one of paragraphs [61]-[121], wherein the APC of any one of paragraphs [61]-[63] or [66]-[121], or an APC of the APC preparations of any one of paragraphs [64]-[121], is derived from a CD14+ monocyte, or is a CD14 enriched APC, or is a CD141 enriched APC.

[123] The method of any one of paragraphs [61]-[122], wherein the APC of any one of paragraphs [61]-[63] or [66]-[122], or an APC of the APC preparations of any one of paragraphs [64]-[122], is enriched from a biological sample.

[124] The method of any one of paragraphs [61]-[123], wherein the APC of any one of paragraphs [61]-[63] or [66]-[123], or an APC of the APC preparations of any one of paragraphs [64]-[123], is stimulated with one or more cytokines or growth factors.

[125] The method of paragraph [124], wherein the one or more cytokines or growth factors comprise GM-CSF, IL-4, FLT3L, TNF-α, IL-1β, PGE1, IL-6, IL-7, IFN-α, R848, LPS, ss-rna40, poly I:C, or a combination thereof.

[126] The method of any one of paragraphs [61]-[125], wherein the APC of any one of paragraphs [61]-[63] or [66]-[125], or an APC of the APC preparations of any one of paragraphs [64]-[125], is from a second biological sample.

[127] The method of paragraph [126], wherein the second biological sample is from the same subject.

[128] The method of any one of paragraphs [61]-[127], wherein the biological sample comprises peripheral blood mononuclear cells (PBMCs).

[129] The method of any one of paragraphs [61]-[128], wherein a percentage of the at least one antigen specific T cell is at least about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4+ T cells, total CD8+ T cells, total T cells or total immune cells.

[130] The method of any one of paragraphs [61]-[129], wherein a percentage of at least one antigen specific CD8+ T cell is at least about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4+ T cells, total CD8+ T cells, total T cells or total immune cells.

[131] The method of any one of paragraphs [61]-[130], wherein a percentage of at least one antigen specific CD4+ T cell is at least about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90% or 95% of total CD4+ T cells, total CD8+ T cells, total T cells or total immune cells.

[132] The method of any one of paragraphs [61]-[131], wherein a percentage of the at least one antigen specific T cell in the biological sample is at most about 0.00001%, 0.00005%, 0.0001%, 0.0005%, 0.001%, 0.005%, 0.01%, 0.05%, 0.1% or 0.5% of total CD4+ T cells, total CD8+ T cells, total T cells or total immune cells.

[133] The method of any one of paragraphs [61]-[132], wherein a percentage of at least one antigen specific CD8+ T cell in the biological sample is at most about 0.00001%, 0.00005%, 0.0001%, 0.0005%, 0.001%, 0.005%, 0.01%, 0.05%, 0.1% or 0.5% of total CD4+ T cells, total CD8+ T cells, total T cells or total immune cells.

[134] The method of any one of paragraphs [61]-[133], wherein a percentage of at least one antigen specific CD4+ T cell in the biological sample is at most about 0.00001%, 0.00005%, 0.0001%, 0.0005%, 0.001%, 0.005%, 0.01%, 0.05%, 0.1% or 0.5% of total CD4+ T cells, total CD8+ T cells, total T cells or total immune cells.

[135] The method of any one of paragraphs [61]-[134], wherein the method further comprises administering one or more of the at least one antigen specific T cell to a subject.

[136] The method of any one of paragraphs [61]-[135], wherein a total time period of the separate time periods is less than 28 days.

[137] The method of any one of paragraphs [61]-[136], wherein incubating comprises incubating a first APC preparation of the APC preparations to the T cells for more than 7 days.

[138] The method of any one of paragraphs [61]-[137], wherein incubating comprises incubating a first APC preparation of the APC preparations to the T cells for more than 7, 8, 9, 10, 11, 12, 13, 14, 15, 16, 17, 18, 19, or 20 days.

[139] The method of any one of paragraphs [61]-[138], wherein the biological sample is freshly obtained from a subject or is a frozen sample.

[140] The method of any one of paragraphs [61]-[139], wherein the method comprises incubating the APC or one or more of the APC preparations with a first medium comprising at least one cytokine or growth factor for a first time period.

[141] The method of paragraph [140], wherein the at least one cytokine or growth factor comprises GM-CSF, IL-4, FLT3L, TNF-α, IL-1β, PGE1, IL-6, IL-7, IFN-α, R848, LPS, ss-rna40, poly I:C, or any combination thereof.

[142] The method of paragraph [140] or [141], wherein the method comprises incubating one or more of the APC preparations with at least one peptide for a second time period.

[143] The method of any one paragraphs [140]-[142], wherein the method comprises incubating the APC of any one of paragraphs [61]-[63] or [66]-[142], or one or more of the APC preparations of any one of paragraphs [64]-[142], with a second medium comprising one or more cytokines or growth factors for a third time period, thereby obtaining a matured APC.

[144] The method of paragraph [143], wherein the one or more cytokines or growth factors comprises GM-CSF, IL-4, FLT3L, TNF-α, IL-1β, PGE1, IL-6, IL-7, IFN-α, R848, LPS, ss-rna40, poly I:C, or a combination thereof.

[145] The method of paragraph [143] or [144], wherein the method further comprises removing the one or more cytokines or growth factors of the second medium after the third time period and before a start of the fourth time period.

[146] The method of any one of paragraphs [61]-[145], wherein an APC of the APC preparations is stimulated with one or more cytokines or growth factors.

[147] The method of any one of paragraphs [61]-[146], wherein the antigen is a neoantigen, a tumor associated antigen, a viral antigen, a minor histocompatibility antigen or a combination thereof.

[148] The method of any one of paragraphs [61]-[147], wherein the method is performed ex vivo.

[149] The method of any one of paragraphs [61]-[148], wherein the at least one antigen specific T cell comprises a plurality of antigen specific T cells.

[150] The method of any one of paragraphs [61]-[149], wherein the method comprises obtaining a biological sample from a subject comprising at least one APC and at least one PBMC or at least on T cell.

[151] The method of any one of paragraphs [61]-[150], wherein the method comprises depleting cells expressing CD14 and/or CD25 and/or CD19 from a biological sample, thereby obtaining a CD14 and/or CD25 and/or CD19 cell depleted sample.

[152] The method of any one of paragraphs [61]-[151], wherein the method comprises incubating a CD14 and/or CD25 and/or CD19 cell depleted sample with FLT3L for a first time period.

[153] The method of any one of paragraphs [61]-[152], wherein the method comprises incubating at least one peptide with a CD14 and/or CD25 and/or CD19 cell depleted sample for a second time period, thereby obtaining a first matured APC peptide loaded sample.

[154] The method of any one of paragraphs [61]-[153], wherein the method comprises incubating the first APC peptide loaded sample with at least one T cell for a third time period, thereby obtaining a first stimulated T cell sample.

[155] The method of paragraph [154], wherein incubating the first APC peptide loaded sample with the at least one T cell is performed in the presence of IL-7, IL-15, or a combination thereof.

[156] The method of paragraph [155], wherein incubating the first APC peptide loaded sample with the at least one T cell is performed in the presence of an indoleamine 2,3-dioxygenase-1 (IDO) inhibitor, an anti-PD-1 antibody, IL-12, or a combination thereof.

[157] The method of paragraph [156], wherein the IDO inhibitor is epacadostat, navoximod, 1-Methyltryptophan, or a combination thereof.

[158] The method of any one of paragraphs [61]-[157], wherein the method comprises incubating a T cell of a first stimulated T cell sample with a FLT3L-stimulated APC of a matured APC sample for a fourth time period, thereby obtaining a second stimulated T cell sample.

[159] The method of any one of paragraphs [61]-[157], wherein the method comprises incubating a T cell of a first stimulated T cell sample with FLT3L and a second APC peptide loaded sample of a matured APC sample for a fourth time period, thereby obtaining a second stimulated T cell sample.

[160] The method of any one of paragraphs [61]-[157], wherein the method comprises incubating a T cell of a first stimulated T cell sample with FLT3L and a FLT3L-stimulated APC of a matured APC sample for a fourth time period, thereby obtaining a second stimulated T cell sample.

[161] The method of any one of paragraphs [158]-[160], wherein incubating the T cell of the first stimulated T cell sample is performed in the presence of IL-7, IL-15, or a combination thereof.

[162] The method of paragraph [161], wherein incubating the T cell of the first stimulated T cell sample is performed in the presence of an indoleamine 2,3-dioxygenase-1 (IDO) inhibitor, an anti-PD-1 antibody, IL-12, or a combination thereof.

[163] The method of paragraph [162], wherein the IDO inhibitor is epacadostat, navoximod, 1-methyltryptophan, or a combination thereof.

[164] The method of any one of paragraphs [61]-[163], wherein the method comprises incubating a T cell of a second stimulated T cell sample with a FLT3L-stimulated APC of a matured APC sample for a fifth time period, thereby obtaining a third stimulated T cell sample.

[165] The method of any one of paragraphs [61]-[163], wherein the method comprises incubating a T cell of a second stimulated T cell sample with FLT3L and a third APC peptide loaded sample of a matured APC sample for a fifth time period, thereby obtaining a third stimulated T cell sample

[166] The method of any one of paragraphs [61]-[163], wherein the method comprises incubating a T cell of a second stimulated T cell sample with FLT3L and a FLT3L-stimulated APC of a matured APC sample for a fifth time period, thereby obtaining a third stimulated T cell sample.

[167] The method of any one of paragraphs [164]-[166], wherein incubating the T cell of the second stimulated T cell sample is performed in the presence of IL-7, IL-15, or a combination thereof.

[168] The method of paragraph [167], wherein incubating the T cell of the second stimulated T cell sample is performed in the presence of an indoleamine 2,3-dioxygenase-1 (IDO) inhibitor, an anti-PD-1 antibody, IL-12, or a combination thereof.

[169] The method of paragraph [168], wherein the IDO inhibitor is epacadostat, navoximod, 1-methyltryptophan, or a combination thereof.

[170] The method of any one of paragraphs [61]-[169], wherein the one or more separate time periods, the 3 or less separate time periods, the first time period, the second time period, the third time period, the fourth time period, or the fifth time period is at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, at least 24 hours, at least 25 hours, at least 26 hours, at least 27 hours, at least 28 hours, at least 29 hours, at least 30 hours, at least 31 hours, at least 32 hours, at least 33 hours, at least 34 hours, at least 35 hours, at least 36 hours, at least 37 hours, at least 38 hours, at least 39 hours, or at least 40 hours.

[171] The method of any one of paragraphs [61]-[170], wherein the one or more separate time periods, the 3 or less separate time periods, the first time period, the second time period, the third time period, the fourth time period, or the fifth time period is from 1 to 4 hours, from 1 to 3 hours, from 1 to 2 hours, from 4 to 40 hours, from 7 to 40 hours, from 4 to 35 hours, from 4 to 32 hours, from 7 to 35 hours or from 7 to 32 hours.

[172] The method of any one of paragraphs [61]-[171], wherein the method comprises administering at least one T cell of a first or a second or a third stimulated T cell sample to a subject in need thereof.

[173] A method comprising: (a) obtaining a biological sample from a subject comprising at least one antigen presenting cell (APC); (b) enriching cells expressing CD14 from the biological sample, thereby obtaining a CD14+ cell enriched sample; (c) incubating the CD14+ cell enriched sample with at least one cytokine or growth factor for a first time period; (d) incubating at least one peptide with the CD14+ cell enriched sample of (c) for a second time period, thereby obtaining an APC peptide loaded sample; (e) incubating the APC peptide loaded sample with one or more cytokines or growth factors for a third time period, thereby obtaining a matured APC sample; (f) incubating APCs of the matured APC sample with a CD14 and/or CD25 and/or CD19 depleted sample comprising T cells for a fourth time period; (g) incubating the T cells with APCs of a matured APC sample for a fifth time period; (h) incubating the T cells with APCs of a matured APC sample for a sixth time period; and (i) administering at least one T cell of the T cells to a subject in need thereof.

[174] A method comprising: (a) obtaining a biological sample from a subject comprising at least one APC and at least one T cell; (b) depleting cells expressing CD14 and/or CD25 and/or CD19 from the biological sample, thereby obtaining a CD14 and/or CD25 and/or CD19 cell depleted sample; (c) incubating the CD14 and/or CD25 and/or CD19 cell depleted sample with FLT3L for a first time period; (d) incubating at least one peptide with the CD14 and/or CD25 and/or CD19 cell depleted sample of (c) for a second time period, thereby obtaining an APC peptide loaded sample; (e) incubating the APC peptide loaded sample with the at least one T cell for a third time period, thereby obtaining a first stimulated T cell sample; (f) incubating a T cell of the first stimulated T cell sample with an APC of a matured APC sample for a fourth time period, thereby obtaining a second stimulated T cell sample; (g) optionally, incubating a T cell of the second stimulated T cell sample with an APC of a matured APC sample for a fifth time period, thereby obtaining a third stimulated T cell sample; (h) administering at least one T cell of the first, the second or the third stimulated T cell sample to a subject in need thereof.

[175] A method comprising: (a) obtaining a biological sample from a subject comprising at least one APC and at least one T cell; (b) depleting cells expressing CD14 and/or CD25 and/or CD19 from the biological sample, thereby obtaining a CD14 and/or CD25 and/or CD19 cell depleted sample; (c) incubating the CD14 and/or CD25 and/or CD19 cell depleted sample with FLT3L for a first time period; (d) incubating at least one peptide with the CD14 and/or CD25 and/or CD19 cell depleted sample of (c) for a second time period, thereby obtaining an APC peptide loaded sample; (e) incubating the APC peptide loaded sample with the at least one T cell for a third time period, thereby obtaining a first stimulated T cell sample; (f) optionally, incubating a T cell of the first stimulated T cell sample with a FLT3L-stimulated APC of a matured APC sample for a fourth time period, thereby obtaining a second stimulated T cell sample; (g) optionally, incubating a T cell of the second stimulated T cell sample with a FLT3L-stimulated APC of a matured APC sample for a fifth time period, thereby obtaining a third stimulated T cell sample; (h) administering at least one T cell of the first, the second or the third stimulated T cell sample to a subject in need thereof.

[176] A method comprising: (a) obtaining a biological sample from a subject comprising at least one APC and at least one T cell; (b) depleting cells expressing CD14 and/or CD25 and/or CD19 from the biological sample, thereby obtaining a CD14 and/or CD25 and/or CD19 cell depleted sample; (c) incubating the CD14 and/or CD25 and/or CD19 cell depleted sample with FLT3L for a first time period; (d) incubating at least one peptide with the CD14 and/or CD25 and/or CD19 cell depleted sample of (c) for a second time period, thereby obtaining a first APC peptide loaded sample; (e) incubating the first APC peptide loaded sample with the at least one T cell for a third time period, thereby obtaining a first stimulated T cell sample; (f) optionally, incubating a T cell of the first stimulated T cell sample with FLT3L and a second APC peptide loaded sample of a matured APC sample for a fourth time period, thereby obtaining a second stimulated T cell sample; (g) optionally, incubating a T cell of the second stimulated T cell sample with FLT3L and a third APC peptide loaded sample of a matured APC sample for a fifth time period, thereby obtaining a third stimulated T cell sample; (h) administering at least one T cell of the first, the second or the third stimulated T cell sample to a subject in need thereof.

[177] A method comprising: (a) obtaining a biological sample from a subject comprising at least one APC and at least one T cell; (b) depleting cells expressing CD14 and/or CD25 and/or CD19 from the biological sample, thereby obtaining a CD14 and/or CD25 and/or CD19 cell depleted sample; (c) incubating the CD14 and/or CD25 and/or CD19 cell depleted sample with FLT3L for a first time period; (d) incubating at least one peptide with the CD14 and/or CD25 and/or CD19 cell depleted sample of (c) for a second time period, thereby obtaining a first APC peptide loaded sample; (e) incubating the first APC peptide loaded sample with the at least one T cell for a third time period, thereby obtaining a first stimulated T cell sample; (f) optionally, incubating a T cell of the first stimulated T cell sample with FLT3L and a FLT3L-stimulated APC of a matured APC sample for a fourth time period, thereby obtaining a second stimulated T cell sample; (g) optionally, incubating a T cell of the second stimulated T cell sample with FLT3L and a FLT3L-stimulated APC of a matured APC sample for a fifth time period, thereby obtaining a third stimulated T cell sample; (h) administering at least one T cell of the first, the second or the third stimulated T cell sample to a subject in need thereof.

[178] A method comprising (a) incubating FLT3L and at least one peptide with a population of immune cells from a biological sample, wherein the FLT3L is incubated with the population of immune cells for a first time period and wherein the at least one peptide is incubated with the population of immune cells for a first peptide stimulation time period, thereby obtaining a first stimulated T cell sample, wherein the population of immune cells comprises at least one T cell and at least one APC; (b) optionally, incubating FLT3L and at least one peptide with at least one APC, wherein the FLT3L is incubated with the at least one APC for a second time period and wherein the at least one peptide is incubated with the at least one APC for a second peptide stimulation time period, thereby obtaining a first matured APC peptide loaded sample; and incubating the first matured APC peptide loaded sample with the first stimulated T cell sample, thereby obtaining a second stimulated T cell sample; (c) optionally, incubating FLT3L and at least one peptide with at least one APC, wherein the FLT3L is incubated with the at least one APC for a third time period and wherein the at least one peptide is incubated with the at least one APC for a third peptide stimulation time period, thereby obtaining a second matured APC peptide loaded sample; and incubating the second matured APC peptide loaded sample with the second stimulated T cell sample, thereby obtaining a third stimulated T cell sample; and (d) administering at least one T cell of the first stimulated T cell sample, the second stimulated T cell sample or the third stimulated T cell sample to a subject in need thereof.

[179] A method comprising (a) determining expression of one or more cell markers of at least one immune cell of a stimulated immune cell sample, and (b) determining binding of the at least one immune cell of the stimulated immune cell sample to a peptide-MHC complex; wherein determining expression and determining binding are performed simultaneously.

[180] The method of paragraph [179], wherein the stimulated immune cell sample comprises a population of immune cells stimulated with APCs comprising a peptide-MHC complex.

[111] The method of paragraph [179] or [180], wherein the population of immune cells is from a biological sample.

[182] A method comprising: (a) incubating a population of immune cells from a biological sample with APCs comprising a peptide-MHC complex, thereby obtaining a stimulated immune cell sample; (b) determining expression of one or more cell markers of at least one immune cell of the stimulated immune cell sample; and (c) determining binding of the at least one immune cell of the stimulated immune cell sample to a peptide- MHC complex; wherein determining expression and determining binding are performed simultaneously.

[183] The method of any one of paragraphs [179]-[182], wherein the one or more cell markers comprise TNF-α, IFN-γ, LAMP-1, 4-1BB, IL-2, IL-17A, Granzyme B, PD-1, CD25, CD69, TIM3, LAG3, CTLA-4, CD62L, CD45RA, CD45RO, FoxP3, or any combination thereof.

[184] The method of any one of paragraphs [179]-[183], wherein determining binding of the at least one immune cell of the stimulated immune cell sample to the peptide-MHC complex comprises determining binding of the at least one immune cell of the stimulated immune cell sample to a MHC tetramer comprising the peptide and the MHC of the peptide-MHC complex.

[185] The method of any one of paragraphs [179]-[184], wherein the MHC is a class I MHC or a class II MHC.

[186] The method of any one of paragraphs [179]-[185], wherein the peptide-MHC complex comprises one or more labels.

[187] The method of any one of paragraphs [179]-[186], wherein the population of immune cells from a biological sample comprise two or more samples each comprising a population of immune cells from one or more biological samples.

[188] The method of paragraph [187], wherein the two or more samples are labeled with two or more sample labels.

[189] The method of any one of paragraphs [179]-[188], wherein determining expression and determining binding comprises fluorescent activated cell sorting (FACS).

[190] The method of any one of paragraphs [179]-[189], wherein determining expression and determining binding comprises single cell analysis.

[191] The method of any one of paragraphs [179]-[190], wherein determining expression and determining binding comprises determining a percentage of immune cells that both express the one or more cell markers and that bind to the peptide-MHC complex.

[192] The method of paragraph [186] or [187], wherein the labels comprise a fluorophore.

[193] The method of any one of paragraphs [179]-[192], wherein the population of immune cells comprises a population of immune cells representative of the population of immune cells of the composition of any one of paragraphs [1]-[58].

EXAMPLES

The present disclosure will be described in greater detail by way of the following specific examples. The following examples are offered for illustrative purposes, and are not intended to limit the invention in any manner. Those of skill in the art will readily recognize a variety of non-critical parameters that can be changed or modified to yield alternative embodiments according to the invention. All patents, patent applications, and printed publications listed herein are incorporated herein by reference in their entirety.

Summary of Examples

Examples 1 and 2 below are examples of T cell manufacturing protocols (protocol 1 and protocol 2). Schematics of the example protocols are shown in FIG. 1A and FIG. 1B. Examples 21-23 depicts the steps for preparing APCs and of these two protocols. Examples 12 and 14-16 and Tables 2-5 summarize results obtained from protocols 1 and 2. Example 13 describes parameters of the protocols that will be tested.

Examples 3-7 and 20 are examples of results of $CD4^+$ memory T cell expansion and $CD8^+$ naïve T cell inductions using protocol 1 and protocol 2. Flow cytometric analyses results are show in FIG. 2B, FIGS. 5A and B, FIG. 7, FIG. 10, and FIGS. 12-23.

Figure 25:
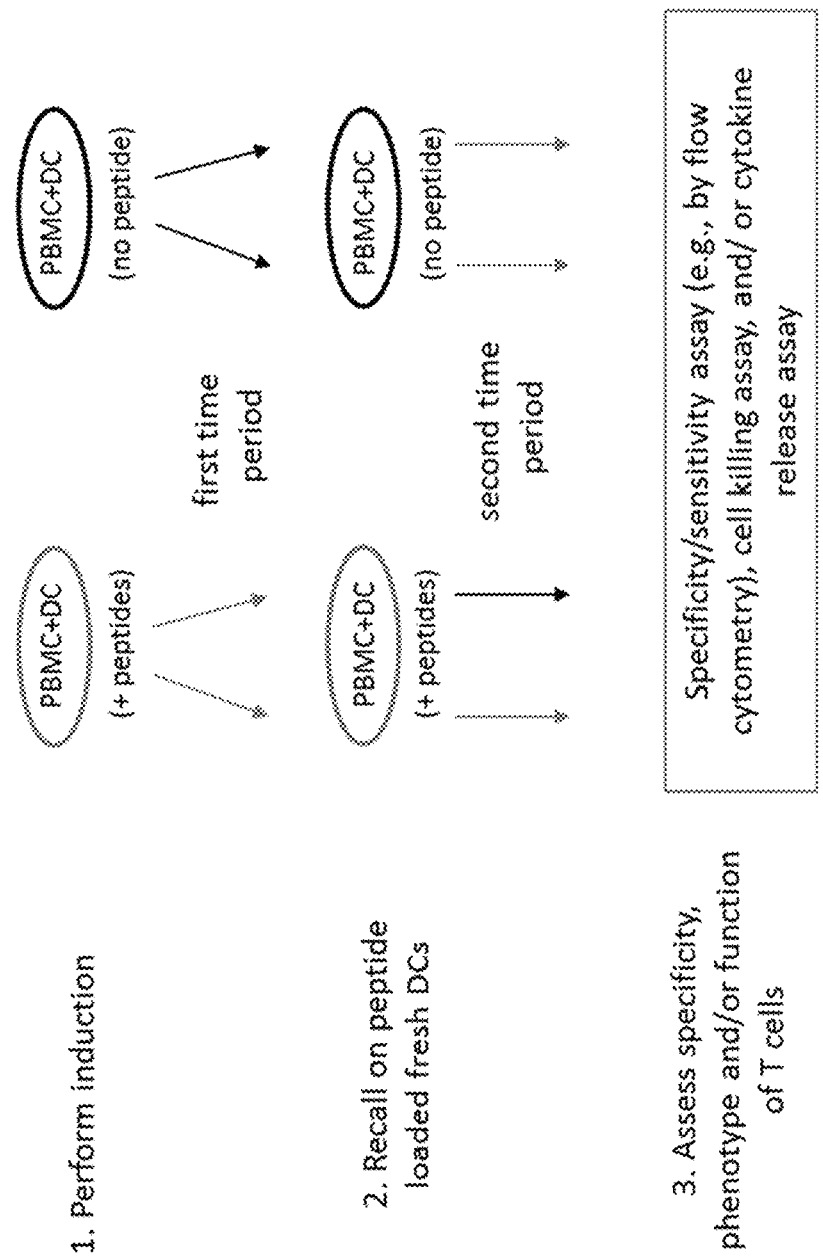
FIG. 25 depicts an example of a method to test functionality, phenotype and/or function of T cells and/or T cell responses.

Examples 8-11 and 16-19 are examples of results of assays used to assess specificity, phenotype and/or function of T cells expanded or induced using the methods described herein. FIG. 25 depicts a general overview of the T cell manufacturing process and use of these assays specificity, phenotype and/or function of the T cells.

Example 1—T Cell Manufacturing Protocol 1

This example provides an example of T cell manufacturing protocol 1 as illustrated in FIG. 1.
Materials:
  DC media (Cellgenix)
  CD14 microbeads, human, Miltenyi #130-050-201
  Cytokines and/or growth factors
  T cell media (AIM V+RPMI 1640 glutamax$^+$serum+ PenStrep)
  Peptide stocks—1 mM per peptide (HIV A02—5-10 peptides, HIV B07—5-10 peptides, DOM—4-8 peptides, PIN—6-12 peptides)

Step 1: Monocyte Isolation for DC Prep
 1. Calculate the approximate number of PBMCs to thaw based on expected DC yield for each donor.
 2. Thaw PBMCs and resuspend at ~$1\times10^6$-$1\times10^8$ cells/mL in DC media.
 3. Add benzonase (1:1000 dilution) and place in incubator with cap loosened.
 4. Perform $CD14^+$ monocyte enrichment according to manufacturer protocol.
 5. Plate enriched cells in 6-well plates at $1\times10^5$-$1\times10^7$ per well in DC media with one or more cytokines and/or growth factors selected from GM-CSF, IL-4, FLT3L, TNF-α, IL-1β, PGE1, IL-6, IL-7, IFN-α, R848, LPS, ss-rna40, and polyI:C.

Step 2: Peptide Loading and Maturation
 1. Count DCs and split the cells according to the experimental conditions in 15 mL tubes; 0.01-1 million cells per condition.
 2. Spin @ 1200 rpm for 5 min and resuspend in 50-400 μL DC medium. Add peptide(s) and place in incubator with loosened cap for 0.5-3 hrs. Volumes were calculated for peptide pools at a concentration of 1 mM per peptide. A volume of each separate pool of A02 (5 peptides) and B07 (5 peptides) was added per well for a final concentration of 0.001-100 μM per peptide.
 3. After 0.5-3 hrs add 200 μL to 1.5 mL of DC media containing maturation mix and transfer the cells to 24 well plate.

The maturation mix contains one or more cytokines selected from GM-CSF, IL-4, FLT3L, TNF-α, IL-1β, PGE1, IL-6, IL-7, IFN-α, R848, LPS, ss-rna40, and polyI:C.

Step 3: Setting Up Long Term Stimulation (LTS) Experiment
 1. Carefully remove all media from the wells of the DC plates, transferring each well to a separate well in a 24-well deepwell block.
 2. Wash each well with 0.5-3 mL T cell media and combine with DC media in the deepwell block.
 3. Add 100 μL to 2 mL T cell media to each well.

4. Spin down DCs at 1200 rpm for 5 min.
5. Remove all supernatant, resuspend DCs in 100 μL to 2 mL T cell media and transfer back into the correct wells.
6. Thaw PBMCs in T cell media and resuspend at 0.5× $10^6$-4×$10^6$ cells/mL in T cell media with IL-7 and IL-15.
7. Add 0.5-3 mL of prepared PBMCs to each well.

Step 4: Feeding LTS
Check with glucose meter if the media is yellow. If glucose remains high, feed culture with IL-7 and IL-15 to the well. If glucose is low, expand the cells to 6 well plate (4 mL/well) and supplement with IL-15 and IL-7. If glucose is very low, expand to 6 mL/well in a 6-well plate.

Step 5: Feeding LTS
Feed cultures every 1-4 days, adding fresh IL-15/IL-7 and expanding the culture volume as needed when glucose concentration becomes low.

Step 6: Re-Stimulation
Count T cells and repeat from step 3 on a new batch of peptide-loaded DCs. Freeze leftover cells for analysis.

Step 7: Feeding LTS
Feed cultures every 1-5 days.

Step 8: Re-Stimulation
Count T cells and repeat from step 3 on a new batch of peptide-loaded DCs. Freeze leftover cells for analysis.

Step 9: Feeding LTS
Feed cultures every 1-5 days.

Step 10
Count T cells and freeze for analysis.

Example 2—T Cell Manufacturing Protocol 2

This protocol can be an alternative to the protocol described in Example 1.
Example 2 provides an example T cell manufacturing protocol (protocol 2) as illustrated in FIG. 1.
Materials:
AIM V media (Invitrogen)
Media 1 (RPMI 1640 glutamax+serum+PenStrep)
Media 2 (AIM V+RPMI 1640 glutamax+serum+PenStrep)
Procedure:
Step 1: Plate 4 million PBMCs in each well of 24 well plate with one or more cytokines in Media 2. The one or more cytokines are selected from GM-CSF, IL-4, FLT3L, TNF-α, IL-1β, PGE1, IL-6, IL-7, IFN-α, R848, LPS, ss-rna40, and polyI:C.

Step 2: Peptide loading and maturation in Media 2
1. Make stock peptide pool of interest (except for no peptide condition) at 0.001-100 μM for shortmers and 0.001-100 μM for longmers final concentration in respective wells and mix.
2. Incubate for 0.5-3 hr.
3. Make stock maturation cocktail and add to each well after incubation and mix. The maturation cocktail contains one or more cytokines selected from GM-CSF, IL-4, FLT3L, TNF-α, IL-1β, PGE1, IL-6, IL-7, IFN-α, R848, LPS, ss-rna40, and polyI:C.

Step 3: Add human serum to each well at a final concentration of 2.5-20% by volume and mix.

Step 4: Carefully replace 50-90% of the media with fresh Media 1 supplemented with IL-7 and IL-15 to a final concentration of 0.005-500 ng/mL each.

Step 5: Carefully replace 50-90% of the media with fresh Media 1 supplemented with IL-7 and IL-15 to a final concentration of 0.005-500 ng/mL each every 1-5 days.

In case the wells turn orange to yellow on non-feeding days (glucose readout in case of clear media), change 25-75% of existing media with fresh Media 1 and IL-7/IL-15.

Step 6: Count and freeze (or proceed to the following steps to carry the T cell simulation to step 8 and/or step 10 of protocol 1).

During the culturing steps from step 1 to step 6, peptide-loaded DCs can be prepared in parallel according to the procedures in protocol 1 "Step 1" and "Step 2".

Count T cells and stimulate T cells with a new batch of peptide-loaded DCs. Freeze leftover cells for analysis. The T cell stimulation procedure can be carried out according to the procedures in protocol 1 "Step 3".

Step 7: Count T cells and repeat T cell stimulation procedures in protocol 1 "step 3" on a new batch of peptide-loaded DCs. Freeze leftover cells for analysis.

Step 8: Count T cells and freeze for analysis.

Example 3—$CD8^+$ T Cell Induction

PBMC samples from a human donor were used to perform antigen specific T cell induction according to protocol 1 or protocol 2. $CD8^+$ memory and naïve T cell inductions were analyzed after manufacturing T cells using different protocols. Cell samples can be taken out at different time points for analysis. pMHC multimers were used to monitor the fraction of antigen specific $CD8^+$ T cells in the induction cultures and used to detect multiple T cell responses in parallel by using combinatorial coding. FIG. 2 depicts an exemplary result showing the fraction of antigen specific $CD8^+$ memory T cells induced with long peptides or short peptides using protocol 1 (prot. 1) and protocol 2 (prot. 2). "Bulk" indicates the sample containing T cells used for induction is whole PBMC. "Treg-" indicates the sample containing T cells used for induction is PBMCs depleted of CD25 expressing cells. FIG. 3 depicts an exemplary result of a T cell response assay showing fraction of antigen specific $CD8^+$ naïve T cell responded to GAS7 peptide analyzed by flow cytometry after short term stimulation or induction (the length of the culture in this example is calculated from the beginning of the stimulation). Increase in fraction of antigen specific memory T cells and naïve PIN specific T cells can be observed after short term stimulation.

Figure 6:
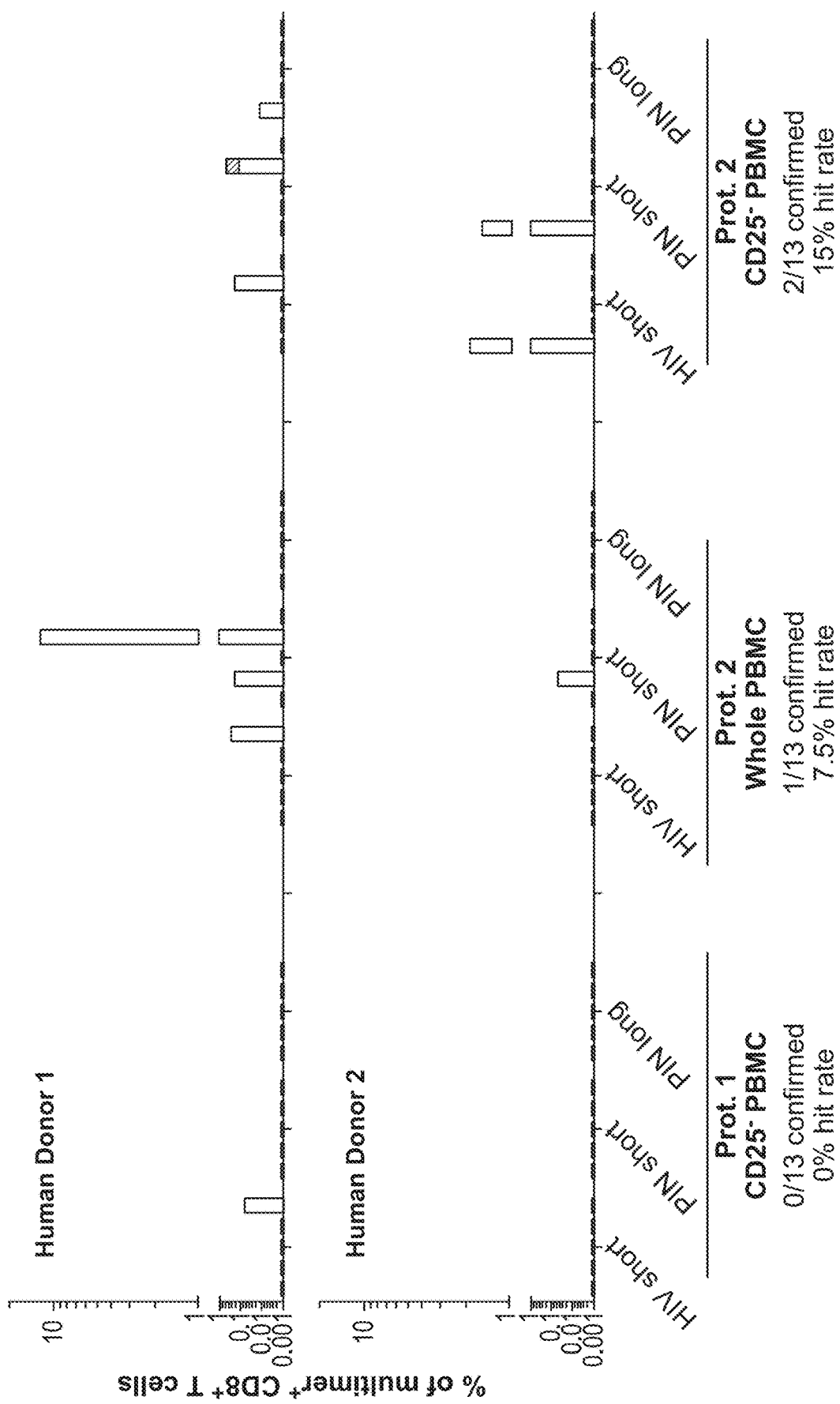
FIG. 6 depicts example results showing antigen specific CD8$^+$ T cell responses to the indicated peptides using PBMC samples from two human donors.

Example 4—$CD8^+$ T Cell Induction $CD8^+$ T cell induction were analyzed after manufacturing T cells using different protocols. The induced T cells were incubated with different antigen peptides in test wells and the fraction of T cells that responded to the peptides were analyzed by flow cytometry. pMHC multimers were used to monitor the fraction of antigen specific $CD8^+$ T cells in the induction cultures and used to detect multiple T cell responses in parallel by using combinatorial coding. Hit rate can be used to depict how responsive the T cells are to antigen peptides. The hit rate is defined as the number of positive response test wells divided by the total number of test wells. The experiment was done in duplicates, and the hit rate was confirmed in the duplicate wells. FIG. 4 depicts an example of results showing the fraction of $CD8^+$ T cells induced with HIV short peptides, previously identified neoantigen (PIN) short peptides, or PIN long peptides after induction using protocol 1 (prot. 1) and protocol 2 (prot. 2). "Whole PBMC" indicates the sample containing T cells used for induction is whole PBMC. "CD25-PBMC" indicates the sample containing T cells used for induction is depleted of $CD25^+$ cells. Both short and long term inductions are shown. FIG. 6 depicts exemplary results showing the fraction of long-term induced $CD8^+$ T cells using PBMC samples from two human donors.

Figure 10:
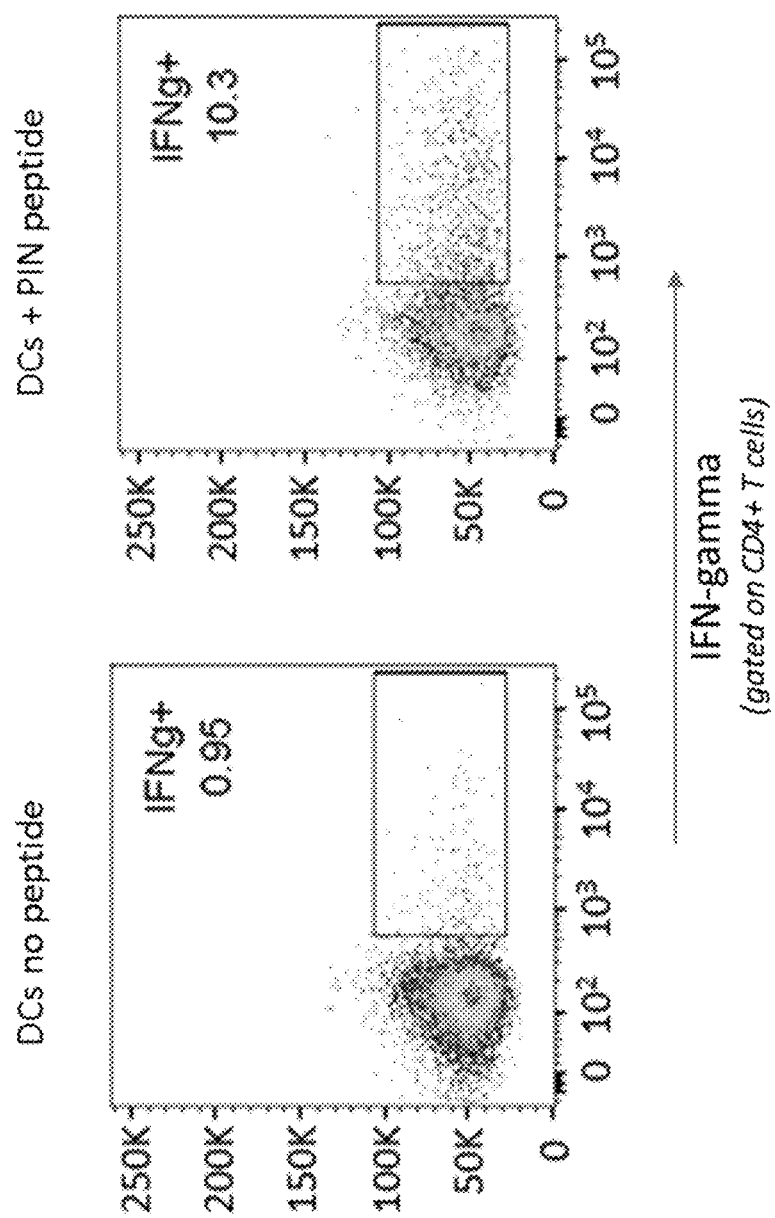
FIG. 10 depicts an example flow cytometric analysis of antigen specific CD4+ T cell responses to peptide loaded antigen presenting cells and then incubated with APCs with and without loaded PINs. The percentage of CD4+ T cells releasing IFNγ are shown.
Figure 11:
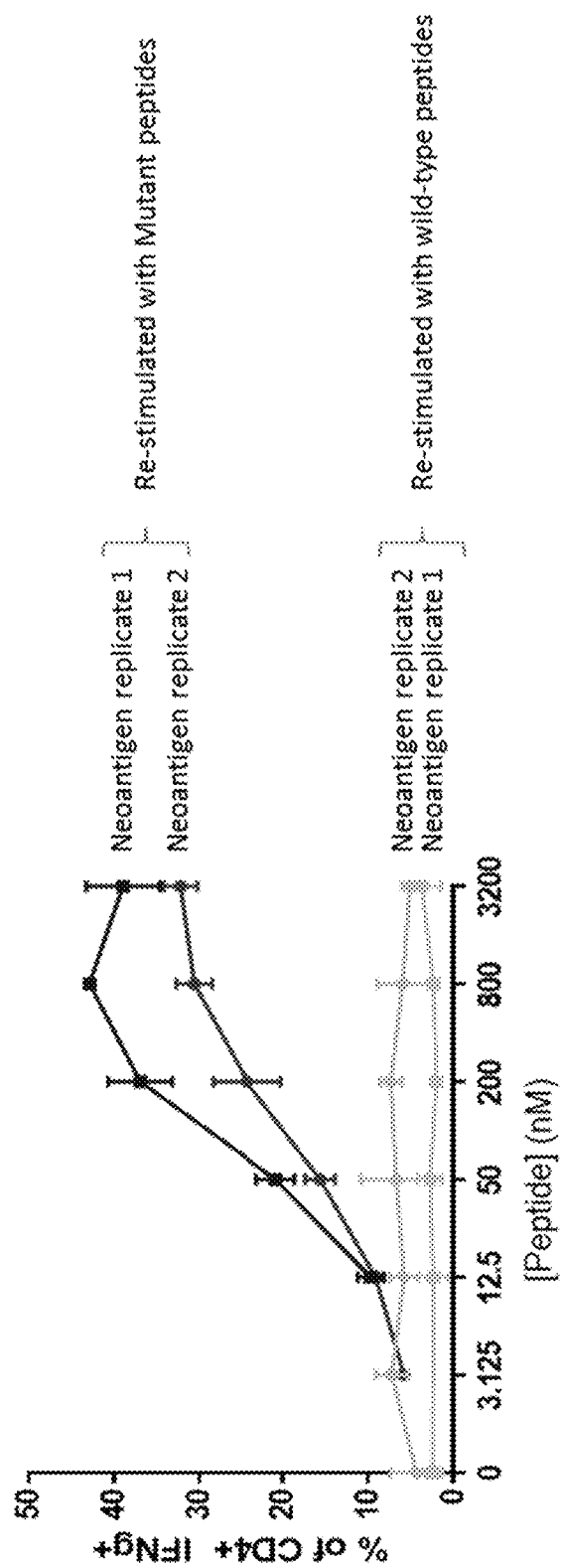
FIG. 11 depicts an example result of the percentage of antigen specific CD4+ T cells releasing IFNγ after being restimulated with mutant peptides or wild-type peptides.
Figure 12:
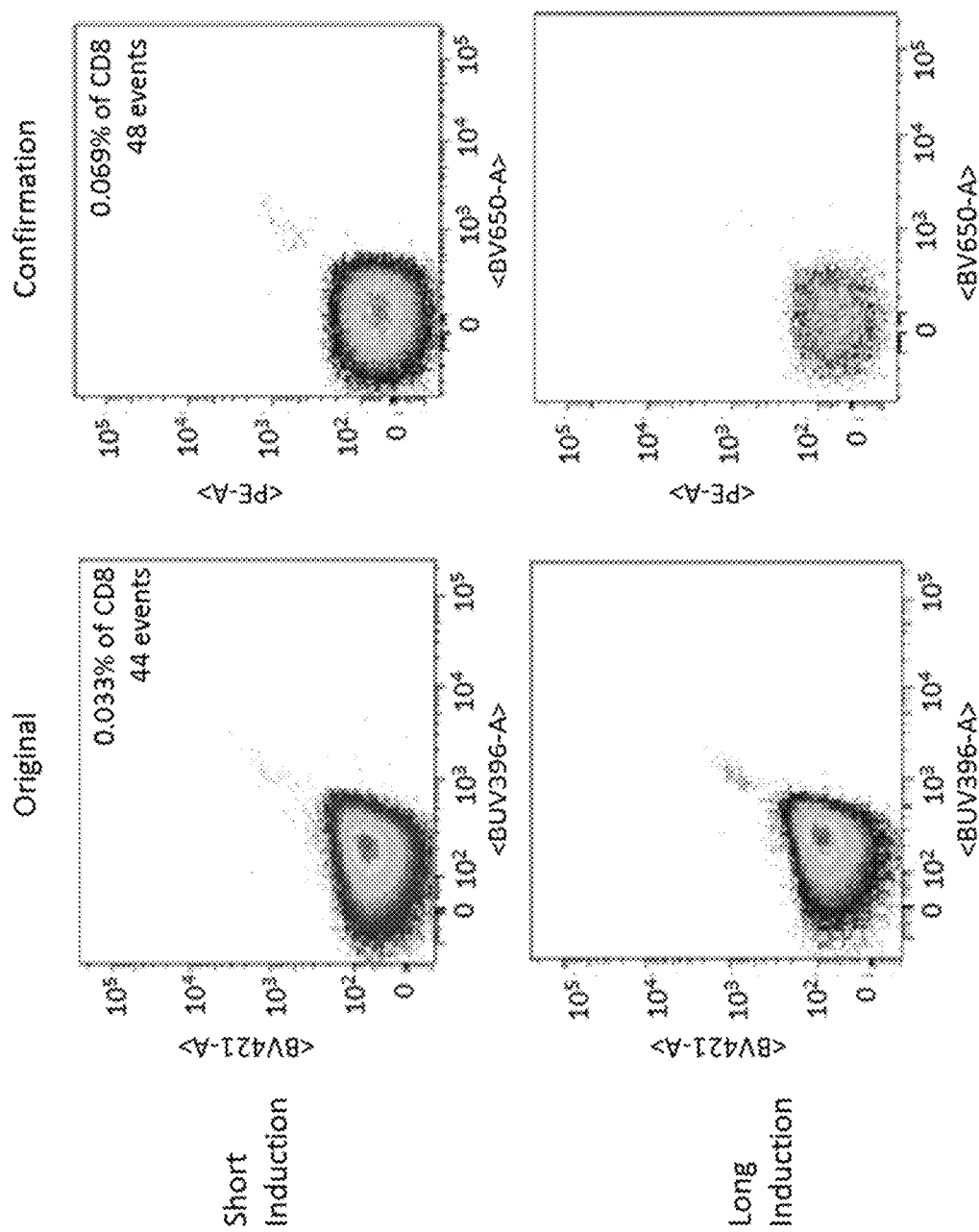
FIG. 12 depicts example flow cytometric analyses showing antigen specific CD8+ naïve T cell responses to short HIV5 peptides. Both short and long term inductions are shown.
Figure 13:
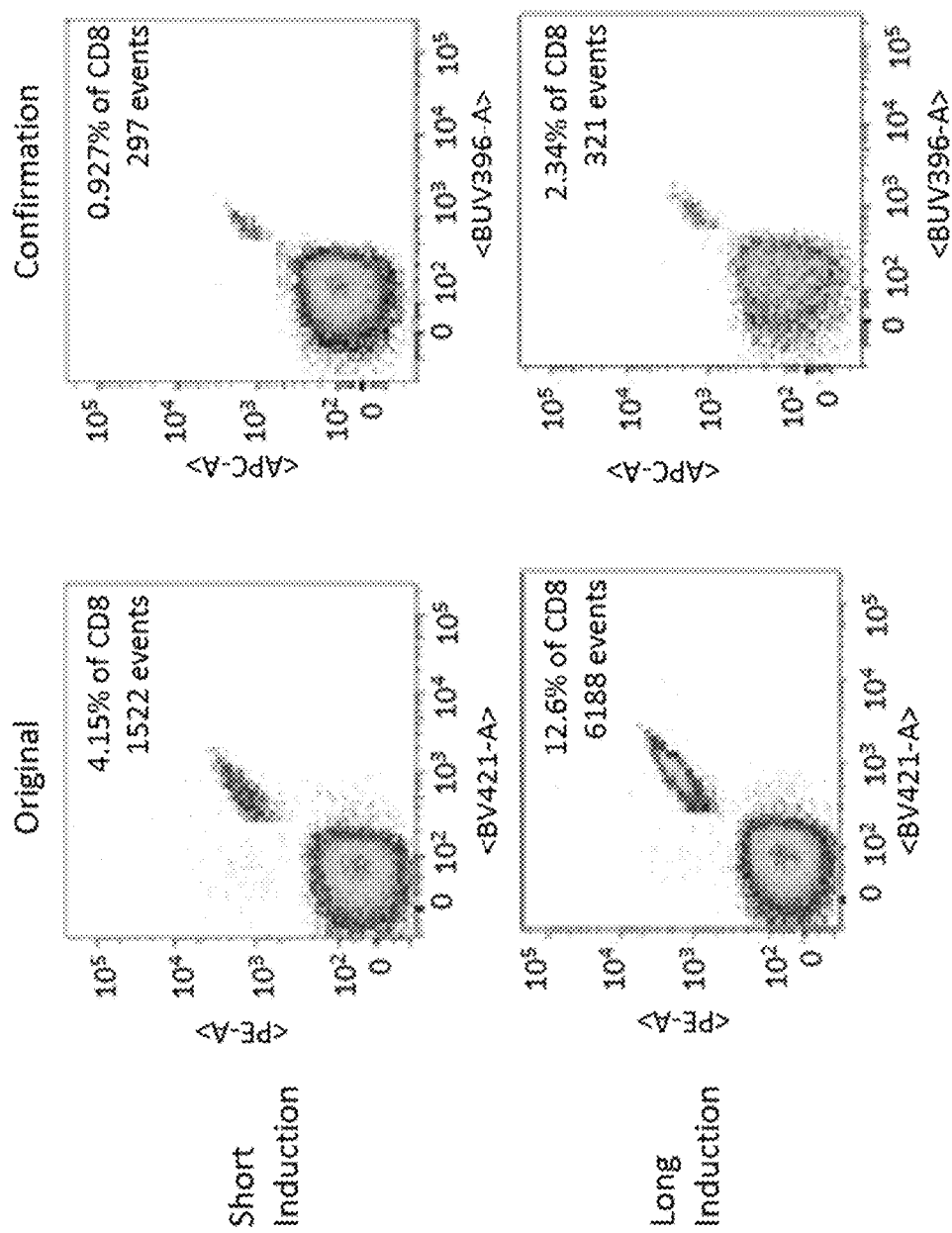
FIG. 13 depicts exemplary flow cytometric analyses showing the fraction of antigen specific CD8+ naïve T cell responses to short ME1 peptides using a whole PBMC sample from a human donor. Both short and long term inductions are shown.
Figure 14:
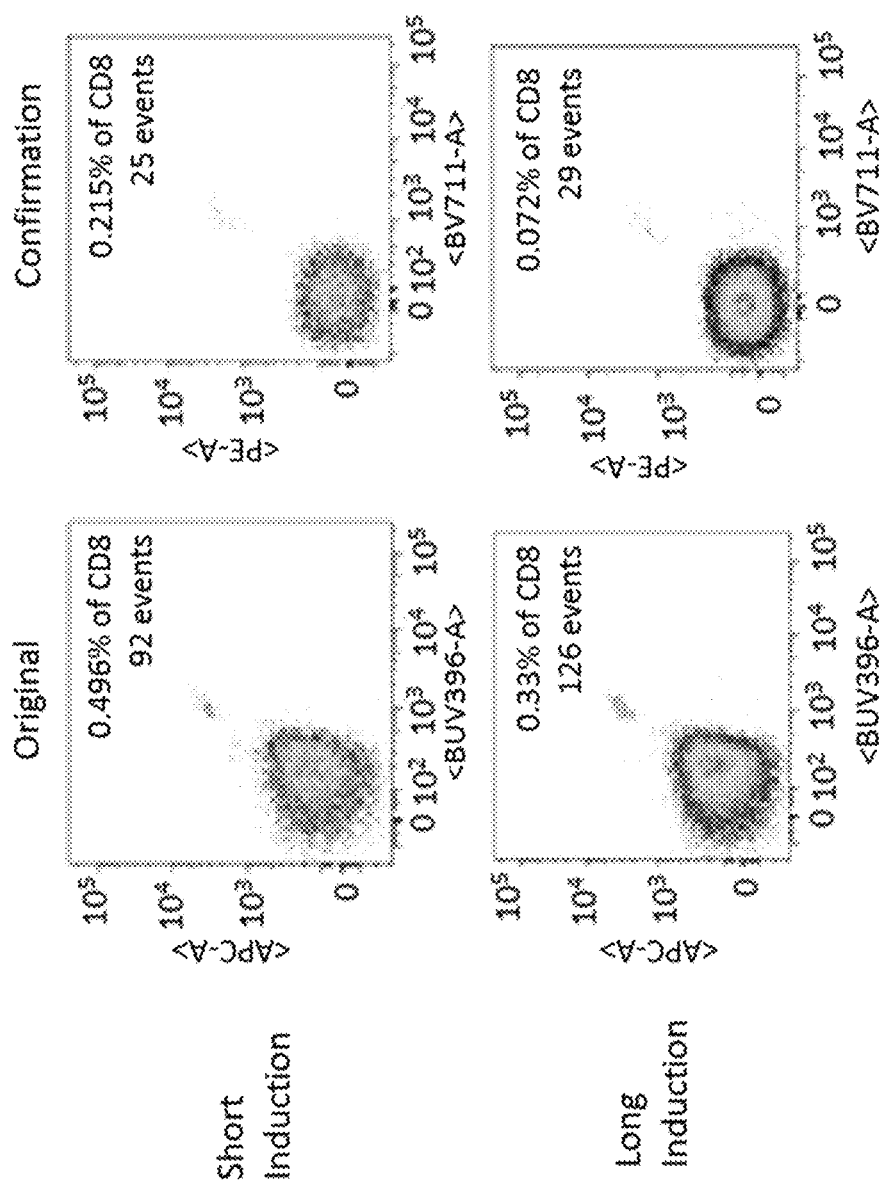
FIG. 14 depicts example flow cytometric analyses showing antigen specific CD8+ naïve T cell responses to short HIV3 peptides using a whole PBMC sample from a human donor. Both short and long term inductions are shown.
Figure 15:
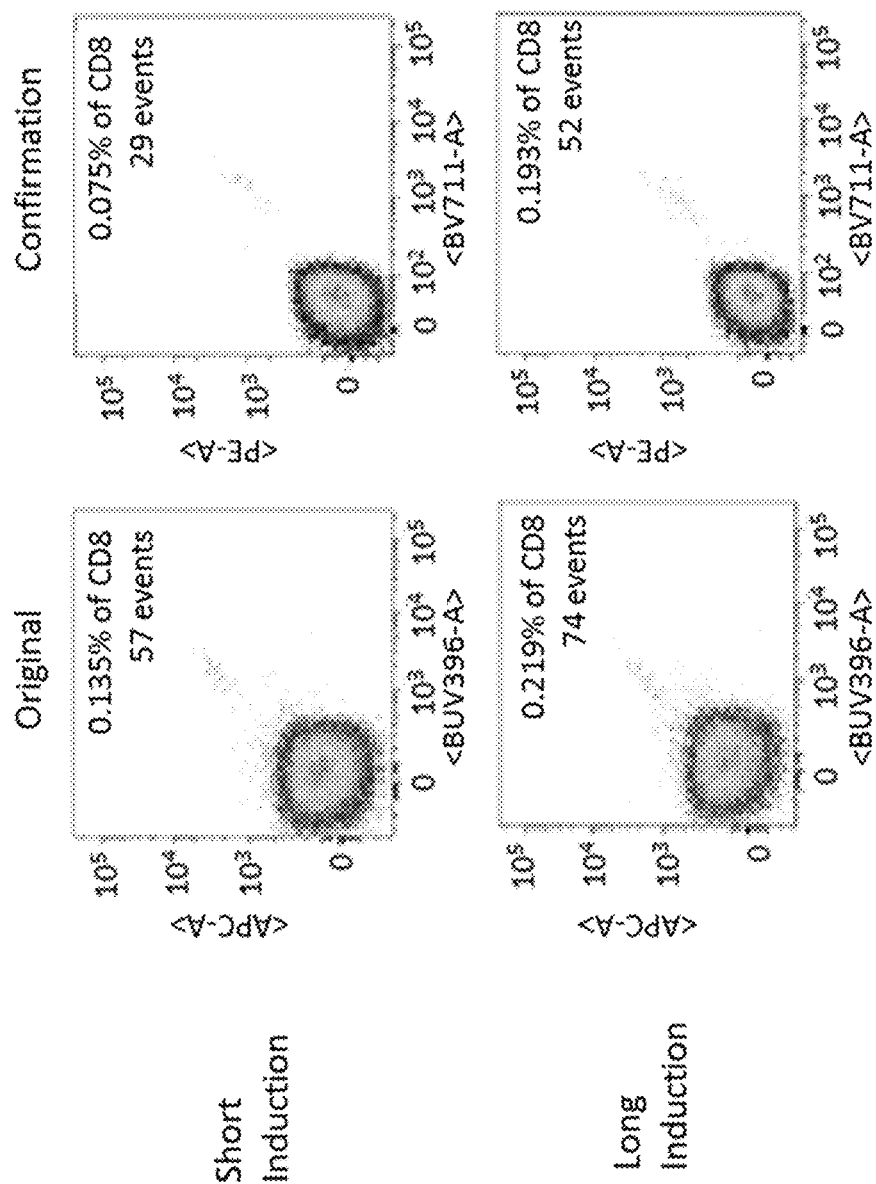
FIG. 15 depicts example flow cytometric analyses showing antigen specific CD8+ naïve T cell responses to long CSNK1A1 peptides using a whole PBMC sample from a human donor. Both short and long term inductions are shown.
Figure 16:
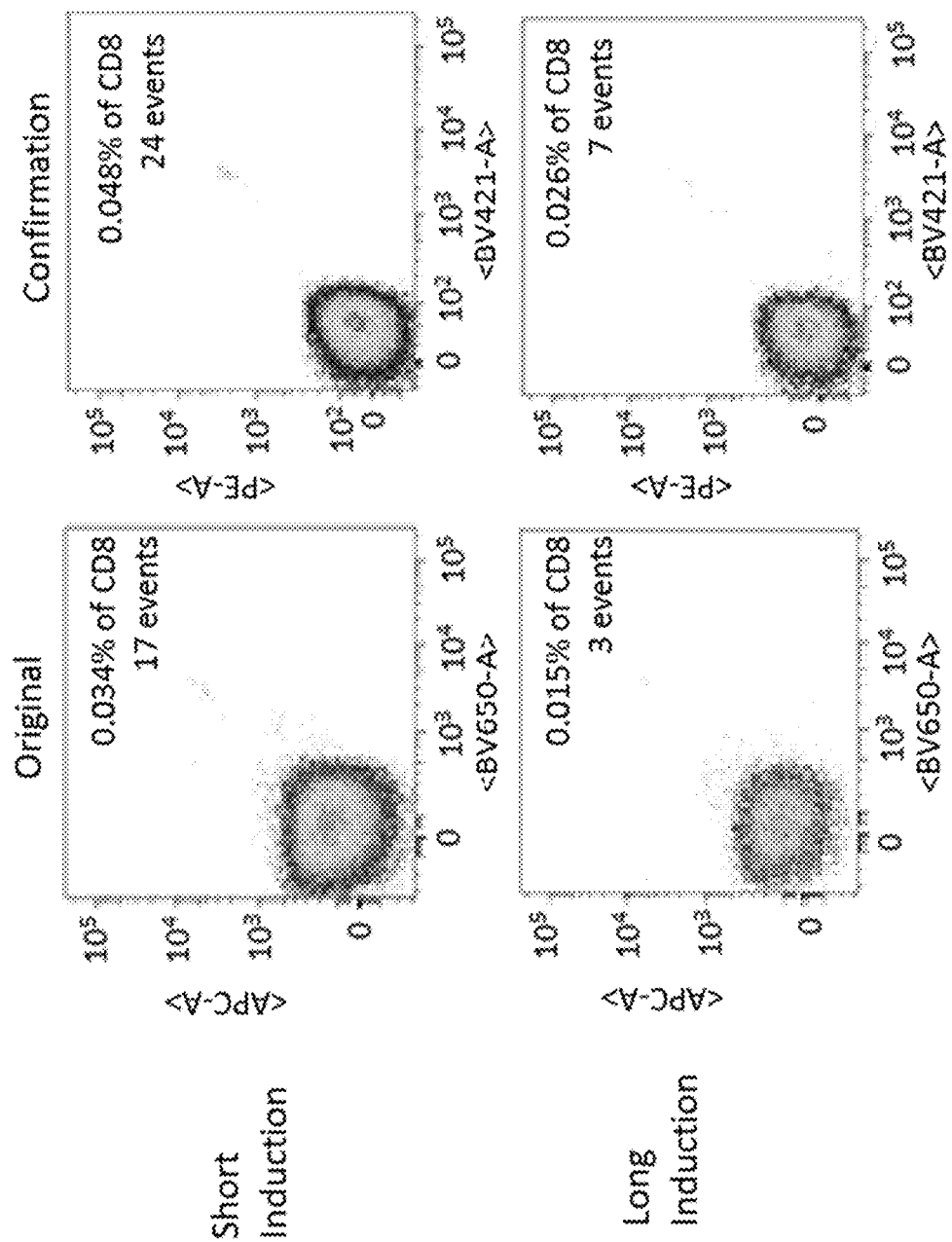
FIG. 16 depicts example flow cytometric analyses showing antigen specific CD8+ naïve T cell responses to long CSNK1A1 peptides using a PBMC sample from a human donor that was depleted of CD25+ cells. Both short and long inductions are shown.
Figure 17:
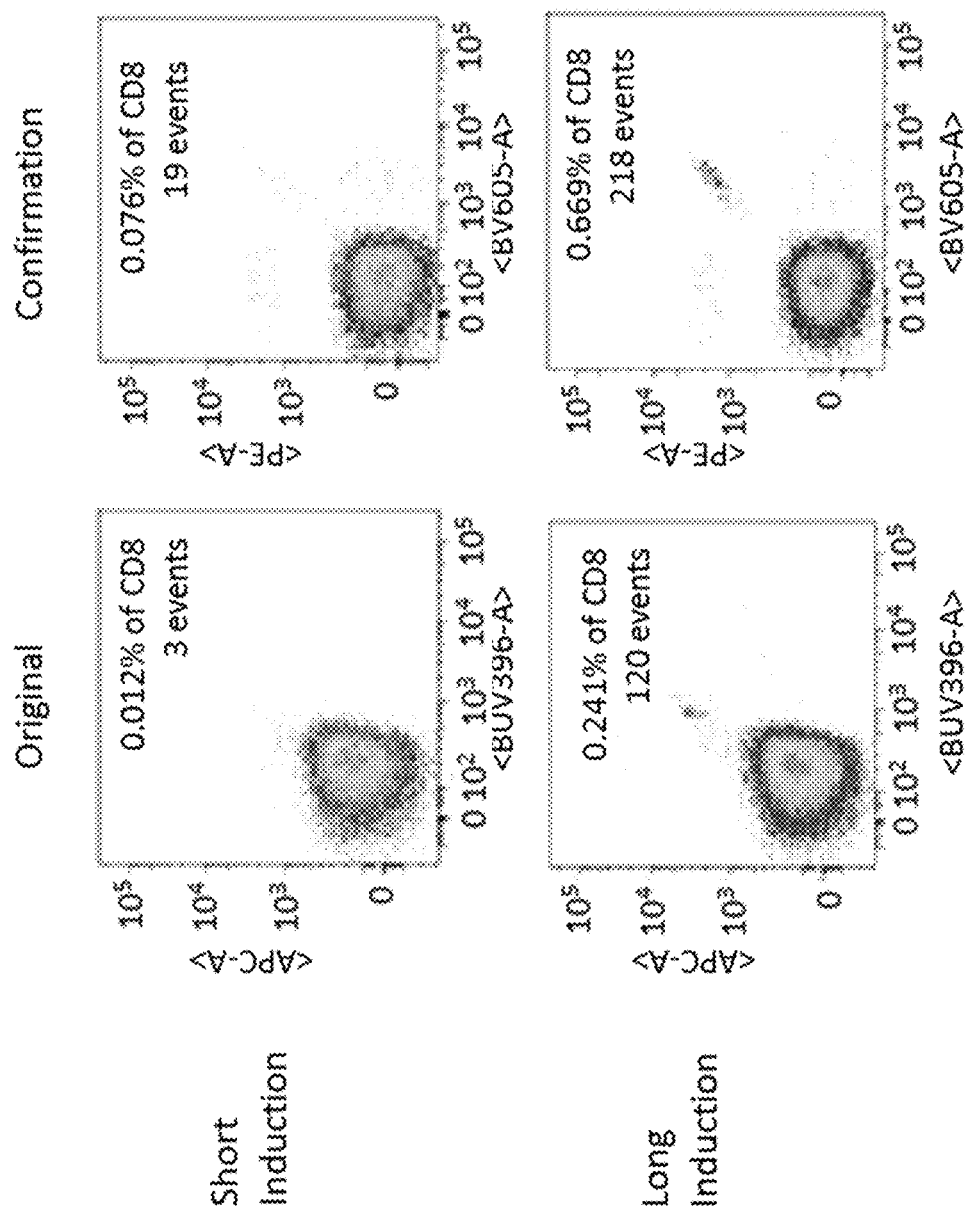
FIG. 17 depicts example flow cytometric analyses showing antigen specific CD8+ naïve T cell responses to short GAS7 peptides using a PBMC sample from a human donor that was depleted of CD25+ cells. Both short and long term inductions are shown.
Figure 18:
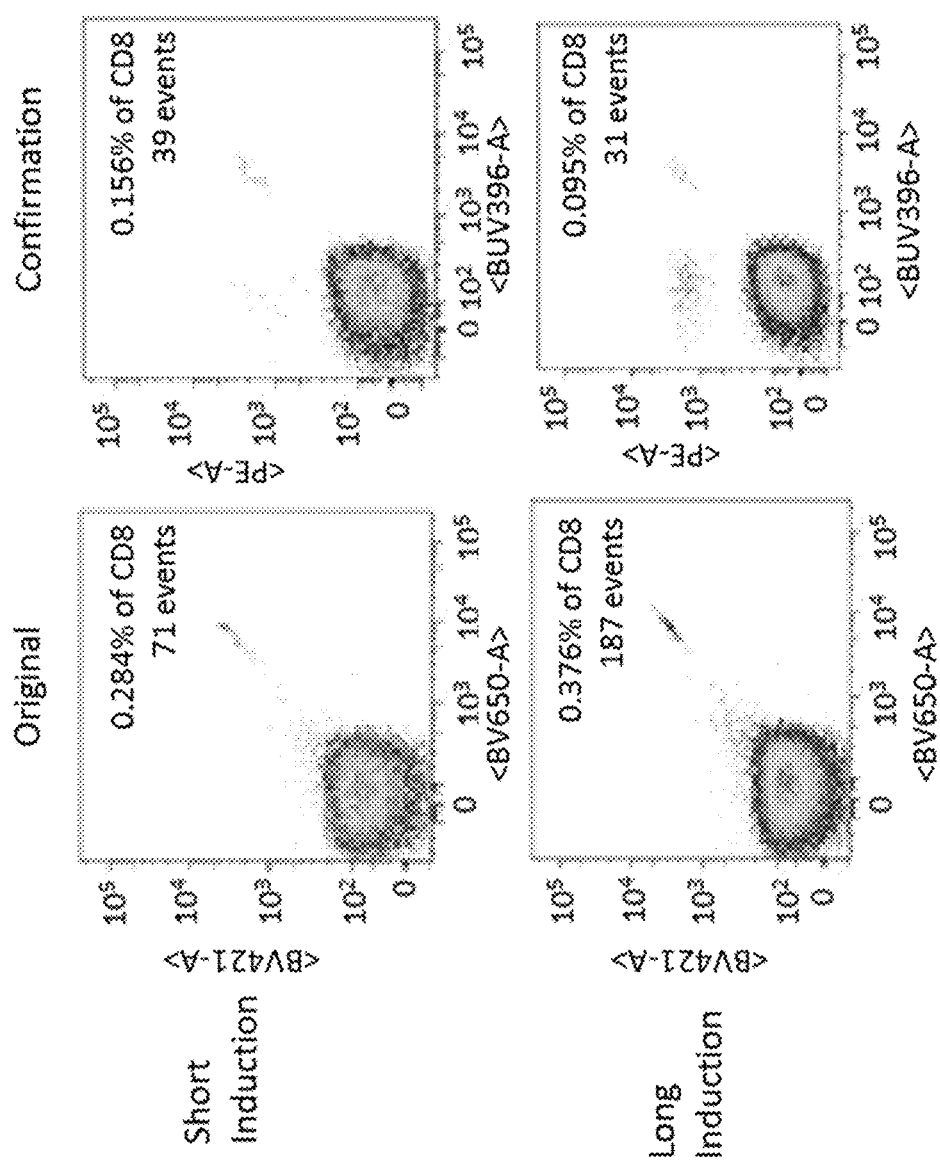
FIG. 18 depicts example flow cytometric analyses showing antigen specific CD8+ naïve T cell responses to short ACTN4 peptides using a PBMC sample from a human donor that was depleted of CD25+ cells. Both short and long term inductions are shown.
Figure 19A:
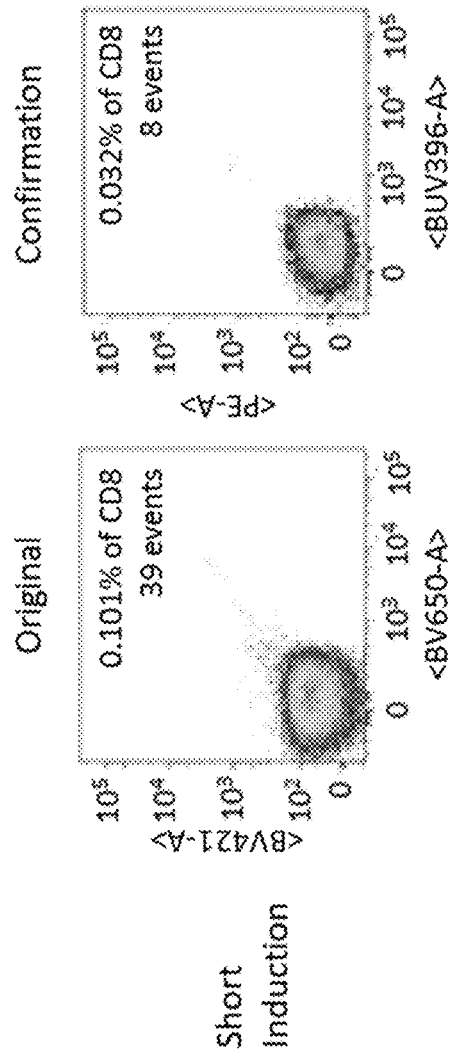
FIG. 19A depicts example flow cytometric analyses showing antigen specific CD8+ naïve T cell responses to short ACTN4 peptides using a PBMC sample from a human donor that was depleted of CD25+ cells. A short term induction is shown.
Figure 19B:
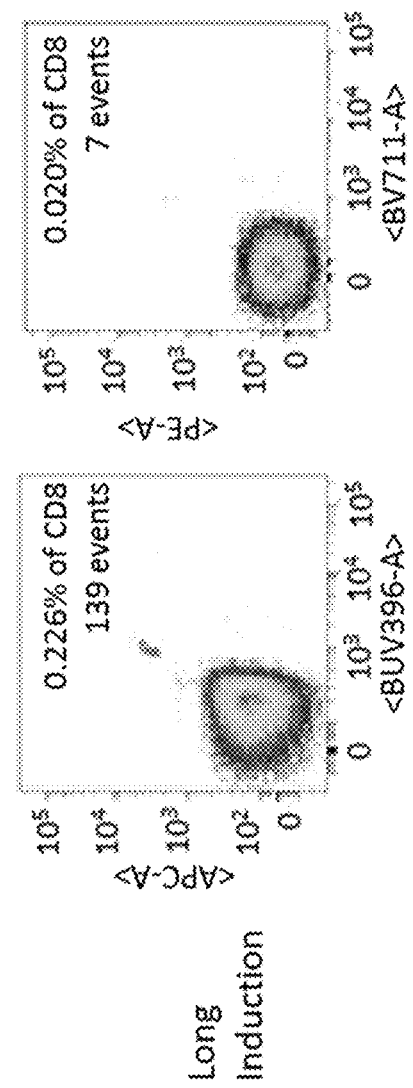
FIG. 19B depicts example flow cytometric analyses showing antigen specific CD8+ naïve T cell responses to short HIV3 peptides using a PBMC sample from a human donor that was depleted of CD25+ cells. A long term induction is shown.
Figure 20:
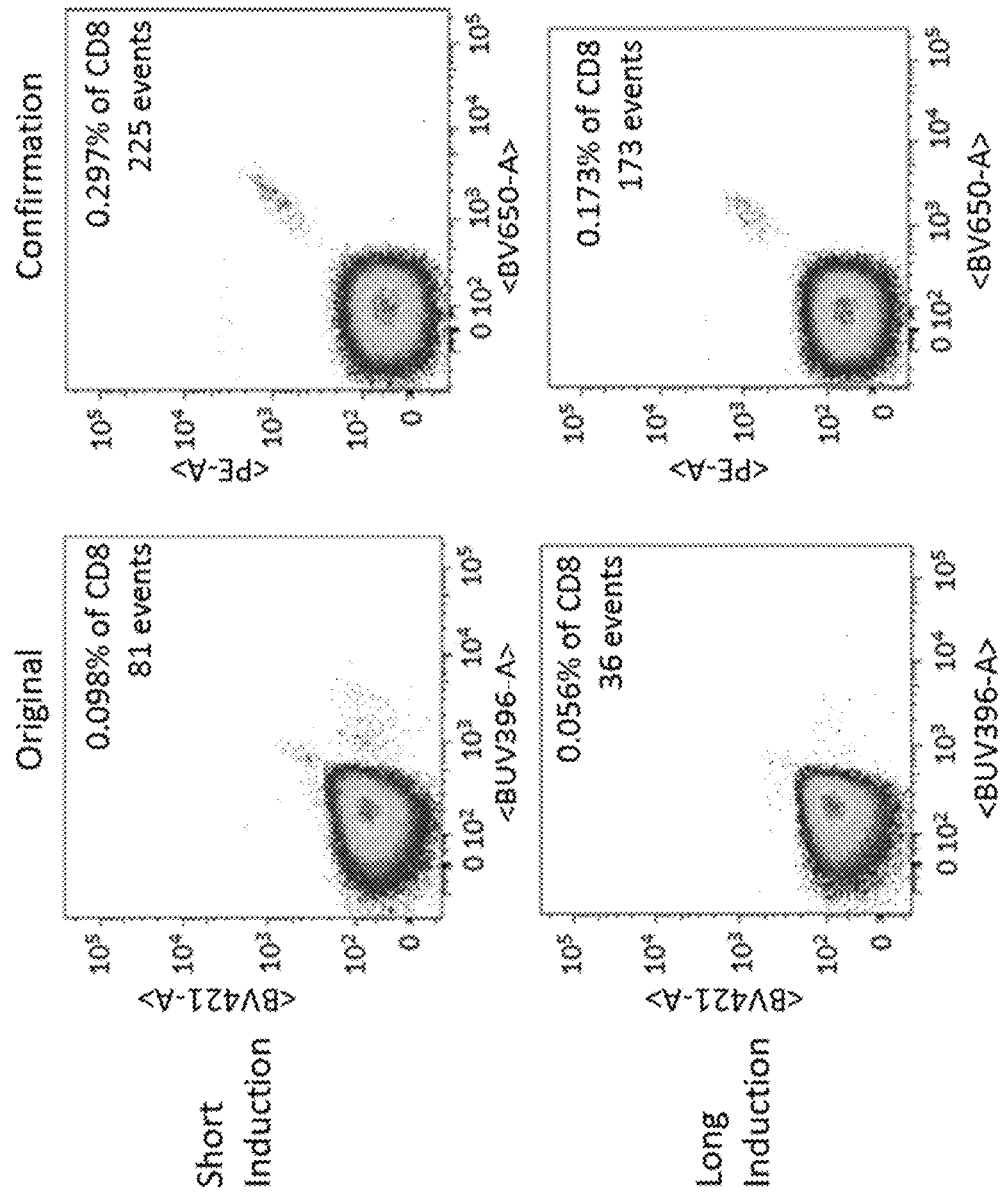
FIG. 20 depicts example flow cytometric analyses of antigen specific CD8+ naïve T cell responses to short HIV5 peptides using a whole PBMC sample from a human donor. Both short and long term inductions are shown.
Figure 21:
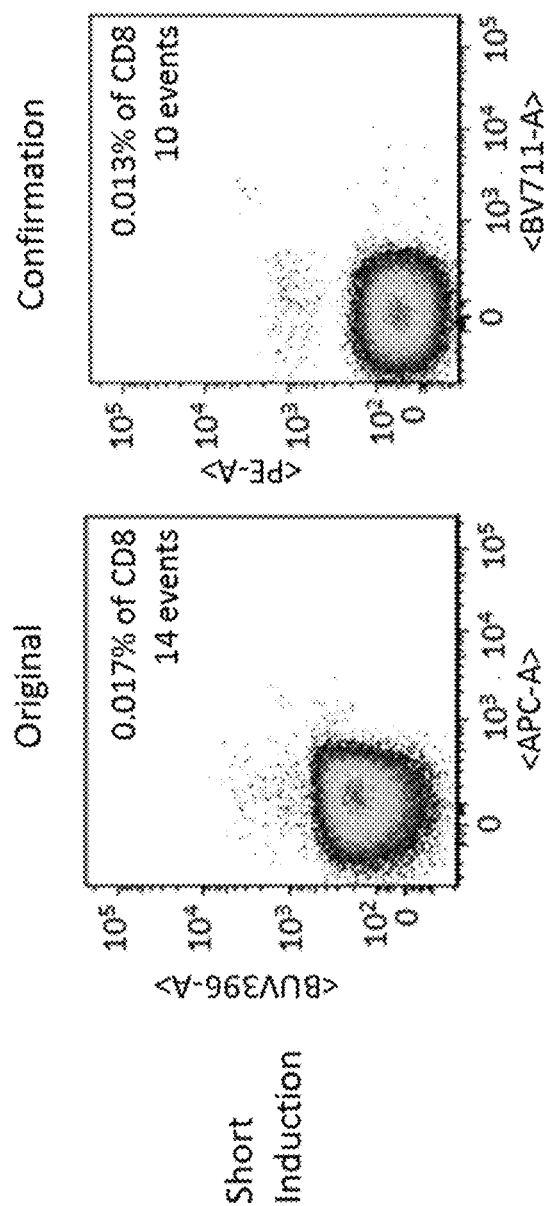
FIG. 21 depicts example flow cytometric analyses showing antigen specific CD8+ naïve T cell responses to short HIV3 peptides using a whole PBMC sample from a human donor. A short term induction is shown.
Figure 22:
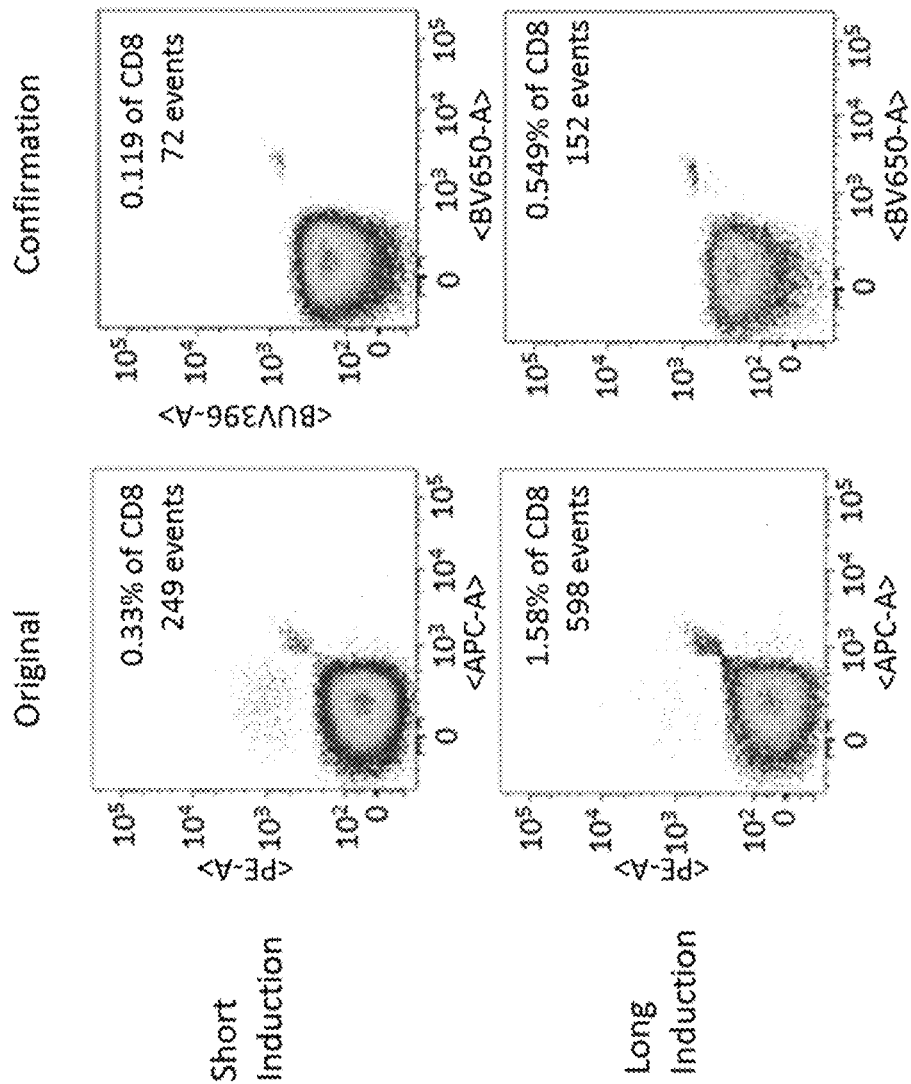
FIG. 22 depicts example flow cytometric analyses showing antigen specific CD8+ naïve T cell responses to short PRDX5 peptides using a PBMC sample from a human donor that was depleted of CD25+ cells. Both very short and long term inductions are shown.
Figure 23:
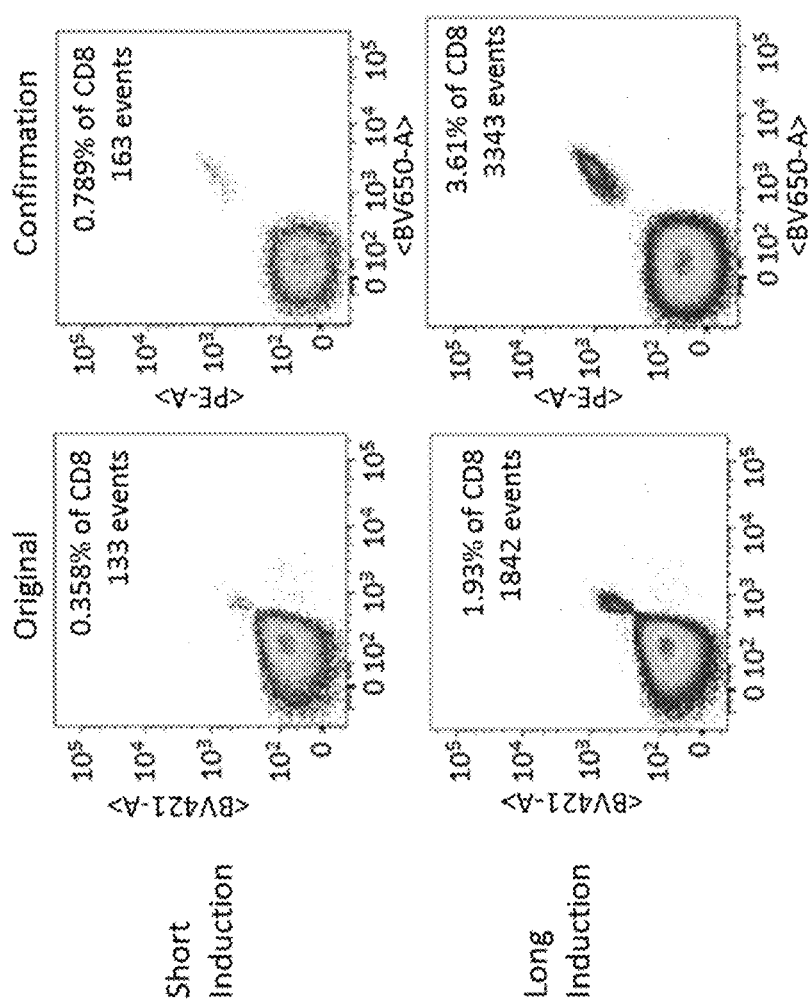
FIG. 23 depicts example flow cytometric analyses showing antigen specific CD8+ naïve T cell responses to short HIV5 peptides using a PBMC sample from a human donor that was depleted of CD25+ cells tides. Both short and long term inductions are shown.
Figure 24:
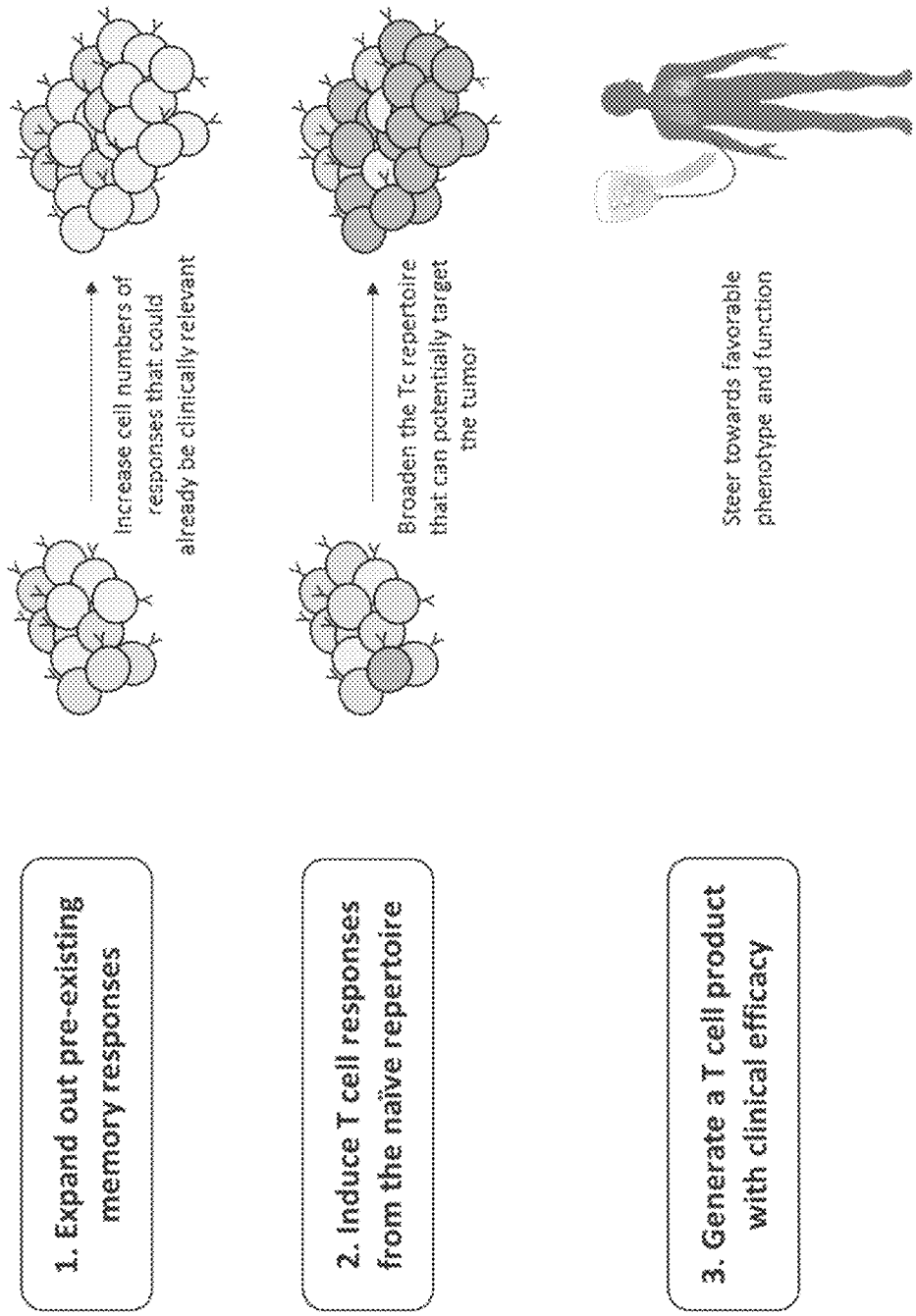
FIG. 24 depicts schematics of examples of methods for generating a therapeutic T cell composition including expansion of memory T cells and induction of naïve T cells.

Example 5—$CD4^+$ T Cell Responses $CD4^+$ T cell responses towards previously identified neoantigens (PINs) can be induced using the ex vivo induction protocol. In this example, CD4+ T cell responses were identified by monitoring IFNγ production in an antigen specific manner. FIG. 10 shows representative examples of such flow cytometric analysis. Finally, specificity of CD4+ T cell responses for the mutant peptide and not the wildtype was shown by stimulation the induced T cell populations either with mutant or wildtype peptide (FIG. 11).

Example 6—Naïve CD8+ T Cell Induction

Naïve CD8+ T cell induction was analyzed by flow cytometry after T cell manufacturing using protocol 1 or protocol 2. The PBMC samples were from a human donor 1 or human donor 2, and either whole PBMCs or CD25− depleted PBMCs. The cell samples were analyzed after short or long induction according to the protocols in FIG. 1. Naïve CD8+ Responses of the induced CD8+ T cells were analyzed against different peptides and were plotted in FIGS. 12-23.

Example 7—CD8+ Naïve T Cell Responses

Figure 7:
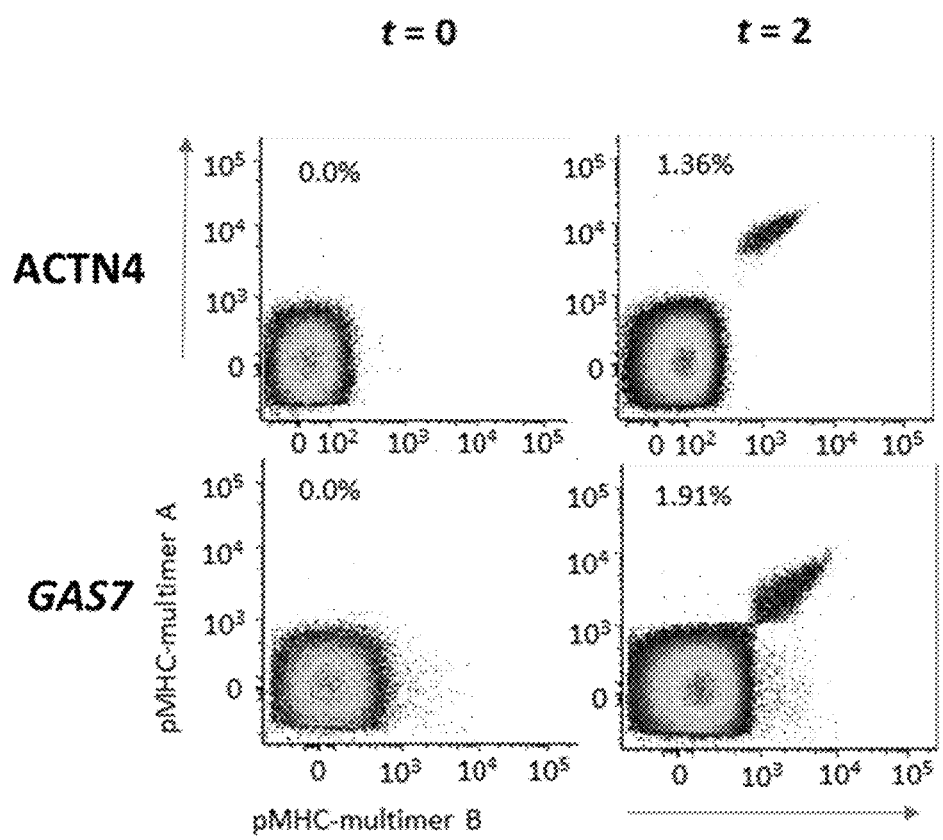
FIG. 7 depicts example flow cytometry plots of antigen specific CD8$^+$ T cell responses to the indicated mutated epitopes in a healthy donor prior to stimulation and after up to three rounds of stimulation.
Figure 8A:
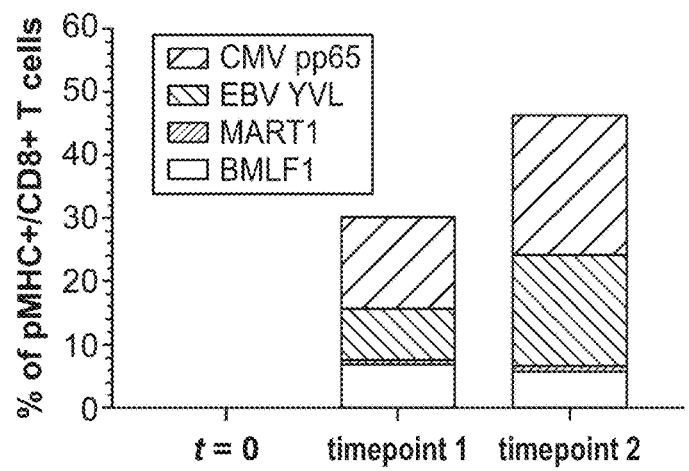
FIG. 8A depicts an example bar graph showing results of antigen specific memory CD8+ T cell responses to viral antigens. After up to three rounds of stimulation, approximately 50% of all CD8+ T cells were specific for the indicated viral epitopes (CMV pp65, EBV YVL, EBV BMLF1 and Mart-1).
Figure 8B:
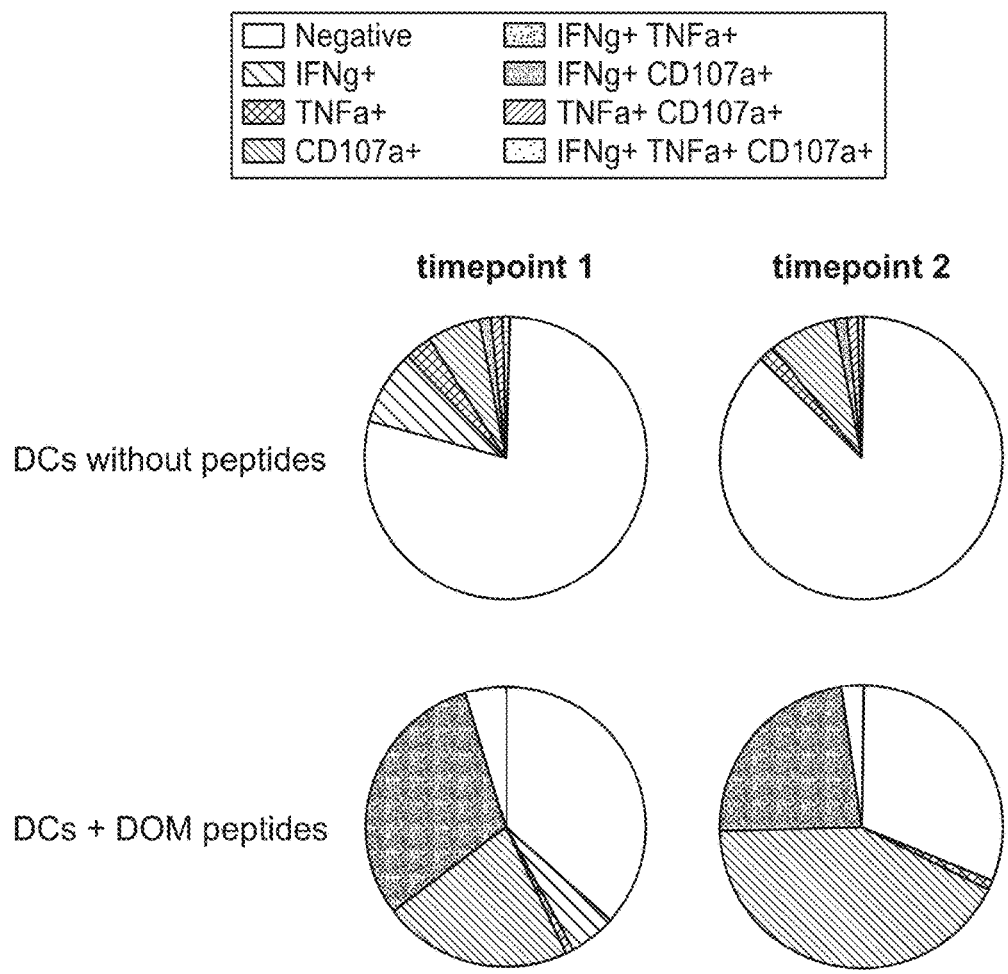
FIG. 8B depicts example results of a recall assay of antigen specific memory CD8+ T cell responses to peptide loaded antigen presenting cells and then incubated with APCs with and without loaded viral antigens. The fraction of CD8+ T cells from two time points that release the indicated cytokines are depicted in the charts.

The T cell manufacturing protocols in Example 1 can successfully be used to induce CD8+ T cell responses from the naïve compartment. FIG. 7 shows representative flow plots of two CD8+ T cell responses that were generated toward mutated epitopes in a healthy donor after two rounds of stimulation. Moreover, CD8+ T cell responses from the memory compartment can be expanded to high numbers. In the representative example shown in FIG. 8A, after up to three rounds of stimulation, approximately 50% of all CD8+ T cells were specific for the immune dominant epitopes, CMV pp65, EBV YVL, EBV BMLF1 and Mart-1. The induced CD8+ memory responses demonstrate poly-functionality in a peptide recall assay (degranulation and cytokine release, FIG. 8B).

Example 8—Flow Cytometry Analysis of T Cells

Figure 5A:
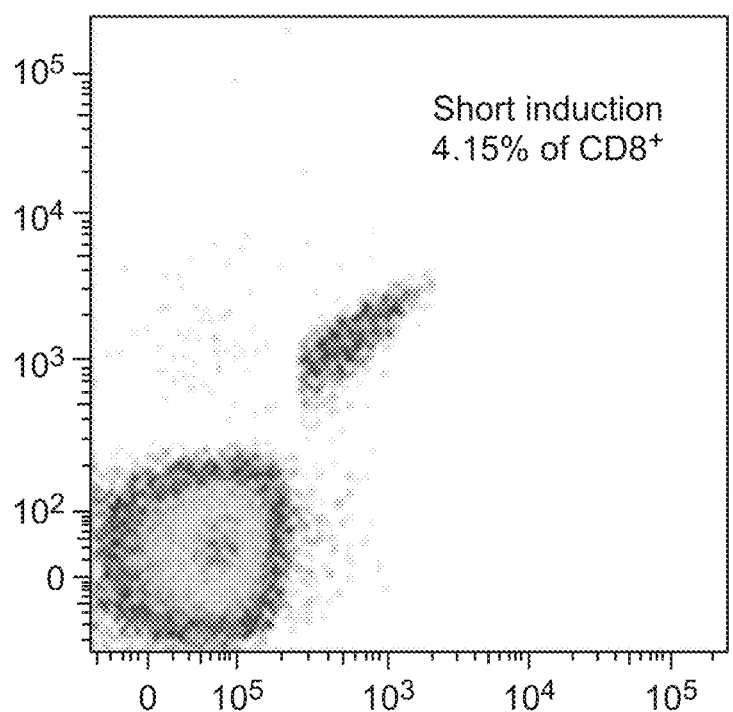
FIG. 5A depicts an example flow cytometry analysis of antigen specific CD8$^+$ naïve T cell responses to a single previously identified neoantigen (PIN) under the indicated conditions.
Figure 5B:
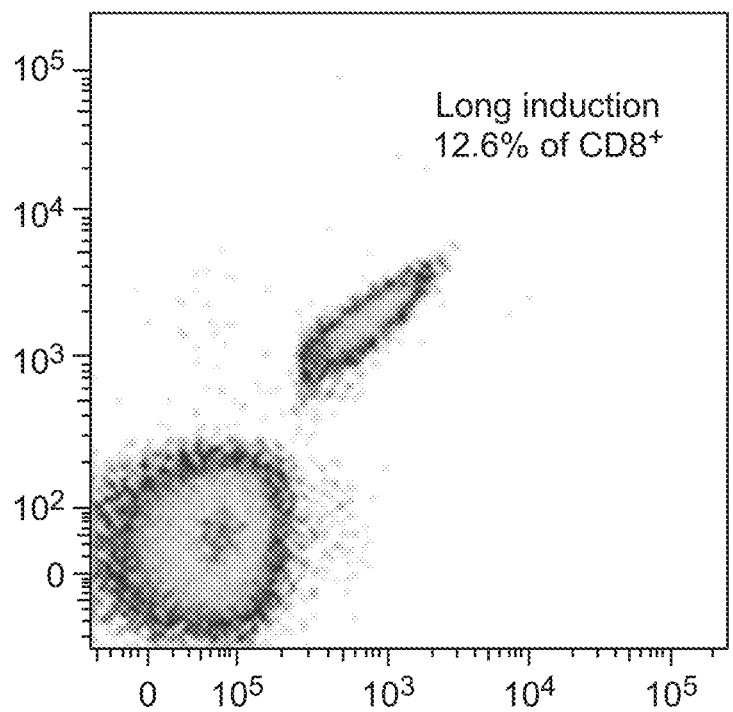
FIG. 5B depicts an example flow cytometry analysis of antigen specific CD8$^+$ naïve T cell responses to a single previously identified neoantigens (PIN) under the indicated conditions.

FIG. 5A depicts an exemplary flow cytometry analysis of ME-1 response of CD8+ naïve T cells induced under condition indicated in the figure using protocol 2. FIG. 5B depicts an example of flow cytometry analysis of ME-1 response of CD8+ naïve T cells induced under condition indicated in the figure. 12.6% of CD8+ T cells were observed to be specific to ME-1 after a long induction.

Example 9—Cytotoxicity Assay of Induced T Cells

Figure 9:
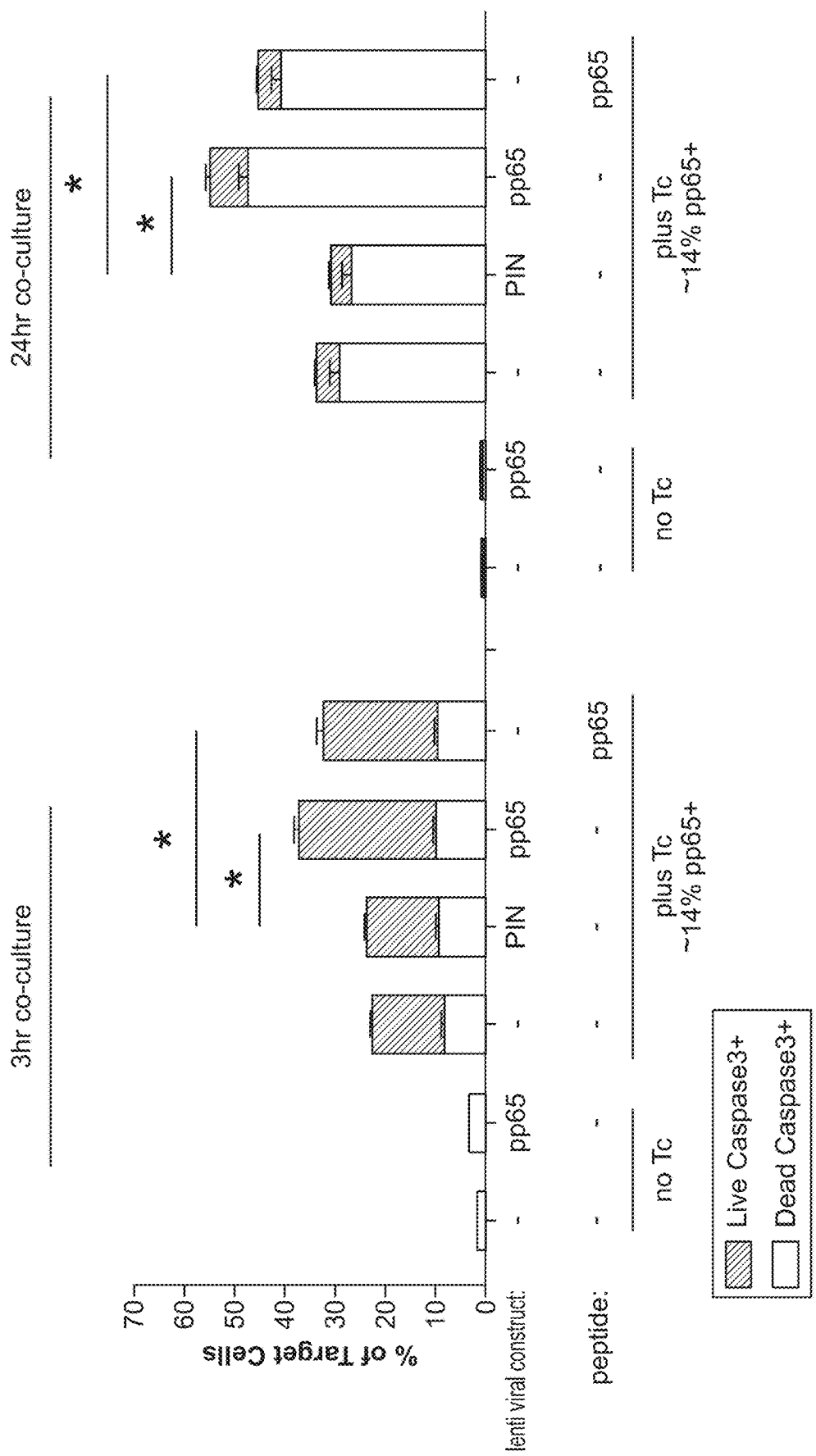
FIG. 9 depicts an example result of a cytotoxicity assay used to assess whether the induced T cell cultures can kill antigen expressing tumor lines. The fractions of live and dead caspase 3 positive tumor cells to total tumor cells are shown. Caspase 3 positive alive tumor cells indicate cells undergoing early cell death.

A cytotoxicity assay was used to assess whether the induced T cell cultures can kill antigen expressing tumor lines. In this example, expression of active caspase 3 on alive and dead tumor cells was measured to quantify early cell death and dead tumor cells. In FIG. 9, the induced CD8+ memory responses were capable of killing antigen expressing tumor targets.

Example 10—Phenotypic Analysis of Generated CD8+ T Cells

CD8+ T cell lines produced in Example 1 can be characterized for phenotypic expression, cytokine profile and specific cytotoxic activity toward autologous target cells. To analyze the phenotypic expression, $1 \times 10^4$-$1 \times 10^6$ T cells of each culture can be washed in PBS containing 0.1-10% FBS and 0.1% sodium azide (FBS-PBS) and resuspended in FBS-PBS containing a 1:100 dilution of fluorochrome-labeled antibody (CD45RA and CD62L). After incubation on ice, the cells are washed and fixed for flow cytometric analysis. If the selected CD8+ T cell cultures express CD62L but not CD45RA, regardless of their reactivity to the various peptides, it can indicate that the selected T cell cultures belong to the CD8+ memory T cell subset.

Example 11—Cytokine Production of CD8+ T Cells

The cytokine profile of CD8+ T cell cultures can be analyzed. T cell cultures will be first challenged with autologous APC pulsed with the antigen peptides. The cytokine profile will be determined quantitatively using ELISA kits (PharMingen, San Diego, Calif.). Microtiter plates (96-Wells, NUNC Maxisorp) will be coated overnight at 4° C. with 0.2-4 µg/well of a purified mouse capturing monoclonal antibody to human cytokine (IL-4, IL-10, TNF-α, IFN-γ) (PharMingen). Plates will be washed and non-specific binding sites will be saturated with 10% (w/v) fetal bovine serum (FBS) for 0.5-3 hours and subsequently washed. Supernatants and cytokine standards will be diluted with PBS and added in duplicate Wells. Plates will be incubated at 37° C. for 1-3 hours and subsequently washed with PBS-T. Matched biotinylated detecting antibody will be added to each well and incubated at room temperature for 1-3 hours. After washing, avidin-conjugated horseradish peroxidase will be added and incubated for 0.5-3 hours. 3,3′,5,5′-tetramethylbenzidine (TMB, Sigma) will be used as a substrate for color development. Optical density will be measured at 450 nm using an ELISA reader (Bio-Rad Laboratories, Hercules, Calif.) and cytokine concentrations will be quantitated by Microplate computer software (Bio-Rad) using a double eight-point standard curve.

Example 12—Prot. 1 and Prot. 2: Summary

TABLE 1

Summary of results from protocols 1 and 2

| | | Prot. 1 | | Prot. 2 | | | |
|---|---|---|---|---|---|---|---|
| | | $CD14^{depleted}/$ $CD25^{depleted}$ | | $CD25^{depleted}$ | | $CD14^{depleted}$ $CD25^{depleted}$ | FLT3L x3 |
| | | LTS 37 | LTS 38 | LTS 37 | LTS 38 | LTS 38 | LTS 38 |
| CD8 Memory | Bulk Fold expansion | 30-1200 | 20-5000 | 20-100 | 5-100 | 5-100 | 5-100 |
| | Absolute # | 1-50 × $10^6$ | 20-1000 × $10^6$ | 0.1-1 × $10^6$ | 2-10 × $10^6$ | 2-20 × $10^6$ | 0.5-10 × $10^6$ |
| | Functionality | decreased at stim 3 | decreased at stim 3 | maintained at stim 3 | maintained at stim 3 | maintained at stim 3 | maintained at stim 3 |

TABLE 1-continued

Summary of results from protocols 1 and 2

| | | Prot. 1 | | Prot. 2 | | | |
|---|---|---|---|---|---|---|---|
| | | CD14$^{depleted}$/CD25$^{depleted}$ | | CD25$^{depleted}$ | | CD14$^{depleted}$ CD25$^{depleted}$ | FLT3L x3 |
| | | LTS 37 | LTS 38 | LTS 37 | LTS 38 | LTS 38 | LTS 38 |
| CD8 Naïve | Hit rate per well | 20-40% | 0-40% | 20-30% | 0-20% | 10% | 0-10% |
| | Hit rate per peptide | 1-3 out of 11 | 0-4 out of 11 | 2 out of 11 | 1 out of 11 | 1-3 out of 11 | 1-2 out of 11 |
| | Absolute # | 0.1-1 × 10$^6$ | — | 0.01-0.5 × 10$^6$ | — | — | — |
| | Functionality | TBD* | TBD | TBD | TBD | TBD | TBD |
| CD4 Naïve | Hit rate/well | 78-100% | 56% | 10-100% | 50% | 70% | TBD |
| | Hit rate/peptide | TBD | TBD | TBD | TBD | TBD | TBD |
| | Absolute # | TBD | TBD | TBD | TBD | TBD | TBD |
| | Functionality | good | good | good | TBD | TBD | TBD |

TBD* = To be determined

Example 13—Protocol 1 and 2 Parameter Testing

An example experiment for testing parameters of the protocols can be to test protocol 1 in patient samples at small scale. Another example experiment for testing parameters of the protocols can be to characterize the T cell products generated in previous batches, including testing functionality of CD4$^+$ T cells and CD8$^+$ T cells and sorting antigen specific cells and characterizing by single cell RNAseq. Another example an experiment for testing parameters of the protocols can be to test addition of poly-ICLC/aCD40L during DC Prep and quantify T cell enrichment. Another example experiment for testing parameters of the protocols can be to test functionality of induced CD8$^+$ naïve T cell responses, including assessing antigen specific cytotoxicity in killing assay, performing peptide recall assay with broader flow panel to measure differentiation and exhaustion, determining sensitivity (peptide titration) and specificity (WT vs mutant, pool deconvolution) for a subset of hits, and enriching for CD8$^+$ to remove possibility of bystander effects from antigen specific CD4$^+$ T cells. Another example experiment for testing parameters of the protocols can be interrogate functionality, determining sensitivity (peptide titration) and specificity (WT vs mutant, pool deconvolution) for a subset of hits, performing recall assay with differentiation and exhaustion flow panel to better understand phenotype. Another example experiment for testing parameters of the protocols can be to sort antigen specific T cells (CD8$^+$ memory, CD8$^+$ naïve, CD4$^+$ naïve) and profile by single cell RNAseq, including comparing phenotype of different inductions, comparing phenotype of inductions from different compartments, examining kinetics.

Example 14—T Cell Inputs Depleted of CD14 and/or CD25 Expressing Cells Improve Induction of CD4$^+$ and CD8$^+$ Naïve T Cells Table 2 below shows results from the protocol 1 T cell preparation method demonstrating that CD14$^-$/CD25$^-$ depletion can increase CD8$^+$ naïve hit rate and have a consistent CD4$^+$ hit rate.

TABLE 2

| CD14$^-$/CD25$^-$ depletion results | | | | |
|---|---|---|---|---|
| LTS#33 | | CD14$^-$ | CD25$^-$ | CD14$^-$/CD25$^-$ |
| CD8 naïve hit rate % | HD34 | 20 | 30 | 50 |
| | HD35 | 0 | 0 | 10 |
| | Average | 10 | 15 | 30 |
| CD4 naïve hit rate % | HD34 | 100 | 80 | 90 |
| | HD35 | 100 | 100 | 100 |
| | Average | 100 | 90 | 95 |

Example 15—CD8$^+$ Naïve Inductions Significantly Improved with Use of Protocol 1 and Protocol 2

Tables 3A and 3B below shows results from both protocol 1 and protocol 2 T cell preparation method described herein. In the two human donors tested, CD8$^+$ naïve inductions significantly improved using depletion of CD25 expressing cells or depletion of CD25 and CD14 expressing cells compared to using depletion of CD14 expressing cells. CD8$^+$ naïve inductions also significantly improved using FLT3L stimulation.

TABLE 3A

| CD8$^+$ naïve induction results from HD35 | | | | | |
|---|---|---|---|---|---|
| | Prot. 1 (CD25 depleted) 1/13 confirmed 7.5% success rate | | | Prot. 2 (bulk) 3/13 confirmed 23% success rate | |
| | day 19 | | day 26 | day 19 | day 26 |
| HD35 | initial | confirmation | initial confirmation | initial confirmation | initial |
| Induced with | HIV replicate 1 | | | | |

TABLE 3A-continued

| | | CD8+ naïve induction results from HD35 | | | | | | |
|---|---|---|---|---|---|---|---|---|
| short peptides | HIV replicate 2 | | | | | | | |
| | HIV replicate 3 | | | | | | | |
| | HIV replicate 4 | | | | | | | |
| | HIV replicate 5 | HIV-5 * 0.0327% | HIV-5 * 0.0691% | HIV-5 | HIV-5 | HIV-3 0.496% | HIV-3 0.215% | HIV-3 0.33% |
| | PIN replicate 1 | | | | | | | |
| | PIN replicate 2 | | | | | CSNK1A1 0.135% | CSNK1A1 0.0747% | CSNK1A1 0.219% |
| | PIN replicate 3 | | | | | | | |
| | PIN replicate 4 | | | | | ME-1 4.15% | ME-1 0.927% | ME-1 12.6% |
| | PIN replicate 5 | | | | | | | |
| Long | PIN LONG replicate 1 | | | | | | | |
| | PIN LONG replicate 2 | | | | | | | |
| | PIN LONG replicate 3 | | | | | | | |

| | | Prot. 2 (bulk) 3/13 confirmed 23% success rate | Prot. 2 (CD25 depleted) 5/13 confirmed 39% success rate | | | |
|---|---|---|---|---|---|---|
| | | day 26 | day 19 | | day 26 | |
| | HD35 | confirmation | initial | confirmation | initial | confirmation |
| Induced with short peptides | HIV replicate 1 | | | | | |
| | HIV replicate 2 | | | | | |
| | HIV replicate 3 | | | | | |
| | HIV replicate 4 | | | | HIV-3 0.226% | HIV-3 0.0203% |
| | HIV replicate 5 | HIV-3 0.0722% | | | | |
| | PIN replicate 1 | | | | | |
| | PIN replicate 2 | CSNK1A1 0.193% | | | | |
| | PIN replicate 3 | | | | | |
| | PIN replicate 4 | ME-1 2.34% | GAS7/ACTN4 0.012/0.284% | GAS7/ACTN4 0.076/0.156% | GAS7/ACTN4 0.241/0.376% | GAS7/ACTN4 0.669/0.095% |
| | PIN replicate 5 | | ACTN4 0.101% | ACTN4 0.032% | | |
| Long | PIN LONG replicate 1 | | CSNK1A1 0.0342% | CSNK1A1 0.0482% | CSNK1A1 0.0156% | CSNK1A1 0.0265% |
| | PIN LONG replicate 2 | | | | | |
| | PIN LONG replicate 3 | | | | | |

TABLE 3B

CD8+ naïve induction results from HD34

| | | Prot. 1 0/13 confirmed 0% success rate | | | | Prot. 2 bulk input 2/13 confirmed 15% success rate | | | | Prot. 2 CD25 depleted input 2/13 confirmed 15% success rate | | | |
|---|---|---|---|---|---|---|---|---|---|---|---|---|---|
| | | day 19 | | day 26 | | day 19 | | day 26 | | day 19 | | day 26 | |
| HD34 | | initial | confirmation | initial | confirmation | initial | confirmation | initial | confirmation | initial | confirmation | initial | confirmation |
| Induced with short peptides | HIV replicate 1 | | | | | | | | | HIV-5 0.358% | HIV-5 0.789% | HIV-5 1.93% | HIV-5 3.61% |
| | HIV replicate 2 | | | | | HIV-3 & HIV-5 0.017/0.098% | HIV-3 & HIV-5 0.013/0.279% | HIV-5 0.056% | HIV-5 0.173% | | | | |
| | HIV replicate 3 | | | | | | | | | | | | |
| | HIV replicate 4 | | | | | | | | | | | | |
| | HIV replicate 5 | | | | | | | | | | | | |
| | PIN replicate 1 | | | | | | | | | PRDX5 0.33% | PRDX5 0.119% | PRDX5 1.58% | PRDX5 0.549% |
| | PIN replicate 2 | | | | | | | | | | | | |
| | PIN replicate 3 | | | | | | | | | | | | |
| | PIN replicate 4 | | | | | | | | | | | | |
| | PIN replicate 5 | | | | | | | | | | | | |

Example 16—UV Mediated Peptide Exchange Assay

UV-mediated cleavage of the conditional ligand can be time dependent. With the set-up described below, peptide cleavage can be detected after 1 min and can be essentially complete after approximately 15 min. A 30 to 60 min incubation time can be normally used to ensure optimal exchange of the conditional ligand with the peptide of interest. Protein concentration may influence the rate of UV-mediated cleavage, as both the nitrophenyl moiety and the reaction product absorb long wavelength UV light. In addition, path length may affect the reaction speed. Empty, peptide receptive MHC molecules that are formed upon UV exposure can be rescued by performing the UV-mediated cleavage in the presence of an MHC ligand of interest. In most experiments, a 100 fold molar excess of peptide over MHC is used. UV induced peptide exchange is routinely performed using 25 μg/mL of UV sensitive MHC class I complexes. However, peptide exchange reactions may be performed with MHC class I concentrations up to 100-200 μg/mL.

Materials:
96-well plates (cat. #: 651201 polypropylene microplate 96 well V sharp, Greiner Bio-one) UV-lamp 366 nm CAMAG UV Cabinet 3 (cat. #: 022.9070, CAMAG) fitted with UV Lamp long-wave UV, 366 nm, 2×8 W (cat. #: 022.9115, CAMAG) or Uvitec tube light, with 2×15W, 365 nm blacklight blue tubes (Model-LI215BLB sizes L×W×H 505×140×117 mm) Centrifuge with rotor for microtiter plates.

Procedure:
1. In a 96-well plate, add the following reagents to each well:

| Reagent | Amount | Final concentration |
|---|---|---|
| PBS | 100 μL | Not applicable |
| 10× Exchange peptide (500 μM in PBS) | 12.5 μL | 50 μM |
| 10× UV-sensitive MHC class I molecules (250 μg/mL: ~5 μM) | 12.5 μL | 25 μg/mL (approx. 0.5 μM) |

2. Place the 96-well plate under a UV lamp (366 nm) for 1 hr, with a distance between the UV lamp and sample of approximately 5 cm.
3. Spin the plate at 3,300 g for 5 minutes. Transfer 100 μL of supernatant (keep the plate at an angle to avoid transferring any pellet) to a new 96-well plate for downstream applications.

Example 17—Assemble Fluorochrome Conjugated pMHC Multimers

MHC class I complexes may be complexed with fluorophore-labeled streptavidin to form MHC class I tetramers for T cell analysis. Commonly used fluorophores include allophycocyanin and phycoerythrin, and the formation of MHC multimers with these conjugates is described below. However, streptavidin-coated quantum dots may also be used to prepare MHC multimers for T cell detection.

Materials:
PE-streptavidin solution 1 mg/mL (cat. #: S866, Molecular Probes) or APC streptavidin solution 1 mg/mL (cat. #: S868, Molecular Probes)
Microtiter plates with exchanged MHC class I complexes, containing 25 μg/mL of pMHC in 100 μL/well. This corresponds to 2.5 μg or 0.05 nmol MHC class I per well.

Procedure:
1. Generate dilutions of 27 μg/mL of streptavidin-PE in PBS, or of 14.6 μg/mL of streptavidin-APC in PBS, preparing 100 μL for each well of MHC class I.
2. Add streptavidin-PE or -APC to MHC class I by four sequential additions of 25 μL with 10 minute intervals.

Example 18—Combinatorial Encoding of MHC Multimers

UV-Mediated MHC Peptide Exchange
1. Thaw the stock solution of biotinylated p*MHC complexes on ice.
2. Dilute the biotinylated p*MHC complexes of interest in PBS to 200 μg/mL. A volume of 60 μL is needed per exchange reaction. For the pMHC complexes to be conjugated to Qdot585, 80 μL is needed per exchange reaction.
3. Dilute peptide stocks to 400 μM in PBS. Prepare a minimum of 70 μL per peptide; for peptides used to make pMHC complexes to be conjugated to Qdot585, prepare a minimum of 90 μL per peptide.
4. In a 96-well polypropylene microplate with a V-bottom, mix 60 μL 200 μg/mL p*MHC of the chosen allele and 60 μL of a 400 μM peptide solution per well (final concentrations: 100 μg/mL p*MHC and 200 μM peptide). For the pMHC complexes to be conjugated to Qdot585, mix 80 μL of 200 μg/mL p*MHC and 80 μL of 400 μM peptide solution.
5. Expose the 96-well microplate to UV light (~366 n) for 1 h at RT. The distance to the UV lamp should be 2-5 cm.
6. Centrifuge the plate at 3,300 g for 5 min at RT.
7. Repeat Step 6 if the pause point was included, and transfer 2×50 μL of the supernatant to two fresh 96-well polypropylene microplates with V-bottoms and keep them on ice. For the pMHC complexes to be conjugated to Qdot585, transfer 2×70 μL. Be careful not to transfer the bottom pellet (often invisible), as the transfer of aggregates will potentially increase the background of the final MHC multimer staining.
8. Multimerize the pMHC monomers by conjugation to fluorochrome-streptavidin conjugates. The differential conjugation is described below: option A for conjugation to Qdot605-, 625-, 655- or 705-streptavidin; option B for conjugation to Qdot585-streptavidin; and option C for conjugation to PE-, APC- or PE-Cy7-streptavidin.

(A) Conjugation to Qdot605-, 625-, 655- or 705-streptavidin: (i) Add 3.5 μL of Qdot-streptavidin conjugate (stock concentration 1 μM) per 50 μL of pMHC monomer (to a final concentration of 66 nM).

(B) Conjugation to Qdot585-streptavidin: (i) Add 4.9 μL of Qdot585-streptavidin conjugate (stock concentration 1 μM) per 70 μL of pMHC monomer (to a final concentration of 66 nM).

(C) Conjugation to PE-, APC- or PE-Cy7-streptavidin: (i) Add 4.6 μL of PE-, APC- or PE-Cy7-streptavidin conjugate (stock concentration 200 μg/mL) per 50 μL of pMHC monomer (to a final concentration of 16.8 μg/mL).

9. Mix well and leave to conjugate for 30 min on ice.
10. Add D-biotin and $NaN_3$ to a final concentration of 25 μM D-biotin and 0.02% (wt/vol) $NaN_3$. Do this by adding 2.5 μL of a 20-fold stock solution (500 μM D-biotin with 0.4% (wt/vol) $NaN_3$) to each well; for MHC multimers conjugated to Qdot585, add 3.5 μL to each well. Mix well and incubate on ice for 20 min.
11. Add 50 μL of PBS containing 25 μM D-biotin and 0.02% (wt/vol) $NaN_3$ to the MHC multimers conjugated to PE, APC or PE-Cy7 (twofold dilution).
12. Mix the different complexes. When mixing, use a 2:1 ratio of Qdot585 to every other color complex. Mix all other color complexes in a 1:1 ratio.

T Cell Staining with MHC Multimers
13. Mix MHC multimers for all the 27 color combinations to obtain one ready-to-use sample and centrifuge it at 3,300 g for 5 min at 4° C. and transfer the supernatant. In total, 54 μL of supernatant will be required for each T cell staining (i.e., 2 μL for each individual pMHC complex present in the mix).
14. Thaw the PBMC samples (or other relevant T cell samples) and wash them twice with RPMI. It is recommended to treat with DNase upon thawing to reduce clotting of the cells (e.g., by thawing cells in medium containing 0.025 mg/mL Pulmozyme and 2.5 mM $MgCl_2$).
15. Resuspend cells in PBS with 2% (vol/vol) FBS (FACS buffer) and distribute them a 96-well polystyrene U-bottom microplate, up to 3×10⁶ cells per well in 200 μL of FACS buffer.
16. Spin the plate at 490 g for 5 min at RT.
17. Throw out buffer by tipping the plate upside down-cells are left as a pellet in the bottom of the well.
18. Add 54 μL of the MHC multimers from Step 13 and mix well.
19. Incubate for 15 min at 37° C.
20. Move the plate onto ice and add 20 μL of antibody mix from a 5× stock.
21. Add 4 μL of a 40-fold dilution of the near-IR dead cell stain and mix well.
22. Incubate for 30 min on ice.
23. Spin the plate at 490 g for 5 min at 4° C.
24. Throw out the supernatant by tipping the plate upside down.
25. Wash twice with 200 μL of FACS buffer (centrifuge twice at 490 g for 5 min at 4° C. and tip the plate upside down after each spin to remove the supernatant).
26. Resuspend the pellet in 50-100 μL of FACS buffer and transfer it to 1.4 mL or 5 mL FACS tubes. The samples are now ready for acquisition on the flow cytometer.

Single Color Compensation Controls
27. Add 100 μL of FACS buffer and one drop of negative compensation beads to 11 FACS tubes (nos. 1-11).
28. Add one drop of anti-mouse Ig-κ compensation beads to tubes 1-10 from Step 27 and one drop of ArC amine reactive beads to a new tube (no. 12).
29. Add 5 μL of 1 mg/mL anti-CD8-biotin to tubes 1-8 and mix.
30. Incubate tubes 1-8 for 20 min on ice.
31. Wash tubes 1-8 twice with 2 mL of FACS buffer (centrifuge at 490 g for 5 min at 4° C.).
32. Add 1 μL of near-IR dead cell stain to tube 12 (from Step 28); mix and incubate for 30 min at RT in the dark.
33. Dilute the streptavidin-fluorochrome conjugates tenfold (except for Qdot585), add 5 μL of each to tubes 1-7, add 1 μL of undiluted Qdot585-streptavidin to tube 8, and then incubate for 20 min on ice in the dark.
34. Add 5 μL of FITC antibody (use one of the dump channel antibodies) or 5 μL of the Alexa Fluor 700 anti-CD8a antibody to tubes 9 and 10 (from Step 28); incubate for 20 min on ice in the dark.
35. Wash tubes 1-11 twice with 2 mL of FACS buffer, and wash tube 12 twice with 2 mL of PBS (centrifuge at 490 g for 5 min at 4° C.).
36. Resuspend all tubes in 150 μL of FACS buffer. Add one drop of ArC-negative beads to tube 12 and mix. The compensation controls are ready for acquisition on the flow cytometer.

Gating Strategy
37. Gate first on lymphocytes, and subsequently on single cells (FSC-α, FSC-W), live cells, dump channel-negative cells and CD8⁺ cells.
38. Draw separate gates that define positive events in the eight different MHC multimer channels.
39. Invert the eight MHC multimer-positive gates, to obtain eight gates that select CD8⁺ and MHC multimer-negative cells for each MHC multimer channel.

40. Intersect gates for two MHC multimer-positive populations with the inverted gates for each of the other six MHC multimer populations. This combination of gates selects for CD8$^+$ cells that are positive in two and only two MHC multimer channels (i.e., if a cell is positive in one or in three or more MHC multimer channels, it is gated out). An example of such a gate is PE$^+$ and APC$^+$ and PE-Cy7$^-$ and Qdot585$^-$ and Qdot605$^-$ and Qdot625$^-$ and Qdot655$^-$ and Qdot705$^-$.

41. Make these intersected gates (described in Step 40) for all 28 possible two-color combinations of MHC multimers.

42. Join all the 28 gates from Step 41 (e.g., gate 1 or gate 2 or . . . or gate 28).

43. Intersect the eight inverted gates from Step 39 (PE$^-$ and APC$^-$ and PE-Cy7$^-$ and Qdot585$^-$ and Qdot605$^-$ and Qdot625$^-$ and Qdot655$^-$ and Qdot705$^-$).

44. Join the two gates from Steps 42 and 43.

45. Make 28 dot plots with all the possible two-color codes, showing the events gated for in Step 44. These plots will only show CD8$^+$ cells that are negative for all MHC multimers or positive for two; all background events are gated out.

46. Also make 28 dot plots with all the possible two-color codes, showing all CD8$^+$ cells. These plots will provide a good indication of the background level in the sample and can also be used to reveal improper compensation. It is recommended comparing these 'nongated' plots with the gated plots in order to gain experience in separating responses from background. This may be especially of importance for low-intensity populations.

Example 19—Fluorescent Cell Barcoding Phospho Flow

Cellular barcoding can be used to perform multiplexed phenotypic and functional analysis by flow cytometry. The phospho flow can be performed with slight modifications to include FCB labeling. After formaldehyde fixation, samples will be resuspended in 100% 20-25° C. methanol (typically 500 µL per 10$^6$ cells) containing the indicated concentration of Alexa Fluor or Pacific Blue succinimidyl esters, with each sample receiving a different concentration of fluorescent dye. In some cases, samples can be resuspended in methanol and then FCB fluorophores dissolved in DMSO (typically at 1:50 dilution) will be added. This can be done to allow prior preparation and storage of FCB staining matrices in DMSO, necessary for 96-well plate experiments. After labeling for 15 min at 20-25° C., cells will be washed twice with staining medium (phosphate-buffered saline (pH 7.0) containing 0.5% BSA and 0.02% sodium azide). Labeling at 4° C. or colder can produce very low labeling intensities, allowing storage of samples at −80° C. in the methanol staining solution without increasing FCB staining levels.

The differentially labeled samples will be combined into one FACS tube or well, and pelleted again if the resulting volume is greater than 100 µL. The combined, barcoded sample (typically 100 µL) will be stained with phospho-specific and/or surface marker antibodies, washed and analyzed by flow cytometry. Flow cytometry can be performed on a BD LSR2 flow cytometer, equipped with 405 nm, 488 nm and 633 nm lasers, and manufacturer's stock filters, with replacement of the 405 nm octagon bandpass filter for Cascade Yellow with a 610/20 bandpass filter for detection of Quantum Dot 605.

Example 20—CD4$^+$ Naïve Inductions

Protocol 1 and 2 were carried out using PIN peptides. Antigen specific CD4$^+$ naïve inductions were assessed. The results can be seen below in Table 4.

TABLE 4

CD4$^+$ naïve induction results from donors 1 and 2

| long term induction read-out LTS#35 | Donor 2 | | | Donor 1 | | |
|---|---|---|---|---|---|---|
| | Prot. 1 (CD25$^-$) | Prot. 2 whole PBMC | Prot. 2 CD25$^-$ | Prot. 1 (CD25$^-$) | Prot. 2 whole PBMC | Prot. 2 CD25$^-$ |
| Induced with PIN replicate 1 | Y | Y | Y | Y | Y | Y |
| Long peptide PIN replicate 2 | Y | Y | Y | Y | — | — |
| PIN replicate 3 | — | Y | Y | Y | Y | — |
| Results | 2/366% | 3/3100% | 3/3100% | 3/3100% | 2/366% | 1/333% |

Example 21—Manufacturing Process: DC Derivation

| Step 1 | Monocyte Enrichment and DC Culture | Autologous Cells Apheresis Bag #1 |
|---|---|---|
| Step 2 | | Monocyte Enrichment |
| Step 3 | | DC culture |
| Step 4 | Peptide Loading and DC Maturation | DC Harvest, resuspension in DC Media |
| Step 5 | | Addition Patient Specific Peptides and incubation |
| Step 6 | | DC Maturation |

Example 22—T Cell Induction Protocol 1

T Cell Induction #1

| Step 7 | Autologous Cells Apheresis Bag #2 |
|---|---|
| Step 8 | CD25$^+$ depletion ($^+$/− CD14$^+$ depletion) |
| Step 9 | DC wash and resuspension in T Cell culture Media |
| Step 10 | Incubation of T cells with Matured DCs (from DC Derivation) |

T Cell Induction #2

| Step 11 | T Cell Washing and Resuspension in T cell Media |
|---|---|
| Step 12 | Incubation of T cells with Matured DC (from DC Derivation) |

T cell induction #3

| Step 11 | T Cell Washing and Resuspension in T cell Media |
|---|---|
| Step 12 | Incubation of T cells with Matured DC (from DC Derivation) |

Harvest & Cryopreservation

| Step 15 | | T Cell Harvest | Release Testing: Mycoplasma |
|---|---|---|---|
| Step 16 | Drug Substance (DS) | Wash and Suspension in Final Formulation | Release Testing: Sterility, Endotoxin, Cell Phenotype, TNC Count, Viability, Cell Concentration, Potency |
| Step 17 | Drug Product (DP) | DS Fill and Cryopreservation Store in vapor phase of liquid nitrogen | |

Example 23—T Cell Induction Protocol 2

T Cell Induction #1

| Step 7 | Autologous Cells Apheresis Bag #2 |
|---|---|
| Step 8 | CD25$^+$ depletion ($^+$/– CD14$^+$ depletion) |
| Step 8a | Add FLT3L |
| Step 9 | Addition Patient Specific Peptides and incubation |
| Step 10 | Incubation of depleted PMBCs with FLT3L and peptides |

T Cell Induction #2

| Step 11 | T Cell Washing and Resuspension in T cell Media |
|---|---|
| Step 12 | Incubation of T cells with Matured DC (from DC Derivation) |

T Cell Induction #3

| Step 11 | T Cell Washing and Resuspension in T cell Media |
|---|---|
| Step 12 | Incubation of T cells with Matured DC (from DC Derivation) |

Harvest & Cryopreservation

| Step 15 | | T Cell Harvest | Release Testing: Mycoplasma |
|---|---|---|---|
| Step 16 | Drug Substance (DS) | Wash and Suspension in Final Formulation | Release Testing: Sterility, Endotoxin, Cell Phenotype, TNC Count, Viability, Cell Concentration, Potency |
| Step 17 | Drug Product (DP) | DS Fill and Cryopreservation Store in vapor phase of liquid nitrogen | |

Example 24—Simultaneous Detection and Functional Characterization of CD4$^+$ and CD8$^+$ Neoantigen-Specific T Cell Responses Using Multiplexed, Multiparameter Flow Cytometry Neoantigens, which arise in cancer cells from somatic mutations that alter protein-coding gene sequences, are emerging as an attractive target for immunotherapy. They are uniquely expressed on tumor cells as opposed to healthy tissue and may be recognized as foreign antigens by the immune system, increasing immunogenicity. T cell manufacturing processes were developed to raise memory and de novo CD4$^+$ and CD8$^+$ T cell responses to patient-specific neoantigens through multiple rounds of ex-vivo T cell stimulation, generating a neoantigen-reactive T cell product for use in adoptive cell therapy. Detailed characterization of the stimulated T cell product can be used to test the many potential variables these processes utilize.

Figure 26:
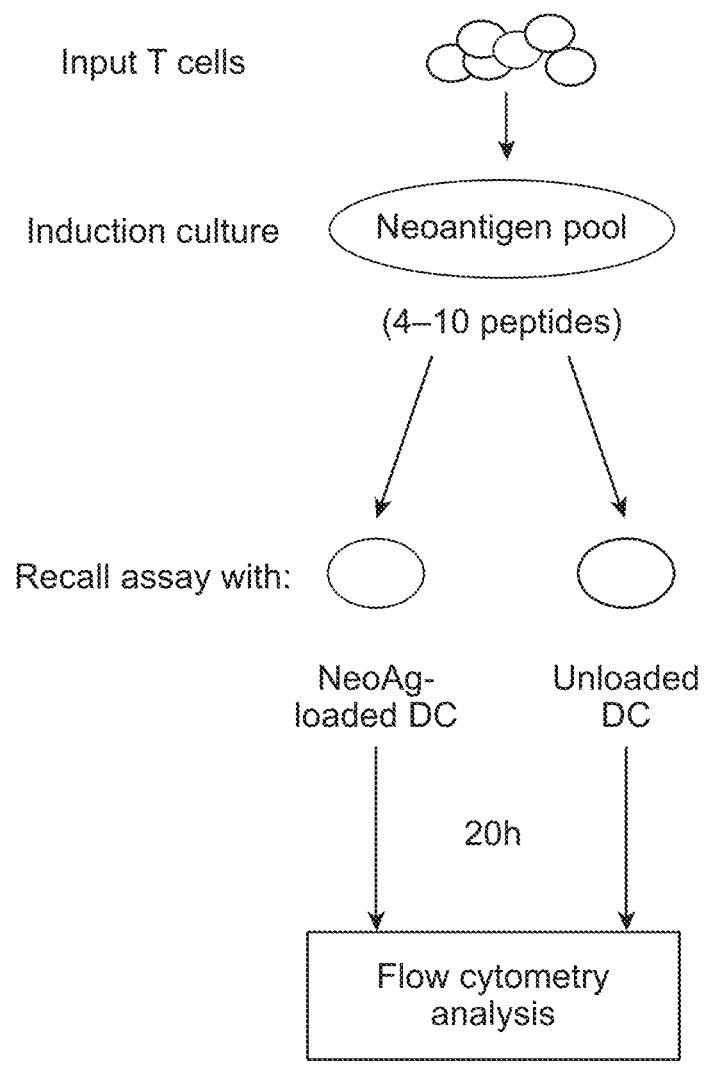
FIG. 26 depicts an example of a recall assay to test functionality, phenotype and/or function of T cells and/or T cell responses.

To probe T cell functionality and/or specificity, an assay was developed to simultaneously detect antigen-specific T cell responses and characterize their magnitude and function. This assay employed the following steps. First T cell-APC co-cultures were used to elicit reactivity in antigen-specific T cells. Optionally, sample multiplexing using fluorescent cell barcoding was employed. To identify antigen-specific CD8$^+$ T cells and to examine T cell functionality, staining of peptide-MHC multimers and multiparameter intracellular and/or cell surface cell marker staining were probed simultaneously using FACS analysis. The results of this streamlined assay demonstrated its application to study T cell responses induced from a healthy donor. Neoantigen-specific T cell responses induced toward peptides were identified in a healthy donor. The magnitude, specificity and functionality of the induced T cell responses were also compared. FIG. 25 and FIG. 26 depict exemplary processes for simultaneous analysis of a cell marker profile and MHC tetramer staining of a T cell sample.

Briefly, different T cell samples were barcoded with different fluorescent dyes at different concentrations (see, e.g., Example 19). Each sample received a different concentration of fluorescent dye or combination of multiple dyes at different concentrations. Samples were resuspended in phosphate-buffered saline (PBS) and then fluorophores dissolved in DMSO (typically at 1:50 dilution) were added to a maximum final concentration of 5 μM. After labeling for 5 min at 37° C., excess fluorescent dye was quenched by the addition of protein-containing medium (e.g. RPMI medium containing 10% pooled human type AB serum). Uniquely barcoded T cell cultures were challenged with autologous APC pulsed with the antigen peptides as described above.

The differentially labeled samples were combined into one FACS tube or well, and pelleted again if the resulting volume is greater than 100 μL. The combined, barcoded sample (typically 100 μL) was stained with surface marker antibodies including LAMP-1 (see, e.g., Example 11) and incubated with assembled fluorochrome conjugated peptide-MHC multimers (see, e.g., Examples 17 and 18 above). After fixation and permeabilization, the sample was additionally stained intracellularly with antibodies targeting TNF-α and IFN-γ.

The cell marker profile and MHC tetramer staining of the combined, barcoded T cell sample were then analyzed simultaneously by flow cytometry on flow cytometer. Unlike other methods that analyze cell marker profiles and MHC tetramer staining of a T cell sample separately, the simultaneous analysis of the cell marker profile and MHC tetramer staining of a T cell sample described in this example provides information about the percentage of T cells that are both antigen specific and that have increased cell marker staining. Other methods that analyze cell marker profiles and MHC tetramer staining of a T cell sample, separately determine the percentage of T cells of a sample that are antigen specific, and separately determine the percentage of T cells that have increased cell marker staining, only allowing correlation of these frequencies. The simultaneous analysis of the cell marker profile and MHC tetramer staining of a T cell sample described in this example does not rely on correlation of the frequency of antigen specific T cells and the frequency of T cells that have increased cell marker staining; rather, it provides a frequency of T cells that are both antigen specific and that have increased cell marker staining. The simultaneous analysis of the cell marker profile and MHC tetramer staining of a T cell sample described in this example allows for determination on a single cell level, those cells that are both antigen specific and that have increased cell marker staining.

To evaluate the success of a given induction process, a recall response assay was used followed by a multiplexed, multiparameter flow cytometry panel analysis. A sample taken from an induction culture was labeled with a unique two-color fluorescent cell barcode. The labeled cells were incubated on antigen-loaded DCs or unloaded DCs overnight to stimulate a functional response in the antigen-specific cells. The next day, uniquely labeled cells were combined prior to antibody and multimer staining according to the table below.

| Marker | Fluorochrome | Purpose |
| --- | --- | --- |
| CD19/CD16/CD14 | BUV39 | Cell exclusion |
| Live/Dead | Near-IR | Dead cell exclusion |
| CD3 | BUV805 | Lineage gating |
| CD4 | Alexa Fluor 700 | Lineage gating |
| CD8 | PerCP-Cy5.5 | Lineage gating |
| Barcode 1 | CFSE | Sample multiplexing |
| Barcode 2 | TagIT Violet | Sample multiplexing |
| Multimer 1 | PE | CD8+ antigen specificity |
| Multimer 2 | BV650 | CD8+ antigen specificity |
| IFNγ | APC | Functionality |
| TNFα | BV711 | Functionality |
| CD107a | BV786 | Cytotoxicity |
| 4-1BB | PE/Dazzle 594 | Activation |

Figure 27A:
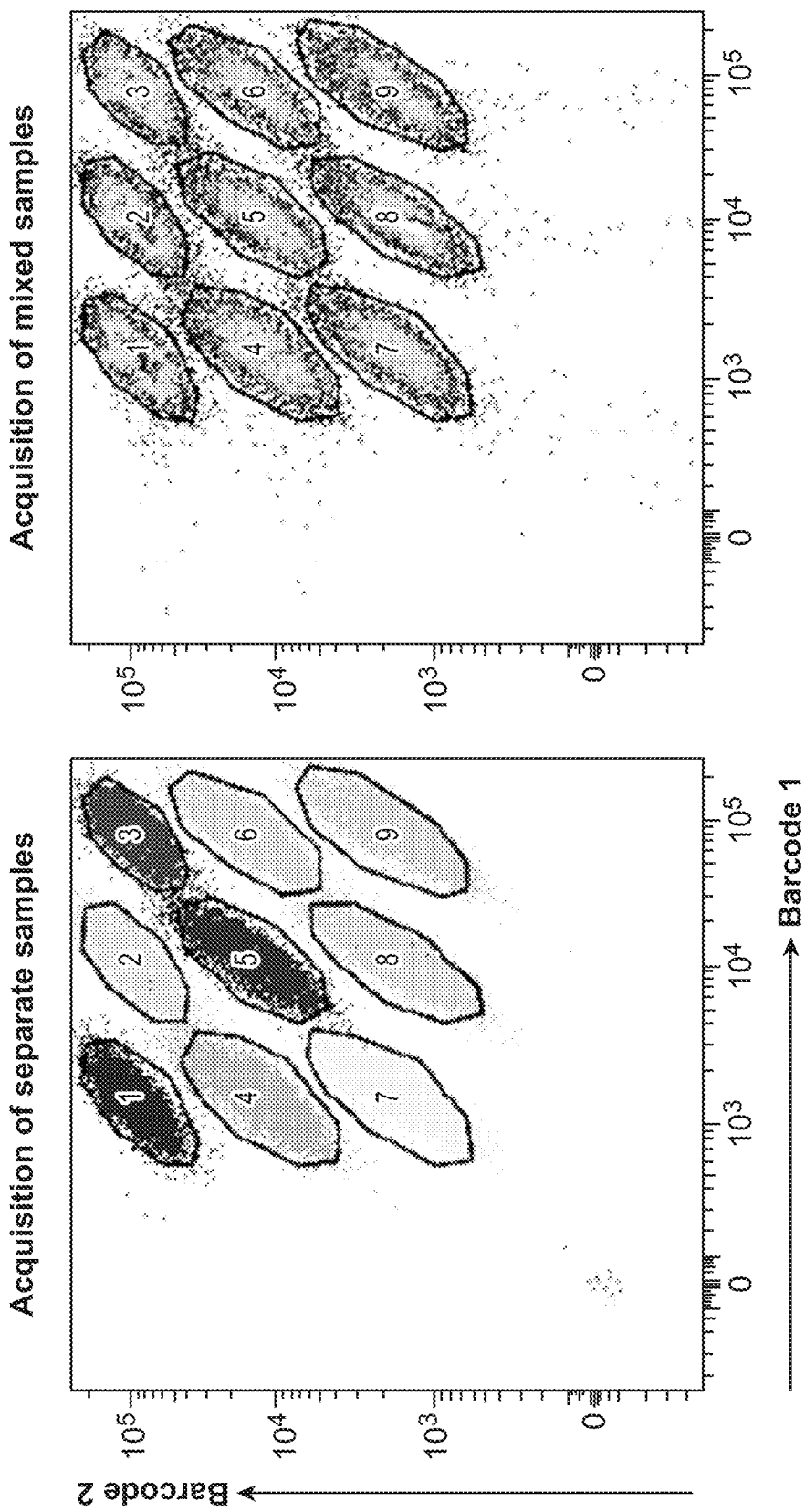
FIG. 27A depicts example flow cytometric analyses showing the ability to deconvolute multiplexed samples by labeled samples, acquired either separately or as a mixture, in a recall assay. Uniquely labeled samples were resolved with minimal to no cross-contamination to other barcodes.
Figure 27B:
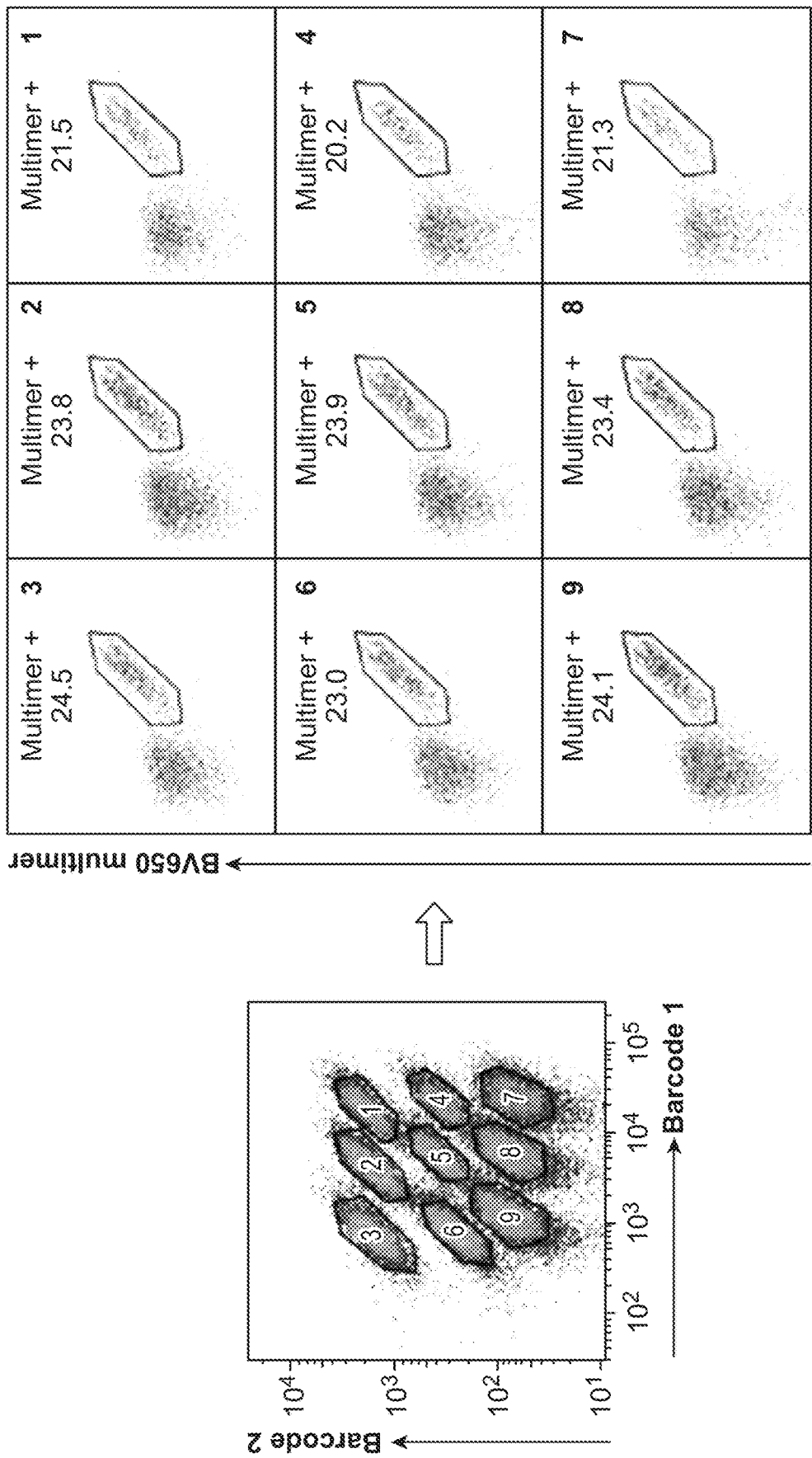
FIG. 27B depicts example flow cytometric analyses showing detection of antigen-specific CD8+ T cells by multimer staining of a mixture of nine uniquely labeled samples in a recall assay.

The ability to fully deconvolute multiplexed samples by labeled, acquired either separately or as a mixture, was determined (FIG. 27A). Uniquely labeled samples could be fully resolved with minimal to no cross-contamination to other barcodes. Detection of antigen-specific CD8+ T cells by multimer staining was maintained with sample multiplexing. A sample of an induction culture containing~20% of CD8+ T cells with specificity for CMV pp65, EBV BRLF1, EBV BMLF1 and/or MART-1 was split, labeled with nine unique two-color barcodes, and then combined for staining with tetramers targeting all four specificities in the same two-color combinations (brilliant violet 650 [BV650] and phycoerythrin [PE]) (FIG. 27B). All nine barcodes yielded comparable tetramer staining pattern and detected frequency of tetramer+ cells.

Figure 28B:
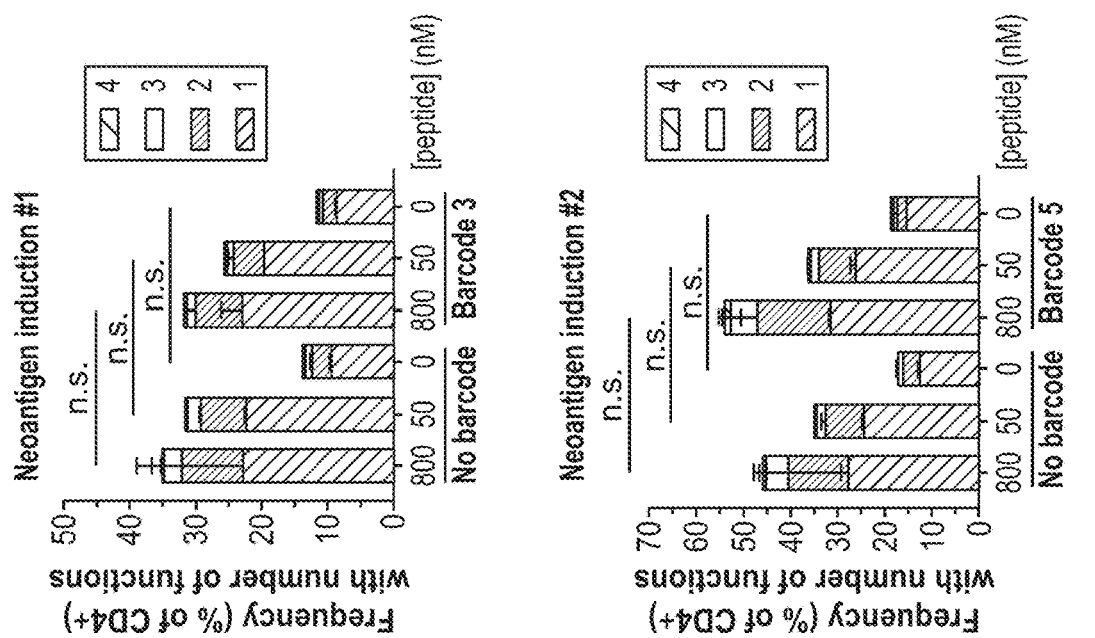
FIG. 28B depicts example bar graphs of the percent of CD4+ T cells with number of functions incubated with DCs loaded with the indicated concentration of peptide in a recall response assay. Samples of two induced cultures containing de novo CD4+ T cell responses were analyzed either alone without barcoding or mixed with irrelevant samples. Barcoding did not alter detectable functionality. The number of functions and magnitude of response elicited from the cells was not significantly changed with sample barcoding.
Figure 28A:
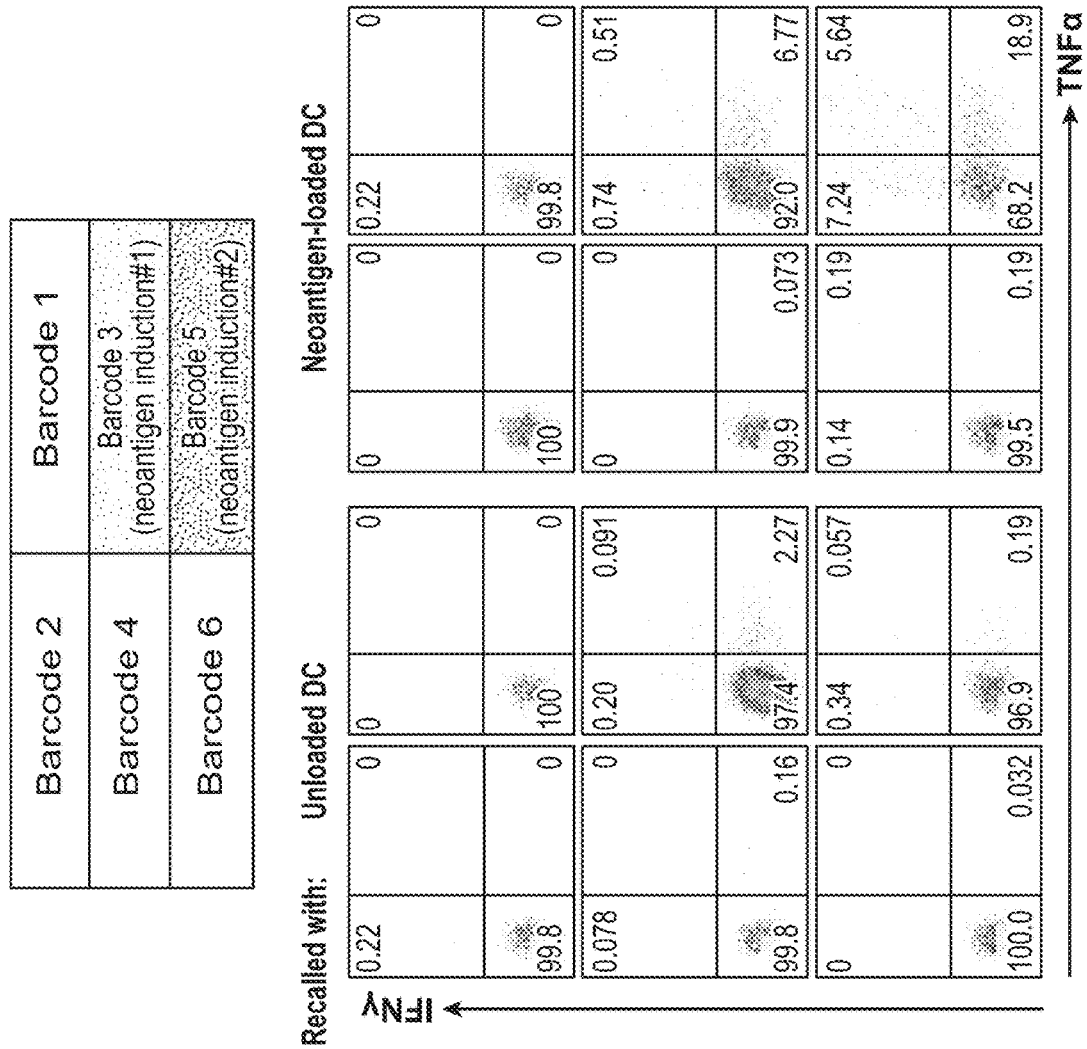
FIG. 28A depicts example flow cytometric analyses of a recall assay using six uniquely barcoded samples recalled with unloaded DCs and neoantigen-loaded DCs.

Samples of two induced cultures containing de novo CD4+ T-cell responses were also analyzed in a recall response assay, either alone without barcoding or mixed with irrelevant samples (FIG. 28A and FIG. 28B). The number of functions and magnitude of response elicited from the cells was not significantly changed with sample barcoding.

Figures 29A, 29B:
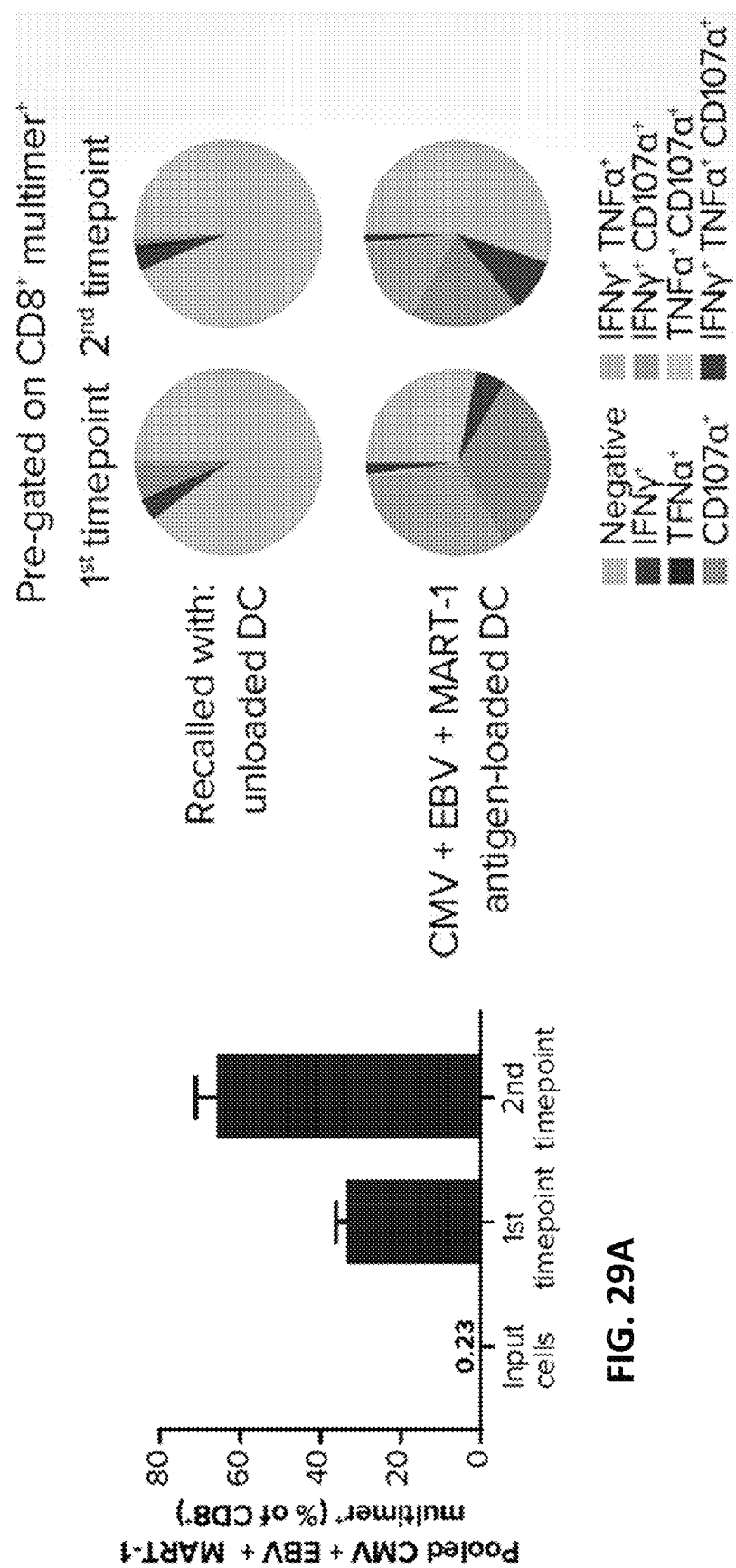
FIG. 29A depicts an example bar graph showing results of antigen specific memory CD8+ T cell responses to viral antigens. CD8+ memory responses toward CMV pp65, MART-1 and EBV BRLF1 and BMLF1 epitopes could be raised from 0.23% of CD8+ T cells in the starting healthy donor material to >60%.
FIG. 29B depicts example results of a recall assay of antigen specific memory CD8+ T cell responses to viral antigens and then recalled with DCs loaded with and without viral antigens. The fraction of CD8+ T cells from two time points that release the indicated cytokines are depicted in the charts.

Simultaneous analysis of specificity and functionality of induced CD8+ memory responses demonstrated that CD8+ memory responses toward CMV pp65, MART-1 and EBV BRLF1 and BMLF1 epitopes could be raised from 0.23% of CD8+ T cells in the starting healthy donor material to >60% (FIG. 29A)

By pre-gating on the CD8+ multimer+ cells, the function of antigen-specific T cells was selectively interrogated (FIG. 29B). Cells exhibited cytotoxic function (CD107a surface exposure) and IFNγ secretion upon exposure to antigen-loaded DCs.

Figure 30A:
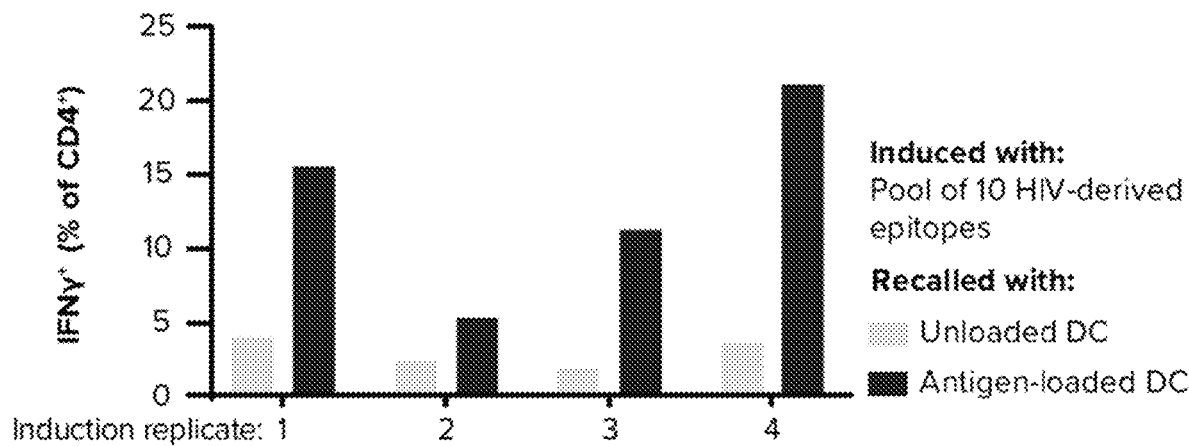
FIG. 30A depicts an example result of hit identification by detection and functional characterization of de novo induced CD4+ responses with multiple specificities in the same culture. In the example shown, an induction was performed in four replicate cultures targeting 10 HIV-derived epitopes, which are naïve targets in an HIV-negative healthy donor. Antigen-specific responses were detected in 4/4 biological replicates, with varying magnitude of response.
Figure 30B:
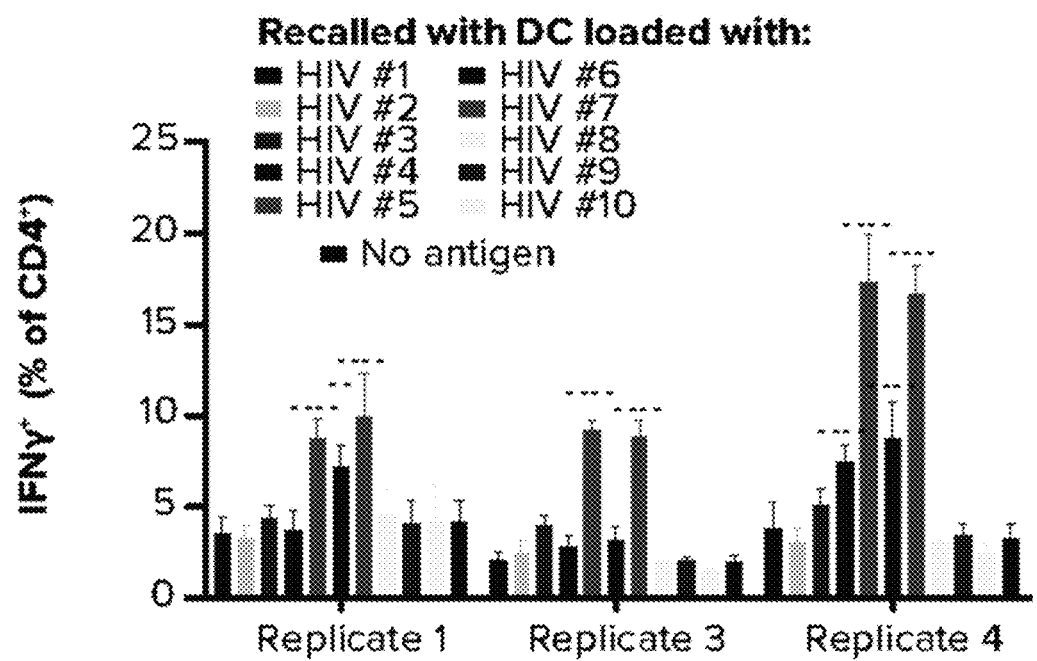
FIG. 30B depicts an example result of pool deconvolution by detection and functional characterization of de novo induced CD4+ responses with multiple specificities in the same culture. Multiple responses were detected in each replicate tested, and the same two epitopes (HIV #5 and HIV #7) yielded the highest magnitude response in each case.
Figure 31:
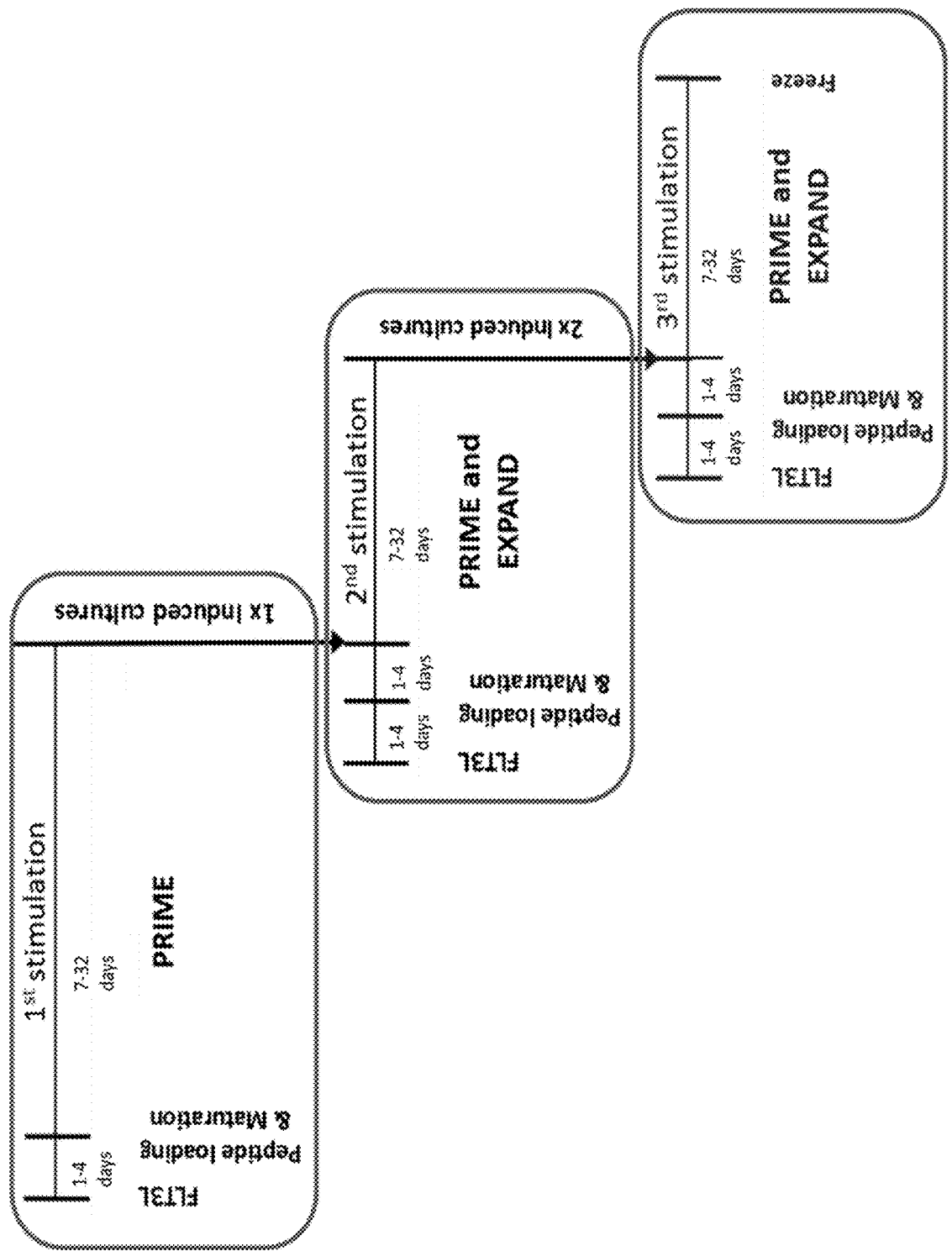
FIG. 31 depicts an example schematic of an antigen specific T cell manufacturing protocol.
Figure 32:
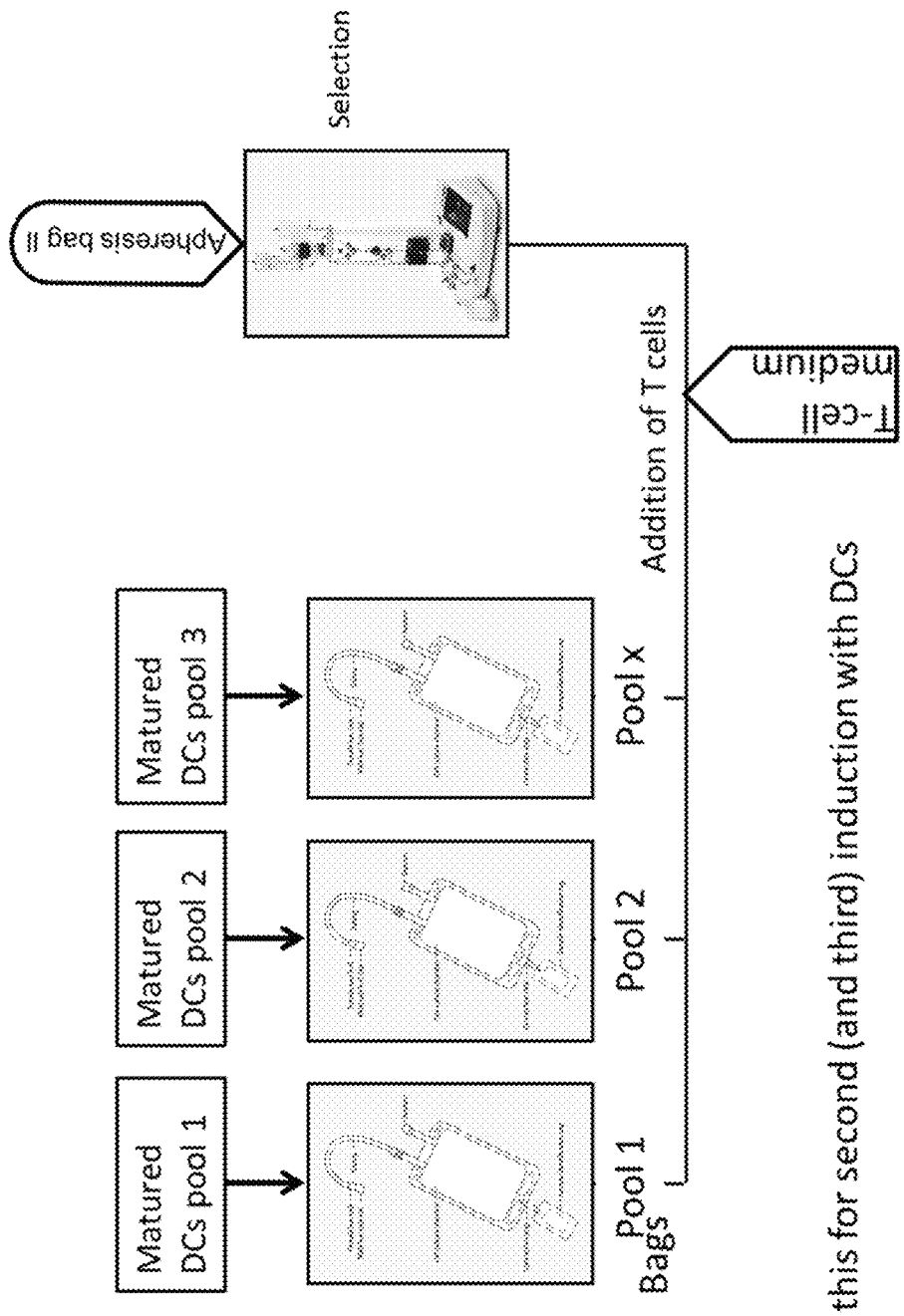
FIG. 32 depicts an example schematic of a T cell induction protocol.
Figure 33:
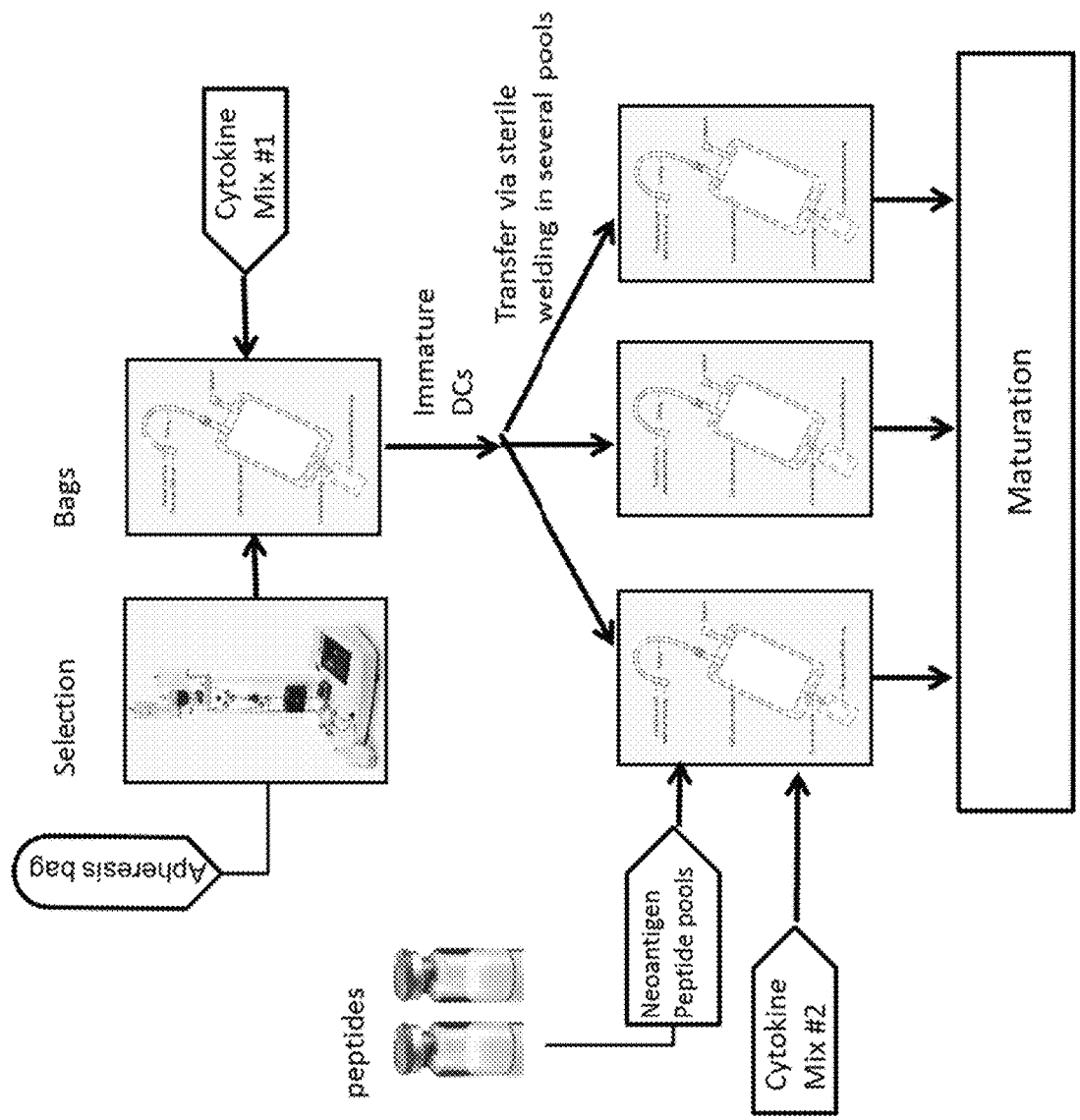
FIG. 33 depicts an example schematic of a dendritic cell generation protocol.

Detection and functional characterization of de novo induced CD4+ responses with multiple specificities in the same culture was also demonstrated. Antigen-specific functionality was utilized to identify induced CD4+ T-cell responses (FIG. 30A). In the example shown, an induction was performed in four replicate cultures targeting 10 HIV-derived epitopes, which are naïve targets in an HIV-negative healthy donor. Antigen-specific responses were detected in all four biological replicates. Three of the detected responses were selected for further follow-up by pool deconvolution to identify the specificity of the induced responses (FIG. 30B). Multiple responses were detected in each replicate tested, and the same two epitopes (HIV #5 and HIV #7) induced the highest magnitude response in each case. Without being bound to any theory, this may reflect greater immunogenicity of these epitopes in this donor due to MHC class II haplotype or a greater precursor frequency of T cells targeting these epitopes in the naïve repertoire. Sensitivity to antigen was determined for three selected responses by peptide titration during DC loading (FIG. 30C). The responses to HIV #5, HIV #6 and HIV #4 demonstrated an $EC_{50}$ of 0.45 µM, 0.43 µM and 9.1 µM, respectively.

Example 25—T Cell Manufacturing Protocol 3

Materials:
AIM V media (Invitrogen)
Human FLT3L, preclinical CellGenix #1415-050 Stock 50 ng/µL
TNF-α, preclinical CellGenix #1406-050 Stock 10 ng/µL
IL-1β, preclinical CellGenix #1411-050 Stock 10 ng/µL
PGE1 or Alprostadil—Cayman from Czech republic Stock 0.5 µg/µL
R10 media—RPMI 1640 glutamax+10% Human serum+1% PenStrep
20/80 Media—18% AIM V+72% RPMI 1640 glutamax+10% Human Serum+1% PenStrep
IL7 Stock 5 ng/µL
IL15 Stock 5 ng/µL Procedure:
Step 1: Plate 5 million PBMCs (or cells of interest) in each well of 24 well plate with FLT3L in 2 mL AIM V media
Step 2: Peptide loading and maturation—in AIMV
1. Mix peptide pool of interest (except for no peptide condition) with PBMCs (or cells of interest) in respective wells.
2. Incubate for 1 hr.
3. Mix Maturation cocktail (including TNF-α, IL-1β, PGE1, and IL-7) to each well after incubation.
Step 3: Add human serum to each well at a final concentration of 10% by volume and mix.
Step 4: Replace the media with fresh RPMI+10% HS media supplemented with IL7+IL15,
Step 5: Replace the media with fresh 20/80 media supplemented with IL7+IL15 during the period of incubation every 1-6 days.
Step 6: Plate 5 million PBMCs (or cells of interest) in each well of new 6-well plate with FLT3L in 2 ml AIM V media
Step 7: Peptide loading and maturation for re-stimulation—(new plates)
1. Mix peptide pool of interest (except for no peptide condition) with PBMCs (or cells of interest) in respective wells
2. Incubate for 1 hr.
3. Mix Maturation cocktail to each well after incubation Step 8: Re-stimulation:
1. Count first stimulation FLT3L cultures and add 5 million cultured cells to the new Re-stimulation plates.
2. Bring the culture volume to 5 mL (AIM V) and add 500 ul of Human serum (10% by volume)

Step 9: Remove 3 ml of the media and add 6 ml of RPMI+10% HS media supplemented with IL7+IL15.

Step 10: Replace 75% of the media with fresh 20/80 media supplemented with IL7+IL15.

Step 11: Repeat re-stimulation if needed.

Example 26—Experimental Data Using T Cell Manufacturing Protocol 3

Figure 34:
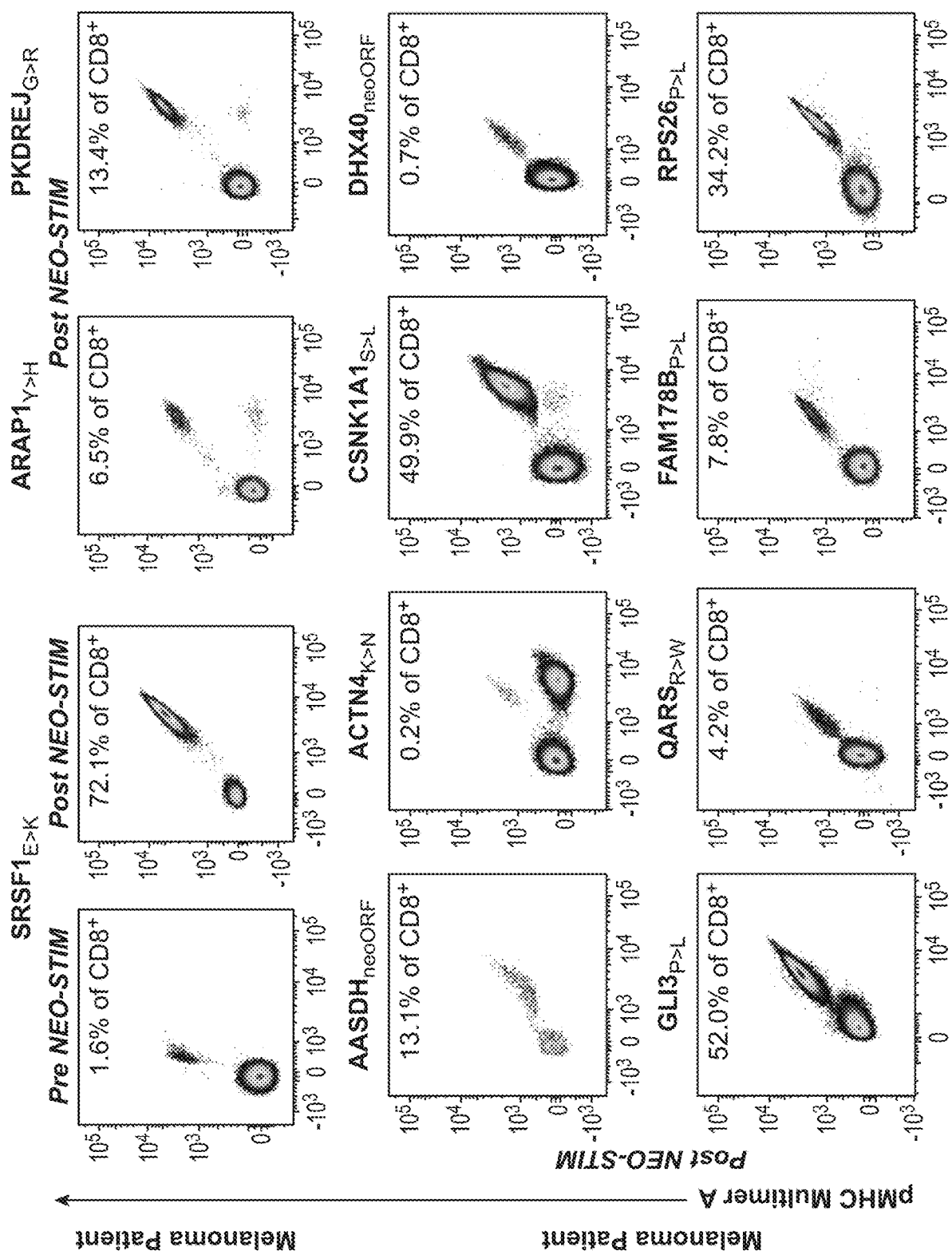
FIG. 34 depicts example pMHC multimer plots showing CD8+ T cell responses induced in leukapheresis material from a melanoma patient targeting patient-specific epitopes: $SRSF1_{E>K}$, $ARAP1_{Y>H}$ & $PKDREJ_{G>R}$, a melanoma patient targeting a patient-specific epitope (AASDHneoORF and seven model neoantigens: $ACTN4_{K>N}$, $CSNK1A1_{S>L}$, DHX40neoORF, $GLI3_{P>L}$ $QARSR_{>W}$, $FAM178B_{P>L}$ and $RPS26_{P>L}$. The first panel plots in the first and second rows indicate memory responses and the remaining plots indicate de novo responses.
Figure 35:
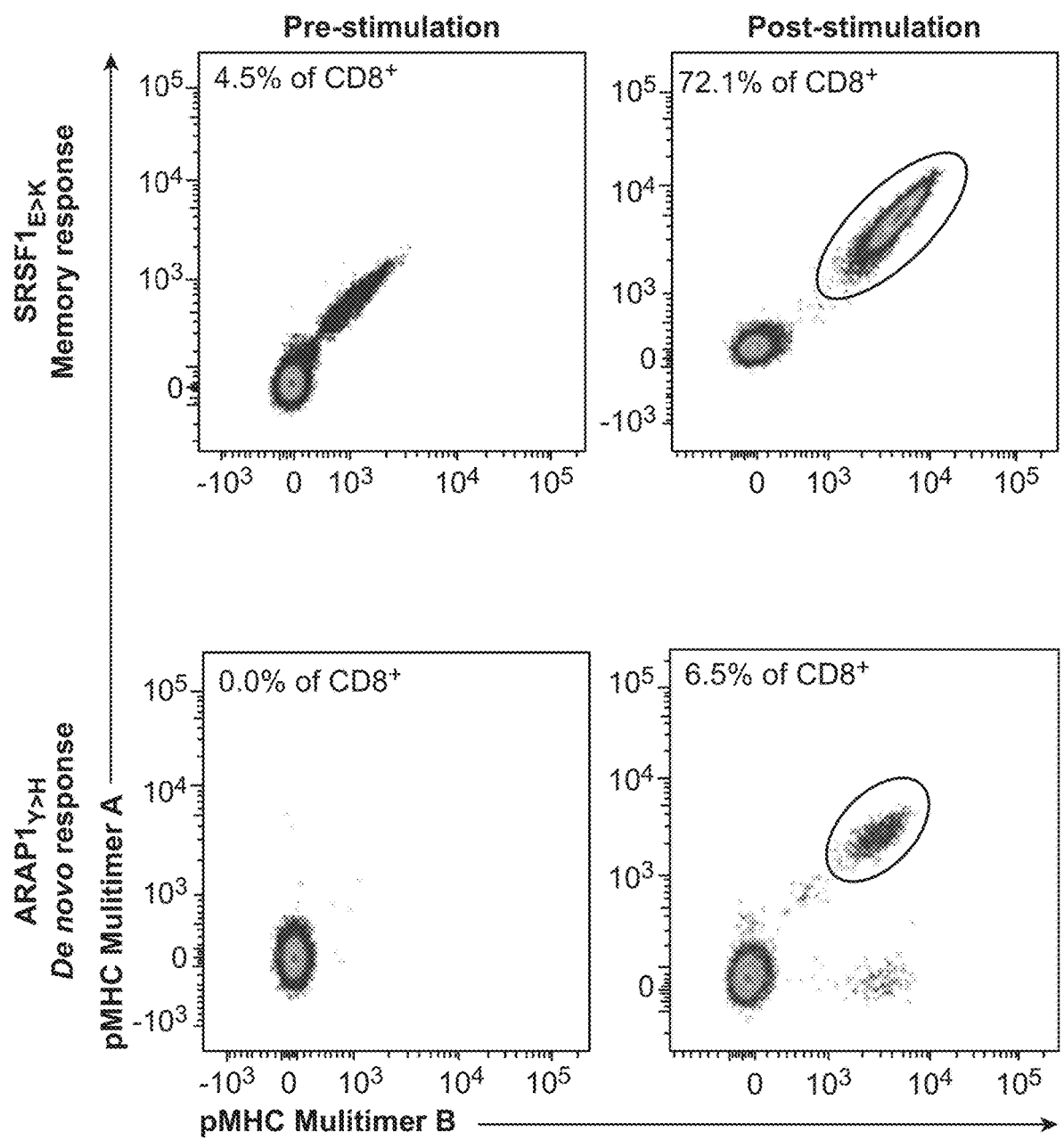
FIG. 35 depicts example data of pMHC multimer plots of $SRSF1_{E>K}$ and $ARAP1_{Y>H}$ pre and post peptide stimulation (left panels), pie charts depicting the functionality of neoantigen specific T cells upon re-challenge with neoantigen loaded DCs; gated on pMHC multimer+ CD8+ or CD4+ T cells. The polyfunctional profile of a CD8+ memory, CD8+ de novo and CD4+ de novo responses induced in a patient with melanoma are shown by a combination of 1, 2, or 3 functions (e.g., the one or more functions are production of one or more factors selected from IFNγ, TNFα, CD107a and 4-1BB).
Figure 35:
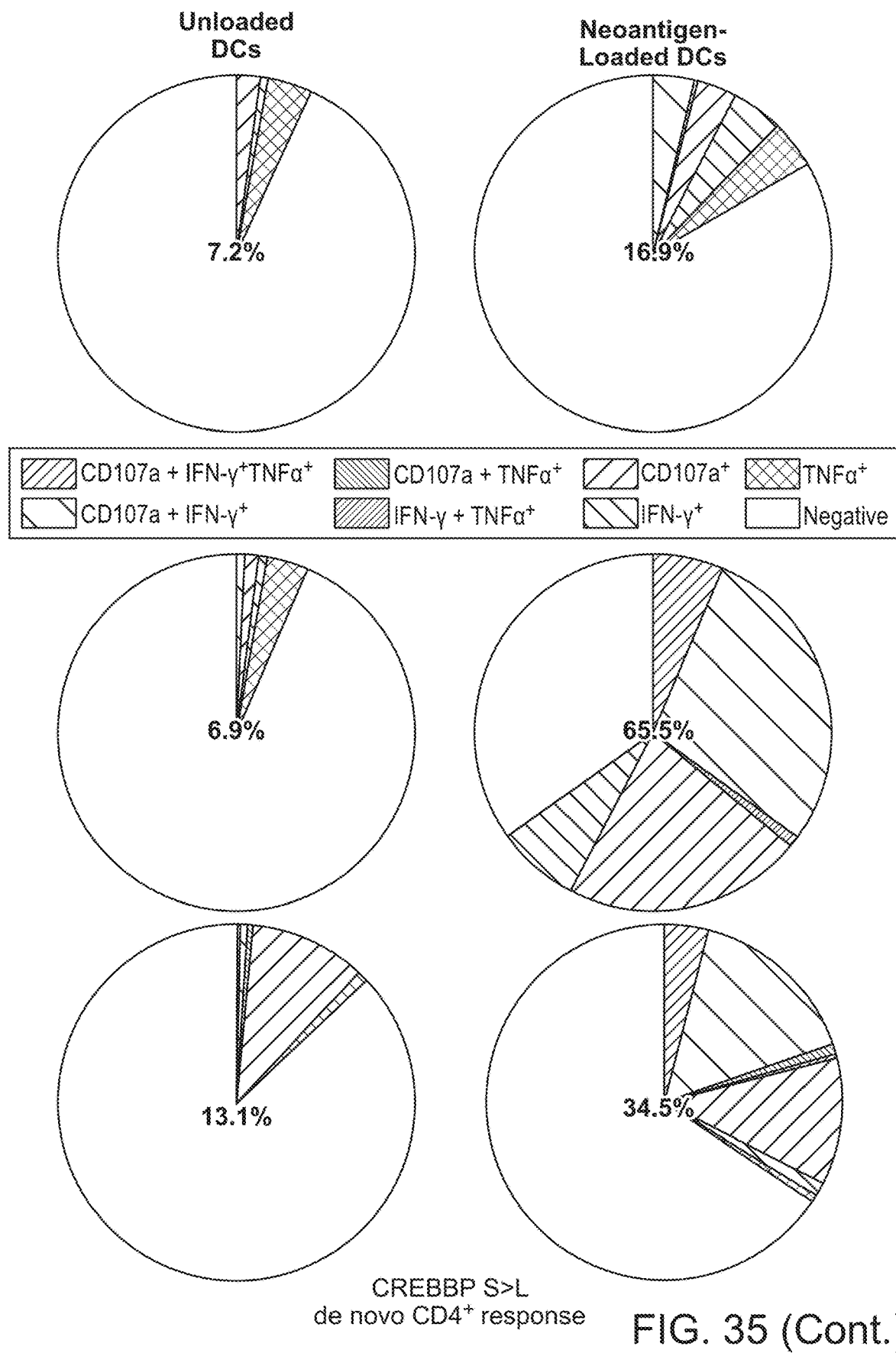
Figure 36:
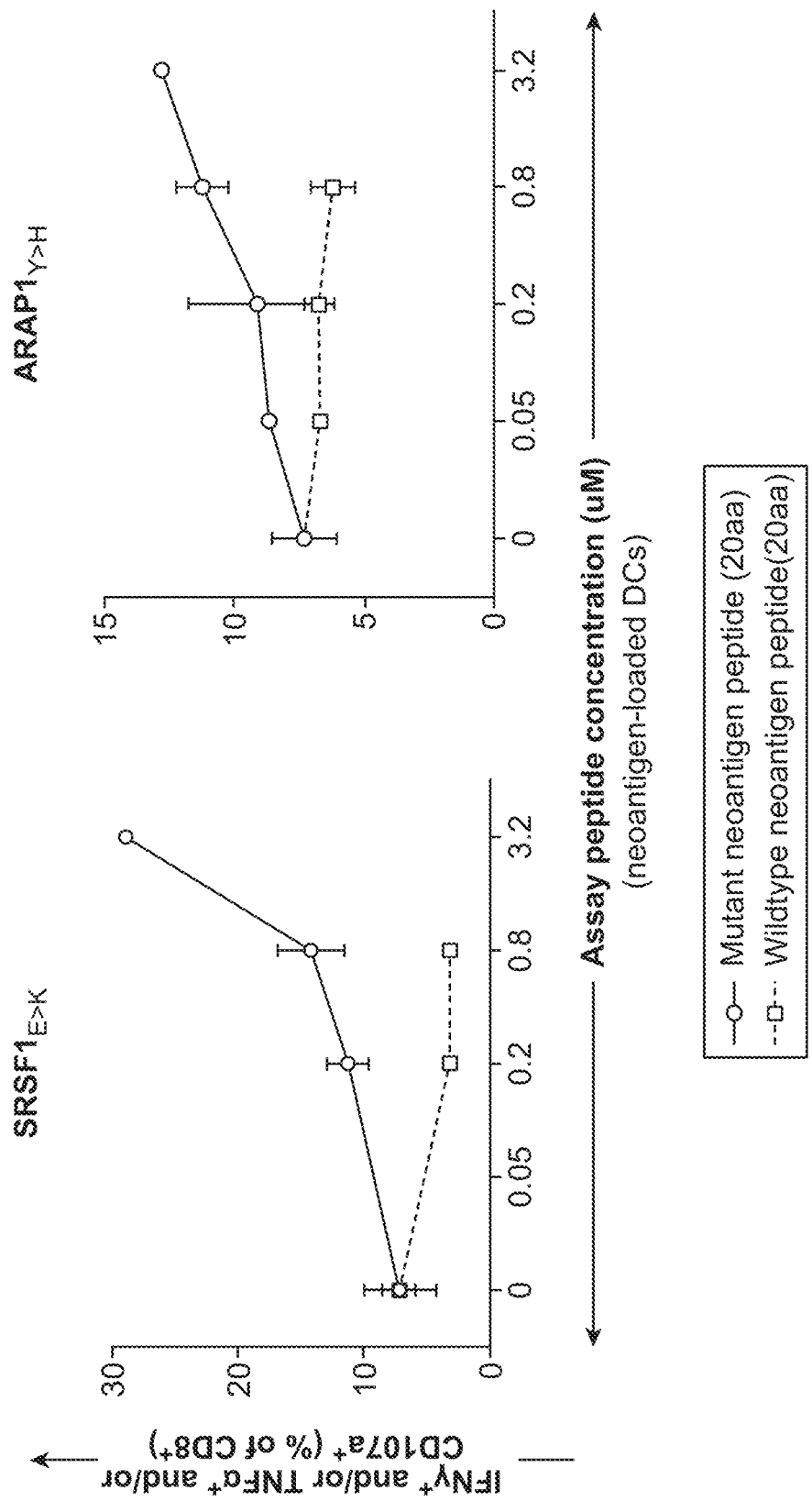
FIG. 36 depicts the specificity of a memory and de novo response induced in a patient with melanoma towards mutated and wildtype peptide. $SRSF1_{E>K}$ and $ARAP1_{Y>H}$ specific T cell responses were challenged with DCs loaded with mutant or wildtype neoantigen peptides at different concentrations (X axis: 0 µM, 0.05 µM, 0.2 µM, 0.8 µM, and 3.2 µM) and measured IFN-γ+ and/or TNFα+ and/or CD107a+ of total CD8+ T cells (Y axis) in the samples; Both responses show significant difference to 0 µM concentration and not responsive to wild type neoantigen peptide. Statistical analysis: FDR for adjusted p value, P values: *≤0.05, *≤0.001, **≤0.0001.
Figure 37A:
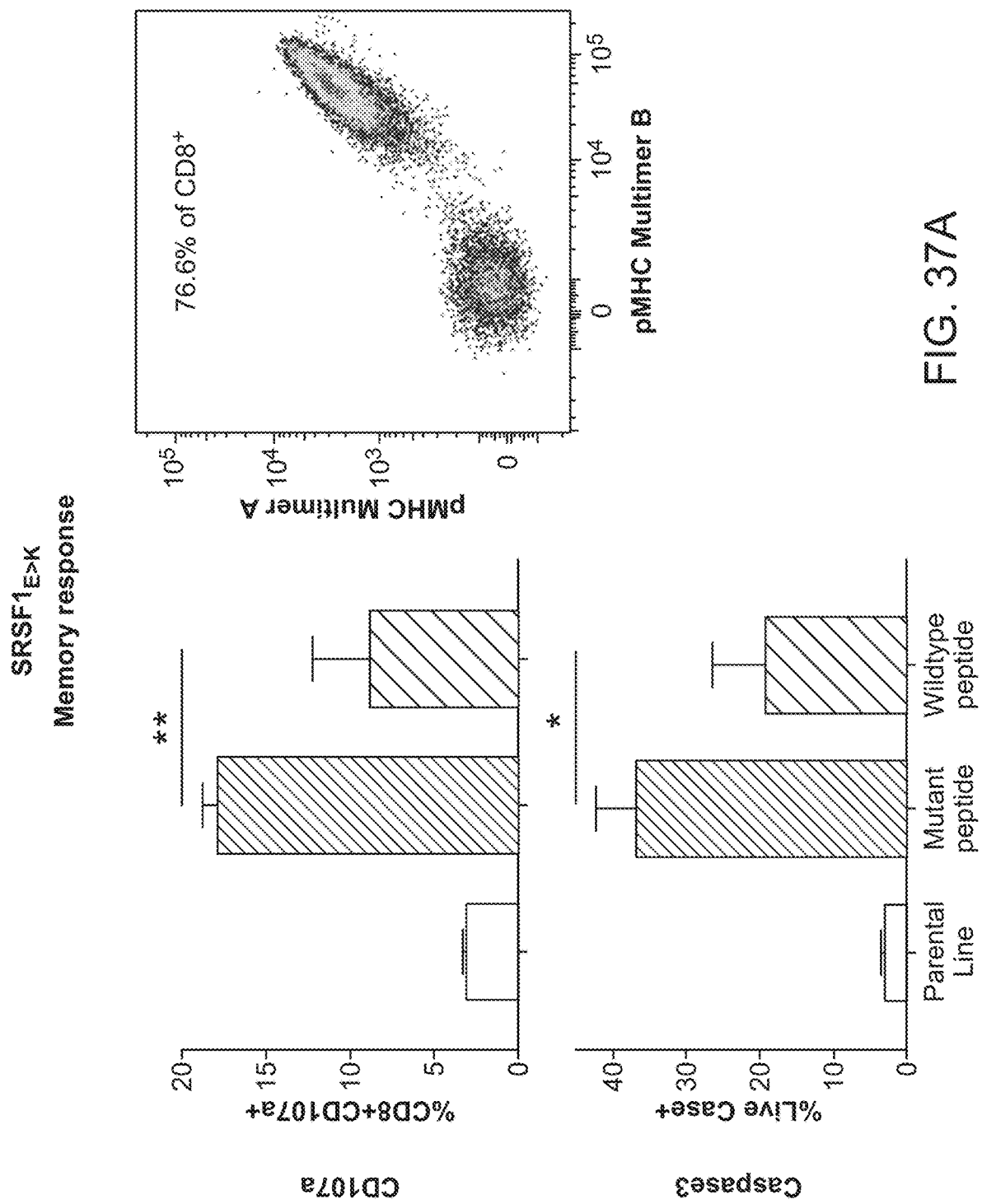
FIG. 37A depicts the cytotoxicity profile of a memory response induced in a patient with melanoma as quantified by the frequency of CD8+CD107a+ T cells. It also depicts target cell killing by these T cell responses as quantified by the frequency of aCAS3+ tumor cells. The cytotoxic capacity of the induced CD8+ T cell responses was assessed by re-challenging with mutant or wildtype neoantigen transduced tumor cells. Un-transduced tumor cells (parental A375 line) or tumor cells transduced with a 200 aa construct were used. The construct either contained the mutant or wildtype sequence, mutation in the center. Upregulation of CD107a on CD8+ T cells and active Caspase3 on tumor cells was measured upon co-culture. Target ratio: 3.3:1 ($SRSF1_{E>K}$).
Figure 37B:
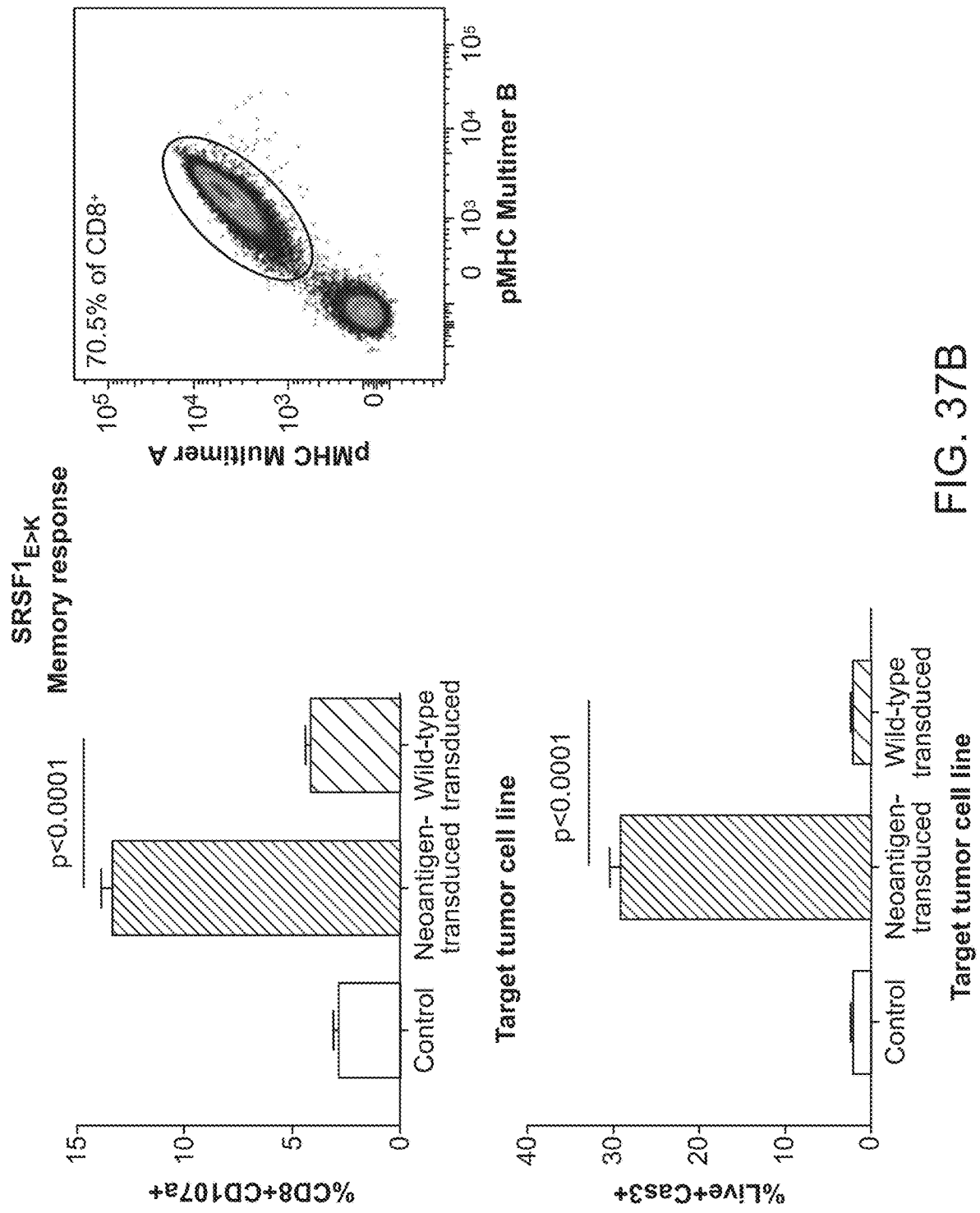
FIG. 37B depicts another example of the cytotoxicity profile of a memory response induced in a patient with melanoma as quantified by the frequency of CD8+CD107a+ T cells. It also depicts target cell killing by these T cell responses as quantified by the frequency of aCAS3+ tumor cells. The cytotoxic capacity of the induced CD8+ T cell responses was assessed by re-challenging with mutant or wildtype neoantigen transduced tumor cells. Un-transduced tumor cells (parental A375 line) or tumor cells transduced with a 200 aa construct were used. The construct either contained the mutant or wildtype sequence, mutation in the center. Upregulation of CD107a on CD8+ T cells and active Caspase3 on tumor cells was measured upon co-culture. Red circles highlight the pMHC+ fractions. Effector:Target ratio: 5:1 ($SRSF1_{E>K}$). Statistical analysis: unpaired T test, P values ≤0.01, **≤0.0001.
Figure 37C:
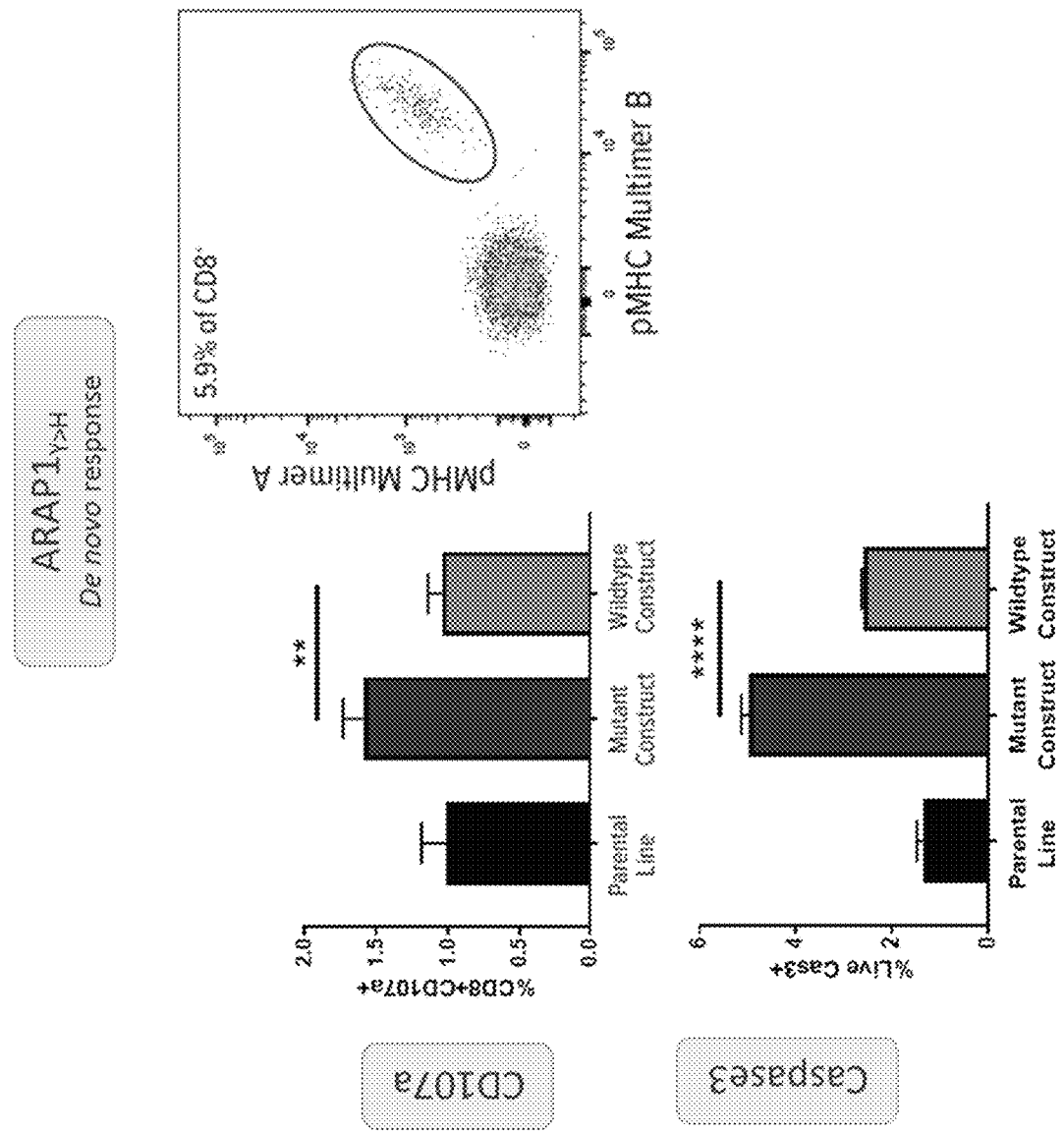
FIG. 37C depicts the cytotoxicity profile of a de novo response induced in a patient with melanoma as quantified by the frequency of CD8+CD107a+ T cells. It also depicts target cell killing by these T cell responses as quantified by the frequency of aCAS3+ tumor cells. The cytotoxic capacity of the induced CD8+ T cell responses was assessed by re-challenging with mutant or wildtype neoantigen transduced tumor cells. Un-transduced tumor cells (parental A375 line) or tumor cells transduced with a 200 aa construct were used. The construct either contained the mutant or wildtype sequence, mutation in the center. Upregulation of CD107a on CD8+ T cells and active Caspase3 on tumor cells was measured upon co-culture. Red circles highlight the pMHC+ fractions. Effector:Target ratio: 0.66:1 ($ARAP1Y>H$). Statistical analysis: unpaired T test, P values ≤0.01, **≤0.0001.
Figure 38A:
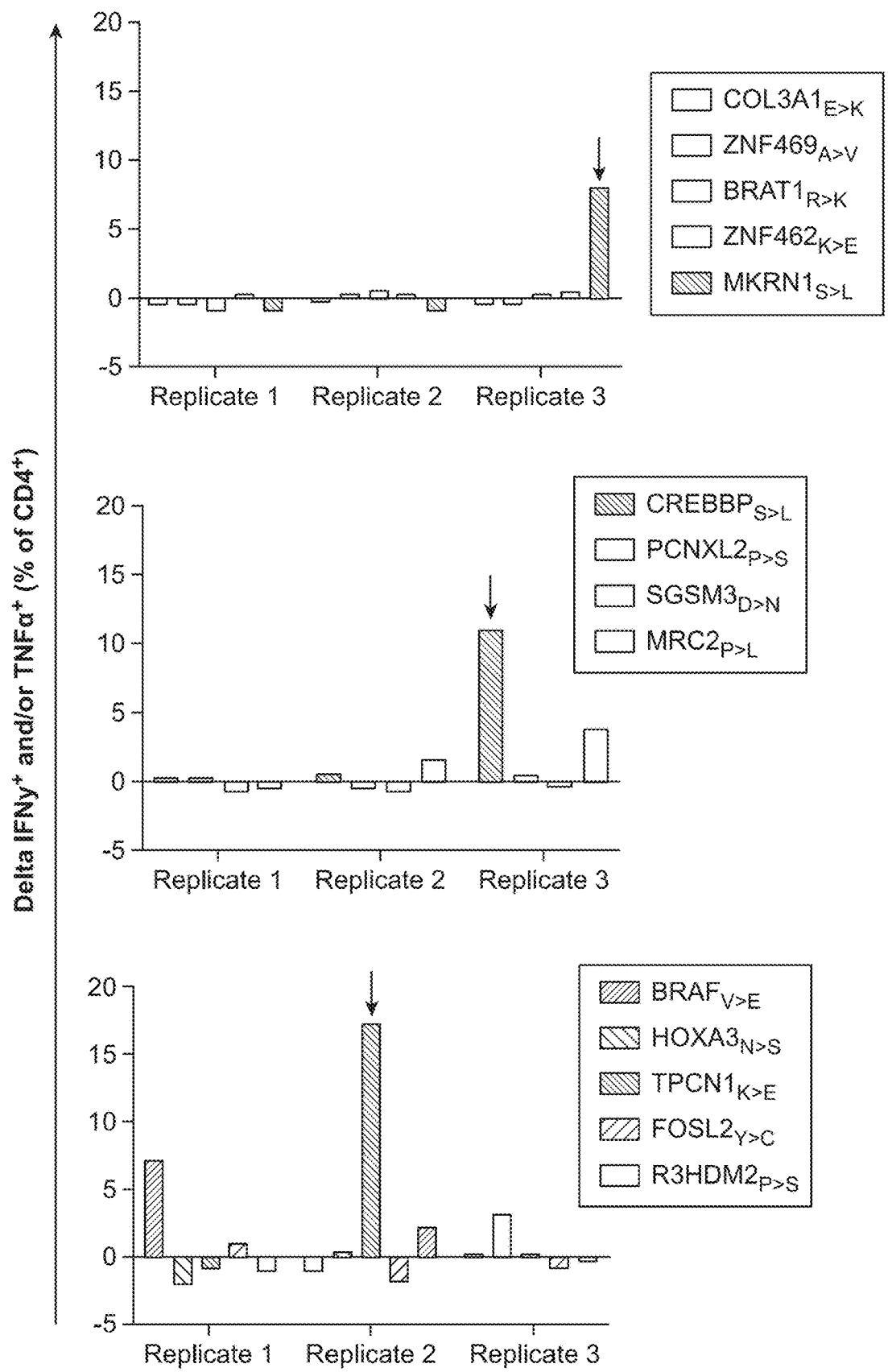
FIG. 38A depicts the identification of neoantigen specific CD4+ T cell responses in a melanoma patient. Responses are identified based on the production of IFN-γ & TNFα (Y axis) when re-challenged with mutant neoantigen peptide loaded DCs (0.8 µM). $MKRN1_{S>L}$, $CREBBP_{S>L}$, and TPCN1K>E were identified as positive responses.
Figure 38B:
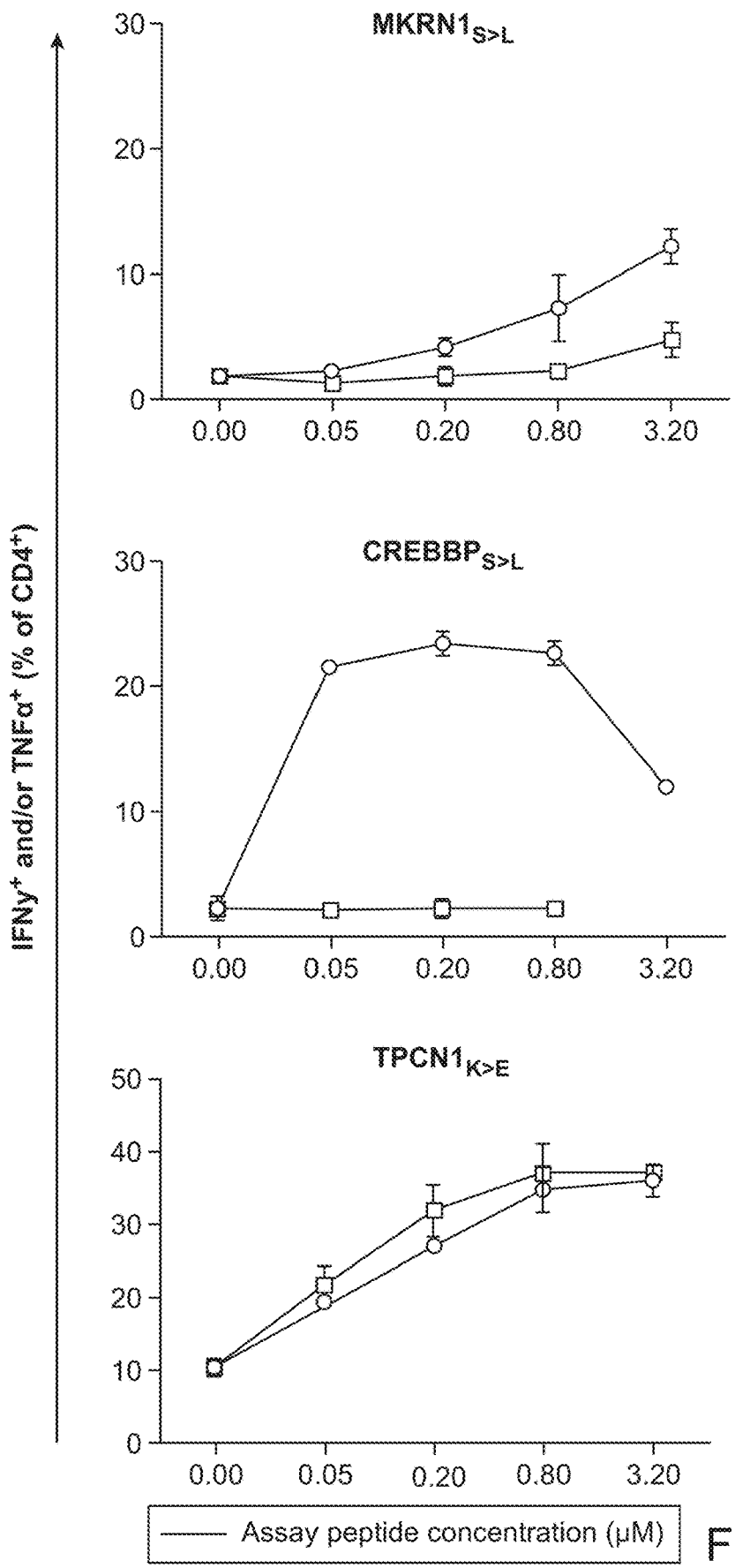
FIG. 38B depicts the specificity of the CD4+ T cell responses depicted in FIG. 38A towards the indicated mutated and wildtype peptides. In a confirmatory study the CD4 T cell responses shown in FIG. 38A were challenged with different concentrations (X axis—0 µM, 0.05 µM, 0.2 µM, 0.8 µM and 3.2 µM) of mutant and wildtype neoantigen peptides and measured IFNγ+ and/or TNFα+ of total CD4+ (Y axis) in the samples. Two of the CD4+ T cell responses ($MKRN1_{S>L}$ and $CREEBP_{S>L}$) show significant difference to 0 µM concentration and not responsive to wild type neoantigen peptide but $TPCN1_{K>E}$ response was reactive to both mutant and wildtype neoantigen peptide. Statistical analysis: FDR for adjusted p value, P value<0.05)
Figure 38C:
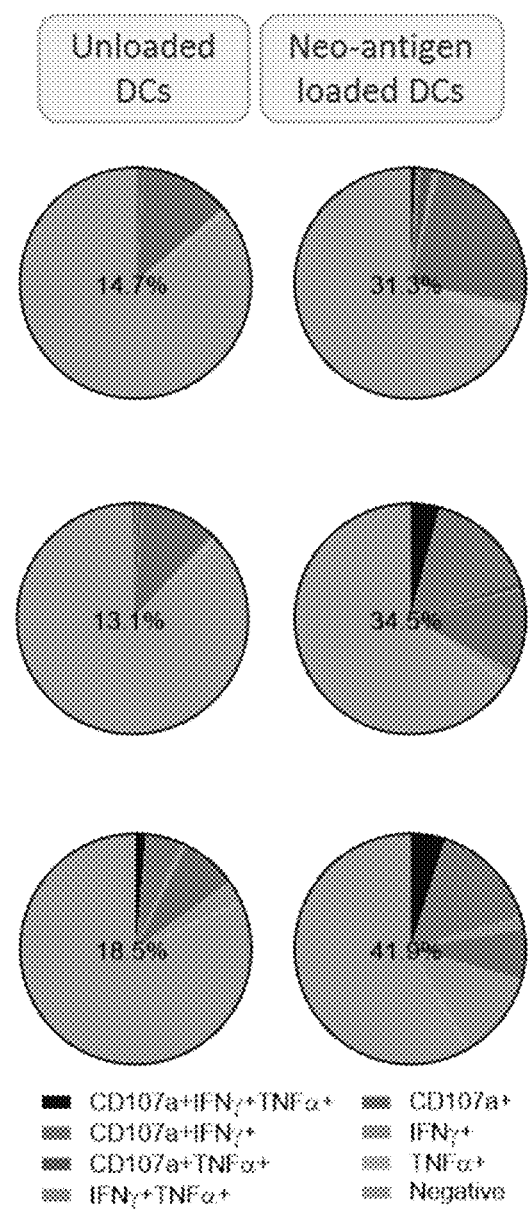
FIG. 38C depicts the polyfunctionality profile of these CD4+ T cell responses, as shown by a combination of 1, 2, 3, or 4 functions (e.g., the one or more functions are production of one or more factors selected from IFNγ, TNFα, CD107a and 4-1BB). The poly-functionality of identified CD4+ T cell responses was assessed by re-challenge with mutant neoantigen peptide loaded DCs (0.8 µm). Percentages in the pie charts represent percentage functional CD4+ T cells (1, 2 and/or 3 functions). Representative data depicted, generated from post-stimulation CD4+ T cell responses induced in a patient.

T cells were prepared using the T cell manufacturing protocol 3 and the stimulated T cells were analyzed. The samples were obtained from two patients with melanoma. T cells were analyzed using similar assays as described in Example 24. FIG. 34 shows pMHC multimer plots quantifying $CD8^+$ T cell responses induced from the two patients with melanoma. As used herein, NEO-STIM refers to the T cell manufacturing protocol. FIG. 35 shows data of the polyfunctional profile of a memory and de novo response induced in a patient with melanoma, as shown by a combination of 1, 2, 3, or 4 functions. The one or more functions are production of one or more factors selected from IFNγ, TNFα, CD107a and 4-1BB). FIG. 36 shows the specificity of a memory and de novo response induced in a patient with melanoma towards mutated and wildtype peptide. FIGS. 37A and 37B and 37C show the cytotoxicity profile of a memory and de novo response induced in a patient with melanoma as quantified by the frequency of $CD8^+CD107a^+$ T cells (top panels). The bottom panels of FIGS. 37A and 37B and 37C show target cell killing by these T cell responses as quantified by the frequency of $aCAS3^+$ tumor cells. FIG. 38A shows the identification of neoantigen specific $CD4^+$ T cell responses in a melanoma patient. FIG. 38B shows the specificity of these $CD4^+$ T cell responses identified in FIG. 38A towards mutated and wildtype peptides. FIG. 38C shows the polyfunctionality profile of these $CD4^+$ T cell responses, as shown by a combination of 1, 2, 3, or 4 functions. The one or more functions are production of one or more factors selected from IFNγ, TNFα, CD107a and 4-1BB).

Example 27—Experimental Data Using T Cell Manufacturing Protocol 1 or 2

Figure 39:
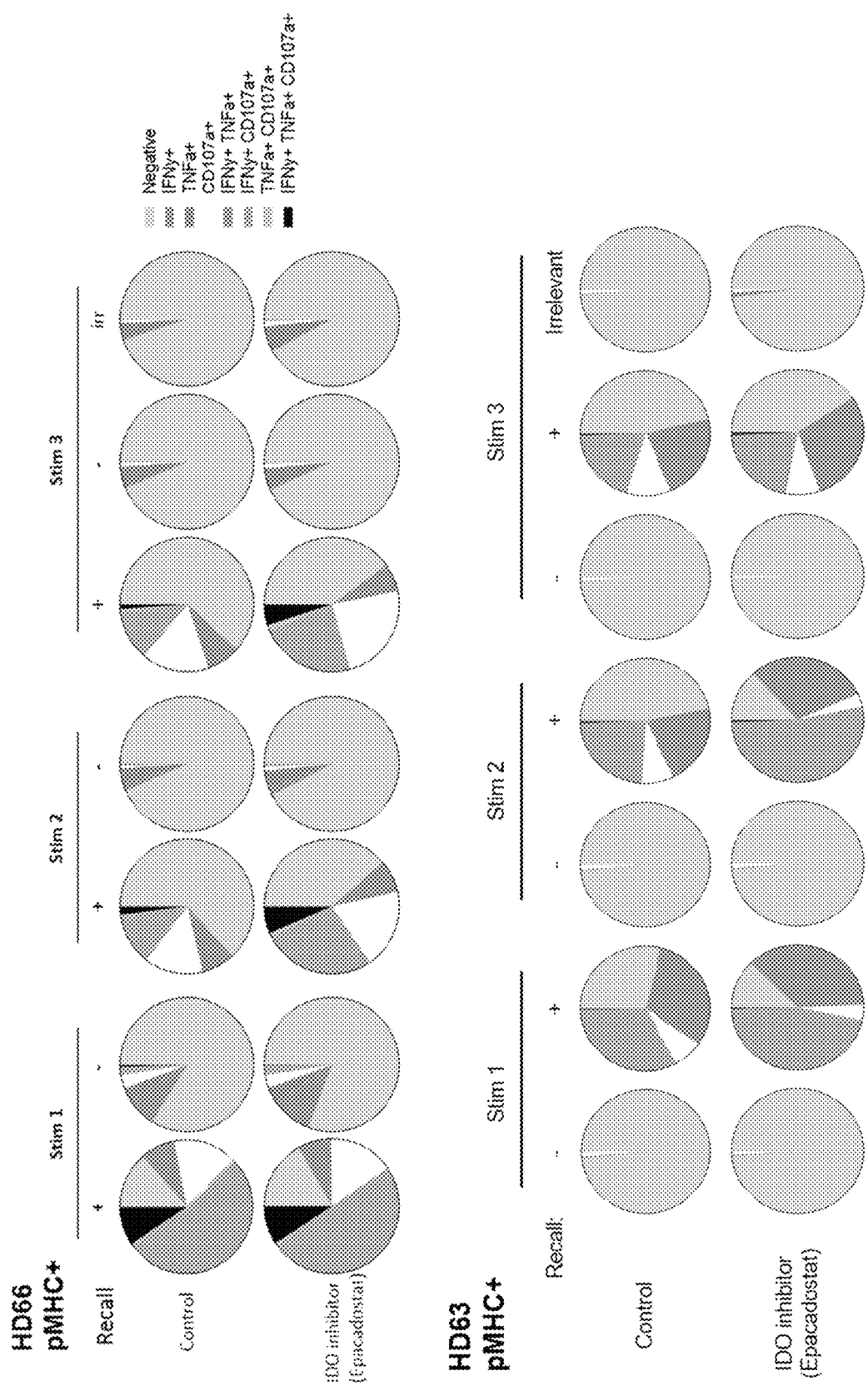
FIG. 39 depicts the functionality of memory responses induced in two healthy donors (e.g., HD66 and HD63) with or without the addition of Epacadostat, as shown by a combination of 1, 2 or 3 functions (e.g., the one or more functions are production of one or more factors selected from IFNγ, TNFα and CD107a).
Figure 40:
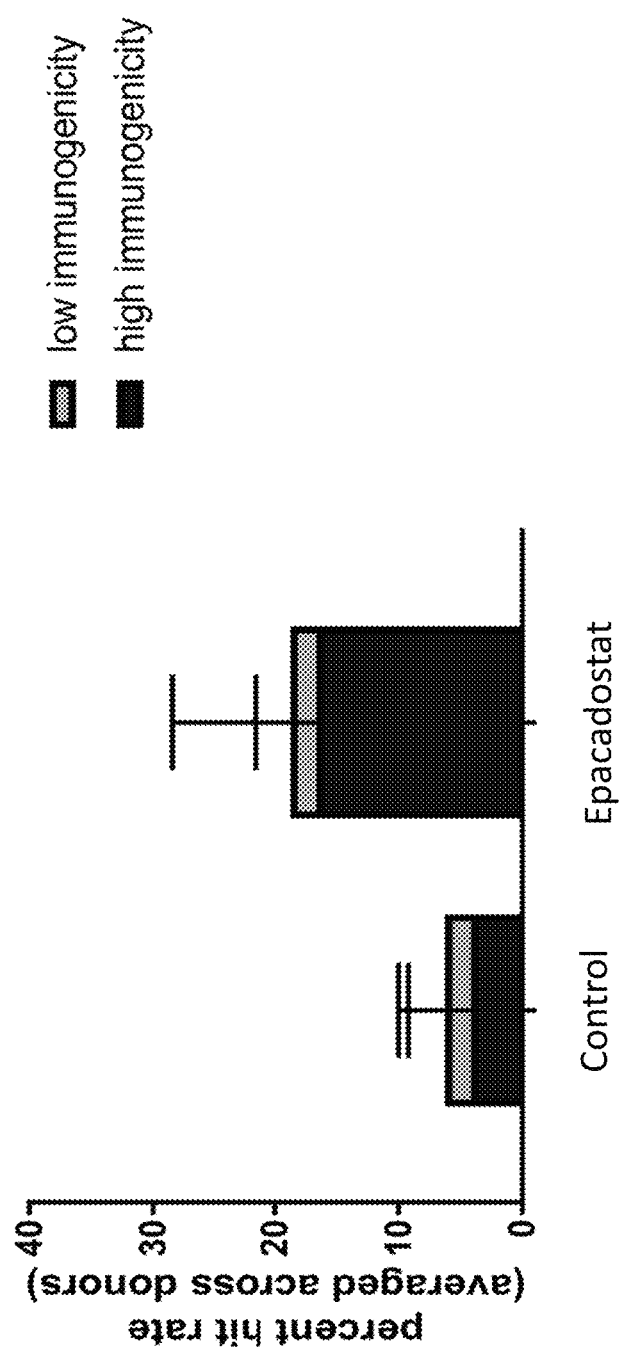
FIG. 40 depicts the percent induced de novo CD8⁺ T cell responses ('hit rate', averaged across four healthy donors) in six replicate inductions with or without the addition of Epacadostat.
Figure 41B:
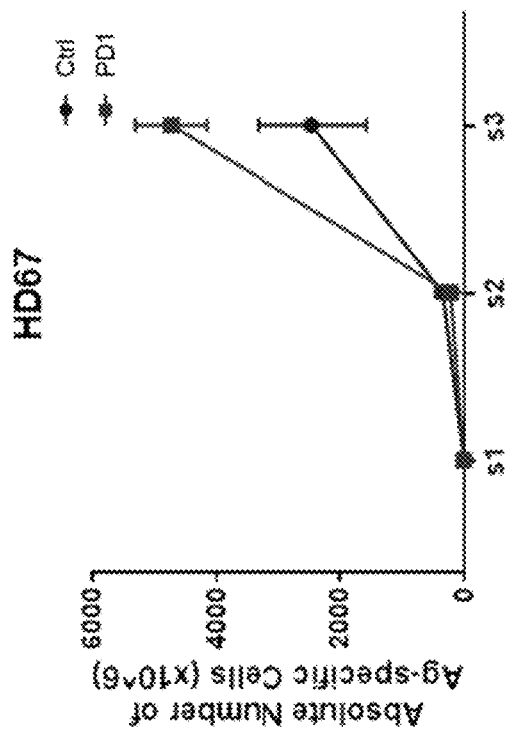
FIG. 41B depicts the absolute number of antigen specific cells from donor HD67 after induction with T cell manufacturing protocol provided herein, with or without the addition of PD-1 blocking antibody.
Figure 41A:
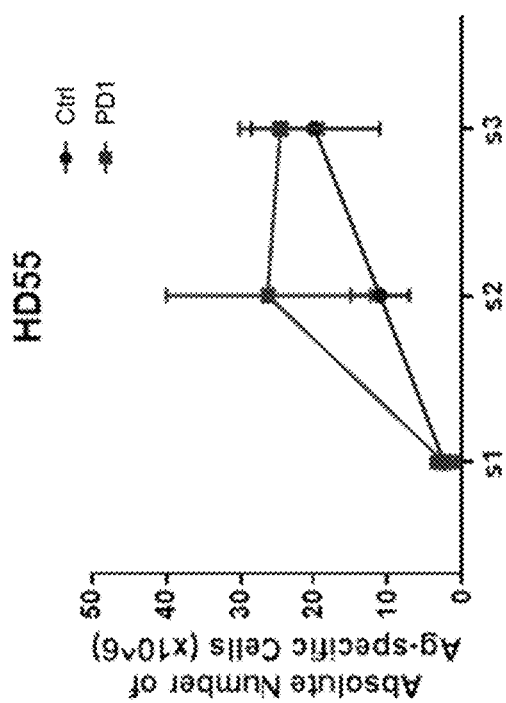
FIG. 41A depicts the absolute number of antigen specific cells from donor HD55 after induction with T cell manufacturing protocol provided herein, with or without the addition of PD-1 blocking antibody.
Figure 42B:
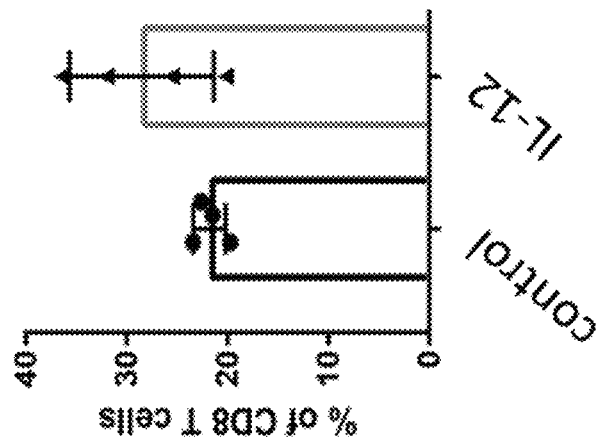
FIG. 42B depicts the percentage of CD8+ T cells within the de novo CD8+ T cell responses with or without the addition of IL-12.
Figure 42A:
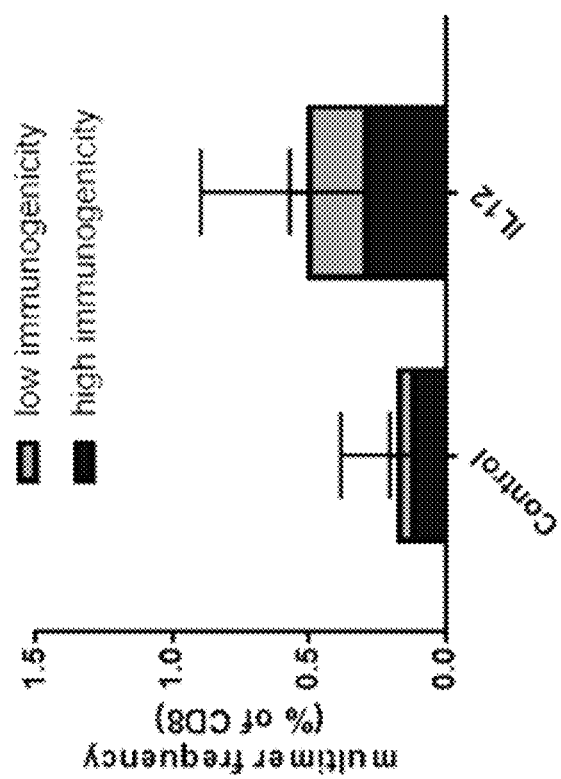
FIG. 42A depicts the fraction of pMHC⁺ CD8⁺ T cells of de novo CD8⁺ T cell responses with or without the addition of IL-12.
Figure 43:
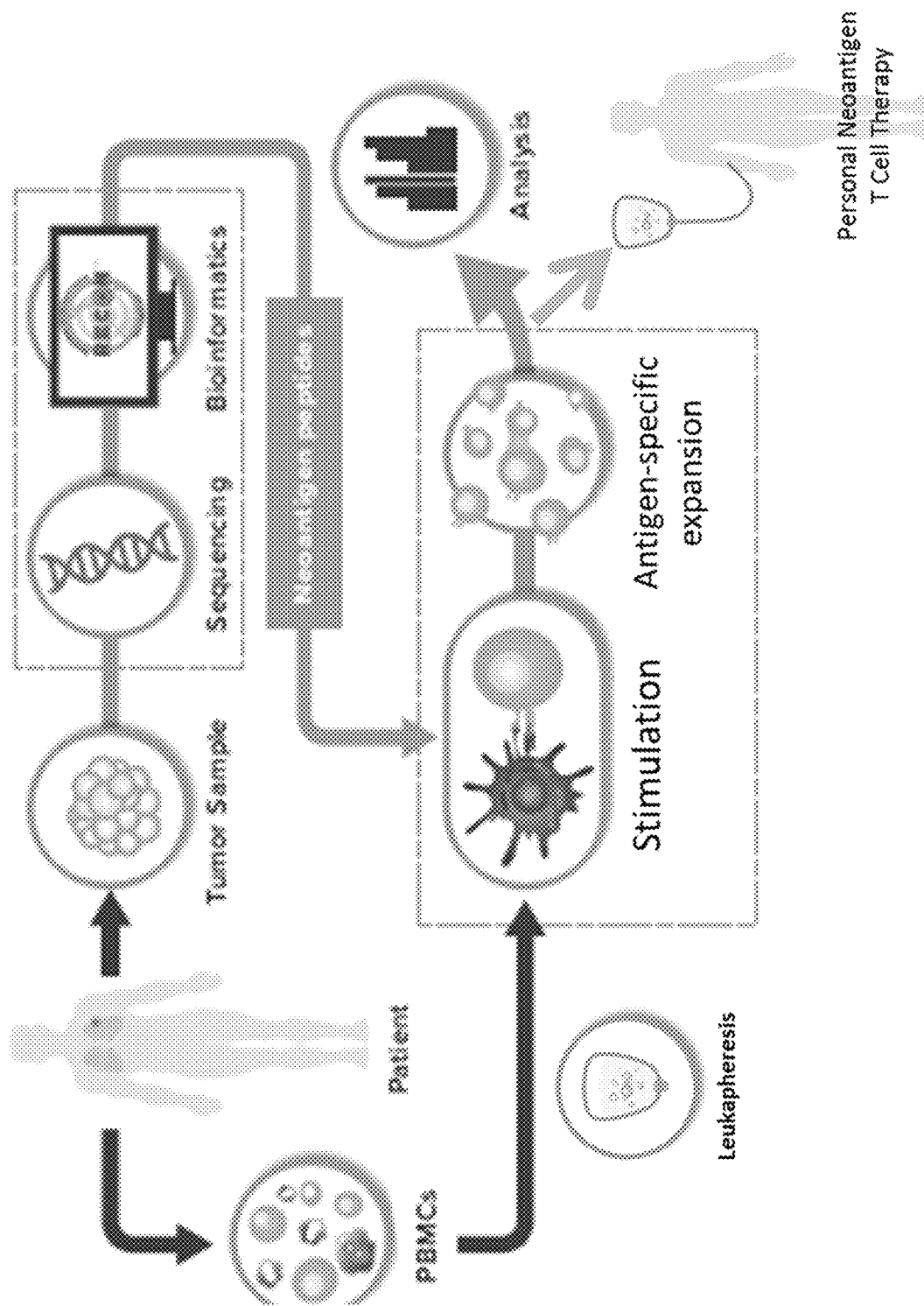
FIG. 43 depicts an example of methods described herein. Patient-specific neoantigens are predicted using a bioinformatics engine, Synthetic long peptides covering the predicted neoantigens are used as immunogens in stimulation protocols to assess immunogenic capacity. The stimulation protocol involves feeding these neoantigen-encoding peptides to patient-derived APCs, which are then co-cultured with patient-derived T cells to prime neoantigen specific T cells.

T cells were prepared using the T cell manufacturing protocol 1 or, as an alternative, protocol 2. The stimulated T cells were analyzed using similar assays as described in Example 24. FIG. 39 shows the functionality of memory responses induced in two healthy donors (e.g., HD66 and HD63) with or without the addition of Epacadostat, as shown by a combination of 1, 2 or 3 functions (e.g., the one or more functions are production of one or more factors selected from IFNγ, TNFα and CD107a). FIG. 40 shows the percent induced de novo CD8+ T cell responses ('hit rate', averaged across four healthy donors) in six replicate inductions with or without the addition of Epacadostat. FIG. 41A shows the absolute number of antigen specific cells from donor HD55 after induction with T cell manufacturing protocol provided herein, with or without the addition of PD-1 blocking antibody. FIG. 41B shows the absolute number of antigen specific cells from donor HD 67 after induction with T cell manufacturing protocol provided herein, with or without the addition of PD-1 blocking antibody. FIG. 42A shows the fraction of $pMHC^+$ $CD8^+$ T cells of de novo $CD8^+$ T cell responses with or without the addition of IL-12. FIG. 42B shows the percentage of $CD8^+$ T cells within the de novo $CD8^+$ T cell responses with or without the addition of IL-12.

Example 28: In-Depth Characterization of Immune Responses Induced Against Patient-Specific Neoantigens Using Patient-specific neoantigens were predicted using bioinformatics engine. Synthetic long peptides covering the predicted neoantigens were used as immunogens in the stimulation protocol to assess the immunogenic capacity. The stimulation protocol involves feeding these neoantigen-encoding peptides to patient-derived APCs, which are then co-cultured with patient-derived T cells to prime neoantigen specific T cells.

Multiple rounds of stimulations are incorporated in the stimulation protocol to prime, activate and expand memory and de novo T cell responses. The specificity, phenotype and functionality of these neoantigen-specific T cells was analyzed by characterizing these responses with the following assays: Combinatorial coding analysis using pMHC multimers was used to detect multiple neoantigen-specific CD8+ T cell responses. A recall response assay using multiplexed, multiparameter flow cytometry was used to identify and validate CD4+ T cell responses. The functionality of CD8+ and CD4+ T cell responses was assessed by measuring production of pro-inflammatory cytokines including IFN-γ and TNFα, and upregulation of the CD107a as a marker of degranulation. A cytotoxicity assay using neoantigen-expressing tumor lines was used to understand the ability of CD8+ T cell responses to recognize and kill target cells in response to naturally processed and presented antigen. The cytotoxicity was measured by the cell surface upregulation of CD107a on the T cells and upregulation of active Caspase3 on neoantigen-expressing tumor cells. In this study, melanoma patient samples (NV6 and NV10) were obtained under IRB approval.

The stimulation protocol was successful in the expansion of pre-existing CD8+ T cell responses, as well as the induction of de novo CD8+ T cell responses (Table 1).

TABLE 1

| Patient | HUGO Symbol | Full Gene Name | Type |
|---|---|---|---|
| NV10 | $SRSF1_{E>K}$ | Serine And Arginine Rich Splicing Factor 1 | CD8 |
| | $ARAP1_{Y>H}$ | Ankyrin Repeat And PH Domain | |
| | $PKDREJ_{G>R}$ | Polycystin Family Receptor For Egg Jelly | |
| | $MKRN1_{S>L}$ | Makorin Ring Finger Protein 1 | CD4 |
| | $CREBBP_{S>L}$ | CREB Binding Protein | |
| | $TPCN1_{K>E}$ | Two Pore Segment Channel 1 | |
| NV6 | $AASDH_{neoORF}$ | Aminoadipate-Semialdehyde Dehydrogenase | CD8 |
| | $ACTN4_{K>N}$ | Actinin Alpha 4 | |
| | $CSNK1A1_{S>L}$ | Casein Kinase 1 Alpha 1 | |
| | $DHX40_{neoORF}$ | DEAH-Box Helicase 40 | |
| | $GLI3_{P>L}$ | GLI Family Zinc Finger 3 | |

TABLE 1-continued

| Patient | HUGO Symbol | Full Gene Name | Type |
|---|---|---|---|
| | $QARS_{R>W}$ | Glutaminyl-TRNA Synthetase | |
| | $FAM178B_{P>L}$ | Family With Sequence Similarity 178 Member B | |
| | $RPS26_{P>L}$ | Ribosomal Protein S26 | |

Using PBMCs from melanoma patient NV10, expansion of a pre-existing CD8+ T cell response was observed from 4.5% of CD8+ T cells to 72.1% of CD8+ T cells ($SRSF1E_{>K}$). Moreover, the stimulation protocol was effective in inducing two presumed de novo CD8+ T cell responses towards patient-specific neoantigens ($ARAP1_{Y>H}$: 6.5% of CD8+ T cells and $PKDREJ_{G>R}$: 13.4% of CD8+ T cells; no cells were detectable prior to the stimulation process) (FIG. 34). The stimulation protocol successfully induced seven de novo CD8+ T cell responses towards both previously described and novel model neoantigens using PBMCs from another melanoma patient, NV6, up to varying magnitudes ($ACTN4_{K>N}$ $CSNK1A1_{S>L}$ DHX40neoORF 7, $GLI3_{P>L}$, $QARS_{R>W}$, $FAM178B_{P>L}$ and $RPS26_{P>L}$, range: 0.2% of CD8+ T cells up to 52% of CD8+ T cells). Additionally, a CD8+ memory T cell response towards a patient-specific neoantigen was expanded (AASDHneoORF, up to 13% of CD8+ T cells post stimulation).

The induced CD8+ T cells from patient NV10 was characterized in more detail. Upon re-challenge with mutant peptide loaded DCs, neoantigen-specific CD8+ T cells exhibited one, two and/or all three functions (16.9% and 65.5% functional CD8+pMHC+ T cells for $SRSF1_{E>K}$ and $ARAP1_{Y>H}$, respectively (FIG. 35).

When re-challenged with different concentrations of neoantigen peptides, the induced CD8+ T cells responded significantly to mutant neoantigen peptide but not to the wildtype peptide (FIG. 36).

In patient NV10, CD4+ T cell responses were identified using a recall response assay with mutant neoantigen loaded DCs (FIGS. 38A-C). Three CD4+ T cell responses were identified ($MKRN1_{S>L}$, $CREBBP_{S>L}$ and $TPCN1_{K>E}$) based on the reactivity to DCs loaded with mutant neoantigen peptide. These CD4+ T cell responses also showed a polyfunctional profile when re-challenged with mutant neoantigen peptide. 31.3%, 34.5% & 41.9% of CD4+ T cells exhibited one, two and/or three functions; $MKRN1_{S>L}$, $CREBBP_{S>L}$ and $TPCN1_{K>E}$ responses, respectively.

The cytotoxic capacity of the induced CD8+ responses from patient NV10 was also assessed (FIGS. 37A-C). Both $SRSF1_{E>K}$ and $ARAP1_{Y>H}$ responses showed a significant upregulation of CD107a on the CD8+ T cells and active Caspase3 on the tumor cells transduced with the mutant construct after co-culture.

Using the stimulation protocol, predicted patient-specific neoantigens, as well as model neoantigens, were confirmed to be immunogenic by the induction of multiple neoantigen-specific CD8+ and CD4+ T cell responses in patient material. The ability to induce polyfunctional and mutant-specific CD8+ and CD4+ T cell responses proves the capability of predicting high-quality neoantigens and generating potent T cell responses. The presence of multiple enriched neoantigen-specific T cell populations (memory and de novo) at the end of the stimulation process demonstrates the ability to raise new T cell responses and generate effective cancer immunotherapies to treat cancer patients.

What is claimed is:

1. A method of preparing cancer antigen-specific T cells ex vivo suitable for T cell therapy in a human subject, the method comprising:
   (a) depleting CD25+ cells from a population of immune cells comprising antigen presenting cells (APCs) and T cells, thereby forming a depleted population of immune cells comprising a first population of APCs and T cells, wherein the population of immune cells is from a biological sample from a human subject; and
   (b) incubating the depleted population of immune cells for a first time period in the presence of:
      (i) FMS-like tyrosine kinase 3 receptor ligand (FLT3L), and
      (ii) (A) a polypeptide comprising one or more cancer antigen epitope sequences expressed by cancer cells of a human subject with cancer; or (B) a polynucleotide encoding the polypeptide comprising the one or more cancer antigen epitope sequences expressed by the cancer cells of the human subject with cancer; thereby forming a population of stimulated T cells; and
   (c) expanding the population of stimulated T cells, thereby forming an expanded population of T cells, wherein expanding comprises expanding T cells derived from naïve CD8+ T cells or naïve CD4+ T cells; wherein the expanded population of T cells comprises T cells that are specific to a complex comprising (i) a first cancer antigen epitope sequence of the one or more cancer antigen epitope sequences and (ii) an MHC protein expressed by the cancer cells or APCs of the human subject with cancer; wherein:
      (i) at least 0.1% of CD8+ T cells that are specific to the complex in the expanded population of T cells are derived from the naïve CD8+ T cells from the biological sample from the human subject, or
      (ii) at least 0.1% of CD4+ T cells that are specific to the complex in the expanded population of T cells are derived from the naïve CD4+ T cells from the biological sample from the human subject.

2. The method of claim 1, wherein steps (b) and (c) are performed in less than 28 days.

3. The method of claim 1, wherein a fraction of CD8+ T cells of total number of CD8+ T cells in the expanded population of T cells that are specific to the complex is at least two-fold higher than a fraction of CD8+ T cells of total number of CD8+ T cells in the biological sample that are specific to the complex.

4. The method of claim 1, wherein a fraction of CD4+ T cells of total number of CD4+ T cells in the expanded population of T cells that are specific to the complex is at least two-fold higher than a fraction of CD4+ T cells of total number of CD4+ T cells in the biological sample that are specific to the complex.

5. The method of claim 1, wherein the biological sample is from the human subject with cancer.

6. The method of claim 1, wherein expanding further comprises contacting the population of stimulated T cells with a second population of mature APCs that has been incubated with FLT3L.

7. The method of claim 6, wherein the second population of mature APCs has been incubated with FLT3L for at least 1 day prior to contacting the population of stimulated T cells with the second population of mature APCs.

8. The method of claim 6, wherein expanding further comprises contacting the population of stimulated T cells with a third population of mature APCs, wherein the third population of mature APCs has been incubated with FLT3L prior to contacting the population of stimulated T cells with the third population of mature APCs.

9. The method of claim 1, wherein the biological sample is a peripheral blood sample, a leukapheresis sample or an apheresis sample.

10. The method of claim 1, wherein incubating comprises incubating the depleted population of immune cells in the presence of FLT3L and an RNA encoding the polypeptide.

11. The method of claim 1, wherein the polypeptide is from 8 to 50 amino acids in length.

12. The method of claim 1, wherein each of the one or more cancer antigen epitope sequences contains a mutation and binds to an MHC protein expressed by cancer cells of the human subject with cancer with a stronger affinity than a corresponding wild-type epitope sequence.

13. The method of claim 1, wherein the one or more cancer antigen epitope sequences comprises two or more cancer antigen epitope sequences that are expressed by cancer cells of the human subject with cancer.

14. The method of claim 13, wherein the expanded population of T cells comprises T cells that are specific to:
(A) a first complex comprising (i) a first cancer antigen epitope sequence of the two or more cancer antigen epitope sequences and (ii) an MHC protein expressed by the cancer cells or APCs of the human subject with cancer, and
(B) a second complex comprising (i) a second cancer antigen epitope sequence of the two or more cancer antigen epitope sequences and (ii) an MHC protein expressed by the cancer cells or APCs of the human subject with cancer.

15. The method of claim 1, wherein depleting comprises contacting the population of immune cells with a CD25 binding agent.

16. The method of claim 1, wherein depleting further comprises depleting CD14+ cells from the population of immune cells.

17. The method of claim 1, wherein depleting further comprises depleting CD19+ cells from the population of immune cells.

18. The method of claim 1, wherein the expanded population of T cells comprises at least $1\times10^6$ total CD8+ T cells or at least $1\times10^6$ total CD4+ T cells.

19. The method of claim 1, wherein the method further comprises harvesting the expanded population of T cells, cryopreserving the expanded population of T cells, preparing a pharmaceutical composition containing the expanded population of T cells or administering a pharmaceutical composition comprising the expanded population of T cells to the human subject with cancer.

20. The method of claim 1, wherein the method further comprises stimulating one or more populations of APCs with one or more cytokines or growth factors, thereby obtaining one or more APC preparations comprising matured APCs, and wherein expanding comprises contacting the population of stimulated T cells with the one or more APC preparations comprising matured APCs.

21. The method of claim 20, wherein the one or more cytokines or growth factors comprise GM-CSF, IL-4, FLT3L, TNF-α, IL-1β, PGE1, IL-6, IL-7, IFN-α, R848, LPS, ss-rna40, poly I:C, or a combination thereof.

* * * * *

UNITED STATES PATENT AND TRADEMARK OFFICE
CERTIFICATE OF CORRECTION

| | |
|---|---|
| PATENT NO. | : 12,258,581 B2 |
| APPLICATION NO. | : 17/494633 |
| DATED | : March 25, 2025 |
| INVENTOR(S) | : Van Buuren et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 546 days.

Signed and Sealed this
Sixteenth Day of December, 2025

John A. Squires
*Director of the United States Patent and Trademark Office*